(12) United States Patent
Lissilaa et al.

(10) Patent No.: US 10,640,564 B2
(45) Date of Patent: May 5, 2020

(54) ANTIBODIES THAT BIND TO CCR6 AND THEIR USES

(71) Applicant: Ichnos Sciences SA, La Chaux-de-Fonds (CH)

(72) Inventors: Rami Lissilaa, La Chaux-de-Fonds (CH); Adrian Walmsley, La Chaux-de-Fonds (CH); Stanislas Blein, La Chaux-de-Fonds (CH); Romain Ollier, La Chaux-de-Fonds (CH); Samuel Hou, La Chaux-de-Fonds (CH); Jeremy Loyau, La Chaux-de-Fonds (CH)

(73) Assignee: Ichnos Sciences SA, La Chaux-de-Fonds (CH)

( * ) Notice: Subject to any disclaimer, the term of this patent is extended or adjusted under 35 U.S.C. 154(b) by 0 days.

(21) Appl. No.: 15/519,413

(22) PCT Filed: Oct. 19, 2015

(86) PCT No.: PCT/EP2015/074178
§ 371 (c)(1),
(2) Date: Apr. 14, 2017

(87) PCT Pub. No.: WO2016/059253
PCT Pub. Date: Apr. 21, 2016

(65) Prior Publication Data
US 2018/0086836 A1 Mar. 29, 2018

(30) Foreign Application Priority Data

Oct. 17, 2014 (EP) ..................................... 14189374

(51) Int. Cl.
*A61K 39/395* (2006.01)
*C07K 16/28* (2006.01)
*A61K 47/68* (2017.01)
*C07K 14/715* (2006.01)

(52) U.S. Cl.
CPC ...... *C07K 16/2866* (2013.01); *A61K 47/6849* (2017.08); *C07K 14/715* (2013.01); *C07K 2317/14* (2013.01); *C07K 2317/24* (2013.01); *C07K 2317/30* (2013.01); *C07K 2317/31* (2013.01); *C07K 2317/35* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/622* (2013.01); *C07K 2317/626* (2013.01); *C07K 2317/76* (2013.01); *C07K 2317/92* (2013.01); *C07K 2317/94* (2013.01); *C07K 2319/30* (2013.01); *C07K 2319/70* (2013.01)

(58) Field of Classification Search
None
See application file for complete search history.

(56) References Cited

U.S. PATENT DOCUMENTS

| | | |
|---|---|---|
| 5,585,089 A | 12/1996 | Queen et al. |
| 5,624,821 A | 4/1997 | Winter et al. |
| 5,648,260 A | 7/1997 | Winter et al. |
| 5,677,425 A | 10/1997 | Bodmer et al. |
| 5,693,762 A | 12/1997 | Queen et al. |
| 5,869,046 A | 2/1999 | Presta et al. |
| 6,121,022 A | 9/2000 | Presta et al. |
| 6,165,745 A | 12/2000 | Ward et al. |
| 6,180,370 B1 | 1/2001 | Queen et al. |
| 6,194,551 B1 | 2/2001 | Idusogie et al. |
| 6,277,375 B1 | 8/2001 | Ward |

(Continued)

FOREIGN PATENT DOCUMENTS

| | | |
|---|---|---|
| WO | WO-9429351 A2 | 12/1994 |
| WO | WO-0042072 A2 | 7/2000 |

(Continued)

OTHER PUBLICATIONS

Paul, W.E. Fundamental Immunology, Third Edition (textbook), "Fv Structure and Diversity in Three Dimensions" pp. 292-295; Raven Press, New York; (1993). (Year: 1993).*

(Continued)

*Primary Examiner* — Elizabeth C. Kemmerer
*Assistant Examiner* — Regina M DeBerry
(74) *Attorney, Agent, or Firm* — Sterne, Kessler, Goldstein & Fox P.L.L.C.

(57) ABSTRACT

The present invention relates to antibodies or fragments thereof that bind to CCR6. More specifically, the present invention relates to an antibody or fragment thereof that binds to CCR6 comprising a heavy chain CDR1 comprising the amino acid sequence of SEQ ID NO: 31, and/or a heavy chain CDR2 comprising the amino acid sequence of SEQ ID NO: 32, SEQ ID NO: 190, SEQ ID NO: 239, SEQ ID NO: 240, SEQ ID NO: 241, SEQ ID NO: 242, SEQ ID NO: 254 or SEQ ID NO: 255 and/or a heavy chain CDR3 comprising the amino acid sequence of SEQ ID NO: 33; and/or comprising a light chain CDR1 comprising the amino acid sequence of SEQ ID NO: 34, SEQ ID NO: 191, SEQ ID NO:244, SEQ ID NO:245, SEQ ID NO: 246 or SEQ ID NO: 256, and/or a light chain CDR2 comprising the amino acid sequence of SEQ ID NO: 35, SEQ ID NO: 247, SEQ ID NO: 248 or SEQ ID NO:257 and/or a light chain CDR3 comprising the amino acid sequence of SEQ ID NO: 36 or SEQ ID NO: 192 or SEQ ID NO: 193.

9 Claims, 20 Drawing Sheets

Specification includes a Sequence Listing.

(56) References Cited

U.S. PATENT DOCUMENTS

| | | | |
|---|---|---|---|
| 2004/0197329 A1 | 10/2004 | Nakayama et al. | |
| 2012/0148592 A1* | 6/2012 | Imai | C07K 16/24 424/139.1 |
| 2013/0052670 A1* | 2/2013 | Savage | C07K 16/18 435/7.94 |

FOREIGN PATENT DOCUMENTS

| | | |
|---|---|---|
| WO | WO-03035835 A2 | 5/2003 |
| WO | WO-2013184218 A1 | 10/2004 |
| WO | WO-2010095031 A2 | 8/2010 |
| WO | WO-2013005649 A1 | 1/2013 |
| WO | WO-2016059253 A1 | 4/2016 |

OTHER PUBLICATIONS

Casset et al. A peptide mimetic of an anti-CD4 monoclonal antibody by rational design. Biochem Biophys Res Comm. vol. 307:198-205 (2003). (Year: 2003).*
Holm et al. Functional mapping and single chain construction of the anti-cytokeratin 8 monoclonal antibody TS1. Mol Immunol. vol. 44(6):1075-1084 (2007). (Year: 2007).*
MacCallum et al. Antibody-antigen interactions: Contact analysis and binding site topography. J Mol Biol. vol. 262:732-745 (1996). Year: 1996).*
Vajdos et al. Comprehensive functional maps of the antigen-binding site of an anti-ErbB2 antibody obtained with shotgun scanning mutagenesis. J Mol Biol. vol. 320(2):415-428 (2002). (Year: 2002).*
Tokuriki et al. Stability effects of mutations and protein evolvability; Current Opinion in Structural Biology, 19:596-604 (2009). (Year: 2009).*
Baba, M., et al., "Identification of CCR6, the Specific Receptor for a Novel Lymphocyte-directed CC Chemokine LARC," The Journal of Biological Chemistry 272(23):14893-14898, American Society for Biochemistry and Molecular Biology, United States (Jun. 1997).
Barbas, S.M., et al., "Recognition of DNA by Synthetic Antibodies," Journal of the American Chemical Society 116(5):2161-2162, American Chemical Society, United States (Mar. 1994).
Beiboer, S.H., et al., "Guided Selection of a Pan Carcinoma Specific Antibody Reveals Similar Binding Characteristics yet Structural Divergence between the Original Murine Antibody and its Human Equivalent," Journal of Molecular Biology 296(3):833-849, Elsevier, England (Feb. 2000).
Bensmana, M,, et al., "The Human Immunoglobulin Pseudo-gamma Ighgp Gene Shows No Major Structural Defect," Nucleic Acids Research 16(7):3108, Oxford University Press, England (Apr. 1988).
Dariavach, P., et al., "Human Immunoglobulin C Lambda 6 Gene Encodes the Kern+Oz—λChain and $C_\lambda 4$ and $C_\lambda 5$ are Pseudogenes," Proceedings of the National Academy of Sciences of the United States of America 84(24):9074-9078, National Academy of Sciences, United States (Dec. 1987).
Edelman, G.M, et al., "The Covalent Structure of an Entire γG Immunoglobulin Molecule," Proceedings of the National Academy of Sciences USA 63(1):78-85, National Academy of Sciences, United States (1969).
Frangione, B., et al., "Human λ Light-chain Constant Region Gene C Mor λ: the Primary Structure of AVI Bence Jones Protein Mor," Proceedings of the National Academy of Sciences of the United States of America 82(10)3415-3419, National Academy of Sciences, United States (May 1985).
Greaves, D.R., et al., "CCR6, a CC Chemokine Receptor That Interacts With Macrophage Inflammatory Protein 3alpha and Is Highly Expressed in Human Dendritic Cells," The Journal of Experimental Medicine 186(6):837-844, Rockefeller University Press, United States (Sep. 1997).
Kearney, J.F., et al., "A New Mouse Myeloma Cell Line That Has Lost Immunoglobulin Expression but Permits the Construction of Antibody-secreting Hybrid Cell Lines," Journal of Immunology 123(4):1548-1550, American Association of Immunologists, United States (Oct. 1979).
Klimka, A., et al., "Human Anti-CD30 Recombinant Antibodies by Guided Phage Antibody Selection Using Cell Panning," British Journal of Cancer 83(2):252-260, Nature Publishing Group, England (Jul. 2000).
Liao, F., et al., "CC-Chemokine Receptor 6 is Expressed on Diverse Memory Subsets of T Cells and Determines Responsiveness to Macrophage Inflammatory Protein 3 Alpha," Journal of Immunology (Baltimore, Md., : 1950) 162(1):186-194, American Association of Immunologists, United states (Jan. 1999).
Longmore, G.E., et al., "Product-Identification and Substrate-Specificity Studies of the GDP-L-Fucose:2-Acetamido-2-Deoxy-Beta-d-Glucoside (FUC Goes to Asn-Linked GlcNAc) 6-Alpha-I-Fucosyltransferase in a Golgi-Rich Fraction From Porcine Liver," Carbohydrate Research 100:365-392, Elsevier, Netherlands (1982).
Power, CA., et al,, "Cloning and Characterization of a Specific Receptor for the Novel Cc Chemokine Mip-3alpha From Lung Dendritic Cells ," The Journal of Experimental Medicine 186(6):825-835, Rockefeller University Press, United States (Sep. 1997).
Rader, C., et al., "A Phage Display Approach for Rapid Antibody Humanization: Designed Combinatorial V Gene Libraries," Proceedings of the National Academy of Sciences USA 95(15):8910-8915, National Academy of Sciences, United States (Jul. 1998).
Romagnani, S., et al., "Properties and Origin of Human Th17 Cells ," Molecular immunology 47(1):3-7, Pergamon Press, England (Nov. 2009).
Rossi, D.L., et al., "Identification Through Bioinformatics of Two New Macrophage Proinflammatory Human Chemokines: Mip-3alpha and Mip-3beta," Journal of immunology (Baltimore, Md. : 1950) 158(3)1033-1036, American Association of Immunologists, United States (Feb. 1997).
Swiss-Prot, "CC chemokine receptor 6," Accession No. Q8HZR7, accessed at https://www.ncbi.nlm.nih.gov/protein/Q8HZR7, accessed on Nov. 13, 2018.
Swiss-Prot, "Chemokine (C—C motif) receptor 6," Accession No. Q5BK58, accessed at https://www.ncbi.nlm.nih.gov/protein/Q5BK58, accessed on Nov. 13, 2018.
Swiss-Prot, "RecName: Full=C—C chemokine receptor type 6, Short=C—C CKR-6, Short=CC-CKR-6, Short=CCR-6, AltName: Full=Chemokine receptor-like 3, Short=CKR-L3, AltName: Full=DRY6, AltName: Full=G-protein coupled receptor 29, AltName: Full=GPR-CY4, Short=GPRCY4, AltName: Ful . . . ," Accession No. P51684.2, accessed at https://www.ncbi.nlm.nih.gov/protein/P51684, accessed on Nov. 13, 2018.
Swiss-Prot, "RecName: Full=C—C chemokine receptor type 6, Short=C—C CKR-6, Short=CC-CKR-6, Short=CCR-6, AltName: Full=KY411, AltName: CD_antigen=CD196," Accession No. 054689. 1, accessed at https://www.ncbi.nlm.nih.gov/protein/O54689, accessed on Nov. 14, 2018.
Swiss-Prot, "RecName: Full=C—C motif chemokine 20, AltName: Full=Beta-chemokine exodus-1, AltName: Full=CC chemokine LARC, AltName: Full=Liver and activation-regulated chemokine, AltName: Full=Macrophage inflammatory protein 3 alpha, Short=MIP-3-alpha, AltName: Full=Small- . . . ," Accession No. P78556.1, accessed at https://www.ncbi.nlm.nih.gov/protein/P78556, accessed on Nov. 14, 2018.
Trail, P.A., et al., "Monoclonal Antibody Drug Immunoconjugates for Targeted Treatment of Cancer," Cancer Immunology, Immunotherapy : CII 52(5):328-337, Springer Verlag, Germany (May 2003).
Zaballos, A., et al., "Molecular Cloning and RNA Expression of Two New Human Chemokine Receptor-like Genes," Biochemical and Biophysical Research Communications 227(3):846-853, Elsevier, United States (Oct. 1996).
International Search Report and Written Opinion for International Application No. PCT/EP2015/074178, European Patent Office, Netherlands, dated Apr. 18, 2017.
Hirota, K., et al., "Preferential recruitment of CCR6 expressing Th17 cells to inflamed joints via CCL20 in rheumatoid arthritis and its animal model," J Exp. Medicine 204(12):2803-812, Rockefeller University Press, United States (2007).

(56) References Cited

OTHER PUBLICATIONS

Vongsa, R.A., et al., "CCR6 Regulation of the Actin Cytoskeleton Orchestrates Human Beta Defensin-2- and CCL20 mediated Restitution of Colonic Epithelial Cells," J Biol Chemistry 284(15)10034-10045, American Society for Biochemistry and Molecular Biology, United States (2009).

* cited by examiner

FIG. 1
A
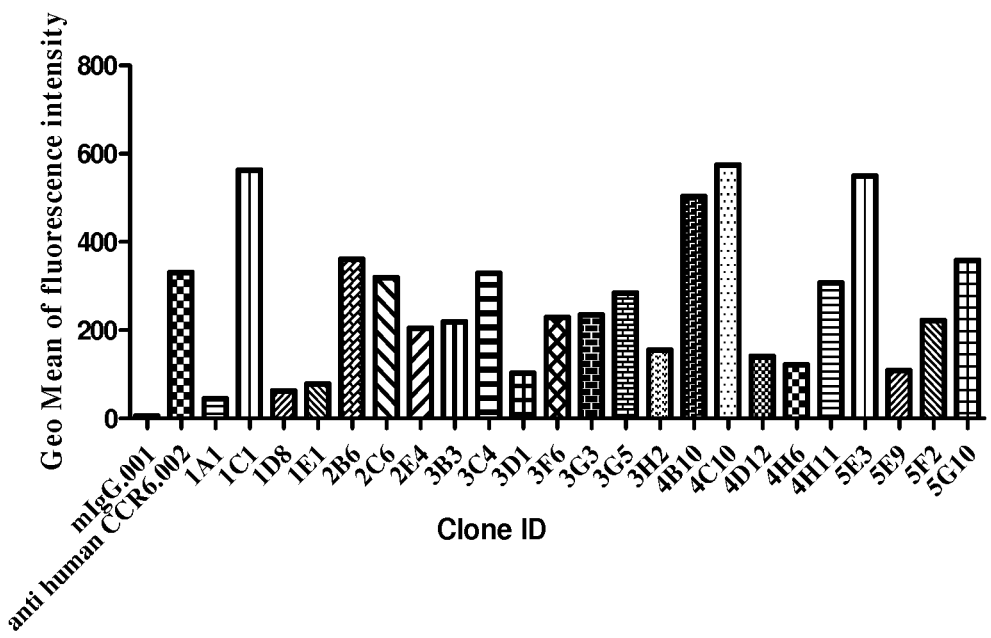
B
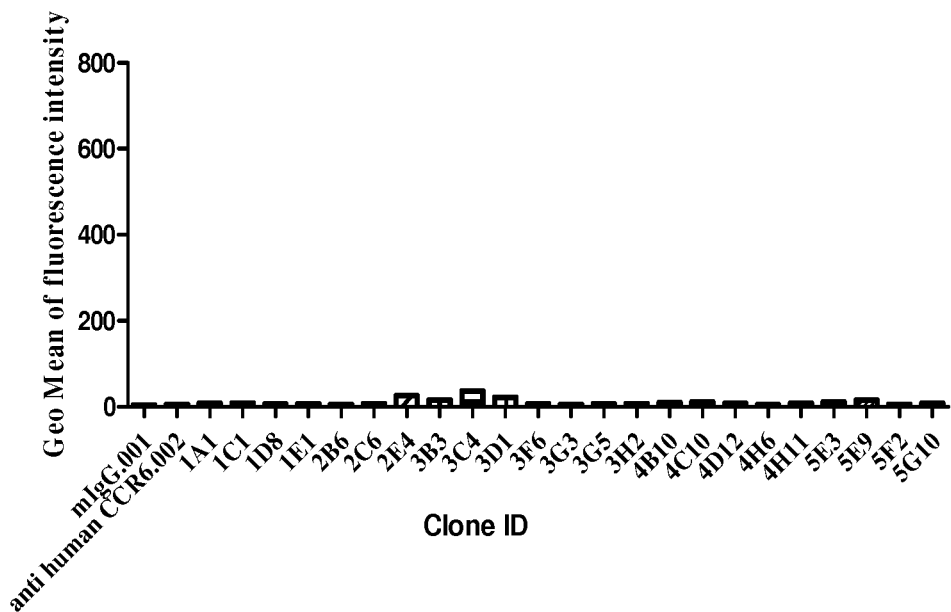

FIG. 2
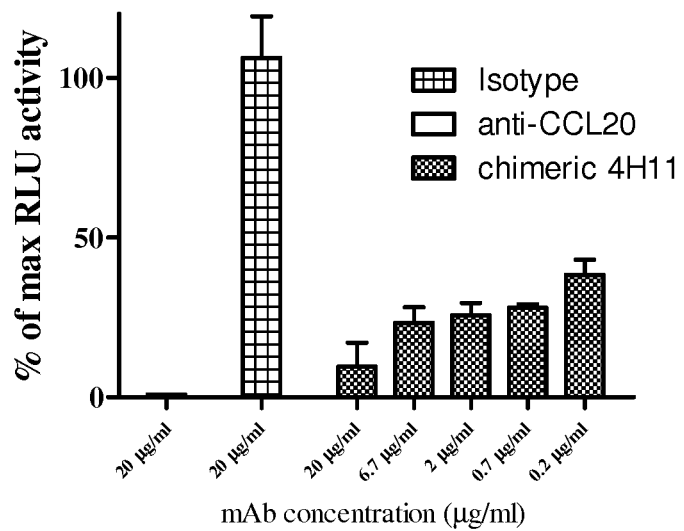
A
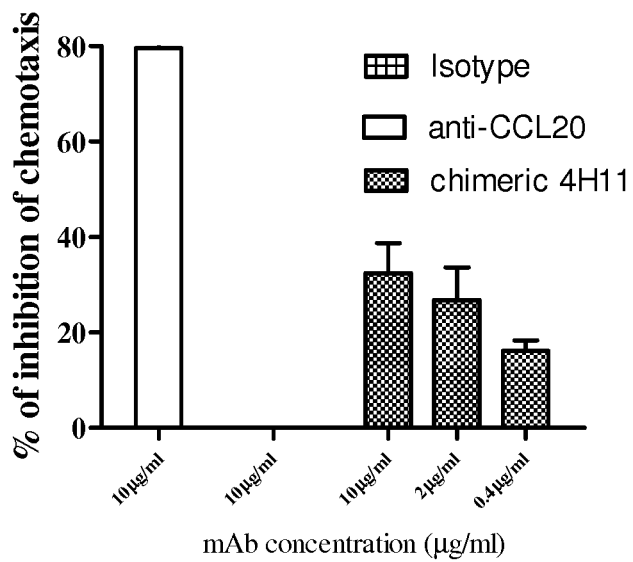
B

FIG. 3
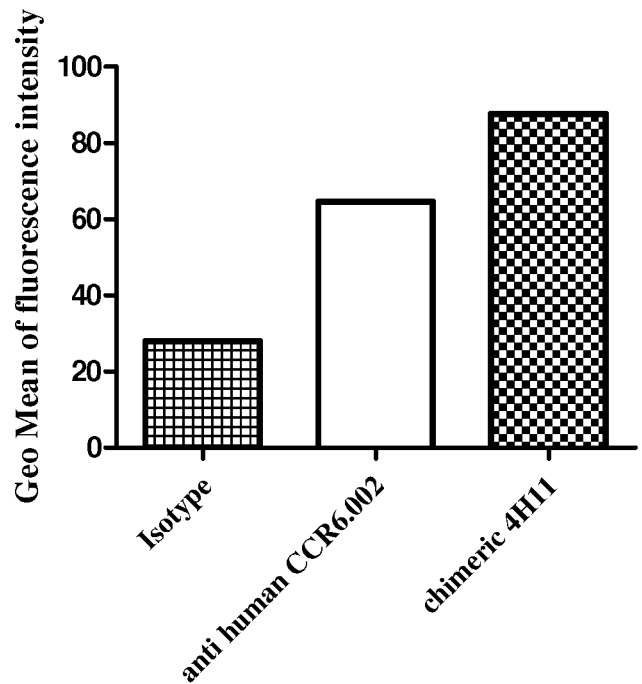
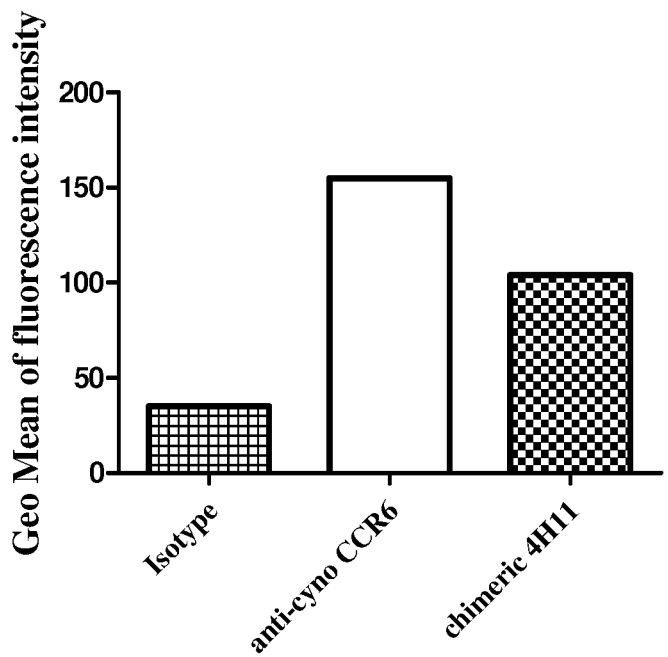

FIG. 5
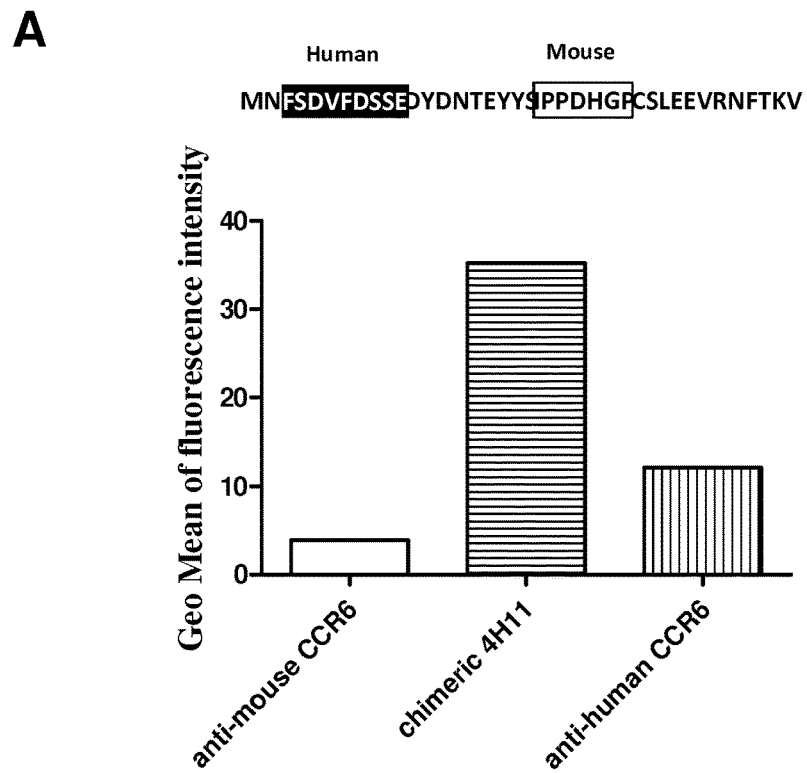
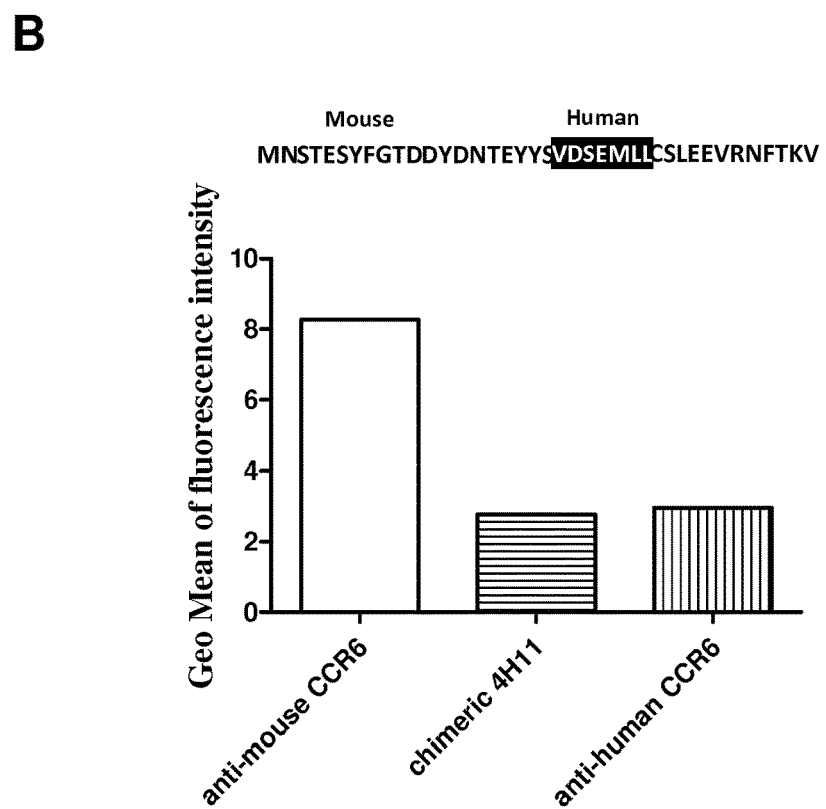

FIG.8
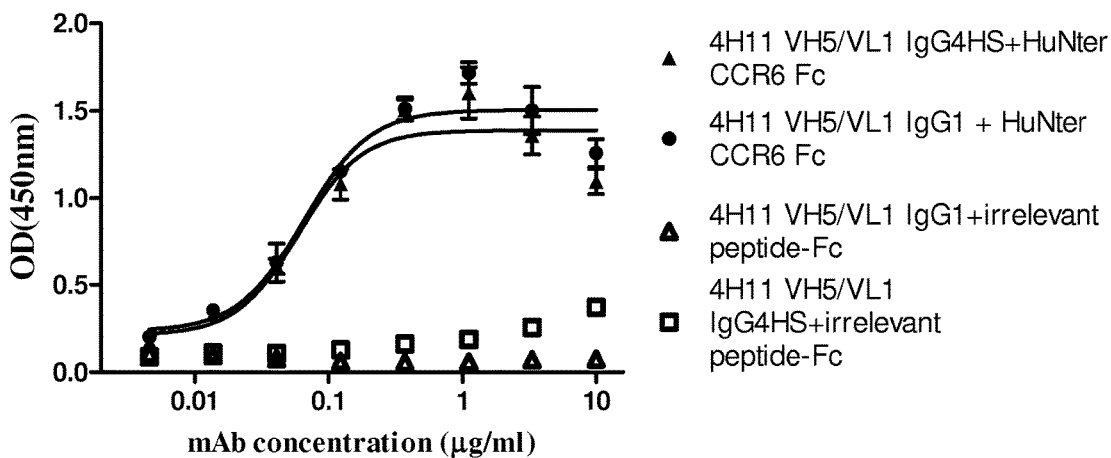
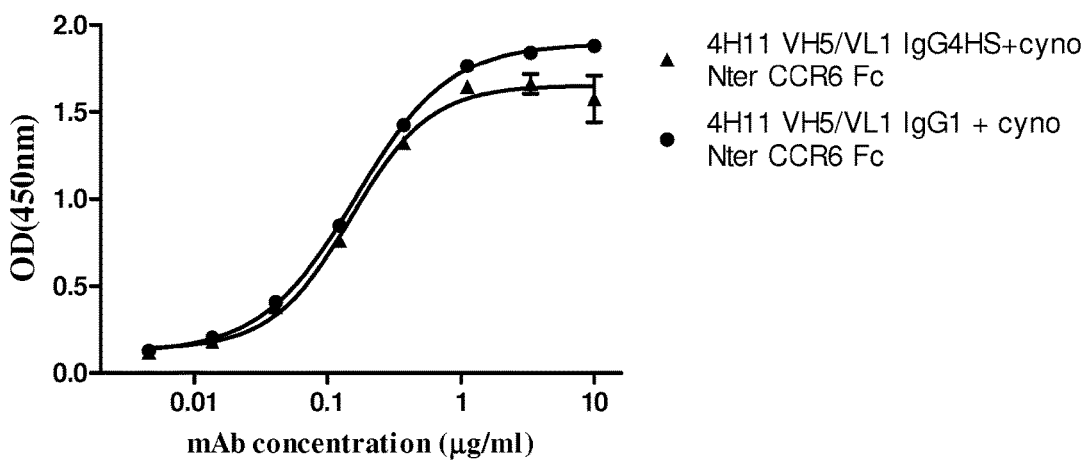

FIG.9
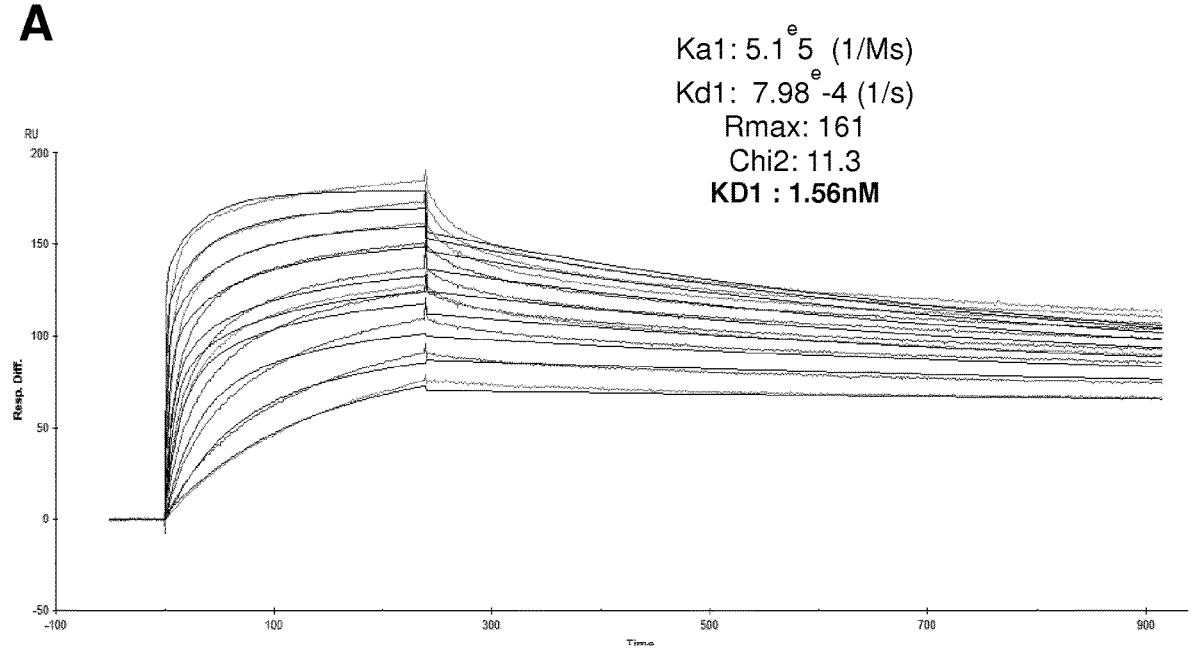
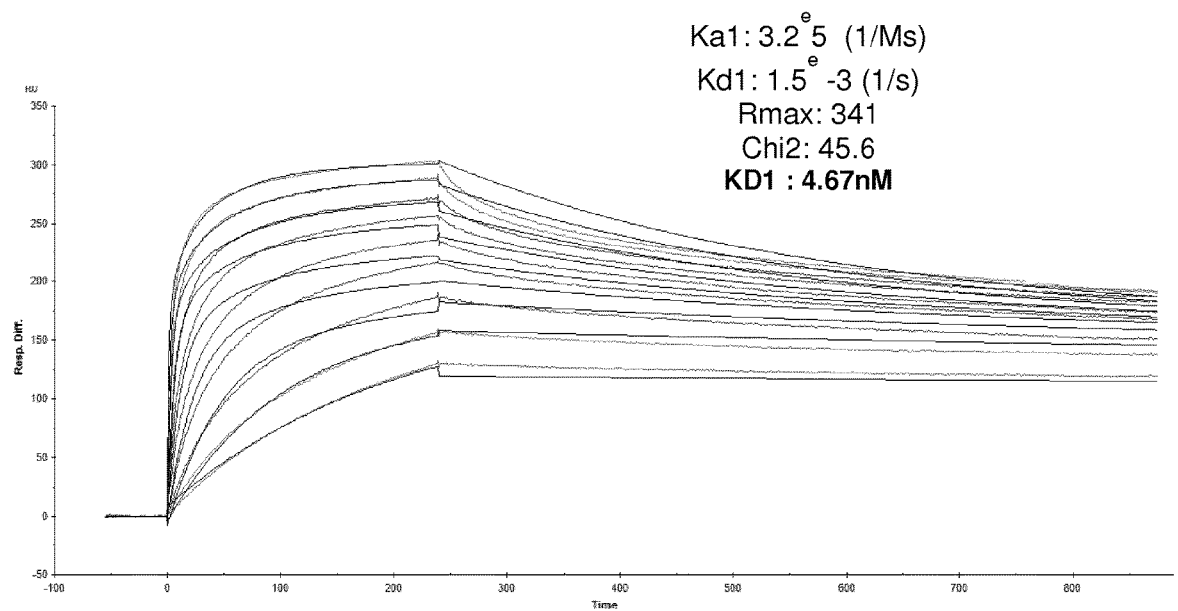

FIG. 14A

|  | Kabat: | H52 | H52a | H53 | H54 | H55 | H56 | H57 | H58 | Biacore binding |
|---|---|---|---|---|---|---|---|---|---|---|
| H2: | | T | - | N | G | G | I | T | Y | |
| Diversification | | X | - | X | G | G | X | T | X | |
| | | | | | | | | | | |
| scFv clones: | | | | | | | | | | |
| VH5/VL1-H2-H1 | | S | | | | | K | | | = |
| VH5/VL1-H2-D1 | | | | S | | | K | | | - |
| VH5/VL1-H2-B1 | | | | M | | | K | | | - |
| VH5/VL1-H2-C3 | | | | R | | | K | | | - |
| VH5/VL1-H2-A3 | | | | | | | K | | | =/+ |
| VH5/VL1-H2-C1 | | | | T | | | D | | | - |
| VH5/VL1-H21-C2 | | | N | T | | | G | | | = |
| VH5/VL1-H2-G2 | | | | T | | | T | | | = |
| VH5/VL1-H2-B3 | | | | T | | | R | | | =/+ |
| VH5/VL1-H2-E1 | | | | T | | | S | | | - |
| VH5/VL1-H2-G1 | | | | K | | | K | | F | - |
| VH5/VL1-H2-E3 | | | N | A | | | S | | L | 0 |

KEYS:
(-) weaker off-rate
(=) off-rate similar to H5/L1 parental scFv
(+) better off-rate
(++) significantly better off-rate
(0) no binding
(ND) not determined
(X) diversity: NNK – all 20 amino-acids

FIG.14B

| | Kabat: | L92 | L93 | L94 | L95 | L96 | Biacore binding |
|---|---|---|---|---|---|---|---|
| L3: | | S | H | V | P | L | |
| Diversification: | | X | X | X | P | x | |
| ScFv clones: | | | | | | | |
| VH5/VL1-L3-H7 | | | L | L | | | ++ |
| VH5/VL1-L3-F9 | | T | Y | M | | | ++ |
| VH5/VL1-L3-B8 | | T | Y | N | | | ++ |
| VH5/VL1-L3-G8 | | T | Y | L | | | ++ |
| VH5/VL1-L3-D8 | | T | K | L | | | + |
| VH5/VL1-L3-E8 | | | Y | L | | | + |
| VH5/VL1-L3-A9 | | | L | M | | I | ND |
| VH5/VL1-L3-B9 | | | Y | I | | | ND |
| VH5/VL1-L3-C9 | | T | Y | Y | | | ++ |
| VH5/VL1-L3-G7 | | T | F | L | | | ++ |
| VH5/VL1-L3-F8 | | | Y | S | | | 0 |
| VH5/VL1-L3-C8 | | T | Y | L | | I | ++ |
| VH5/VL1-L3-B10 | | | K | L | | | + |
| VH5/VL1-L3-D9 | | S | X | M | | L | ++ |

KEYS:
(-) weaker off-rate
(=) off-rate similar to H5/L1 parental scFv
(+) better off-rate
(++) significantly better off-rate
(0) no binding
(ND) not determined

FIG.17

|  | Human FAB HC/LC SEQ ID NO: | Human IgG1 HC/LC SEQ ID NO: | Human monovalent BEAT® HC1/HC2/LC SEQ ID NO: | Human IgG4 HC/LC SEQ ID NO: |
|---|---|---|---|---|
| VH5/VL1-B3G8-G29A | 206/207 | 198/199 | 227/228/229 | 214/215 |
| VH5/VL1-B3C9-G29A | 208/209 | 200/201 | 230/231/232 | 216/217 |
| VH5/VL1-G8-G29A | 202/203 | 194/195 | 221/222/223 | 210/211 |
| VH5/VL1-C9-G29A | 204/205 | 196/197 | 224/225/226 | 212/213 |
| VH5/VL1 | 233/234 | 10/30 | 218/219/220 | 235/236 |

FIG.18A

| FAB | Ka human CCR6 | Kd human CCR6 | KD human CCR6 | Ka cynomolgus CCR6 | Kd cynomolgus CCR6 | KD cynomolgus CCR6 |
|---|---|---|---|---|---|---|
| VH5/VL1-B3G8-G29A | 6.46e6 | 3.39e-3 | 526 pM | 1.72e6 | 2.02e-3 | 1.17 nM |
| VH5/VL1-B3C9-G29A | 6.96e6 | 3.79e-3 | 544 pM | 1.83e6 | 2.25e-3 | 1.23 nM |
| VH5/VL1-G8-G29A | 2.65e6 | 2.66e-3 | 1.0 nM | 8.97e5 | 1.96e-3 | 2.19 nM |
| VH5/VL1-C9-G29A | 2.66e6 | 3.41e-3 | 1.28 nM | 8.75e5 | 2.44e-3 | 2.79 nM |
| VH5/VL1 | 1.58e6 | 3.11e-2 | 19.6 nM | 7.44e5 | 2.50e-2 | 33.6 nM |

ANTIBODIES THAT BIND TO CCR6 AND THEIR USES

REFERENCE TO SEQUENCE LISTING SUBMITTED ELECTRONICALLY

The content of the electronically submitted sequence listing (Name: 3305_0230001_Seqlisting_ST25; Size: 307,352 bytes; and Date of Creation: Jun. 5, 2019) is incorporated herein by reference in its entirety.

FIELD OF THE INVENTION

The present invention relates to improved antibodies or fragments thereof that bind to CCR6. More specifically, the present invention relates to an antibody or fragment thereof that binds to CCR6 comprising a heavy chain CDR1 comprising the amino acid sequence of SEQ ID NO: 31, and/or a heavy chain CDR2 comprising the amino acid sequence of SEQ ID NO: 32, SEQ ID NO: 190, SEQ ID NO: 239, SEQ ID NO: 240, SEQ ID NO: 241, SEQ ID NO: 242, SEQ ID NO: 254 or SEQ ID NO: 255 and/or a heavy chain CDR3 comprising the amino acid sequence of SEQ ID NO: 33; and/or comprising a light chain CDR1 comprising the amino acid sequence of SEQ ID NO: 34, SEQ ID NO: 191, SEQ ID NO:244, SEQ ID NO:245, SEQ ID NO: 246 or SEQ ID NO: 256, and/or a light chain CDR2 comprising the amino acid sequence of SEQ ID NO: 35, SEQ ID NO: 247, SEQ ID NO: 248 or SEQ ID NO:257 and/or a light chain CDR3 comprising the amino acid sequence of SEQ ID NO: 36 or SEQ ID NO: 192 or SEQ ID NO: 193. The present invention also relates to medicaments and related materials comprising the specified anti-CCR6 antibodies and the use of these to treat diseases.

BACKGROUND OF THE INVENTION

Chemokines are a family of chemoattractant, proinflammatory cytokines which are essential for homeostasis and activation of the immune system. They direct migration of immune cells into sites of inflammation and infection. Chemokines bind to specific cell surface receptors belonging to the family of 7-transmembrane domain, G protein-coupled receptors (GPCRs).

CCR6 is a chemokine receptor belonging to Class A of the GPCR superfamily and it is expressed on human dendritic cells, memory T cells and on B cells (Zaballos et al., (1996) Biochem & Biophys Res Com, 227: 846-853; Greaves et al., (1997) J Exp Med, 186: 837-844; Power et al., (1997) J Exp Med 186: 825-835; Liao et al., (1999) J Immunol 162: 186-94). The only known ligand for CCR6 is the chemokine CCL20 also known as MIP-3α, LARC or exodus (Rossi et al., (1997) J Immunol 158: 1033-1036). The CCR6 receptor was first cloned from human genomic DNA as an orphan receptor (Zaballos et al., supra). Northern blot analysis has revealed that CCR6 is expressed mainly in spleen, lymph nodes, thymus, appendix, and PBMCs among various human tissues (Baba et al., (1997) J Biol Chem, 272: 14893-14898). Among various leukocyte subsets, CCR6 mRNA has been detected in lymphocytes (CD4$^+$ and CD8$^+$ T cells and B cells) but not in natural killer cells, monocytes, or granulocytes (Baba et al., supra). The chemokine ligand/receptor pairing CCL20/CCR6 is interesting because these molecules display characteristics of both homeostatic and activation functions and these dual characteristics suggest a role for CCR6 in the priming and effector phases of the immune response.

Due to its expression on Th17 cells (Romagnani S et al., (2009) Mol Immunol 47: 3-7), CCR6 is involved in a plethora of autoimmune and inflammatory diseases, for example, atopic dermatitis, contact dermatitis, mycosis fungoides, psoriasis, chronic hepatitis, periodontal disease, HPV, IBD, rheumatoid arthritis, allergic asthma, COPD, delayed-type hypersensitivity, B-cell malignancies, breast adenocarcinoma, hepatocellular carcinoma, pancreatic adenocarcinoma, thyroid papillary carcinoma and glioblastoma.

Workers have generated antibodies against CCR6 using a variety of methods for instance using Phage Display WO2013184218 (MSM PROTEIN TECHNOLOGIES). Anti-CCR6 antibodies have also been generated using conventional immunisation methods WO2001017558A3 (SCHERING CORPORATION). All such prior art antibodies do not have the properties necessary to be suitable as therapeutic antibodies. That is although some or all of these antibodies have binding affinity for human CCR6, they do not have or have not been demonstrated to have the ability to modulate the activity of the human CCR6 receptor, for instance the ability to prevent CCR6 dependent cell migration. Such prior art antibodies have also not been shown to be suitable for use as diagnostic antibodies, as they are not CCR6 specific.

Therefore there remains a need in the art for compositions that can be used in the treatment and diagnosis of diverse immune and inflammatory diseases and disorders.

SUMMARY OF THE INVENTION

The present disclosure relates generally to antibodies or fragments thereof that bind to CCR6, methods for their preparation and use, including methods for treating CCR6 mediated disorders. The antibodies or fragments thereof of the present invention that bind to CCR6 exhibit numerous desirable properties and may be useful for the treatment of various diseases that include but are not limited to inflammatory diseases and/or auto immune diseases.

In one aspect, the present disclosure provides an antibody or fragment thereof that binds to CCR6 comprising a heavy chain CDR1 comprising the amino acid sequence of SEQ ID NO: 31, and/or a heavy chain CDR2 comprising the amino acid sequence of SEQ ID NO: 32, SEQ ID NO: 190, SEQ ID NO: 239, SEQ ID NO: 240, SEQ ID NO: 241 or SEQ ID NO: 242, and/or a heavy chain CDR3 comprising the amino acid sequence of SEQ ID NO: 33; and/or comprising a light chain CDR1 comprising the amino acid sequence of SEQ ID NO: 34, SEQ ID NO: 191, SEQ ID NO:244, SEQ ID NO:245 or SEQ ID NO: 246, and/or a light chain CDR2 comprising the amino acid sequence of SEQ ID NO: 35, SEQ ID NO: 247, SEQ ID NO: 248 or SEQ ID NO:257, and/or a light chain CDR3 comprising the amino acid sequence of SEQ ID NO: 36 or SEQ ID NO: 192 or SEQ ID NO: 193.

In accordance with another aspect of the present disclosure there is provided provides an antibody or fragment thereof that binds to CCR6 comprising a heavy chain CDR1 comprising the amino acid sequence of SEQ ID NO: 31, and/or a heavy chain CDR2 comprising the amino acid sequence of SEQ ID NO: 241, and/or a heavy chain CDR3 comprising the amino acid sequence of SEQ ID NO: 33; and/or comprising a light chain CDR1 comprising the amino acid sequence of SEQ ID NO: 245, and/or a light chain CDR2 comprising the amino acid sequence of SEQ ID NO: 191 and/or a light chain CDR3 comprising the amino acid sequence of SEQ ID NO: 192.

In a further aspect the present invention provides an antibody or fragment thereof that binds to CCR6 comprising a heavy chain variable region sequence comprising the amino acid sequence of SEQ ID NO: 7, 37, 39, 40, 41, 42, 75, 177, 178, 179, 249.

Preferably the antibody or fragment thereof that binds to CCR6 comprising a heavy chain variable region sequence comprising the amino acid sequence of SEQ ID NO: 7, 37, 75, 177, 178 and 179 and most preferably SEQ ID NO: 7, 37 or 249.

In a further aspect the present invention provides an antibody or fragment thereof that binds to CCR6 comprising a heavy chain variable framework region that is the product of or derived from a human gene selected from the group consisting of: IGHV3-11*04 (SEQ ID NO: 77), IGHV3-11*01 (SEQ ID NO: 78), IGHV3-48*03 (SEQ ID NO: 79), IGHV3-23*04 (SEQ ID NO: 80) and IGHV3-66*04 (SEQ ID NO: 81). Most preferably the human gene is IGHV3-23*04 (SEQ ID NO: 80) and wherein the heavy chain variable framework region comprises at least one amino acid modification in comparison to the corresponding framework region of the heavy chain variable region of the corresponding murine or intermediary antibody sequence.

According to the present invention an intermediary antibody means any version of a starting antibody which differs from the original by at least one residue and in particular refers to one or more of the antibodies generated according to the present invention by way of humanising or improving a murine antibody.

In a further aspect the present invention provides an antibody or fragment thereof comprising a light chain variable sequence comprising the amino acid sequence of SEQ ID NO: 8, 38, 43, 44, 45, 46, 181, 182, 250, 251, 252 or 253.

Preferably the antibody or fragment thereof that binds to CCR6 comprising a light chain variable region sequence comprising the amino acid sequence of SEQ ID NO: 8, 38, 181, 182, 250, 251, 252 or 253 and most preferably SEQ ID NO: 8, 38, 251 or 253.

In a further aspect the present invention provides an antibody or fragment thereof that binds to CCR6 comprising a light chain variable framework region that is the product of or derived from a human gene selected from the group consisting of: germline FW regions IGKV2-30*02 (SEQ ID NO: 82), IGKV2-30*01 (SEQ ID NO: 83) IGKV2D-30*01 (SEQ ID NO: 84), IGKV2-29*02 (SEQ ID NO: 85), and IGKV2-29*03 (SEQ ID NO: 86).

In a further aspect the present invention provides an antibody or fragment thereof comprising a light chain variable framework region that is the product of or derived from human gene IGKV2-30*02 (SEQ ID NO: 82) and wherein the light chain variable framework region comprises at least one amino acid modification from the corresponding framework region of the light chain variable region of the corresponding murine antibody or intermediary antibody sequence.

In a further aspect the present invention provides an antibody or fragment thereof that binds to CCR6 comprising a heavy chain sequence selected from the group consisting of SEQ ID NOS: 10, 19, 20, 21, 22, 23, 24, 173, 175, 183, 184, 194, 196, 198, 200, 202, 204, 206, 208, 210, 212, 214, 216, 218, 221, 224, 227, 230, 233 and 235. In a further aspect the present invention provides an antibody or fragment thereof that binds to CCR6 comprising a light chain sequence selected from the group consisting of SEQ ID NOS: 25, 26, 27, 28, 29, 30, 176, 186, 187, 195, 197, 199, 201, 203, 205, 207, 209, 211, 213, 215, 217, 219, 222, 225, 228, 231 and 236.

In a further aspect the present invention provides an antibody or fragment thereof that binds to CCR6 comprising:
(a) a heavy chain sequence comprising the amino acid sequence of SEQ ID NO: 19, 24, 214 or 216; and
(b) a light chain sequence comprising the amino acid sequence of SEQ ID NO: 25, 30, 215 or 217.

In a further aspect the present invention provides an antibody or fragment thereof that binds to CCR6, wherein the antibody comprises a human IgG4 Fc region, wherein the antibody has no Fc-mediated cytotoxicity activity. In a further aspect the present invention provides an antibody or fragment thereof that binds to CCR6, wherein the antibody comprises a human IGHG1 Fc region, wherein the antibody is competent for cytotoxicity mechanisms such as antibody dependent cellular cytotoxicity (ADCC). In a preferred aspect, the antibody or fragment thereof that binds to CCR6 has a non fucosylated IGHG1 Fc region and exhibits enhanced Fc-mediated cytotoxicity mechanisms such as ADCC.

In another aspect, the present invention provides a cross-reactive antibody of fragment thereof which binds to human CCR6 and which also binds to cynomologous CCR6. By "cross-reactive antibody" is meant an antibody that binds to an antigen from one species, e.g. human, and which also binds to the corresponding antigen in a different species, e.g. *Macacca mulata* and *Macacca fascicularis*.

In another aspect, the disclosure of the present invention also describes humanized antibodies or fragments thereof that bind with a similar affinity to CCR6 as the corresponding chimeric antibody e.g. retain at least 85% of the CCR6 binding affinity ($K_D$) of the corresponding chimeric antibody or have at least equivalent or higher CCR6 binding affinity ($K_D$) when compared to the corresponding chimeric antibody.

In another aspect, the present invention also relates to anti-CCR6 antibodies or fragments thereof, which can inhibit the CCL20 mediated migration of a cell population expressing CCR6. The inventors have surprisingly found that antibodies according to the present invention have the unexpected property of inhibiting and in some cases completely abrogating the chemotaxis mediated by CCL20 of cells which express CCR6.

In another aspect, the present invention also relates to anti-CCR6 antibodies or fragments thereof, which affect CCL20 binding to CCR6 in vivo. The inventors have surprisingly found that antibodies according to the present invention interact in the binding of CCR6 and its ligand CCL20, so reducing and in some cases preventing completely ligand receptor binding.

In another aspect, the present invention also relates to anti-CCR6 antibodies or fragments thereof, which acts as an antagonist upon CCR6 in vivo.

In another aspect, the present invention also relates to anti-CCR6 antibodies or fragments thereof which exhibit enhanced thermostability.

The disclosure of the present invention also provides isolated nucleic acids encoding antibodies and fragments thereof that bind to CCR6, vectors and host cells comprising the nucleic acid or the vector. Compositions comprising the anti-CCR6 antibody or fragment thereof and a pharmaceutically acceptable carrier and immunoconjugates comprising the antibody or fragment thereof linked to a therapeutic agent are also provided.

The present disclosure also provides methods for treating CCR6 mediated disorders. In one aspect, in an in vitro model of CCL20-induced cellular migration, an anti-CCR6 antibody or fragment thereof efficiently suppressed the migration of cells expressing CCR6, in response to CCL20.

The present disclosure also provides pharmaceutical compositions comprising an anti-CCR6 antibody or fragments thereof and a carrier, such as a diluent or excipient.

The present disclosure also provides kits and articles of manufacture comprising the antibody or fragments thereof, a composition or an immunoconjugate for the treatment of a CCR6 mediated disorder.

BRIEF DESCRIPTION OF THE FIGURES

FIG. 1: Flow cytometry analysis of hybridoma candidates. Histogram plots show the geometric mean of fluorescence intensity (Y-axis) and the clone ID (X-axis). Binding of hybridoma candidates was evaluated on BAF cells transfected with human CCR6 (FIG. 1A) or BAF expressing irrelevant protein (FIG. 1B).

FIG. 2: Testing blocking effect of chimeric 4H11 in CCR6-bioassays.

(A) Testing Blocking Potential of Chimeric 4H11 in Discoverx Bioassay.

This figure shows the results from a functional Discoverx CCR6-bioassay using chimeric 4H11. In this assay, CCL20-induced chemiluminescence activity was measured on cells containing PathHunter components in the presence of chimeric 4H11 used at five different concentrations (20, 6.7, 2, 0.7 and 0.2 µg/ml). The percentage of relative luminescence unit (RLU) was calculated considering chemiluminescent signal in conditions using chimeric IgG1 isotype control as 100% of luminescent activity (B) Testing Blocking Potential of Chimeric 4H11 in CCL20-Induced Chemotaxis Assay.

This figure shows the results from functional CCR6-dependent migration assay using chimeric 4H11. A migration assay using a 6.5 mm Transwell plate, where migration of BAF cells transfected with full length human CCR6 in response to recombinant human CCL20 was evaluated in the presence of chimeric 4H11 used at three different concentrations (10, 2 and 0.4 µg/ml). As a positive control, a commercial anti-CCL20 antibody was used at 10 µg/ml. Migration was evaluated by counting cells in the upper and lower chambers of the Transwell, using flow cytometer.

FIG. 3: Flow cytometry analysis of chimeric 4H11 antibody.

(A) Staining on Human Activated Peripheral Blood Mononuclear Cells (PBMCs).

Histogram plots shows the geometric mean fluorescence intensity (GeoMean in Y-axis) corresponding to each tested antibody (in X-axis). Binding of chimeric 4H11 to human CCR6 was detected with anti-human IgG-PE. To detect binding of commercial antibody to human CCR6, anti-mouse-PE secondary antibody was used.

(B) Staining on Cynomologus Monkey Peripheral Blood Mononuclear Cells (PBMCs).

Binding of the chimeric 4H11 antibody to cynomologus CCR6 was evaluated by flow cytometry. Peripheral blood mononuclear cells (PBMCs) were isolated from whole blood collected from a cynomologus monkey and $2 \times 10^5$ cells were incubated with 10 µg/ml of either control antibody or chimeric 4H11 antibody. Binding of 4H11 to cynomologus CCR6 was detected with anti-human IgG-PE. To detect binding of commercial antibody to cynomologus CCR6, anti-mouse-PE secondary antibody was used.

Figure 4:
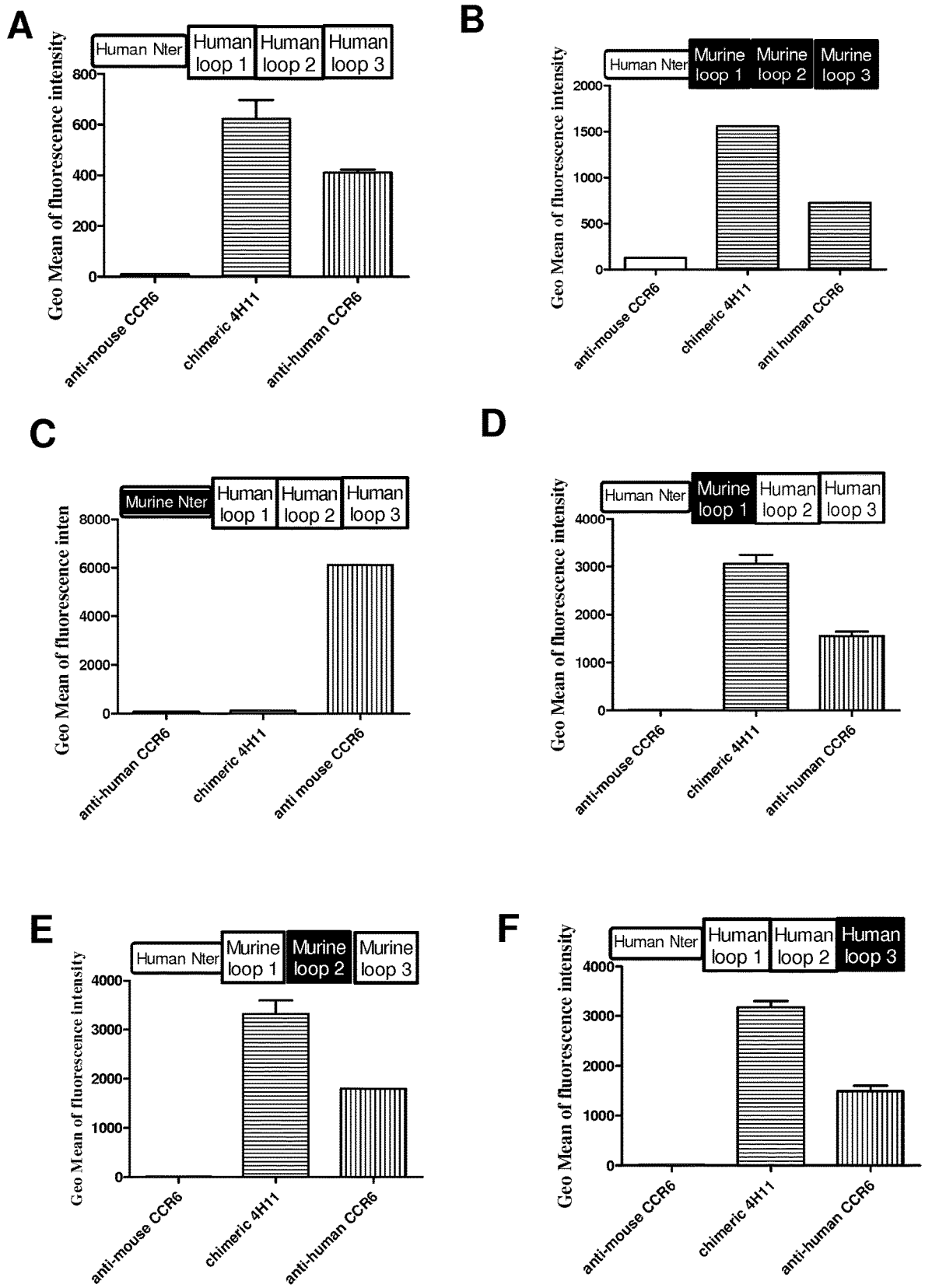

FIG. 4: Evaluation of binding region of chimeric 4H11 antibody using human/mouse CCR6 hybrids transfectants.

Binding of the chimeric 4H11 antibody to human/mouse CCR6 hybrid constructs was evaluated by flow cytometry. Human/mouse CCR6 transfectants were counted and $2 \times 10^5$ cells were incubated with 10 µg/ml of chimeric 4H11 antibody. Binding activity of 4H11 was detected with anti-human IgG-PE. To evaluate good expression of the human/mouse chimera on cells, two commercial antibodies directed against human and mouse CCR6 were used. Histogram plots show the geometric mean of fluorescence intensity (Y-axis) measured by flow cytometry FIG. 5: Evaluation of the epitope of chimeric 4H11 antibody within the N-terminal region of CCR6

Binding of the chimeric 4H11 antibody to human/mouse hybrid of the N-terminal region of CCR6 was evaluated by flow cytometry, as described in FIG. 4.

Figure 6:
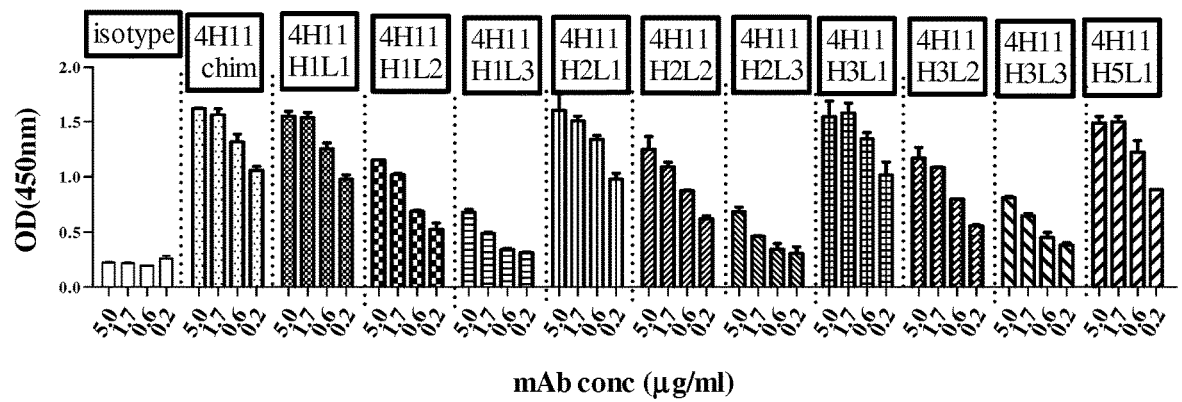

FIG. 6: Testing of humanized anti-human CCR6 candidates by Cell-ELISA.

Binding of humanized 4H11 candidates was evaluated using CHO cells transfected with human CCR6. In this experiment, a 96-well plate was pre-coated with 100 µl of Poly-D diluted at 1 µg/ml in PBS. The day after, cells were washed, plated at $1 \times 10^6$ cells/well and incubated with various concentrations (ranging from 10 to 0.0137 µg/ml) of humanized 4H11 candidates and fixed in 4% PFA. Horseradish Peroxidase (HRP) labelled-goat-anti human Ig Fc fragment specific-HRP was used as secondary antibody. TMB substrate was used to reveal antibody binding activity and the reaction was stopped by adding $H_2SO_4$ and the optical density was read at 450 nM (OD 450 nM)

Figure 7:
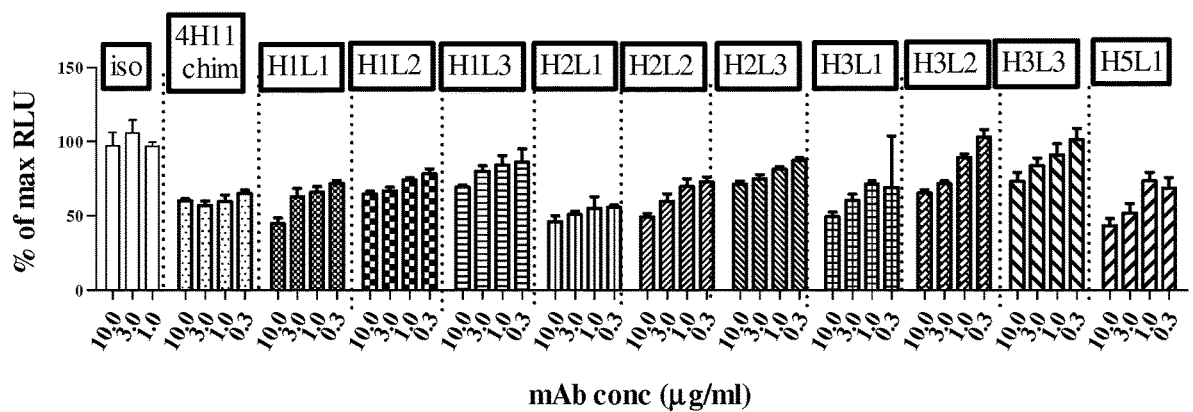

FIG. 7: Testing humanized 4H11 anti-human CCR6 candidates in a functional Ab Hunter CCR6 bioassay. Cells containing PathHunter components were incubated with various concentrations (10, 3, 1 and 0.3 µg/ml) of humanized 4H11 candidates in two different human IgG backbones. Chemiluminescence activity was measured following cell activation with CCL20 and addition of PathHunter detection reagents. Neutralizing activity of humanized 4H11 candidates was evaluated by calculating the percentage of maximum relative luminescence unit (RLU), where RLU max is the light emission at maximum stimulation.

FIG. 8: Direct binding ELISA on immobilized recombinant human N-terminal CCR6 Fc. Binding of humanized 4H11 H5L1 antibody on human N terminus fragment of CCR6 was measured by direct ELISA. Various concentrations (ranging from 10 to 0.00006 µg/ml) of humanized 4H11 H5L1 in IgG1 and IgG4HS backbones were incubated with 2 µg/ml of either recombinant human N terCCR6-Fc tagged protein (FIG. 8A) or recombinant cynomologus N-terminal peptide Fc (FIG. 8B), coated overnight at 4° C. in a 96-well plate. Binding of humanized 4H11 H5L1 antibody to Nter CCR6-Fc protein was detected by horseradish peroxidase (HRP)-conjugated anti-human (Fab)'2-specific antibody.

FIG. 9: Surface Plasmon Resonance Measurements of 4H11 VH5/VL1 IgG4HS antibody. This figure shows kinetic binding affinity constants (KD) measured on human (FIG. 9A) and cyno (FIG. 9B) CCR6 N-terminal peptide Fc fused using a humanized 4H11 (VH5/VL1) Fab antibody as analyte. Data are expressed as number of response (abbreviated RU; Y axis) vs. time (X axis).

Figure 10:
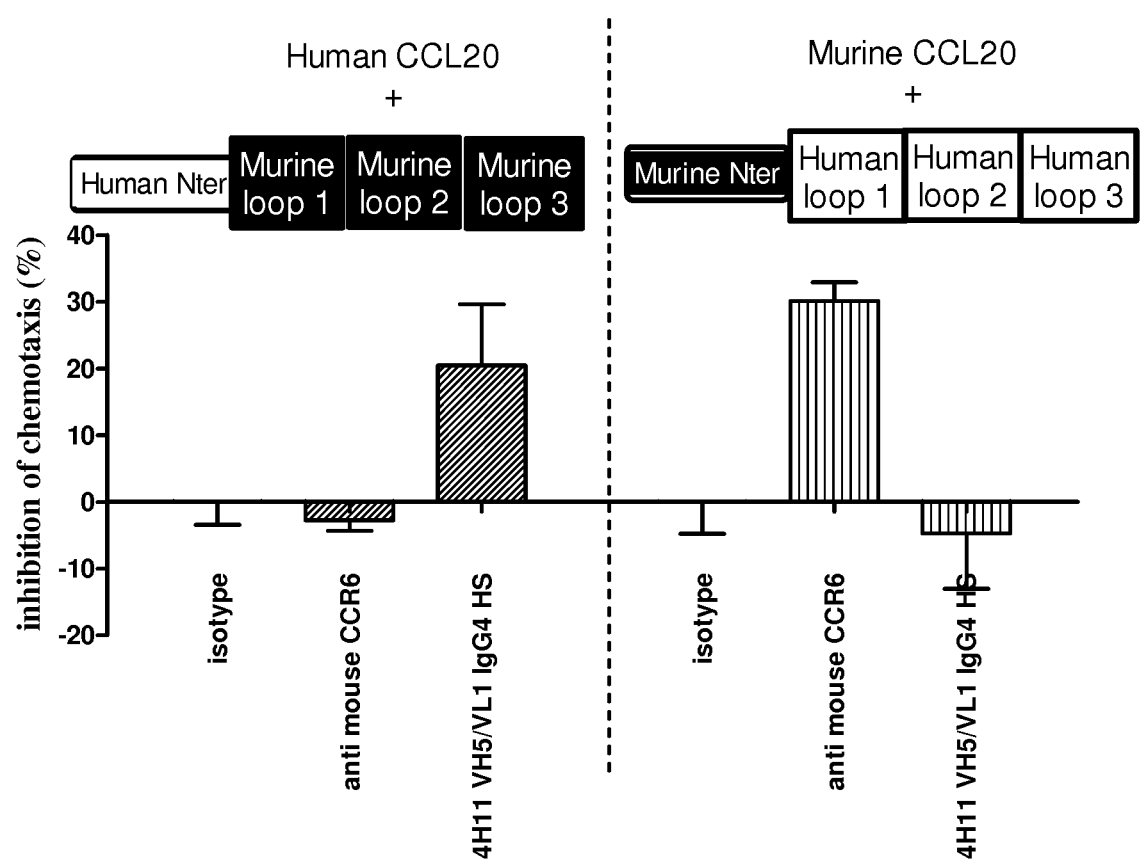

FIG. 10: Testing of 4H11 VH5/VL1 IgG4HS antibody in a migration assay using human-mouse hybrid CCR6 transfectants. This figure shows the results from a migration assay using a 6.5 mm Transwell plate, where migration of BAF cells transfected with human-mouse chimera CCR6 in response to either recombinant human CCL20 (left part of the graph) or mouse CCL20 (right part of the graph) was evaluated in the presence of 4H11 VH5/VL1 IgG4HS used at 10 μg/ml. As a control antibody, a commercial anti-mouse CCL20 antibody was used at 10 μg/ml. Migration was evaluated by counting cells in the upper and lower chambers of the Transwell, using flow cytometer.

Figure 11:
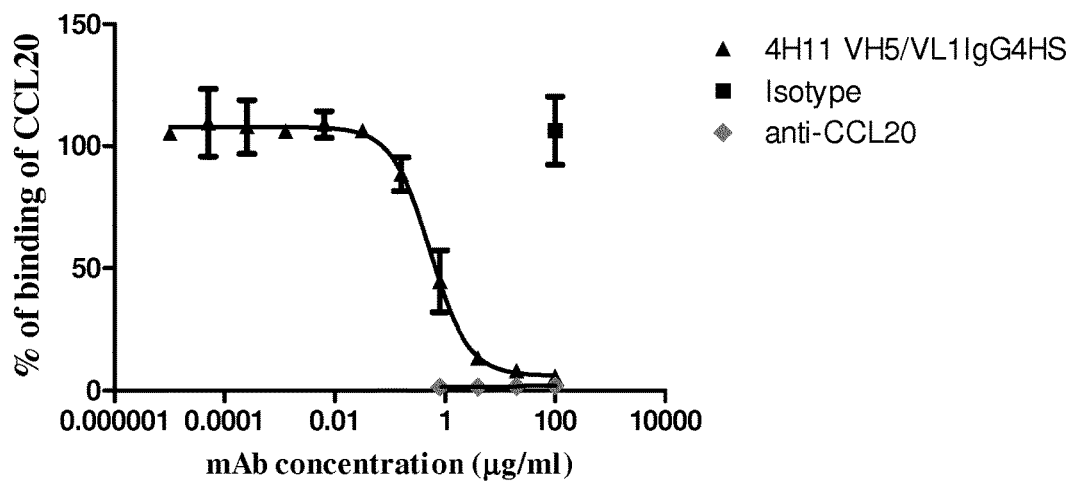

FIG. 11: Testing of neutralizing potential of 4H11 VH5/VL1 IgG4HS antibody by Flow cytometry using CCR6 transfected cells.

Cells transfected with CCR6 were incubated at 4° C. for 20 minutes with humanized 4H11-VH5/VL1 serially diluted (from 100 to 0.00001 μg/ml) in FACS buffer containing 0.1% of azide. Cells were centrifuged and incubated at 4° C. for 20 minutes with 0.5 μg/ml of recombinant human CCL20. To detect CCL20 bound to CCR6, cells were incubated with a biotinylated goat anti-human CCL20, followed by incubation with Allophycocyanin (APC)-labelled Streptavidin diluted at 1/100 in FACS buffer containing 0.1% of azide. To evaluate blocking potential of humanized 4H11 VH5/VL1 IgG4HS, percentage of CCL20 was measured at each concentration of antibody. Maximum binding activity of CCL20 to CCR6 was calculated as a percentage of that seen for the isotype control.

Figure 12:
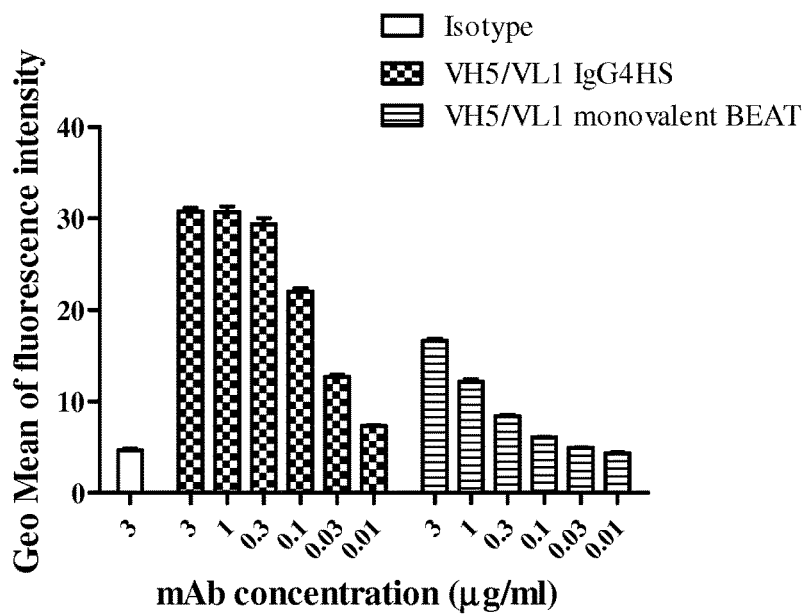

FIG. 12: Testing of 4H11 VH5/VL1 antibody in monovalent and bivalent formats by Flow cytometry using human CCR6 transfected cells.

Binding activities of monovalent and bivalent 4H11 VH5/VL1 antibodies to human CCR6-transfected BAF cells were evaluated by flow cytometry. BAF cells expressing human CCR6 were counted and $2 \times 10^5$ of cells were incubated with various concentrations (ranging from 3 to 0.01 μg/ml) of either monovalent or bivalent 4H11 VH5/VL1 antibody. Binding activity of both antibodies was detected using anti-human IgG-PE. As a control, an irrelevant human IgG antibody was used at 3 μg/ml. Histogram plots show the geometric mean of fluorescence intensity (Y-axis) measured by flow cytometry.

Figure 13:
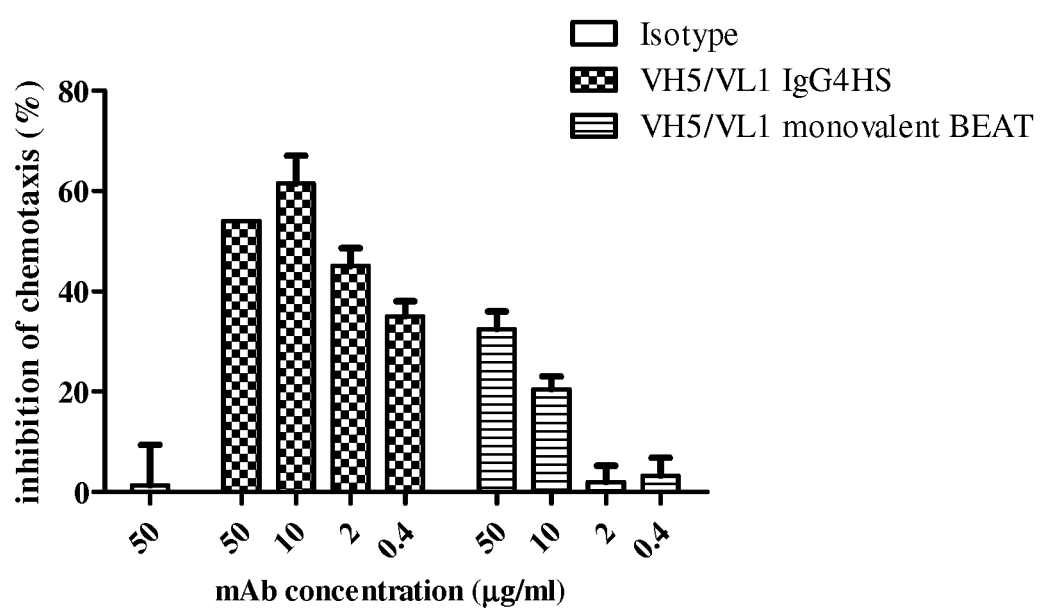

FIG. 13: Testing of 4H11 VH5/VL1 antibody in monovalent and bivalent formats in a migration assay using human CCR6 transfected cells.

The blocking potential of bivalent and monovalent 4H11 VH5/VL1 antibodies was evaluated in a migration assay using a 6.5 mm Transwell plate. In this assay, BAF cells transfected with human CCR6 were counted, and $1 \times 10^5$ cells were incubated with recombinant human CCL20 in the presence of various concentrations (ranging from 50 to 0.4 μg/ml) of either monovalent or bivalent 4H11 VH5/VL1 antibody. As a control antibody, an irrelevant human IgG antibody was used at 50 μg/ml. Migration was evaluated by counting cells in the upper and lower chambers of the Transwell, using flow cytometer.

FIG. 14: Off-rate analysis of VH5/VL1 scFv variants from phage display library.

FIG. 14A: scFv fragments isolated from CDR-H2 library.
FIG. 14B: scFv fragments isolated from CDR-L3 library.

Figure 15:
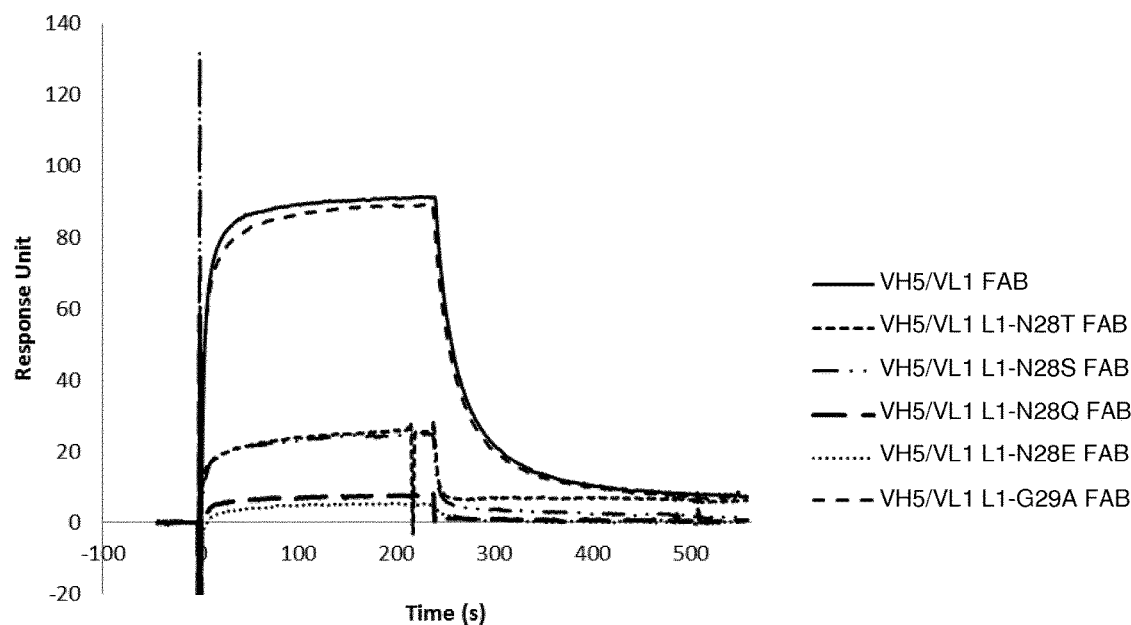

FIG. 15: Surface Plasmon Resonance measurements of VH5/VL1 FAB variants at position CDR-L1 28 and 29.

This figure shows SPR data measured on human CCR6 N-terminal peptide Fc fused using FAB variants as analytes. Data are expressed as number of response (abbreviated RU; Y axis) vs. time (X axis).

Figure 16:
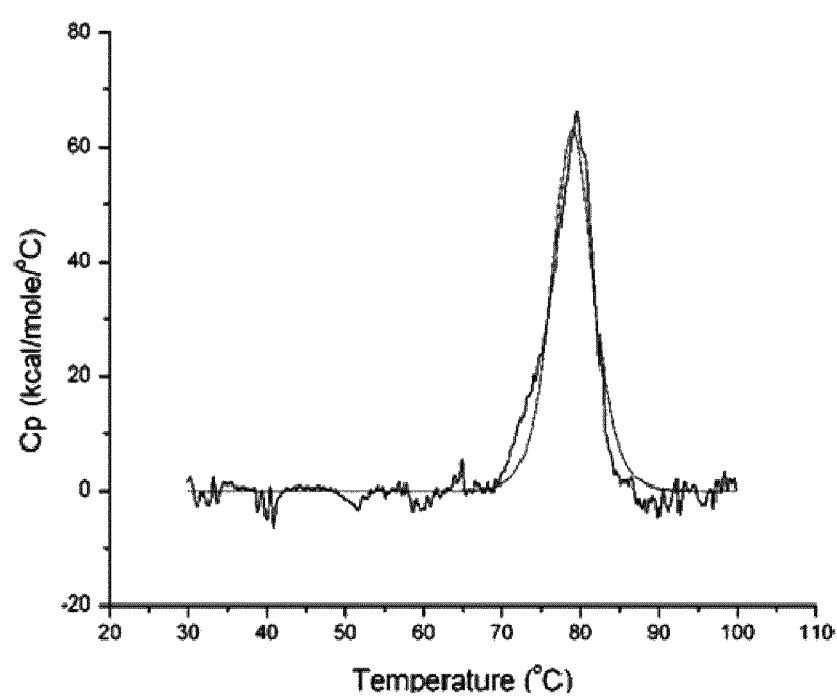

FIG. 16: Thermo-stability measurement of the VH5/VL1 L1-G29A FAB using differential scanning calorimetry.

Data are expressed as excess molar heat capacity (abbreviated Cp [kcal/mol/° C.]; Y axis) vs. temperature (° C.; X axis).

FIG. 17: Sequence details of engineered VH5/VL1 FAB fragments and antibody formats used for affinity and functional testing.

FIG. 18: Binding constants measured for the engineered VH5/VL1 FAB fragments by SPR.

Figure 18B:
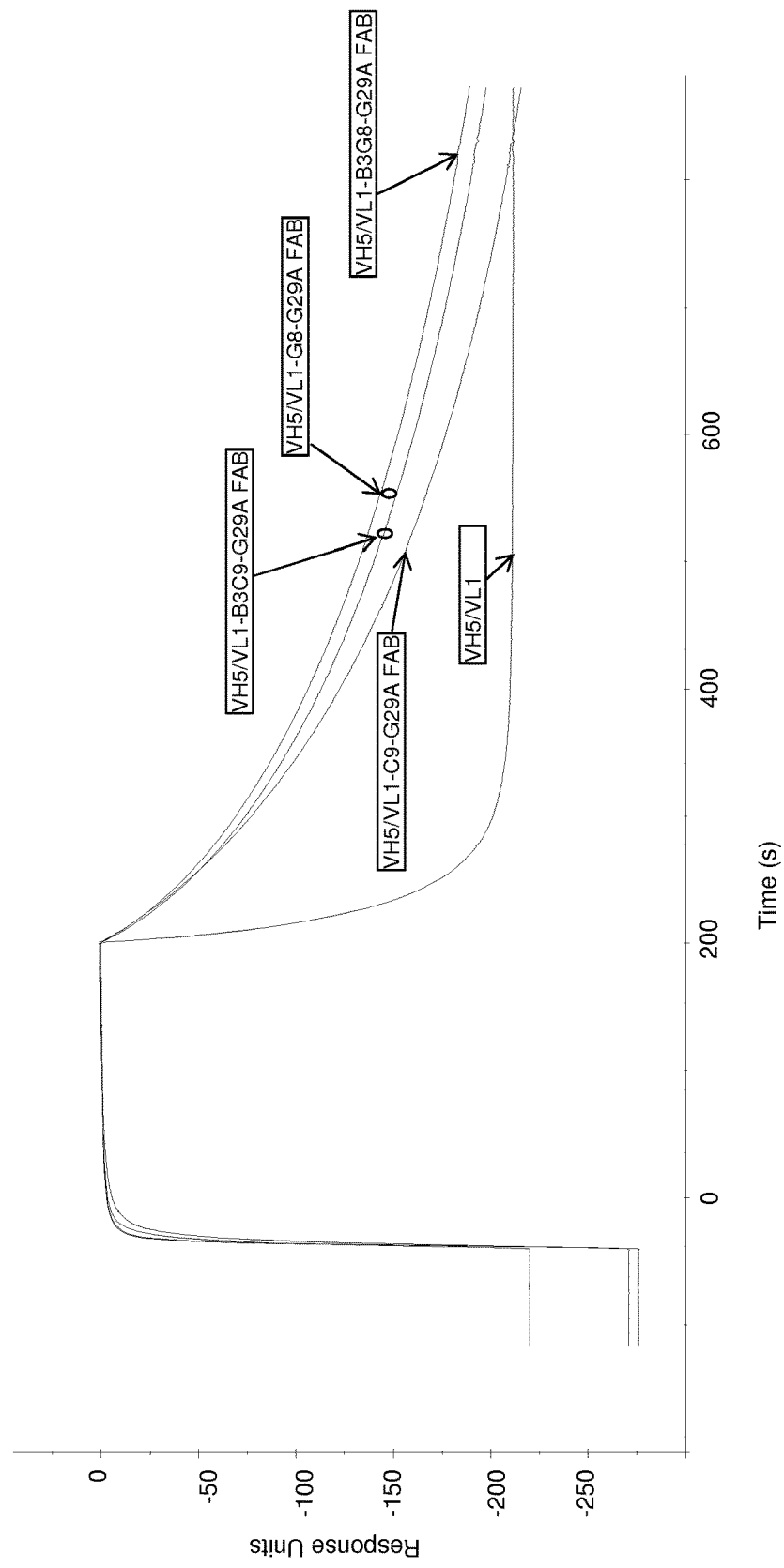

FIG. 18A: summary of the binding constants against human and cynomolgus monkey CCR6 fusion proteins.
FIG. 18B: off-rate comparison between the four different engineered VH5/VL1 FAB fragments.

Figure 19:
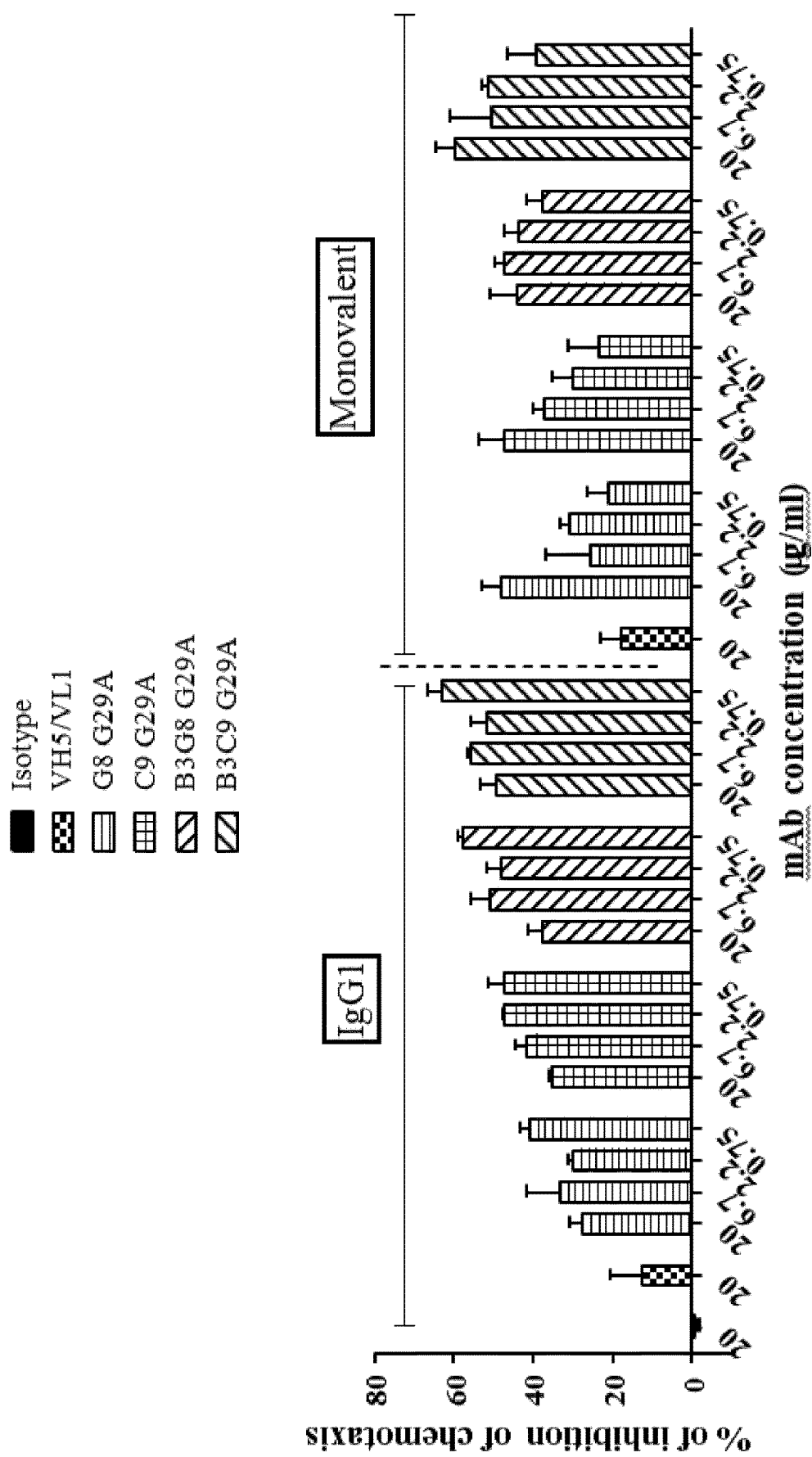

FIG. 19. Testing the blocking potential of affinity-matured bivalent and monovalent 4H11-VH5/VL1 candidates in CCL20-induced chemotaxis assay.

This figure shows the results from a migration assay using various affinity-matured VH5/VL1 variants, tested at four different concentrations (20, 6.67, 2.2 and 0.75 μg/ml). In this assay, migration of BAF cells transfected with full length human CCR6 through a HTS Transwell®-96 permeable supports was evaluated in the presence of either bivalent IgG or monovalent Fab affinity-matured VH5/VL1 candidates in response to CCL20 added to the lower chambers. As a control, the non-affinity matured 4H11 VH5/VL1 IgG1 mAb was used at 20 μg/ml. A human IgG1 isotype control was used at 20 μg/ml in the assay.

Migration was evaluated by counting cells in the upper and lower chambers of the Transwell, using flow cytometer.

DETAILED DESCRIPTION OF THE INVENTION

The present disclosure relates to new antibodies and fragments thereof that bind to CCR6 which are suitable for use as therapeutic agents or as part of a diagnostic reagent.

The term "CCR6" as used herein includes variants, isoforms, and species homologs of CCR6. Accordingly, antibodies of this disclosure may bind to human CCR6 and may cross-react with CCR6 from species other than human, for example, mouse, rat or cynomologous monkey. In certain embodiments, the antibodies may be completely specific for one or more human CCR6 proteins and may not exhibit species or other types of non-human cross-reactivity. The complete amino acid sequence of an exemplary human CCR6 has Swiss-Prot accession number P51684 (CCR6 HUMAN; SEQ ID NO: 71). CCR6 is also known as C—C CKR-6, CC-CKR-6, CCR-6, LARC receptor, GPR-CY4, GPRCY4, Chemokine receptor-like 3, CKR-L3, DRY6 or GPCR 29. CCR6 has also recently been designated CD196 (cluster of differentiation 196). Human CCR6 is designated GeneID: 1235 by Entrez Gene, and HGNC: 1607 by HGNC. CCR6 can be encoded by the gene designated CCR6 gene. The complete amino acid sequence of an exemplary murine CCR6 has Swiss-Prot accession number O54689 (CCR6 MOUSE; SEQ ID NO: 72). Murine CCR6 is designated GeneID: 12458 by Entrez Gene. The complete amino acid sequence of an exemplary rat CCR6 has Swiss-Prot accession number Q5BK58 (Q5BK58 RAT; SEQ ID NO: 73). Rat CCR6 is designated Gene ID: 308163 by Entrez Gene. The complete amino acid sequence of an exemplary rhesus monkey CCR6 (*Macaca mulatta*) has Swiss-Prot accession number Q8HZR7 (Q8HZR7_MACMU; SEQ ID NO: 74). Rhesus monkey CCR6 is designated Gene ID: 574335 by Entrez Gene. The Swiss-Prot database is available at swissmodel.expasy.org, Arnold K et al., (2006) Bioinformatics, 22(2): 195-201.

The use of "CCR6" herein encompasses all known or as yet undiscovered alleles and polymorphic forms of CCR6, preferably of human CCR6. The terms "human CCR6" or "CCR6" are used herein equivalently and mean "human CCR6" if not otherwise specifically indicated.

The term "CCR6 ligand" or "CCL20" are used herein equivalently and include specifically ligands to human CCR6. CCL20 is a small cytokine belonging to the CC chemokine family and is also known as MIP-3α, LARC or Exodus. CCL20 has Swiss-Prot accession number P78556 (CCL20 HUMAN; SEQ ID NO: 76) and is designated Gene ID: 6364 by Entrez Gene. CCL20 is expressed in several tissues with the highest expression observed in peripheral blood lymphocytes, lymph nodes, liver, appendix and fetal lung, and lower levels observed in the thymus, testis, prostate and gut.

The term "antibody or fragment thereof that binds to CCR6" as used herein includes antibodies or a fragment thereof that binds to CCR6 e.g. human CCR6 in isolated form, with an affinity ($K_D$) of 850 pM or less, preferably 700 nM or less, more preferably 300 nM or less, more preferably 260 nM or less, even more preferably 250 nM or less.

The term "antibody or fragment thereof that binds to CCR6" includes antibodies or antigenic binding fragments thereof. The terms "antagonistic antibody" or "antagonist antibody" are used herein equivalently and include an antibody that is capable of inhibiting and/or neutralising the biological signalling activity of CCR6, for example by blocking binding or substantially reducing binding of CCR6 to its ligand and thus inhibiting or reducing the signalisation pathway triggered by CCR6 and/or inhibiting or reducing a CCR6-mediated cell response like B-lineage maturation, antigen-driven B-cell differentiation and/or regulation of the migration and recruitment of dendritic and T cells during inflammatory and immunological responses.

The term "antibody" as referred to herein includes whole antibodies and any antigen binding fragments or single chains thereof. An "antibody" refers to a glycoprotein comprising at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR) with are hypervariable in sequence and/or involved in antigen recognition and/or usually form structurally defined loops, interspersed with regions that are more conserved, termed framework regions (FR or FW). Each VH and VL is composed of three CDRs and four FWs, arranged from amino-terminus to carboxy-terminus in the following order: FW1, CDR1, FW2, CDR2, FW3, CDR3, FW4. The amino acid sequences of FW1, FW2, FW3, and FW4 all together constitute the "non-CDR region" or "non-extended CDR region" of VH or VL as referred to herein.

The term "heavy chain variable framework region" as referred herein may comprise one or more (e.g., one, two, three and/or four) heavy chain framework region sequences (e.g., framework 1 (FW1), framework 2 (FW2), framework 3 (FW3) and/or framework 4 (FW4)). Preferably the heavy chain variable region framework comprises FW1, FW2 and/or FW3, more preferably FW1, FW2 and FW3. The term "light chain variable framework region" as referred herein may comprise one or more (e.g., one, two, three and/or four) light chain framework region sequences (e.g., framework 1 (FW1), framework 2 (FW2), framework 3 (FW3) and/or framework 4 (FW4)). Preferably the light chain variable region framework comprises FW1, FW2 and/or FW3, more preferably FW1, FW2 and FW3.

The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies are grouped into classes, also referred to as isotypes, as determined genetically by the constant region. Human constant light chains are classified as kappa (Cκ) and lambda (Cλ) light chains. Heavy chains are classified as mu (μ), delta (δ), gamma (γ), alpha (α), or epsilon (s), and define the antibody's isotype as IgM, IgD, IgG, IgA, and IgE, respectively. Thus, "isotype" as used herein is meant any of the classes and/or subclasses of immunoglobulins defined by the chemical and antigenic characteristics of their constant regions. The known human immunoglobulin isotypes are IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), and IgE (IGHE). The so-called human immunoglobulin pseudo-gamma IGHGP gene represents an additional human immunoglobulin heavy constant region gene which has been sequenced but does not encode a protein due to an altered switch region (Bensmana M et al., (1988) Nucleic Acids Res. 16(7): 3108). In spite of having an altered switch region, the human immunoglobulin pseudo-gamma IGHGP gene has open reading frames for all heavy constant domains (CH1-CH3) and hinge. All open reading frames for its heavy constant domains encode protein domains which align well with all human immunoglobulin constant domains with the predicted structural features. This additional pseudo-gamma isotype is referred herein as IgGP or IGHGP. Other pseudo immunoglobulin genes have been reported such as the human immunoglobulin heavy constant domain epsilon P1 and P2 pseudo-genes (IGHEP1 and IGHEP2). The IgG class is the most commonly used for therapeutic purposes. In humans this class comprises subclasses IgG1, IgG2, IgG3 and IgG4. In mice this class comprises subclasses IgG1, IgG2a, IgG2b, IgG2c and IgG3.

The term "murine antibody" as used herein includes antibodies in which the variable region sequences and the constant region sequences are derived from a mouse.

The term "chimeric antibody" as used herein includes antibodies in which the variable region sequences are derived from one species and the constant region sequences are derived from another species, such as an antibody in which the variable region sequences are derived from a mouse antibody and the constant region sequences are derived from a human antibody.

The term "humanized antibody" or "humanized anti-CCR6 antibody" as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term "Fab" or "Fab region" as used herein includes the polypeptides that comprise the VH, CH1, VL, and CL immunoglobulin domains. Fab may refer to this region in isolation, or this region in the context of a full length antibody or antibody fragment.

The term "Fc" or "Fc region", as used herein includes the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains C gamma 2 and C gamma 3 (Cγ2 and Cγ3) and the hinge between C gamma 1 (Cγ1) and C gamma 2 (Cγ2). Although the boundaries of the Fc region may vary, the human IgG heavy chain Fc region is usually defined to comprise residues C226 or P230 to its carboxyl-terminus, wherein the numbering is according to the EU numbering system. For human IgG1 the Fc region is herein defined to comprise residue P232 to its carboxyl-terminus, wherein the numbering is according to the EU numbering system (Edelman G M et al., (1969) Proc Natl Acad Sci USA, 63(1): 78-85). Fc may refer to this region in isolation or this region in the context of an Fc polypeptide, for example an antibody.

The term "hinge" or "hinge region" or "antibody hinge region" herein includes the flexible polypeptide comprising the amino acids between the first and second constant domains of an antibody. The "hinge region" as referred to herein is a sequence region of 6-62 amino acids in length, only present in IgA, IgD and IgG, which encompasses the cysteine residues that bridge the two heavy chains. Structurally, the IgG CH1 domain ends at EU position 220, and the IgG CH2 domain begins at residue EU position 237. Thus for IgG the antibody hinge is herein defined to include positions 221 (D221 in IgG1) to 231 (A231 in IgG1), wherein the numbering is according to the EU numbering system (Edelman G M et al., supra).

The term "parent antibody" or "parent immunoglobulin" as used herein includes an unmodified antibody that is subsequently modified to generate a variant. Said parent antibody may be a naturally occurring antibody, or a variant or engineered version of a naturally occurring antibody. Parent antibody may refer to the antibody itself, compositions that comprise the parent antibody, or the amino acid sequence that encodes it. By "parent anti-CCR6 antibody" as used herein is meant an antibody or immunoglobulin that binds the ligand CCL20 and is modified to generate a variant. By "corresponding murine antibody" as used herein is meant a murine antibody or immunoglobulin that binds to CCR6 and that can be modified to generate a variant, specifically the murine antibody 4H11 as disclosed herein. By "corresponding chimeric antibody" as used herein is meant a chimeric antibody or immunoglobulin that binds to CCR6 and that can be modified to generate a variant.

The term "variant antibody" or "antibody variant" as used herein includes an antibody sequence that differs from that of a parent antibody sequence by virtue of at least one amino acid modification compared to the parent. The variant antibody sequence herein will preferably possess at least about 80%, most preferably at least about 90%, more preferably at least about 95% amino acid sequence identity with a parent antibody sequence. Antibody variant may refer to the antibody itself, compositions comprising the antibody variant, or the amino acid sequence that encodes it.

The term "identity" or "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 80%, and more preferably at least about 90%, 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 80% sequence identity, even more preferably at least 90%, 95%, 98% or 99% sequence identity. Preferably, residue positions which are not identical differ by conservative amino acid substitutions.

The term "amino acid modification" herein includes an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution R94K refers to a variant polypeptide, in this case a heavy chain variable framework region variant, in which the arginine at position 94 is replaced with a lysine. For the preceding example, 94K indicates the substitution of position 94 with a lysine. For the purposes herein, multiple substitutions are typically separated by a slash. For example, R94K/L78V refers to a double variant comprising the substitutions R94K and L78V. By "amino acid insertion" or "insertion" as used herein is meant the addition of an amino acid at a particular position in a parent polypeptide sequence. For example, insert –94 designates an insertion at position 94. By "amino acid deletion" or "deletion" as used herein is meant the removal of an amino acid at a particular position in a parent polypeptide sequence. For example, R94-designates the deletion of arginine at position 94.

As used herein, the term "conservative modifications" or "conservative sequence modifications" is intended to refer to amino acid modifications that do not significantly affect or alter the binding characteristics of the antibody containing the amino acid sequence. Such conservative modifications include amino acid substitutions, insertions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions or within the framework regions of an antibody of the invention can be replaced with other amino acid residues from the same side chain family and the altered antibody (variant antibody) can be tested for retained function.

The term "epitope" refers to a region of an antigen that is bound by an antibody. An epitope may be defined as structural or functional. Functional epitopes are generally a subset of structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

For all human immunoglobulin heavy chain constant domains numbering is according to the "EU numbering system" (Edelman G M et al., (1969) Proc Natl Acad Sci USA, 63(1): 78-85). For the human kappa immunoglobulin light chain constant domain (IGKC), numbering is according to the "EU numbering system" (Edelman G M et al., supra).

For the human lambda immunoglobulin light chain constant domains (IGLC1, IGLC2, IGLC3, IGLC6, and IGLC7), numbering is according to the "Kabat numbering system" (Kabat E A et al., (1991) Sequences of proteins of immunological interest. 5th Edition—US Department of Health and Human Services, NIH publication no 91-3242) as described by Dariavach P et al., (1987) Proc Natl Acad Sci USA, 84(24): 9074-8 and Frangione B et al., (1985) Proc Natl Acad Sci USA, 82(10): 3415-9.

The term "variable domain" refers to the domains that mediates antigen-binding and defines specificity of a particular antibody for a particular antigen. In naturally occurring antibodies, the antigen-binding site consists of two variable domains that define specificity: one located in the heavy chain (VH) and the other located in the light chain (VL). In some cases, specificity may exclusively reside in only one of the two domains as in single-domain antibodies from heavy-chain antibodies found in camelids. The V regions are usually about 110 amino acids long, and consist of relatively invariant stretches of amino acid sequence called framework regions (FRs) of 15-30 amino acids separated by shorter regions of extreme variability called "hypervariable regions" that are 9-12 amino acids long. The variable domains of native heavy and light chains comprise four FRs, largely adopting a beat-sheet configuration, connected by three hypervariable regions, which form loops. The hypervariable regions in each chain are held together in close proximity by FRs, and with the hypervariable regions from the other chain, contribute to the formation of the antigen binding site of antibodies (see Kabat E A et al., supra). The term "hypervariable region" as used herein refers to the amino acid residues of an antibody which are responsible for antigen binding. The hypervariable region generally comprises amino acid residues from a "complementary determining region" or "CDR", the latter being of highest sequence variability and/or involved in antigen recognition. For all variable domains numbering is according to Kabat (Kabat E A et al., supra).

A number of CDR definitions are in use and are encompassed herein. The Kabat definition is based on sequence variability and is the most commonly used (Kabat E A et al., supra). Chothia refers instead to the location of the structural loops (Chothia C & Lesk A M (1987) J. Mol. Biol. 196: 901-917). The AbM definition is a compromise between the Kabat and the Chothia definitions and is used by Oxford Molecular's AbM antibody modelling software (Martin A C R et al., (1989) Proc. Natl. Acad. Sci. USA, 86: 9268-72; Martin A C R et al., (1991) Methods Enzymol. 203: 121-153; Pedersen J T et al., (1992) Immunomethods, 1: 126-136; Rees A R et al., (1996) In Sternberg M. J. E. (ed.), Protein Structure Prediction. Oxford University Press, Oxford, 141-172). The contact definition has been recently introduced (MacCallum R M et al., (1996) J. Mol. Biol. 262: 732-745) and is based on an analysis of the available complex structures available in the Protein Databank. The definition of the CDR by IMGT®, the international ImMunoGeneTics information System® (www.imgt.org) is based on the IMGT numbering for all immunoglobulin and T cell receptor V-REGIONs of all species (IMGT®, the international ImMunoGeneTics information System®; Lefranc M P et al., (1991) Nucleic Acids Res. 27(1): 209-12; Ruiz M et al., (2000) Nucleic Acids Res. 28(1): 219-21; Lefranc M P (2001) Nucleic Acids Res. 29(1): 207-9; Lefranc M P (2003) Nucleic Acids Res. 31(1): 307-10; Lefranc M P et al., (2005) Dev. Comp. Immunol. 29(3): 185-203; Kaas Q et al., (2007) Briefings in Functional Genomics & Proteomics, 6(4): 253-64).

All Complementarity Determining Regions (CDRs) discussed in the present invention, are defined preferably according to IMGT®. The variable domain residues for each of these CDRs are as follows (numbering according to Kabat E A, et al., supra): LCDR1: 27-32, LCDR2: 50-52, LCDR3: 89-97, HCDR1: 26-35, HCDR2: 51-57 and HCDR3: 93-102. The "non-CDR region" of the VL region as used herein comprise the amino acid sequences: 1-26 (FR1), 33-49 (FR2), 53-88 (FR3), and 98-approximately 107 (FR4). The "non-CDR region" of the VH region as used herein comprise the amino acid sequences: 1-25 (FR1), 36-50 (FR2), 58-92 (FR3), and 103-approximately 113 (FR4).

The CDRs of the present invention may comprise "extended CDRs" which are based on the aforementioned definitions and have variable domain residues as follows: LCDR1: 24-36, LCDR2: 46-56, LCDR3:89-97, HCDR1: 26-36, HCDR2:47-65, HCDR3: 93-102. These extended CDRs are numbered as well according to Kabat et al., supra. The "non-extended CDR region" of the VL region as used herein comprise the amino acid sequences: 1-23 (FR1), 37-45 (FR2), 57-88 (FR3), and 98-approximately 107 (FR4). The "non-extended CDR region" of the VH region as used herein comprise the amino acid sequences: 1-25 (FR1), 37-46 (FR2), 66-92 (FR3), and 103-approximately 113 (FR4).

The term "full length antibody" as used herein includes the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1 (Cγ1), CH2 (Cγ2), and CH3 (Cγ3). In some mammals, for example in camels and llamas, IgG antibodies may consist of only two heavy chains, each heavy chain comprising a variable domain attached to the Fc region.

Antibody fragments include, but are not limited to, (i) the Fab fragment consisting of VL, VH, CL and CH1 domains, including Fab' and Fab'-SH, (ii) the Fd fragment consisting of the VH and CH1 domains, (iii) the Fv fragment consisting of the VL and VH domains of a single antibody; (iv) the dAb fragment (Ward E S et al., (1989) Nature, 341: 544-546) which consists of a single variable, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird R E et al., (1988) Science 242: 423-426; Huston J S et al., (1988) Proc. Natl. Acad. Sci. USA, 85: 5879-83), (vii) bispecific single chain Fv dimers (PCT/US92/09965), (viii) "diabodies" or "triabodies", multivalent or multispecific fragments constructed by gene fusion (Tomlinson I &

Hollinger P (2000) Methods Enzymol. 326: 461-79; WO94/13804; Holliger P et al., (1993) Proc. Natl. Acad. Sci. USA, 90: 6444-48) and (ix) scFv genetically fused to the same or a different antibody (Coloma M J & Morrison S L (1997) Nature Biotechnology, 15(2): 159-163).

The term "effector function" as used herein includes a biochemical event that results from the interaction of an antibody Fc region with an Fc receptor or ligand. Effector functions include FcγR-mediated effector functions such as ADCC (antibody dependent cell-mediated cytotoxicity) and ADCP (antibody dependent cell-mediated phagocytosis), and complement-mediated effector functions such as CDC (complement dependent cytotoxicity). An effector function of an antibody may be altered by altering, i.e. enhancing or reducing, preferably enhancing, the affinity of the antibody for an effector molecule such as an Fc receptor or a complement component. Effector function may be determined using one or more cell based or in vivo assays. Such assays often involve monitoring the response of cells to the antibody, for example cell survival, cell death, change in cellular morphology or transcriptional activation such as cellular expression of a natural gene or reporter gene. For example, such assays may measure the ability of an antibody to elicit ADCC, ADCP, or CDC. For some assays additional cells or components, that is in addition to the target cells, may need to be added, for example serum complement or effector cells such as peripheral blood monocytes (PBMCs), NK cells, macrophages, and the like. Enhanced effector function can be determined by comparing the effector function of an altered antibody with a control antibody and detecting, for example, an increase in ADCC, ADCP or CDC measured by one of more of the aforementioned assays. Binding affinity will generally be varied by modifying the effector molecule binding site and in this case it is appropriate to locate the site of interest and modify at least part of the site in a suitable way. It is also envisaged that an alteration in the binding site on the antibody for the effector molecule need not alter significantly the overall binding affinity but may alter the geometry of the interaction rendering the effector mechanism ineffective as in non-productive binding. It is further envisaged that an effector function may also be altered by modifying a site not directly involved in effector molecule binding, but otherwise involved in performance of the effector function. By altering an effector function of an antibody it may be possible to control various aspects of the immune response, e.g. enhancing or suppressing various reactions of the immune system, with possible beneficial effects in diagnosis and therapy.

As used herein, the term "CCR6-mediated disorder" includes conditions such as cancer and inflammatory diseases and/or auto immune diseases, including inter alia rheumatoid arthritis, multiple sclerosis (MS), psoriasis, graft versus host disease (GVHD), lupus, Chronic Obstructive Pulmonary Disease (COPD), optic neuritis, age related macular degeneration, SLE, Sjogen's syndrome, Scleroderma, systemic sclerosis, Chronic Kidney disease, Liver Fibrosis, Tuberculosis, Idiopathic pulmonary fibrosis, Tuberculosis induced lung fibrosis, Retroperitoneal Fibrosis, Pulmonary fibrosis, Cystic fibrosis, Endomyocardial fibrosis, Atrial Fibrosis, Mediastinal fibrosis, Myelofibrosis (bone marrow), Retroperitoneal fibrosis, Progressive massive fibrosis, Nephrogenic systemic fibrosis, Arthrofibrosis, inflammatory bowel diseases (e.g., ulcerative colitis and Crohn's disease), atherosclerosis, transplant rejection, central nervous system injury, psoriasis, leukaemia or lymphoma (e.g., chronic lymphocytic leukaemia (CLL)), atherosclerosis, and lung and colon carcinomas.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc. Preferably the subject is human.

Anti-CCR6 Antibodies

In a first aspect the present invention provides an antibody or fragment thereof that binds to CCR6 comprising a heavy chain CDR1 comprising the amino acid sequence of SEQ ID NO: 31, and/or a heavy chain CDR2 comprising the amino acid sequence of SEQ ID NO: 32, SEQ ID NO: 190, SEQ ID NO: 239, SEQ ID NO: 240, SEQ ID NO: 241, SEQ ID NO: 242, SEQ ID NO: 254 or SEQ ID NO: 255 and/or a heavy chain CDR3 comprising the amino acid sequence of SEQ ID NO: 33; and/or comprising a light chain CDR1 comprising the amino acid sequence of SEQ ID NO: 34, SEQ ID NO: 191, SEQ ID NO:244, SEQ ID NO:245, SEQ ID NO: 246 or SEQ ID NO: 256, and/or a light chain CDR2 comprising the amino acid sequence of SEQ ID NO: 35, SEQ ID NO: 247, SEQ ID NO: 248 or SEQ ID NO:257 and/or a light chain CDR3 comprising the amino acid sequence of SEQ ID NO: 36 or SEQ ID NO: 192 or SEQ ID NO: 193.

In accordance with this first aspect of the present invention there is provided an antibody or fragment thereof that binds to CCR6 comprising a heavy chain CDR1 comprising the amino acid sequence of SEQ ID NO: 31, and a heavy chain CDR2 comprising the amino acid sequence of SEQ ID NO: 241, and a heavy chain CDR3 comprising the amino acid sequence of SEQ ID NO: 33; and/or comprising a light chain CDR1 comprising the amino acid sequence of SEQ ID NO:245, and a light chain CDR2 comprising the amino acid sequence of SEQ ID NO: 248 and a light chain CDR3 comprising the amino acid sequence of SEQ ID NO: 192 or SEQ ID NO: 193.

In accordance with this aspect of the present the present invention also relates to anti-CCR6 antibodies that comprise the heavy or light CDRs detailed in the various aspects of the present disclosure.

Preferably, the antibody or fragment thereof binds to human CCR6 and is cross reactive with murine or rat or cynomolgus monkey CCR6.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka A et al., (2000) Br. J. Cancer, 83(2): 252-260 (describing the production of a humanized anti-CD30 antibody using only the heavy chain variable domain CDR3 of murine anti-CD30 antibody Ki-4); Beiboer S H et al., (2000) J. Mol. Biol. 296: 833-849 (describing recombinant epithelial glycoprotein-2 (EGP-2) antibodies using only the heavy chain CDR3 sequence of the parental murine MOC-31 anti-EGP-2 antibody); Rader C et al., (1998) Proc. Natl. Acad. Sci USA, 95: 8910-8915 (describing a panel of humanized anti-integrin αvβ3 antibodies using a heavy and light chain variable CDR3 domain of a murine anti-integrin αvβ3 antibody LM609 wherein each member antibody comprises a distinct sequence outside the CDR3 domain and capable of binding the same epitope as the parental murine antibody with affinities as high or higher than the parental murine antibody); Barbas C et al., (1994) J. Am. Chem. Soc. 116: 2161-62 (disclosing that the CDR3 domain provides the most significant contribution to antigen binding).

Accordingly, the present invention provides antibodies and fragments thereof that bind to CCR6 comprising one or more heavy and/or light chain CDR3 domains, in particular comprising heavy chain CDR3 comprising the amino acid sequence of SEQ ID NO: 33 and/or light chain CDR3 comprising the amino acid sequence of SEQ ID NOs: 36, 192 or 193, wherein the antibody is capable of binding to CCR6. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human e.g. murine antibody.

In a further aspect the present invention provides an antibody or fragment thereof that binds to CCR6 comprising a heavy chain variable region sequence comprising the amino acid sequence of SEQ ID NO: 7, 37, 39, 40, 41, 42, 75, 177, 178, 179 and 249. In another aspect the present invention provides an antibody or fragment thereof that binds to CCR6 comprising a light chain variable region sequence comprising the amino acid sequence of SEQ ID NO: 8, 38, 43, 44, 45, 46, 181, 182, 250, 251, 252 or 253. In some embodiments the antibody or fragment thereof that binds to CCR6 comprises a heavy chain variable region sequence comprising the amino acid sequence of SEQ ID NO: 37 or 249 and a light chain variable region sequence comprising the amino acid sequence of SEQ ID NO: 38 or 250, 251, 252 or 253. Preferably, the antibody or fragment thereof binds to human CCR6 and is cross reactive with cynomolgus monkey CCR6.

In another aspect the present invention provides variants of an antibody or fragment thereof that binds to CCR6. Thus the present invention provides antibodies or fragments thereof that have an amino acid sequence of the non-CDR regions of the heavy and/or light chain variable region sequence which is at least 90% identical (having at least 90% amino acid sequence identity) to the amino acid sequence of the non-CDR regions of the heavy and/or light chain variable region sequence of the parent antibody of either the heavy or the light chain e.g. of either the heavy and light variable region sequences as in SEQ ID NO: 7, 37, 39, 40, 41, 42, 75, 177, 178, 179, 249 or SEQ ID NO: 8, 38, 43, 44, 45, 46, 181, 182, 250, 251, 252 or 253 respectively. As well antibodies or fragments thereof that have an amino acid sequence of the non-extended CDR regions of the heavy and/or light chain variable region sequence which is at least 80% identical to the amino acid sequence of the non-extended CDR regions of the heavy and/or light chain variable region sequence of the parent antibody of either the heavy or the light chain are provided by the present invention. Preferably the amino acid sequence identity of the non-CDR regions or of the non-extended CDR regions of the heavy and/or light chain variable region sequence is at least 85%, more preferably at least 90%, and most preferably at least 95%, in particular 96%, more particular 97%, even more particular 98%, most particular 99%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to an amino acid sequence is defined herein as the percentage of amino acid residues in the candidate sequence that are identical with the antibody or fragment thereof that binds to CCR6, after aligning the sequences and introducing gaps, if necessary, to achieve the maximum percent sequence identity. Thus sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM250 (a standard scoring matrix; see Dayhoff M O et al., (1978) in Atlas of Protein Sequence and Structure, vol 5, supp. 3) can be used in conjunction with the computer program. For example, the percent identity can be calculated as: the total number of identical matches multiplied by 100 and then divided by the sum of the length of the longer sequence within the matched span and the number of gaps introduced into the longer sequences in order to align the two sequences.

In some embodiments the present disclosure thus provides an antibody or fragment thereof that binds to CCR6, wherein the antibody or fragment thereof comprises a heavy chain variable framework region sequence which is at least 65% identical to the framework region sequence of SEQ ID NOS: 77, 78, 79, 80, 81 and/or a light chain variable framework region sequence which is at least 75% identical to the framework region sequence of SEQ ID NOS: SEQ ID NOS: 82, 83, 84, 85, 86. In some embodiments the present disclosure provides an antibody or fragment thereof that binds to CCR6, wherein the antibody or fragment thereof comprises a heavy chain variable framework region sequence which is at least 75% identical to the framework region sequence of SEQ ID NO: 80 and/or a light chain variable framework region sequence which is at least 82% identical to the framework region sequence of SEQ ID NO: 82.

In another aspect the present invention provides an antibody or fragment thereof that binds to CCR6 comprising the heavy and or light chain CDRs as described supra and further comprising a heavy chain variable framework region that is the product of or derived from a human gene selected from the group consisting of IGHV3-11*04 (SEQ ID NO: 77), IGHV3-11*01 (SEQ ID NO: 78), IGHV3-48*03 (SEQ ID NO: 79), IGHV3-23*04 (SEQ ID NO: 80), and IGHV3-66*04 (SEQ ID NO: 81), preferably a heavy chain variable framework region that is the product of or derived from human gene IGHV3-23*04 (SEQ ID NO: 80). The heavy chain variable framework region may comprise one or more (e.g., one, two, three and/or four) heavy chain framework region sequences (e.g., framework 1 (FW1), framework 2 (FW2), framework 3 (FW3) and/or framework 4 (FW4)) present in the product of or derived from those human genes. Preferably the heavy chain variable region framework comprises FW1, FW2 and/or FW3, more preferably FW1, FW2 and FW3 present in the product of or derived from a human gene selected from the group consisting of IGHV3-11*04 (SEQ ID NO: 77), IGHV3-11*01 (SEQ ID NO: 78), IGHV3-48*03 (SEQ ID NO: 79), IGHV3-23*04 (SEQ ID NO: 80), and IGHV3-66*04 (SEQ ID NO: 81). Heavy chain framework region sequences as used herein include FW1 (position 1 to position 25), FW2 (position 36 to position 49), FW3 (position 66 to position 94) and FW 4 (position 103 to position 113), wherein the amino acid position is indicated utilizing the numbering system set forth in Kabat.

In some embodiments the present disclosure provides an antibody or fragment thereof comprising a heavy chain sequence comprising the amino acid sequence of SEQ ID NO: 10, 173, 175, 183, 184, 194, 196, 198, 200, 202, 204, 206, 208, 210, 212, 214, 216, 218, 221, 224, 227, 230, 233 and 235 and wherein the heavy chain variable framework region thereof comprises at least one amino acid modification from the corresponding heavy chain variable framework region of the corresponding murine antibody.

Preferably the amino acid modification comprises an amino acid substitution at amino acid position selected from the group consisting of 24, 49 and 62, wherein the amino acid position of each group member is indicated according to the Kabat numbering.

In another aspect the present invention provides an antibody or fragment thereof that binds to CCR6 comprising a light chain variable framework region that is the product of or derived from a human gene selected from the group consisting of IGKV2-30*02 (SEQ ID NO: 82), IGKV2-30*01 (SEQ ID NO: 83), IGKV2D-30*01 (SEQ ID NO: 84), IGKV2-29*02 (SEQ ID NO: 85), IGKV2-29*03 (SEQ ID NO: 86), preferably a light chain variable framework region that is the product of or derived from human gene IGKV2-30*02 (SEQ ID NO: 82). The light chain variable region framework region may comprise one or more (e.g., one, two, three and/or four) light chain framework region sequences (e.g., framework 1 (FW1), framework 2 (FW2), framework 3 (FW3) and/or framework 4 (FW4)) present in the product of or derived from those human genes. Preferably the light chain variable region framework comprises FW1, FW2 and/or FW3, more preferably FW1, FW2 and FW3 present in the product of or derived from a human gene selected from the group consisting of IGKV2-30*02 (SEQ ID NO: 82), IGKV2-30*01 (SEQ ID NO: 83), IGKV2D-30*01 (SEQ ID NO: 84), IGKV2-29*02 (SEQ ID NO: 85), IGKV2-29*03 (SEQ ID NO: 86). Light chain framework region sequences as used herein include FW1 (position 1 to position 23), FW2 (position 35 to position 49), FW3 (position 57 to position 88) and FW 4 (position 98 to position 108), wherein the amino acid position is indicated utilizing the numbering system set forth in Kabat.

In some embodiments the present disclosure provides an antibody or fragment thereof comprising a light chain variable framework region that is the product of or derived from human gene IGKV2-30*02 (SEQ ID NO: 82) and wherein the light chain variable framework region comprises at least one amino acid modification from the corresponding framework region of the light chain variable region of the corresponding murine antibody.

In some embodiments the present disclosure provides an antibody or fragment thereof comprising a light chain sequence comprising the amino acid sequence of SEQ ID NO: 30, 176, 186, 187, 195, 197, 199, 201, 203, 205, 207, 209, 211, 213, 215, 217, 219, 222, 225, 228, 231 and 236. Alternatively, the light chain variable framework region of the light chain sequence comprises at least one amino acid modification from the corresponding light chain variable framework region of the corresponding murine antibody.

The amino acid modification may comprise an amino acid substitution at an amino acid position selected from the group consisting of 36 and 46, wherein the amino acid position of each group member is indicated according to the Kabat numbering.

Particularly preferred is a light chain sequence comprising the amino acid sequence of SEQ ID NO: 30, 211 or 213, without any amino acid modifications.

In some embodiments the antibody or fragment thereof that binds to CCR6 comprises a heavy chain variable framework region that is the product of or derived from a human gene selected from the group consisting of IGHV3-11*04 (SEQ ID NO: 77), IGHV3-11*01 (SEQ ID NO: 78), IGHV3-48*03 (SEQ ID NO: 79), IGHV3-23*04 (SEQ ID NO: 80), and IGHV3-66*04 (SEQ ID NO: 81) and a light chain variable framework region that is the product of or derived from a human gene selected from the group consisting of IGKV2-30*02 (SEQ ID NO: 82), IGKV2-30*01 (SEQ ID NO: 83), IGKV2D-30*01 (SEQ ID NO: 84), IGKV2-29*02 (SEQ ID NO: 85), IGKV2-29*03 (SEQ ID NO: 86), preferably a heavy chain variable framework region that is the product of or derived from human gene IGHV3-23*04 (SEQ ID NO: 80), and a light chain variable framework region that is the product of or derived from human gene IGKV2-30*02 (SEQ ID NO: 82). As well combinations of heavy chain variable framework regions which are present in the product of or derived from different human genes mentioned supra and/or of light chain variable region framework regions which are present in the product of or derived from different human genes mentioned supra are encompassed by the present invention.

Germline DNA sequences for human heavy and light chain variable region genes can be found in the "VBase" human germline sequence database (available on the Internet at www.mrccpe.cam.ac.uk/vbase), as well as in Kabat E A et al., supra; Tomlinson I M et al., (1992) J. Mol. Biol. 227: 776-798 and Cox J P L et al., (1994) Eur. J. Immunol. 24: 827-836. As another example, the germline DNA sequences for human heavy and light chain variable region genes can be found in the Genbank database.

In another aspect, the present disclosure also provides an antibody or fragment thereof that binds to CCR6, wherein at least one of the heavy chain CDRs and/or at least one of the light chain CDRs comprises at least one amino acid modification. Site-directed mutagenesis or PCR-mediated mutagenesis can be performed to introduce the modification(s) and the effect on antibody binding, or other functional property of interest, can be evaluated in in vitro or in vivo assays. Preferably conservative modifications are introduced. The modification(s) may be amino acid substitutions, additions or deletions, but are preferably substitutions. Typically, no more than five, preferably no more than four, more preferably no more than three, even more preferably no more than two, most preferably no more than one amino acid modifications are performed within a CDR region.

In certain embodiments, framework sequences can be used to engineer variable regions to produce variant antibodies. Variant antibodies of the invention include those in which modifications have been made to framework residues within VH and/or VK, e.g. to improve the properties of the antibody. Typically such framework modifications are made to decrease the immunogenicity of the antibody. For example, one approach is to "backmutate" one or more framework residues to the corresponding murine sequence or to "backmutate" one or more framework residues to a corresponding germline sequence. In the context of the present invention the term backmutate will be used interchangeably to mean either of these operations and more generally to refer to the sequential modification of one or more residues in the amino acid sequence of an antibody so as to alter its properties, such as immunogenicity.

Thus in a further aspect the present disclosure provides an antibody or fragment thereof that binds to CCR6, wherein at least one of the framework region sequences of the heavy chain variable region of the antibody or fragment thereof comprises at least one amino acid modification from the corresponding framework region of the heavy chain variable region of the corresponding murine antibody. Preferably the amino acid modification is an amino acid substitution. Typically, no more than seven, preferably no more than six, preferably no more than five, preferably no more than four, more preferably no more than three, even more preferably no more than two, most preferably no more than one amino acid modifications are performed within a framework region.

The present disclosure also provides an antibody or fragment thereof that binds to CCR6, wherein at least one of the framework region sequences of the light chain variable region of the antibody or fragment thereof may comprise at least one amino acid modification from the corresponding framework region of the light chain variable region of the corresponding murine antibody. Preferably the amino acid modification is an amino acid substitution. Typically, no more than two, more preferably no more than one and most preferably, no amino acid modifications are performed within a framework region.

Given that each of these heavy and light chain variable region sequences can bind to CCR6, the heavy and light chain variable region sequences can be "mixed and matched" to create anti-CCR6 binding molecules of the invention. CCR6 binding of such "mixed and matched" antibodies can be tested using the binding assays described e.g. in the Examples.

In one embodiment of the present disclosure, the antibody or fragment thereof is a humanized antibody. Preferably, the antibody or fragment thereof is a humanized monoclonal antibody.

The present disclosure also provides a monovalent antibody or fragment thereof that binds to CCR6, i.e. an antibody which consists of a single antigen binding arm. The present disclosure also provides a fragment of a antibody that binds to CCR6 selected from the group consisting of Fab, Fab', Fab'-SH, Fd, Fv, dAb, F(ab')2, scFv, bispecific single chain Fv dimers, diabodies, triabodies and scFv genetically fused to the same or a different antibody. Preferred fragments are scFv, bispecific single chain Fv dimers and diabodies. The present disclosure also provides a full length antibody that binds to CCR6.

The present disclosure also provides an antibody or fragment thereof that binds to CCR6 which further comprises a heavy and/or light constant region in particular a human heavy and/or a human light constant region. Human heavy constant regions may be selected from the group of human immunoglobulins consisting of IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), or IgE (IGHE), whereas the human heavy constant region IgG, in particular IgG1 (IGHG1) is preferred. Human light constant region may be selected from the group of human immunoglobulins consisting of kappa or lambda constant regions, whereas human kappa constant region is preferred. In a preferred embodiment the antibody or fragment thereof that binds to CCR6 comprises a human IgG1 (IGHG1) heavy constant domain and a human light kappa constant domain.

In addition or alternative to modifications made within the framework regions or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation. Each of these embodiments is described in further detail below. Modifications within the Fc region as outlined below are according to the EU numbering of residues in the Fc region. In one embodiment, the hinge region of CH1 is modified such that the number of cysteine residues in the hinge region is altered, e.g.,
increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al. In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In a further embodiment Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 to 238 in the N-terminal region of the CH2 domain are altered to thereby alter the ability of the antibody to fix complement. This approach is described further in PCT Publication No: WO1994/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication No: WO2000/42072 by Presta.

The present disclosure also provides an antibody or fragment thereof that binds to CCR6 comprising human heavy and/or light constant regions, wherein the human heavy constant region comprises an isotypic variant comprising the CH1 region, the hinge region, the CH2 region and CH3 region from human IgG4 (IGHG4) and wherein the hinge region comprises a substitution of serine at position 228 to proline. Preferably the antibody comprising the isotypic variant is a full length antibody. A particular preferred antibody or fragment thereof that binds to CCR6 comprising an isotypic variant comprising the CH1 from human IgG4 (IGHG4), the hinge from human IgG4 (IGHG4), having S228P substitution and the CH2 and CH3 from human IgG4 (IGHG4). It has been found that the isotypic variant exhibits no Fc-mediated cytotoxicity mechanisms such as ADCC compared to an antibody or fragment thereof that binds to CCR6 which comprises a human heavy constant region from human IgG1 (IGHG1) (which is usually a native human IgG1), i.e. as compared to an antibody or fragment thereof that binds to CCR6 that only differs from the isotypic variant with regard to the modified heavy constant region.

The present disclosure also provides an antibody or fragment thereof that binds to CCR6 which comprises a human IgG Fc region, wherein the mature core carbohydrate structure attached to the human IgG Fc region lacks fucose (referred herein alternatively as "non fucosylated"). The term "mature core carbohydrate structure" as used herein includes a processed core carbohydrate structure attached to an Fc region which generally consists of the carbohydrate structure GlcNAc (Fucose)-GlcNAc-Man-(Man-GlcNAc)$_2$ typical of biantennary oligosaccharides represented schematically below:

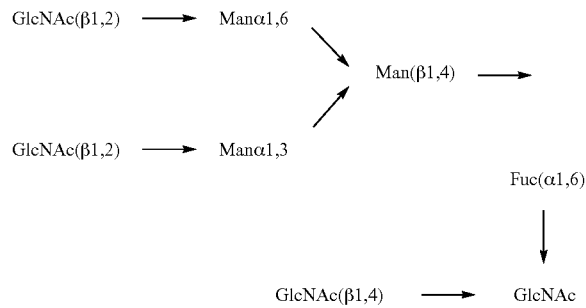

This term specifically includes G-1 forms of the core mature carbohydrate structure lacking a β1,2 GlcNAc residue. Preferably, however, the core carbohydrate structure includes both β1,2 GlcNAc residues. The mature core carbohydrate structure herein generally is not hypermannosylated. The mature core carbohydrate structure is attached to the Fc region of the glycoprotein, generally via N-linkage to Asn297 of a CH2 domain of the Fc region.

In an embodiment of the present invention the antibody comprises a human IgG1 (IGHG1) Fc region, wherein the mature core carbohydrate structure attached to the human IgG1 (IGHG1) Fc region lacks fucose. More preferred is a full-length antibody comprising a human IgG1 (IGHG1) Fc region, wherein the mature core carbohydrate structure attached to the human IgG1 (IGHG1) Fc region lacks fucose. It is known from WO03/035835 that lack of fucose in the mature core carbohydrate structure attached to the human IgG Fc region may enhance ADCC. Thus in a further embodiment the antibody or fragment thereof of the present disclosure comprises a human IgG1 (IGHG1) Fc region, wherein the mature core carbohydrate structure attached to the human IgG1 (IGHG1) Fc region lacks fucose, whereas the antibody lacking fucose exhibits enhanced ADCC compared to the parent antibody or fragment thereof not lacking fucose. Methods to generate antibodies which lack fucose are, for example (a) use of an engineered or mutant host cell that is deficient in fucose metabolism such that it has a reduced ability (or is unable to) fucosylate proteins expressed therein; (b) culturing cells under conditions which prevent or reduce fucosylation; (c) post-translational removal of fucose (e. g. with a fucosidase enzyme); (d) post-translational addition of the desired carbohydrate, e. g. after recombinant expression of a non-glycosylated glycoprotein; or (e) purification of the glycoprotein so as to select for product which is not fucosylated. Preferably used are methods described in Example 14 of WO2010/095031 e,g. methods described in Longmore et al., (1982) Carbohydr. Res. 365-92 or in Imai-Nishiya et al., (2007), BMC Biotechnol. 7: 84.

Also provided by the present invention is an antibody or fragment thereof that binds to CCR6 and which binds to the same epitope as the antibody comprising the heavy chain variable sequence comprising the amino acid sequence of SEQ ID NO: 7, 37, 39, 40, 41, 42, 75, 177, 178, 179, 249 and the light chain variable sequence comprising the amino acid sequence of SEQ ID NO: 8, 38, 43, 44, 45, 46, 181, 182, 250, 251, 252 or 253. This specific region or epitope of the CCR6 polypeptide can be identified by any suitable epitope mapping method known in the art in combination with any one of the antibodies provided by the present invention. Examples of such methods include screening peptides of varying lengths derived from CCR6 for binding to the antibody of the present invention with the smallest fragment that can specifically bind to the antibody containing the sequence of the epitope recognised by the antibody. The CCR6 peptides may be produced synthetically or by proteolytic digestion of the CCR6 polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antibodies which bind the same epitope.

Anti-CCR6 Antibody Properties

Standard assays to evaluate the binding ability of the antibodies toward e.g. CCR6 are known in the art, including for example, ELISAs, BIAcore®, Western blots, RIAs, and flow cytometry analysis. Suitable assays are described in detail in the Examples. The binding kinetics (e.g., binding affinity like KD) of the antibodies also can be assessed by standard assays known in the art, such as by Scatchard or BIAcore® system analysis. The relative binding affinity $K_i$ can be assessed by standard competition assays known in the art.

In a further aspect the present invention provides antibodies or fragment thereof that bind to human, mouse, rat and cynomolgus monkey CCR6 as visualized by ELISA or BIAcore® methods. Binding ELISA can be carried out and measured according to Example 3.

In a further aspect the present invention provides antibodies or fragments thereof that bind to recombinant or naturally produced human CCR6 and prevent activation and cytokine secretion by CD4 T lymphocytes.

In a further aspect the present invention provides antibodies or fragment thereof that bind to CCR6, in particular CCR6 in isolated form, with an affinity ($K_D$) of 850 pM or less, preferably 700 nM or less, more preferably 300 nM or less, more preferably 260 nM or less, even more preferably 250 nM or less, e.g. measured by Surface Plasmon Resonance (SPR) on a BIAcore® instrument (GE Healthcare Europe GmbH, Glattbrugg, Switzerland) by capturing the antibody on a protein-A coupled CM5 research grade sensor chip (GE Healthcare Europe GmbH, Glattbrugg, Switzerland; BR-1000-14) with a human soluble CCR6 polypeptide (encoded by SEQ ID NO: 101) used as analyte as detailed in Example 5. In a preferred aspect, the present invention provides a humanized antibody or fragment thereof that retains at least 85% of the CCR6 binding affinity ($K_D$) of the corresponding chimeric antibody. Preferably the humanized antibody or fragment thereof retains at least 90% of the CCR6 binding affinity ($K_D$) of the corresponding chimeric antibody, more preferably at least 95% of the binding affinity ($K_D$) of the corresponding chimeric antibody. Preferably, the humanized antibody or fragment thereof binds human CCR6 with equivalent affinity to the corresponding chimeric antibody. By "equivalent affinity" is meant an affinity value that is within a range of ±10% of the CCR6 binding affinity of the corresponding chimeric antibody. More preferably, the present invention provides a humanized antibody or fragment thereof that binds human CCR6 with a higher affinity than the corresponding chimeric antibody. Preferably the humanized antibody or fragment thereof binds human CCR6 with two-fold higher affinity than the corresponding chimeric antibody, more preferably with three-fold higher affinity than the corresponding chimeric antibody. In a preferred aspect of the present invention, humanized antibodies or fragment thereof that bind to human CCR6 are provided that have a binding affinity ($K_D$) of 500 nM or less, preferably 250 nM or less, more preferably 100 nM or less, more preferably 50 nM or less, even more preferably 48 nM or less e.g. measured by Surface Plasmon Resonance (SPR) on a BIAcore® instrument (GE Healthcare Europe GmbH, Glattbrugg, Switzerland) by capturing the antibody on a protein-A coupled CM5 research grade sensor chip (GE Healthcare Europe GmbH, Glattbrugg, Switzerland; BR-1000-14) with a human soluble CCR6 polypeptide (encoded by SEQ ID NO: 101) used as analyte as detailed in Example 7.

A further aspect of the present invention provides antibodies or fragments thereof that bind to CCR6 and which have good thermal stability. In a preferred embodiment, an antibody or fragment thereof that binds to CCR6 has a FAB fragment thermostability temperature greater than 70° C., preferably greater than 75° C. and even more preferably greater than 80° C. For analysis of FAB fragment thermostability differential scanning calorimetry measurements are used, whereas a mid-point melting temperature of the FAB fragment in context of a full-length IgG is identified. These kind of calorimetric measurements are known to the skilled person and can be carried out according to e.g. Garber E & Demarest S J (2007) Biochem Biophys Res Commun, 355: 751-7, as further described in Example 5.

Nucleic Acids, Vectors and Host Cells

The present disclosure also provides isolated nucleic acids encoding the antibodies and fragments thereof that bind to CCR6, vectors and host cells comprising the nucleic acid or the vector. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art, see e.g. F. Ausubel, et al., ed. (1987) Current Protocols in Molecular Biology, Greene Publishing and Wiley Interscience, New York. A nucleic acid of the invention can be, for example, DNA or RNA and may or may not contain intron sequences. In a preferred embodiment, the nucleic acid is a cDNA molecule.

Nucleic acids of the invention can be obtained using standard molecular biology techniques e.g. cDNAs encoding the light and heavy chains of the antibody or encoding VH and VL segments can be obtained by standard PCR amplification or cDNA cloning techniques. For antibodies obtained from an immunoglobulin gene library (e.g., using phage display techniques), one or more nucleic acids encoding the antibody can be recovered from the library. The methods of introducing exogenous nucleic acid into host cells are well known in the art, and will vary with the host cell used. Techniques include but are not limited to dextran-mediated transfection, calcium phosphate precipitation, calcium chloride treatment, polyethylenimine mediated transfection, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

Preferred nucleic acids molecules of the invention are those encoding the heavy chain sequence selected from the group consisting of SEQ ID NOS: 88, 90, 92, 94, 96, 98 and/or the light chain sequence selected from the group consisting of SEQ ID NOS: 87, 89, 91, 93, 95, 97.

Preferred nucleic acids molecules of the invention are those encoding the heavy chain variable region of SEQ ID NO: 7, 37 or 249 and/or the light chain variable region of SEQ ID NO: 8, 38, 250, 251, 252 or 253.

Once DNA fragments encoding VH and VL segments are obtained, these DNA fragments can be further manipulated by standard recombinant DNA techniques, for example to convert the variable region genes to full-length antibody chain genes, or to fragments genes corresponding to the fragments described supra like Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat E A et al., supra) and DNA fragments encompassing these regions can be obtained by standard PCR amplification. The heavy chain constant region can be an IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), or IgE (IGHE) constant region, but most preferably is an IgG1 (IGHG1) constant region. For a Fab fragment heavy chain gene, the VH-encoding DNA can be operatively linked to another DNA molecule encoding only the heavy chain CH1 constant region. The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat E A et al., supra.) and DNA fragments encompassing these regions can be obtained by standard PCR amplification. In preferred embodiments, the light chain constant region can be a kappa or lambda constant region, preferably a kappa constant region. To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird R E et al., (1988) Science, 242: 423-426; Huston J S et al., (1988) Proc. Natl. Acad. Sci. USA, 85: 5879-83; McCafferty J et al., (1990) Nature, 348: 552-554). Various techniques have been developed for the production of antibody fragments of antibodies. Traditionally, these fragments were derived via proteolytic digestion of intact antibodies (see, e.g., Morimoto K et al., (1992) J. Biochem. & Biophysical Methods, 24: 107-117 and Brennan M et al., (1985) Science, 229: 81-3). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter P et al., (1992) Bio/Technology, 10: 163-167). According to another approach, F(ab')2 fragments can be isolated directly from recombinant host cell culture. Other techniques for the production of antibody fragments will be apparent to the skilled practitioner. In other embodiments, the antibody of choice is a single-chain Fv fragment (scFv), see e.g. WO 1993/16185; U.S. Pat. Nos. 5,571,894 and 5,587,458. The antibody fragment may also be a "linear antibody", e.g., as described in U.S. Pat. No. 5,641,870, for example.

The nucleic acids that encode the antibodies of the present invention may be incorporated into a vector, preferably an expression vector in order to express the protein. A variety of expression vectors may be utilized for protein expression. Expression vectors may comprise self-replicating extrachromosomal vectors or vectors which integrate into a host genome. Expression vectors are constructed to be compatible with the host cell type. Thus vectors, preferably expression vectors, which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing antibodies.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology, Methods in Enzymology 185, Academic Press, San Diego, Calif. (1990)). Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr− host cells with methotrexate selection/amplification) and the neo gene (for G418 selection).

Suitable host cells for cloning or expressing the DNA in the vectors herein are prokaryote, yeast, or higher eukaryote cells. Suitable prokaryotes for this purpose include eubacteria, including gram-negative or gram-positive organisms, for example, Enterobacteriaceae such as *Escherichia*, e.g., *E. coli*, *Enterobacter*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*. Suitable *E. coli* cloning hosts include *E. coli* 294 (ATCC 31,446), *E. coli* B, *E. coli* X1776 (ATCC 31,537), and *E. coli* W3110 (ATCC 27,325). In addition to prokaryotes, eukaryotic microbes such as filamentous fungi or yeast are suitable cloning or expression hosts. *Saccharomyces cerevisiae*, or common baker's yeast, is the most commonly used among lower eukaryotic host microorganisms. However, a number of other genera, species, and strains are commonly available and useful, such as *Schizosaccharoriyces pombe*; *Kluyveromyces* hosts including *K. lactis*, *K. fragilis* (ATCC 12,424), *K. bulgaricus* (ATCC 16,045), *K. wickeramii* (ATCC 24,178), *K. waith* (ADCC 56,500), *K. drosopmarum* (ATCC 36,906), *K. thermotolerans*, or *K. marxianusyarrowia* (EP402226); *Pichia pastoris* (EP183070); *Candida*; *Trichoderma reesia* (EP244234); *Neurospora crassa*; *Schwanniomyces* such as *Schwanniomyces occidentalis*; and filamentous fungi including *Neurospora, Penicillium, Tolypocladium*, or *Aspergillus* hosts such as *A. nidulans* or *A. niger*.

Suitable host cells for the expression of the antibodies of the invention are derived from multicellular organisms. Examples of invertebrate cells include plaril and insect cells. Numerous baculoviral strains and variants and corresponding permissive insect host cells from hosts such as *Spodoptera frugiperda* (caterpillar), *Aedes augypti* (mosquito), *Aedes albopictus* (mosquito), *Drosophila melanogaster* (fruitfly) and *Bombyx mori* have been identified. A variety of viral strains for transfection are publicly available, for example, the L-1 variant of *Autographa californica* NPV and the Bm-5 strain of *Bombyx mori* NPV, and such viruses may be used, particularly for transfection of *Spodoptera frugiperda* cells. Plant cell cultures of cotton, corn, potato, soybean, *petunia*, tomato, and tobacco can also be utilized as hosts.

Host cells for expressing the recombinant antibodies of the invention are preferably mammalian host cells which include Chinese Hamster Ovary (CHO cells) (including dhfr⁻ CHO cells, described in Urlaub G & Chasin L A (1980) Proc. Natl. Acad. Sci, USA, 77: 4216-4220, used with a DHFR selectable marker, e.g., as described in Kaufman R J & Sharp P A (1982) J. Mol. Biol, 159: 601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP338841 (to Bebbington). When recombinant antibody genes are introduced into mammalian host cells, the antibodies are produced by culturing the host cells for a period of time sufficient to allow for expression of the antibody in the host cells or, more preferably, for secretion of the antibody into the culture medium in which the host cells are grown. Host cells useful for producing antibodies that bind to CCR6 may be cultured in a variety of media. Commercially available media such as Ham's F10 (Sigma-Aldrich Chemie GmbH, Buchs, Switzerland), Minimal Essential Medium (MEM; Sigma-Aldrich Chemie GmbH), RPMI-1640 (Sigma-Aldrich Chemie GmbH, Basel, Switzerland), and Dulbecco's Modified Eagle's Medium ((DMEM; Sigma-Aldrich Chemie GmbH) are suitable for culturing the host cells. Antibodies can be recovered from the culture medium using standard protein purification methods.

Antibodies may be operably linked to a fusion partner to enable targeting of the expressed protein, purification, screening, display, and the like. Fusion partners may be linked to the antibody sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence $G_4S$. A fusion partner may be a targeting or signal sequence that directs antibody and any associated fusion partners to a desired cellular location or to the extracellular media. As is known in the art, certain signalling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both.

Construction and Production of Antibodies

Antibodies generated against the CCR6 polypeptide may be obtained by immunisation of an animal i.e. by administering the polypeptides to an animal, preferably a non-human animal, using well-known and routine protocols, see for example Handbook of Experimental Immunology (Weir D M (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats in particular mice are generally most suitable. Antibodies can be produced as well by recombinant DNA techniques known to the skilled person. In additional antibodies can be produced by enzymatic or chemical cleavage of naturally occurring antibodies. Humanized antibodies of the present invention may be constructed by transferring one or more CDRs or portions thereof from VH and/or VL regions from a non-human animal (e.g., mouse) to one or more framework regions from human VH and/or VL regions. Optionally, human framework residues thus present in the VH and/or VL regions may be replaced by corresponding non-human (e.g., mouse) residues when needed or desired for decreasing immunogenicity of the antibody and/or maintaining binding affinity. Optionally, non-human amino acid residues present in the CDRs may be replaced with human residues. Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al).

Humanized antibodies of the present invention may be constructed wherein the human acceptor molecule for the heavy chain variable region is selected based on homology considerations between potential acceptor molecule variable regions and the heavy chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same heavy chain class as the murine donor molecule, and of the same canonical structural class of the variable region of the murine donor molecule. Secondary considerations for selection of the human acceptor molecule for the heavy chain variable region elude homology in CDR length between the murine donor molecule and the human acceptor molecule. Human acceptor antibody molecules are preferably selected by homology search to the V-BASE database, although other databases such as the Kabat and the public NCBI databases may be used as well.

Humanized antibodies of the present invention may be constructed wherein the human acceptor molecule for the light chain variable region is selected based on homology considerations between potential acceptor molecule variable regions and with the light chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same light chain class as the murine donor molecule, and of the same canonical structural class of the variable region of the murine donor molecule. Secondary considerations for selection of the human acceptor molecule for the light chain variable region include homology in CDR length between the murine donor molecule and the human acceptor molecule. Human acceptor antibody molecules are preferably selected by homology searches to the V-BASE database, and other databases such as the Kabat and the public NCBI databases may be used as well. Methods for humanizing a non-human antibody are described herein, including in Example 6, below.

The present invention provides a method of producing an antibody or fragment thereof that binds to CCR6 comprising culturing a host cell comprising an isolated nucleic acid encoding the antibody or fragment thereof that binds to CCR6 or a vector comprising an isolated nucleic acid encoding the antibody or fragment thereof that binds to CCR6 so that the nucleic acid is expressed and the antibody produced. Preferably the antibody is isolated. For host cells, nucleic acids and vectors, the ones described above can be used. Expression of the nucleic acids can be obtained by, e.g. a combination of recombinant DNA techniques and gene transfection methods as is well known in the art (e.g., Morrison S (1985) Science 229: 1202) and as further outlined above. For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into vectors such as expression vectors. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH1 segment(s) within the vector and the VK segment is operatively linked to the CK segment within the vector.

Characterization and Purification of Anti-CCR6 Antibodies

Screening for antibodies can be performed using assays to measure binding to human CCR6 and/or assays to measure the ability to block the binding of CCR6 to its ligand. An example of a binding assay is an ELISA, in particular, using a fusion protein of human CCR6 and human Fc, which is immobilized on plates, and employing a conjugated secondary antibody to detect anti-CCR6 antibody bound to the fusion protein. An example of a blocking assay is CCL20-mediated migration assay measuring the blocking of ligand protein binding to CCR6 on BAF transfected cells. This assay is looking for a reduction in signal as the antibody in the supernatant blocks the migration of CCR6-expressing cells in response to CCL20. A further example of blocking assay is an assay where the blocking of CCR6 activation is measured by chemiluminescence.

Antibodies of the present invention may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. To purify CCR6 antibodies, selected host cells can be grown in e.g. spinner-flasks for monoclonal antibody purification. Supernatants can be filtered and concentrated before affinity chromatography with protein A-sepharose (Pharmacia, Piscataway, N.J.). Eluted antibodies can be checked by gel electrophoresis and high performance liquid chromatography to ensure purity. A preferred antibody of the present invention is thus an isolated and/or purified antibody that binds to CCR6.

Immunoconjugates

In another aspect, the present invention provides a CCR6 antibody or a fragment thereof that binds to human CCR6, linked to a therapeutic agent, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be linked to an antibody of the invention include duocarmycins, calicheamicins, maytansines and auristatins, and derivatives thereof. An example of a calicheamicin antibody conjugate is commercially available (Mylotarg®; American Home Products). Cytotoxins can be linked to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito G et al., (2003) Adv. Drug Deliv. Rev. 55: 199-215; Trail P A et al., (2003) Cancer Immunol. Immunother. 52: 328-337; Payne G (2003) Cancer Cell, 3: 207-212; Allen T M (2002) Nat. Rev. Cancer, 2: 750-763; Pastan I & Kreitman R J (2002) Curr. Opin. Investig. Drugs, 3: 1089-1091; Senter P D & Springer C J, (2001) Adv. Drug Deliv. Rev. 53: 247-264. Antibodies of the present invention also can be linked to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for preparing radio-immunconjugates are established in the art. Examples of radioimmunoconjugates are commercially available, including Zevalin® (EDEC Pharmaceuticals) and Bexxar® (Corixa Pharmaceuticals) and similar methods can be used to prepare radioimmunoconjugates using the antibodies of the invention. The antibody immunoconjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Techniques for linking such therapeutic agents to antibodies are well known, see, e.g., Anion et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985); Hellstrom et al., "Antibodies For Drug Delivery", in Controlled Drug Delivery (2nd Ed.), Robinson et al., (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al., (eds.), pp. 475-506 (1985); "Analysis, Results, and Future Prospective of the Therapeutic Use of Radiolabeled Antibody in Cancer Therapy", in Monoclonal Antibodies for Cancer Detection and Therapy, Baldwin et al., (eds.), pp. 303-16 (Academic Press 1985), and Thorpe P E & Ross W C (1982) Immunol. Rev. 62: 119-58.

In another aspect, the present invention provides a CCR6 antibody or a fragment thereof that binds to CCR6, administered together with a therapeutic agent, such as a cytotoxin, a drug (e.g., an immunosuppressant) or a radiotoxin.

Pharmaceutical Compositions

In another aspect, the present invention provides a composition, e.g., a pharmaceutical composition, comprising the antibody or fragment thereof, of the present invention, and a pharmaceutically acceptable carrier. Such compositions may include one or a combination of (e.g., two or more different) antibodies, and/or immunoconjugates of the invention and/or a therapeutic agent, such as a cytotoxin, a drug (e.g., an immunosuppressant) or a radiotoxin as described supra. For example, a pharmaceutical composition of the invention can comprise a combination of antibodies (or immunoconjugates) that bind to different epitopes on the target antigen or that have complementary activities. Pharmaceutical compositions of the invention also can be administered in combination therapy, i.e., combined with other agents. For example, the combination therapy can include a CCR6 antibody of the present invention combined with at least one other anti-inflammatory or immunosuppressant agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody or immunoconjugate, may be coated in a material to protect the compound from the action of acids and other natural conditions that may inactivate the compound. Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

In another aspect, the present invention provides a composition comprising an immunoconjugate comprising the antibody or fragment thereof that binds to CCR6 linked to a therapeutic agent and a pharmaceutically acceptable carrier. Immunoconjugates and therapeutic agents which can be used are as described supra.

In another aspect, the present invention provides a composition comprising the antibody or fragment thereof of the present invention which further comprises another pharmaceutically active agent. Preferably the another pharmaceutically active agent is one or more of: a) another antagonist to CCR6, b) an anti-inflammatory agent, c) an immune suppressive agent e.g. TNFα antagonist, cortisone or steroids etc) and/or d) an anti-allergy agent.

A pharmaceutical composition of the invention may also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic-acid (EDTA), sorbitol, tartaric acid, phosphoric acid, and the like. Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic and Other Uses

The antibodies of the present invention have numerous in vitro and in vivo diagnostic and therapeutic utilities involving the diagnosis and treatment of CCR6 mediated disorders. For example, these molecules can be administered to cells in culture, in vitro or ex vivo, or to human subjects, e.g., in vivo, to treat, prevent and to diagnose a variety of CCR6-mediated disorders. Preferred subjects are human and include patients having disorders mediated by CCR6 activity (CCR6 mediated disorders). The neutralizing antibodies of the present invention can be effective in treating patients independent of whether they have an abnormal CCR6 status such as an increase in CCR6 expression in an activated T cell population or an increase in CCR6 expression on memory T cell population or an increase in CCR6 expression on Th17 T cell population, in comparison to a naive T cell population.

More preferred subjects are human and include patients expressing a high level of CCR6.

A "patient" for the purposes of the present invention includes humans and other animals, preferably mammals and most preferably humans. Thus the antibodies of the present invention have both human therapy and veterinary applications. The term "treatment" or "treating" in the present invention is meant to include therapeutic treatment, as well as prophylactic, or suppressive measures for a disease or disorder. Thus, for example, successful administration of an antibody prior to onset of the disease results in treatment of the disease. As another example, successful administration of an antibody after clinical manifestation of the disease to combat the symptoms of the disease comprises treatment of the disease. "Treatment" and "treating" also encompasses administration of an antibody after the appearance of the disease in order to eradicate the disease. Successful administration of an antibody after onset and after clinical symptoms have been developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In a particular embodiment, the antibodies are used in vivo to treat, prevent or diagnose a variety of CCR6-mediated disorders. Thus the invention provides a method for treating a CCR6 mediated disorder in a subject, the method comprising administering to the subject a therapeutically effective amount of the antibody or fragment thereof. Exemplary CCR6 mediated disorders include, but are not limited to, inflammatory diseases and/or autoimmune diseases, for example, inflammatory bowel disease (IBD) including ulcerative colitis and Crohn's disease, rheumatoid arthritis, MS, type 1 and type 2 diabetes, psoriasis, psoriatic arthritis, ankylosing spondylitis, atopic dermatitis; allergic reactions or conditions, including for example, asthma and allergic lung inflammation; cancers, atherosclerosis, infections, neurodegenerative diseases, graft rejection, graft versus host diseases (GVHD) and cardiovascular disorders/diseases. Preferably, the CCR6 mediated disorders include inflammatory diseases and/or auto immune diseases, including inter alia inflammatory bowel diseases (e.g., ulcerative colitis and Crohn's disease), rheumatoid arthritis, MS and atherosclerosis, Chronic Obstructive Pulmonary Disease (COPD), optic neuritis, age related macular degeneration, SLE, Sjogen's syndrome, Scleroderma, systemic sclerosis, Chronic Kidney disease, Liver Fibrosis, Tuberculosis, Idiopathic pulmonary fibrosis, Tuberculosis induced lung fibrosis, Retroperitoneal Fibrosis, Pulmonary fibrosis, Cystic fibrosis, Endomyocardial fibrosis, Atrial Fibrosis, Mediastinal fibrosis, Myelofibrosis (bone marrow), Retroperitoneal fibrosis, Progressive massive fibrosis, Nephrogenic systemic fibrosis, Arthrofibrosis.

Preferred CCR6 mediated disorders to be treated with the antibody of the invention are selected from the group consisting of inflammatory bowel disease, multiple sclerosis, rheumatoid arthritis and asthma. A particular preferred CCR6 mediated disorder to be treated with the antibody of the invention is inflammatory bowel disease.

In one embodiment, the antibodies of the invention can be used to detect levels of CCR6, or levels of cells which contain CCR6 on their membrane surface, which levels can then be linked to certain disease symptoms. Alternatively, the antibodies can be used to inhibit or block CCR6 function which, in turn, can be linked to the prevention or amelioration of certain disease symptoms, thereby implicating CCR6 as a mediator of the disease. This can be achieved by contacting a sample and a control sample with the CCR6 antibody under conditions that allow for the formation of a complex between the antibody and CCR6. Any complexes formed between the antibody and CCR6 are detected and compared in the sample and the control. In light of the specific binding of the antibodies of the invention for CCR6, the antibodies of the invention can be used to specifically detect CCR6 expression on the surface of cells e.g. can be used to detect a patient having low or high expression levels of CCR6. The antibodies of the invention can also be used to purify CCR6 via immunoaffinity purification.

In another embodiment, the antibodies of the invention can be initially tested for binding activity associated with therapeutic or diagnostic use in vitro. For example, compositions of the invention can be tested using flow cytometric assays.

The present disclosure further provides the use of an antibody or fragment thereof as a medicament and the use of an antibody or fragment thereof in the preparation of a medicament for the treatment of a CCR6 mediated disorder. In a further embodiment the present disclosure provides the antibody or fragment thereof for use as a medicament. Also provided by the present disclosure is the antibody or fragment thereof for use in a method for treating a CCR6 mediated disorder. CCR6 mediated disorders are the ones as described supra. The antibody or fragment thereof of the present invention may be particularly useful for treating CCR6 mediated disorders independent of the costimulatory status of a patient. In a preferred embodiment, the antibody or fragment thereof can be used for treating a CCR6 mediated disorder wherein for instance a patient expresses a high level of CCR6.

As previously described, anti-CCR6 antibodies of the invention can be co-administered with one or other more therapeutic agents, e.g., a cytotoxic agent, a radiotoxic agent or an immunosuppressive agent. The antibody can be linked to the agent (as an immunoconjugate as described supra) or can be administered separate from the agent. In the latter case (separate administration), the antibody can be administered before, after or concurrently with the agent or can be co-administered with other known therapies, e.g., an anti-cancer therapy, e.g., radiation.

For administration of the antibody, the dosage ranges from about 0.0001 to 100 mg/kg, and more usually 0.01 to 10 mg/kg, of the host body weight. An exemplary treatment regime entails administration once per week, once every two weeks, once every three weeks, once every four weeks, once a month, once every three months or once every three to six months. The antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml. Alternatively the antibody can be administered as a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated.

Actual dosage levels of the active ingredients, i.e. the antibody in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective amount" of a CCR6 antibody of the invention preferably results in a decrease in severity of disease symptoms, an increase in frequency and duration of disease symptom-free periods, and/or a prevention of impairment or disability due to the disease affliction. The ability of a compound for the treatment of a CCR6 mediated disorder can be evaluated in an animal model system predictive of efficacy in human. Alternatively, this property of a composition can be evaluated by examining the ability of the compound to inhibit cell growth, such inhibition can be measured in vitro by assays known to the skilled practitioner. One of ordinary skill in the art would be able to determine such amounts based on such factors as the subject's size, the severity of the subject's symptoms, and the particular composition or route of administration selected.

The antibody or the composition of the present invention can be administered via one or more routes of administration using one or more of a variety of methods known in the art. As will be appreciated by the skilled artisan, the route and/or mode of administration will vary depending upon the desired results. Preferred routes of administration include intravenous, intramuscular, intradermal, intraperitoneal, subcutaneous, spinal or other parenteral routes of administration, for example by injection or infusion. More preferred routes of administration are intravenous or subcutaneous. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, for example, intranasally, orally, vaginally, rectally, sublingually or topically.

Article of Manufacture and Kit

In another embodiment of the disclosure, an article of manufacture comprising the antibody or fragment thereof, the composition or the immunoconjugate of the invention for the treatment of a CCR6 mediated disorder is provided. The article of manufacture may comprise a container and a label or package insert on or associated with the container. Suitable containers include, for example, bottles, vials or syringes. The containers may be formed from a variety of materials such as glass or plastic. The container holds a composition that may be effective for treating the condition and may have a sterile access port (e.g., the container may be an intravenous solution bag or a vial having a stopper pierceable by a hypodermic injection needle). At least one active agent in the composition may be the antibody described herein. The label or package insert may indicate that the composition may be used for treating the condition of choice, such as cancer. In one embodiment, the label or package insert may indicate that the composition comprising the antibody may be used to treat a CCR6-mediated disorder.

Moreover, the article of manufacture may comprise (a) a first container with a composition contained therein, wherein the composition comprises the antibody herein, and (b) a second container with a composition contained therein, wherein the composition comprises a therapeutic agent other than the antibody. The article of manufacture in this embodiment of the disclosure may further comprise a package insert indicating that the first and second compositions can be used in combination to treat a CCR6 mediated disease or disorder. Such therapeutic agent may be any of the adjunct therapies described in the preceding section (e.g., a thrombolytic agent, an anti-platelet agent, a chemotherapeutic agent, an anti-angiogenic agent, an anti-hormonal compound, a cardioprotectant, and/or a regulator of immune function in a mammal, including a cytokine). Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Also within the scope of the present invention are kits comprising the antibody, the compositions or the immunoconjugates of the invention and instructions for use. The kit can further contain one more additional reagents, such as an immunosuppressive reagent, a cytotoxic agent or a radiotoxic agent, or one or more additional antibodies of the invention (e.g., an antibody having a complementary activity which binds to an epitope on CCR6 distinct from the first antibody).

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Establishment of Stable Human CCR6 Expressing CHO and BAF/3 Cells

Cloning of the Construct:

The gene for human CCR6 was ordered from Imagenes (now SourceBiosciences LifeSciences, Nottingham, UK). The name for the construct attributed by Imagenes was IRATp970E0757D. The target vector for cloning was pGLEX33[IRES-REP], a Glenmark proprietary vector with an expression cassette under control of the mouse CMV promoter. A multiple cloning site (MCS) allowed cloning of the gene of interest, CCR6. The MCS (and hence, in the final construct, the open reading frame of CCR6) was followed by an IRES and a second open reading frame coding for a reporter protein (REP).

In order to clone the open reading frame of CCR6 (SEQ ID NO: 101) in pGLEX33[IRES-REP], the construct of IRATp970E0757D was used as template for PCR using a specific primer pair (GlnPr863 and GlnPr864) that was adding convenient restriction sites (NheI/ClaI) 5' and 3' to the open reading frame. The amplicon was cut using NheI/ClaI and cloned into the backbone of pGLEX33[IRES-REP], that was cut in the MCS using the same enzymes and CIPed in order to prevent recircularization. The resulting construct was named pGLEX33[CCR6-IRES-REP] and confirmed by sequencing (Fastens, Geneva, Switzerland).

CHO[hsCCR6]

Chinese Hamster Ovary cells (CHO—S, Invitrogen, Carlsbad, Calif., USA) were cultured in suspension in PowerCHO-2 CD medium (Lonza, Verviers, Belgium), supplemented with 4 mM L-glutamine (Applichem, Germany) and incubated in a shaking incubator (200 rpm with a circular stroke of 2.5 cm) at 37° C., 5% $CO_2$ and 80% humidity.

Subcultures of CHO—S cells were routinely carried out every 3-4 days using a seeding density of $0.5*10^6$ viable cells/ml in fresh medium. The cells were cultivated using 10 ml of medium in 50 ml bioreactor tubes (Tubespin Bioreactor 50; TPP, Trasadingen, Switzerland) containing a permeable filter allowing gas exchange. The cell viability and concentration were determined with the Countess automated cell counter (Invitrogen, Carlsbad, Calif., USA) using the trypan blue cell exclusion method. Cell concentration was confirmed by determination of the packed cell volume (PCV) method using PCV tubes (TPP, Trasadingen, Switzerland) for CHO—S cells.

Transfection of CHO—S cells was performed using polyethyleneimine (PEI; JetPEI, Polyplus-transfection, Illkirch, France). PEI is a cationic polymer which can complex with negatively charged molecules such as DNA. The positive charged DNA-PEI complex binds to the negatively charged cell surface and is internalized by endocytosis. It reaches the lysosome compartment from where it is released by lysis to the nucleus. The high transfection efficiency with DNA-PEI complexes is due to the ability of PEI to protect DNA from lysosomal degradation. The cells were transfected according to the manual provided by the manufacturer. Two plasmids were simultaneously co-transfected, pGLEX33[CCR6-IRES-REP] expressing the gene of interest as well as the reporter gene and a second vector expressing the PAC gene that provides resistance to the selection marker puromycin. Both vectors were linearized before stable transfection and transfected in a ratio that was known to allow generation of stable cell population.

The day after transfection the cells were diluted at different concentrations that with selective medium and distributed into 96 well plates in order to generate stable cell populations that will be referred to as minipools. The selective medium used was PowerCHO-2, 4 mM glutamine, supplemented with puromycin at a specific concentration that was known to allow selection of stable cell lines.

Seven days after transfection, the selection stringency was renewed by adding selection medium to the cells. As soon as colonies in 96 well plates were confluent, the plates were analysed for reporter gene expression using a fluorescence reader. The 48 highest expressors were expanded into 24 well plate scale. At this scale, the cells were tested for human CCR6 expression using FACS and human CCR6 specific antibodies. The 5 clones #12, 16, 25, 37 and 47 showed the most homogenous expression and the highest expression of CCR6. These cells were further expanded for a research cell bank preparation of 10 cryovials each. The RCB was kept at −80° C. in the cell bank of the protein expression and cell line development group.

BA/F3[CCR6]

BA/F3 is an IL-3 dependent murine pro B cell line most likely derived from C3H mice. The cells with the order number ACC 300 were purchased from DSMZ (Braunschweig, Germany). Cells were routinely cultured in T-Flasks using BA/F3 growth medium (80% RPMI (vol./vol.), 10% heat inactivated FCS (vol./vol.), 10% (vol./vol.) conditioned medium of WEHI-3B cell line (DSMZ catalogue number ACC 26) and incubated in a static incubator (37° C., 5% $CO_2$ and 80% humidity).

Subcultures of BA/F3 cells were routinely carried out every 3-4 days using a seeding density of $0.1*10^6$ viable cells/ml in fresh medium. The cells were cultivated using 20 ml of medium in T-150 flasks (TPP, Trasadingen, Switzerland). The cell viability and concentration were determined with the Countess automated cell counter (Invitrogen, Carlsbad, Calif., USA) using the trypan blue cell exclusion method.

Transfection of BA/F3 cells was performed using electroporation using the NEON device (LifeTechnologies, Carlsbad, Calif.). Electroporation conditions (puls number, puls length, voltage) were optimized using the instructions provided in the manual of the NEON device. Two plasmids were simultaneously co-transfected, pGLEX33 [CCR6-IRES-REP] expressing the gene of interest as well as the reporter gene and a second vector expressing the PAC gene that provides resistance to the selection marker puromycin. Both vectors were linearized before stable transfection and transfected in a ratio that was known to allow generation of stable cell population.

The cells were diluted in growth medium at different concentrations and distributed into 96 well plates. The next day, another volume of selective medium was added to the cells. The selective medium used was BA/F3 growth medium, supplemented with puromycin. The combination of dilution of BA/F3 cells at different concentrations and puromycin treatment was known to allow selection of stable cell lines As soon as colonies in 96 well plates were confluent, the plates were analysed for reporter gene expression using a fluorescence reader. The 96 highest expressors were expanded into 24 well plate scale. At this scale, the cells were tested for human CCR6 expression using FACS and human CCR6 specific antibodies. The 5 clones #7, 17, 21 and 48 showed the most homogenous expression and the highest expression of CCR6. These cells were further expanded for a research cell bank preparation of 10 cryovials each. The RCB was kept at −80° C. in the cell bank of the protein expression and cell line development group.

>Glnpr863

SEQ ID NO: 99

GAGGCTAGCCACCATGAGCGGGGAATCAATGAA

>Glnpr864

SEQ ID NO: 100

AGGGGCATCGATTCACATAGTGAAGGACGACGC

>hsCCR6

SEQ ID NO: 101

ATGAGCGGGGAATCAATGAATTTCAGCGATGTTTTCGACTCCAGTGAAG

ATTATTTTGTGTCAGTCAATACTTCATATTACTCAGTTGATTCTGAGAT

GTTACTGTGCTCCTTGCAGGAGGTCAGGCAGTTCTCCAGGCTATTTGTA

-continued

```
CCGATTGCCTACTCCTTGATCTGTGTCTTTGGCCTCCTGGGGAATATTC
TGGTGGTGATCACCTTTGCTTTTTATAAGAAGGCCAGGTCTATGACAGA
CGTCTATCTCTTGAACATGGCCATTGCAGACATCCTCTTTGTTCTTACT
CTCCCATTCTGGGCAGTGAGTCATGCCACCGGTGCGTGGGTTTTCAGCA
ATGCCACGTGCAAGTTGCTAAAAGGCATCTATGCCATCAACTTTAACTG
CGGGATGCTGCTCCTGACTTGCATTAGCATGGACCGGTACATCGCCATT
GTACAGGCGACTAAGTCATTCCGGCTCCGATCCAGAACACTACCGCGCA
GCAAAATCATCTGCCTTGTTGTGTGGGGGCTGTCAGTCATCATCTCCAG
CTCAACTTTTGTCTTCAACCAAAAATACAACACCCAAGGCAGCGATGTC
TGTGAACCCAAGTACCAGACTGTCTCGGAGCCCATCAGGTGGAAGCTGC
TGATGTTGGGGCTTGAGCTACTCTTTGGTTTCTTTATCCCTTTGATGTT
CATGATATTTTGTTACACGTTCATTGTCAAAACCTTGGTGCAAGCTCAG
AATTCTAAAAGGCACAAAGCCATCCGTGTAATCATAGCTGTGGTGCTTG
TGTTTCTGGCTTGTCAGATTCCTCATAACATGGTCCTGCTTGTGACGGC
TGCAAATTTGGGTAAAATGAACCGATCCTGCCAGAGCGAAAAGCTAATT
GGCTATACGAAAACTGTCACAGAAGTCCTGGCTTTCCTGCACTGCTGCC
TGAACCCTGTGCTCTACGCTTTTATTGGGCAGAAGTTCAGAAACTACTT
TCTGAAGATCTTGAAGGACCTGTGGTGTGTGAGAAGGAAGTACAAGTCC
TCAGGCTTCTCCTGTGCCGGGAGGTACTCAGAAAACATTTCTCGGCAGA
CCAGTGAGACCGCAGATAACGACAATGCGTCGTCCTTCACTATGTGAA
```

Generation and Screening of Mouse Anti-Human CCR6 Antibodies

CHO and BAF cells transfected with human CCR6 were washed with PBS and resuspended in PBS. For the first immunization, CCR6-transfected CHO cells were transferred to 0.5 mL insulin syringes (BD Pharmingen, Allschwil, Switzerland) and BALB/c animals (Harlan, Netherlands) were immunized sub-cutaneously in the back footpads, the base of the tail and the neck with $10 \times 10^6$ transfected cells. The immunization was repeated two weeks later with BAF transfected with CCR6 following the same route of injection.

The presence of circulating anti-human CCR6 antibodies in the immunized mouse sera was evaluated by Flow cytometry using transfected BAF cells and BAF mock as negative control. A serial dilution (from 1:100 to 1:109) of the different mouse sera was added to the cells and the bound antibodies were detected using a PE-labelled goat anti-mouse IgG secondary antibody (BD Biosciences, Allschwil, Switzerland). A final sub-cutaneous boost with $1 \times 10^6$ of CCR6 transfected BAF cells was performed in animals displaying the best anti-human CCR6 IgG serum titer three days before sacrifice.

Animals were euthanized and the inguinal, axillary, brachial, popliteal and sciatic lymph nodes were collected to prepare a single cell suspension by disturbing the lymph node architecture with two 25G needles in a DNAse (Roche Diagnostics (Schweiz) AG, Rotkreuz, Switzerland) and collagenase (Roche Diagnostics (Schweiz) AG, Rotkreuz, Switzerland) solution. Single cell suspensions were fused to a myeloma cell line X63AG8.653 (mouse BALB/c myeloma cell line; ATCC accession number: CRL 1580; Kearney J F et al., (1979) J. Immunol. 123(4): 1548-1550) at a ratio of 7:1 (fusion partner-to-harvested lymph node cells) with polyethylene glycol 1500 (Roche Diagnostics (Schweiz) AG, Rotkreuz, Switzerland). The fused cells were plated into 96 well flat bottom plates containing mouse macrophages in DMEM-10 medium (Invitrogen AG, Basel, Switzerland) supplemented with 10% fetal bovine serum (FBS, PAA Laboratories, Pasching, Austria), 2 mM L-glutamine, 100 U/ml (Biochrom AG, Germany) penicillin, 100 µg/ml streptomycin (Biochrom AG, Germany), 10 mM HEPES (Invitrogen AG, Basel, Switzerland), 50 µM β-mercaptoethanol (Sigma-Aldrich Chemie GmbH, Buchs, Switzerland), HAT (Sigma-Aldrich Chemie GmbH, Buchs, Switzerland) and 1% Growth factor (Hybridokine, Interchim/Uptima, Montluçon, France).

Approximately 800 wells from the fusions were screened by FACS for the presence of mouse IgG that recognized human CCR6. Positive wells were expanded and subjected to two rounds of sub cloning. Cells were collected and the heavy and light chains were cloned and sequenced.

Example 2

Cloning and Sequencing of the VH and VL Chains of the Anti-CCR6 Antibodies from Hybridoma Cells RNA was isolated from hybridomas, reverse-transcribed into cDNA and VH and VL genes were amplified by PCR. These PCR products were ligated into a rescue-vector, allowing the sequencing of individual PCR products and the determination of mono- or poly-clonality of the hybridomas. The pDrive vector (Qiagen, Germany) used for this purpose encoded the LacZ α-peptide when no insert was present. This allowed a blue/white selection on IPTG and X-gal containing LB-agar plates (colonies with no insert were blue because of the degradation of X-gal by the LacZ α-peptide). White colonies were amplified and minipreps were performed to isolate the plasmids, which were sequenced with standard primers (M13rev, M13fwd, T7 or SP6) annealing on the vector. Sequences were analysed using three different softwares: Geneious, Clone Manager and BioEdit. The obtained sequences were then subcloned into an expression vector for recombinant expression of the antibody of interest.

1. RNA Isolation

Total RNA from hybridomas was isolated from $2-10 \times 10^6$ cells using the NucelosSpin RNA II kit from Macherey-Nagel (Germany, Cat. No. 740955) following the manufacturer's protocol (with 600 µl RA1 buffer, syringe homogenization in addition to column homogeneization and 60 µl RNase-free $H_2O$ (provided with the kit) for elution).

The yield of RNA preparations were quantified using a NanoDropND-1000 Spectrophotometer (Thermo Fischer Scientific, USA).

2. One Step RT-PCR

The total RNA preparations described above were further reverse-transcribed into cDNA, and the VH and VL fragments were amplified by PCR using two different mixtures of degenerated primers, each one allowing the recovery of all the different subfamilies of mouse immunoglobulin heavy chain variable fragments and variable heavy chain junction regions or the recovery of all mouse immunoglobulin light chain kappa variable fragments and variable light chain kappa junction regions. Both reverse-transcription and PCR amplification were performed simultaneously using the QiaGen one step RT-PCR kit (Qiagen, Germany, Cat. No. 210212). Since the technique used specific primer, each mRNA sample was then treated in duplicate allowing for the individual reverse-transcription and amplification of either the VH or the VL fragments.

2 μg of total RNA dissolved into RNase-free to a final volume of 30 μl was mixed with: 10 μl of a 5× stock solution of QiaGen OneStep RT-PCR Buffer, 2 μl of a dNTPs mix at a concentration of 10 mM, 3 μl of primer mix at a concentration of 10 μM and 2 μl of QiaGen OneStep RT-PCR Enzyme Mix. The final solution was placed in a PCR tube, and cycled in a PCR-themocycler (BioRad iCycler version 4.006, BioRad, USA) using the following settings:
30 min at 50° C.
15 min at 95° C.
40 cycles: 30 sec at 94° C.
30 sec at 55° C.
1 min at 72° C.
10 min at 72° C.
Hold at 4° C.

3. pDrive Cloning

PCR products were loaded on 2% agarose gel and the products of interest (~450 bp) were excised from the gel, and using the Macherey-Nagel NucloSpin Gel and PCR Clean-up kit (Germany, Cat. No. 740609). For DNA sequencing, the extracted PCR products were cloned into a rescue-vector (pDrive vector, Qiagen, Germany, Cat. No. 231124) and transformed into *E. coli* TOP10 competent cells (Invitrogen AG, Basel, Switzerland, No. C404006)

Miniprep Extraction

Positive colonies were amplified in 1.5 ml LB+100 μg/ml ampicillin in MN Square-well Block (Macherey-Nagel, Germany., Cat. No. 740488) and a miniprep extraction was performed using the NucleoSpin 96 Plasmid kit (Macherey-Nagel, Germany., Cat. No. 740625).

4. Sequencing

Samples were sent for DNA sequencing to the DNA sequencing service company Fastens (Plan-les-Ouates, Switzerland) with the standard primers M13rev, M13fwd, T7 or SP6.

5. Sequence Analysis

Geneious, Clone Manager 9 Professional Edition and BioEdit Sequence Alignment Editor (Hall, T. A. 1999. BioEdit: a user-friendly biological sequence alignment editor and analysis program for Windows 95/98/NT. Nucl. Acids. Symp. Ser. 41:95-98) were used for the analysis of sequences.

6. Cloning of Expression Vector for Recombinant Chimeric Antibody Expression

For recombinant expression in mammalian cells, the isolated murine VH and VL fragments were formatted as chimeric immunoglobulins using assembly based PCR methods. These chimeric antibodies consists of a heavy chain where the murine heavy variable domain is fused to the human IgG1 heavy chain constant domains (γ1, hinge, γ2, aid γ3 regions) and a light chain where the murine light variable domain is fused to a human kappa constant domain (CIO. All chimeric antibodies were cloned into the in house mammalian expression vector pGLEX18 vector for expression and transiently transfect in HEK-293 (ATCC number: CRL-1573)

The very first chimeras (for HC and for LC) were produced by overlapping PCRs. Both the variable part and the constant part were amplified by PCR, and were then fused together by a second PCR reaction. They were then cloned in frame using BspEI/NotI in one in house vector containing a leader peptide upstream of the BspEI restriction site. The resulting coding sequences (leader peptide, variable part, constant part) were subdoned using HindIII/XhoI (for LC) or HindIII/XbaI (for HC) into the pGLEX18 expression vector. Restrictions sites for RsrII (for LC) aid for BbvCI (for HC) were added during the overlapping PCR between the variable part and the constant part of the antibodies. For the next chimeras, VL and VH were amplified by PCR, and cloned directly in frame into the pGLEX18 backbone containing the leader peptide and the corresponding constant part, using BspEI/RsrII for LC and BspEI/BbvCI for HC.

The primers used for reverse transcription and amplification were synthetized by Microsynth, (Balgach, Switzerland) and were HPLC purified. The Primers sequences can be found in Table 1.

TABLE 1

| Primer Mix VH back 100 uM (from 100 uM stocks) (SEQ ID NOs: 102-120) | |
|---|---|
| GTGATC gcc atg gcg tcg acC GAK GTR MAG CTT CAG GAG TC | 3 μl |
| GTGATC gcc atg gcg tcg acC GAG GTB CAG CTB CAG CAG TC | 3 μl |
| GTGATC gcc atg gcg tcg acC CAG GTG CAG CTG AAG SAR TC | 2 μl |
| GTGATC gcc atg gcg tcg acC GAG GTC CAR CTG CAA CAR TC | 2 μl |
| GTGATC gcc atg gcg tcg acC CAG GTY CAG CTB CAG CAR TC | 4 μl |
| GTGATC gcc atg gcg tcg acC CAG GTY CAR CTG CAG CAR TC | 3 μl |
| GTGATC gcc atg gcg tcg acC CAG GTC CAC GTG AAG CAR TC | 2 μl |
| GTGATC gcc atg gcg tcg acC GAG GTG AAS STG GTG GAR TC | 3 μl |
| GTGATC gcc atg gcg tcg acC GAV GTG AWG STG GTG GAG TC | 4 μl |
| GTGATC gcc atg gcg tcg acC GAG GTG CAG STG GTG GAR TC | 2 μl |
| GTGATC gcc atg gcg tcg acC GAK GTG CAM CTG GTG GAR TC | 3 μl |
| GTGATC gcc atg gcg tcg acC GAG GTG AAG CTG ATG GAR TC | 2 μl |
| GTGATC gcc atg gcg tcg acC GAG GTG CAR CTT GTT GAR TC | 2 μl |
| GTGATC gcc atg gcg tcg acC GAR GTR AAG CTT CTC GAR TC | 3 μl |

TABLE 1-continued

| | |
|---|---|
| GTGATC gcc atg gcg tcg acC GAA GTG AAR STT GAG GAR TC | 3 μl |
| GTGATC gcc atg gcg tcg acC CAG GTT ACT CTR AAA SAR TC | 3 μl |
| GTGATC gcc atg gcg tcg acC CAG GTC CAA CTV CAG CAR CC | 3 μl |
| GTGATC gcc atg gcg tcg acC GAT GTG AAC TTG GAA SAR TC | 2 μl |
| GTGATC gcc atg gcg tcg acC GAG GTG AAG GTC ATC GAR TC | 2 μl |
| Primer Mix VH for 100 uM (from 100 uM stocks) (SEQ ID NOs: 121-124) | |
| CCTCCACCACTCGAGCC CGA GGA AAC GGT GAC CGT GGT | 9.5 μl |
| CCTCCACCACTCGAGCC CGA GGA GAC TGT GAG AGT GGT | 9.5 μl |
| CCTCCACCACTCGAGCC CGC AGA GAC AGT GAC CAG AGT | 9.5 μl |
| CCTCCACCACTCGAGCC CGA GGA GAC GGT GAC TGA GGT | 9.5 μl |
| Primer Mix VL back 100 uM (from 100 uM stocks) (SEQ ID NOs: 125-144) | |
| GGCGGTGGC gct agc GAY ATC CAG CTG ACT CAG CC | 2 μl |
| GGCGGTGGC gct agc CAA ATT GTT CTC ACC CAG TC | 2 μl |
| GGCGGTGGC gct agc GAY ATT GTG MTM ACT CAG TC | 3 μl |
| GGCGGTGGC gct agc GAY ATT GTG YTR ACA CAG TC | 3 μl |
| GGCGGTGGC gct agc GAY ATT GTR ATG ACM CAG TC | 3 μl |
| GGCGGTGGC gct agc GAY ATT MAG ATR AMC CAG TC | 4 μl |
| GGCGGTGGC gct agc GAY ATT CAG ATG AYD CAG TC | 4 μl |
| GGCGGTGGCGCT AGC GAY ATY CAG ATG ACA CAG AC | 2 μl |
| GGCGGTGGC gct agc GAY ATT GTT CTC AWC CAG TC | 2 μl |
| GGCGGTGGCgct agc GAY ATT GWG CTS ACC CAA TC | 3 μl |
| GGCGGTGGC gct agc GAY ATT STR ATG ACC CAR TC | 4 μl |
| GGCGGTGGC gct agc GAY RTT KTG ATG ACC CAR AC | 4 μl |
| GGCGGTGGC gct agc GAY ATT GTG ATG ACB CAG KC | 4 μl |
| GGCGGTGGC gct agc GAY ATT GTG ATA ACY CAG GA | 2 μl |
| GGCGGTGGC gct agc GAY ATT GTG ATG ACC CAG WT | 2 μl |
| GGCGGTGGC gct agc GAY ATT GTG ATG ACA CAA CC | 2 μl |
| GGCGGTGGC gct agc GAY ATT TTG CTG ACT CAG TC | 2 μl |
| GGCGGTGGC gct agc GAA ACA ACT GTG ACC CAG TC | 1 μl |
| GGCGGTGGC gct agc GAA AAT GTK CTS ACC CAG TC | 2 μl |
| GGCGGTGGC gct agc CAG GCT GTT GTG ACT CAG GAA TC | 2.8 μl |
| Primer Mix VL back 100 uM (from 100 uM stocks) (SEQ ID NOs: 145-148) | |
| ATGCTGAC gc ggc cgc ACG TTT KAT TTC CAG CTT GG | 1.9 μl |
| ATGCTGAC gc ggc cgc ACG TTT TAT TTC CAA CTT TG | 9.5 μl |
| ATGCTGAC gc ggc cgc ACG TTT CAG CTC CAG CTT GG | 9.5 μl |
| ATGCTGAC gc ggc cgc ACC TAG GAC AGT CAG TTT GG | 2 μl |

The following sequencing primers as indicated in Table 2 were used:

TABLE 2

| | |
|---|---|
| M13-Fwd | GTAAAACGACGGCCAGT (SEQ ID NO: 149) |
| M13-Rev | AACAGCTATGACCATG (SEQ ID NO: 150) |
| T7 | TAATACGACTCACTATAGG (SEQ ID NO: 151) |
| SP6 | GATTTAGGTGACACTATAG (SEQ ID NO: 152) |

Example 3

Biological Characterization of Anti-Human CCR6 Antibodies

CCR6-Specific Antibody Detection by Flow Cytometry

Antibody titers, specificity and production by hybridomas and recombinant antibody candidates were determined by flow cytometry. Briefly, BAF cells transfected with human CCR6 (Generation of these transfected cells is detailed in example 1) were cultured and $2\times10^5$ cells were distributed in a 96 well V bottom plate (TPP, Trasadingen, Switzerland), and centrifuged for three minutes at 1300 rpm; supernatants were discarded, cells were collected and analyzed by flow cytometry as described below. Cells were resuspended in 50 µl of hybridoma supernatant or in 50 µl of FACS buffer (PBS, 2% FBS, 10% Versene (Invitrogen, USA)) with 5 µg/mL of isotype control or commercial mouse anti-human CCR6 antibody (clone 11A9, BD Biosciences, Allschwil, Switzerland). Cells were incubated for 30 minutes on ice, washed two times and resuspended in 50 µl of FACS buffer. An anti-mouse IgG-Phycoerithrin-PE (BD Biosciences, Allschwil, Switzerland) diluted 1/200 was used to detect CCR6-specific mouse hybridoma and the isotype control antibody. Cells were incubated for 15 minutes on ice, washed once, resuspended in 400 µl of FACS buffer and analyzed on the FACS instrument (Cyan, Beckman Coulter International S.A., Nyon, Switzerland). FIG. 1 shows that the parental hybridoma supernatants of various clones recognize the human CCR6 protein expressed on the surface of transfected BAF cells (FIG. 1A) but not on BAF mock cells (FIG. 1B).

4H11 was selected because it showed superior properties over the other candidates, in terms of hybridoma stability and better functional properties amongst all selected recombinant candidates (n=5) as detailed below.

4H11 Chimeric Antibody Neutralizes CCR6-Mediated Cell Activation in Discoverx Bioassay In order to determine whether chimeric 4H11 neutralizes recruitment of β-arrestin upon activation of CCR6 receptor, a bioassay using Ab Hunter anti-CCR6 kit (DiscoveRx corporation, Birmingham, UK) was assessed, according to manufacturer's specifications. Chemiluminescence activity was read using a microplate reader (Biotek, USA; distributor: WITTEC AG, Littau, Switzerland). In the assay, chimeric 4H11 was used at 5 different concentrations (20, 6.7, 2, 0.7 and 0.2 µg/ml). A chimeric IgG1 isotype control and anti-CCL20 (R&D Systems, Minneapolis, USA) were used as negative and positive control, respectively, at 20 µg/ml. The percentage of relative luminescence unit (RLU) was calculated considering chemiluminescent signal in conditions using chimeric IgG1 isotype control as 100% of luminescent activity. FIG. 2A shows that chimeric 4H11 significantly reduces CCR6 receptor signalling in a dose dependent manner as compared to an isotype matched control. In addition, chimeric 4H11 is still active at low concentrations (0.2 µg/ml).

Inhibition of CCL20-Induced Migration of CCR6-Expressing BAF Cells

Generation of BAF cells transfected with human CCR6 is detailed in example 1. The ability of chimeric 4H11 to neutralize the migration of human CCR6-transfected BAF cells in response to human CCL20 was tested. Briefly, 100 µl of BAF-CCR6 diluted at $1\times10^6$ cells/ml were pre-incubated with 3 doses of chimeric 4H11 (10, 2 and 0.4 µg/ml) and added to the upper chamber of a 6.5 mm Transwell® with 8.0 µm Pore Polycarbonate Membrane Insert [Corning, Chemie Brunschwig AG, Switzerland]. The lower chamber of the Transwell contained recombinant human CCL20 (R&D Systems) diluted at 10 ng/ml in 500 µl of BAF medium (RPMI-1640 (Sigma-Aldrich Chemie GmbH, Basel, Switzerland) containing 10% of FCS (Amimed distributed by Bioconcept, Allschwil, Switzerland)). Following incubation, cells from lower and upper chambers were harvested and counted using the Guava Easycyte HT (Millipore AG, Zug, Switzerland). Chimeric IgG1 isotype and anti-CCL20 (R&D Systems) were used at 10 µg/ml as negative and positive controls, respectively. A migration ratio was calculated by dividing the number of cells in the lower chamber by the total number of cells in the upper and lower chamber. The percentage of inhibition of migration was calculated as the percentage of that seen for the isotype control. FIG. 2B demonstrates that chimeric 4H11 reduced the migration of BAFCCR6 cells induced by human CCL20, even at 0.4 µg/ml as compared to an isotype control.

Example 4

Binding of 4H11 Candidate on Human and Other Animal Species Peripheral Blood Mononuclear Cells (PBMC) by Flow Cytometry Human Cells Filters containing human leukocytes were collected from the Blood Collection Center from La Chaux-de-Fonds, Switzerland (Centre de Transfusion Sanguine et Laboratoire de Serologie, rue Sophie-Mairet 29, CH-2300). Cells were removed from the filters by backflushing with 60 mL of PBS containing 10 U/mL of liquemin (Drossapharm AG, Lucern, Switzerland). PBMCs were then purified with 50 mL Blood-Sep-Filter Tubes (Brunschwig, Basel, Switzerland) following manufacturer's instructions. Cells were washed 3 times with Roswell Park Memorial Institute (RPMI, PAA Laboratories, Pasching, Austria) medium with FBS (PAA Laboratories, Pasching, Austria). Cells were counted and $2\times10^5$ cells were distributed in a 96 well V bottom plate (TPP, Trasadingen, Switzerland), and centrifuged for three minutes at 1300 rpm; cells were collected and analyzed by flow cytometry as described below.

Human PBMCs cells prepared as described above were resuspended in 50 µl of FACS buffer (PBS, 2% FBS, 10% Versene (Invitrogen, USA) with 10 µg/mL of chimeric 4H11 antibody, 10 µg/mL or an appropriate isotype control or 10 µg/mL of commercial anti-human CCR6 antibody (clone R6H9, eBioscience, Vienna, Austria). Cells were incubated for 30 minutes on ice, washed once and resuspended in 50 µl of FACS buffer. An anti-human IgG-Phycoerithrin-PE and anti-mouse IgG-Phycoerithrin-PE (BD Biosciences, Allschwil, Switzerland) diluted 1/200 were used to detect the chimeric 4H11 antibody and commercial anti-human CCR6 antibody, respectively. Cells were incubated for 15 minutes on ice, washed once, resuspended in 400 µl of FACS buffer and analyzed on the FACS instrument (Cyan, Beckman Coulter International S.A., Nyon, Switzerland).

Cynomolgus Monkey Primary Cells

Whole blood from Cynomolgus monkeys (obtained from Professor Eric Rouiller, laboratory of Neurophysiology, University of Fribourg, Fribourg, Switzerland), was collected in citrate tubes (BD Biosciences, Allschwil, Switzerland). Two mL of PBS was mixed with 3 mL of blood and the mixture was layered on the top of 10 ml of a 85:15 Ficoll: PBS mixture (GE Healthcare Europe GmbH, Glattbrugg, Switzerland). Samples were centrifuged for 20 minutes at room temperature without break. The PBMC layer was collected and washed three times with PBS. Cells were resuspended in Dulbecco's Modified Eagle Medium (DMEM, PAA Laboratories, Pasching, Austria), 10% FBS (PAA Laboratories, Pasching, Austria), Non-essential amino acids (PAA Laboratories, Pasching, Austria) 1 mM Sodium Pyruvate (PAA Laboratories, Pasching, Austria), 2 mM Ultraglutamine (Lonza, Belgium), 100 U/ml penicillin (Biochrom AG, Germany), 100 µg/ml streptomycin (Biochrom AG, Germany). Cells were counted and $2 \times 10^5$ cells were distributed in a 96 well V bottom plate (TPP, Trasadingen, Switzerland), and centrifuged for three minutes at 1300 rpm. Chimeric 4H11, isotype control or commercial anti-human CCR6 non-human primate cross reactive antibody (clone 11A9, BD Pharmingen, Allschwil, Switzerland) were added to the wells at 10 µg/mL. Cells were washed and anti-human IgG-Phycoerithrin-PE and anti-mouse IgG-Phycoerithrin-PE (BD Biosciences, Allschwil, Switzerland) diluted at 1/200 in FACS buffer were used to detect the chimeric 4H11 antibody and commercial anti-human CCR6 antibody, respectively. Cells were incubated for 15 minutes on ice, washed once, resuspended in 400 µl of FACS buffer and analysed on the FACS instrument (Cyan, Beckman Coulter International S.A., Nyon, Switzerland). FIG. 3 shows that chimeric 4H11 is able to recognize CCR6 receptor expressed on the surface of human (FIG. 3A) and cynomologus monkey (FIG. 3B) lymphocytes, thus provides for cross-reactivity properties highly desired for drug development.

Example 5: CCR6 Epitope Mapping Studies

This study was assessed to identify small regions and individual amino acids of the human CCR6 sequence (hsCCR6) important for the binding of chimeric 4H11 mAb. As chimeric 4H11 does not recognize mouse CCR6 receptor (mmCCR6), a linear approach using human-mouse hybrids, whereby the N-terminal region and the extracellular loops of the human CCR6 receptor were replaced by the equivalent mouse regions was used to determine the epitope of this mAb.

Generation of Mouse-Human Hybrid CCR6 Mutants.

The first mutant called hsCCR6/mmECL1 corresponds to the sequence of the hsCCR6 where amino acids 105 to 119 (ExtraCellular Loop 1 of hsCCR6) were replaced by amino acids 97 to 111 of mmCCR6 sequence (ExtraCellular Loop 1 of mmCCR6). The second mutant called hsCCR6/mmECL2 corresponds to the sequence of the hsCCR6 where amino acids 181 to 211 (ExtraCellular Loop 2 of hsCCR6) were replaced by amino acids 173 to 203 from mmCCR6 sequence (ExtraCellular Loop 2 of mmCCR6). The third mutant called hsCCR6/mmECL3 corresponds to the sequence of the hsCCR6 where amino acids 280 to 303 (ExtraCellular Loop 3 of hsCCR6) were replaced by amino acids 272 to 295 from mmCCR6 sequence (ExtraCellular Loop 3 of mmCCR6)

For the first mutant hsCCR6/mmECL1, the hsECL1 sequence was replaced by mmECL1 sequence by fusion PCR (using 3 PCRs).

A first PCR (PCR1) was performed using the hsCCR6 as template (GSD491), the forward primer GlnPr1778 (containing a NheI restriction site and the beginning of the hsCCR6 sequence) and reverse primer GlnPr1947 (containing 24 bp of hsCCR6 before the hsECL1 and the first 34 bp of mmECL1).

A second PCR (PCR2) was done in parallel of the first PCR using the hsCCR6 as template (GSD491), the forward primer GlnPr1948 (containing the last 33 bp of mmECL1 and 25 bp of hsCCR6 after the hsECL1) and the reverse primer GlnPr1779 (containing the end of the hsCCR6 sequence and a XhoI restriction site).

The third PCR (PCR3) was done using PCR1 and PCR2 as template (overlap 22 bp) and GlnPr1778 and GlnPr1779 as forward and reverse primers.

For the second mutant hsCCR6/mmECL2, the hsECL2 sequence was replaced by mmECL2 sequence by fusion PCR (using 3 PCRs).

A first PCR (PCR1) was done using the hsCCR6 as template (GSD491), the forward primer GlnPr1778 (containing a NheI restriction site and the beginning of the hsCCR6 sequence) and reverse primer GlnPr1949 (containing 28 bp of hsCCR6 before the hsECL2 and the first 54 bp of mmECL2).

A second PCR (PCR2) was done in parallel of the first PCR using the hsCCR6 as template (GSD491), the forward primer GlnPr1950 (containing the last 57 bp of mmECL2 and 25 bp of hsCCR6 after the hsECL2) and the reverse primer GlnPr1779 (containing the end of the hsCCR6 sequence and a XhoI restriction site).

The third PCR (PCR3) was done using PCR1 and PCR2 as template (overlap 18 bp) and GlnPr1778 and GlnPr1779 as forward and reverse primers.

For the third mutant hsCCR6/mmECL3, the hsECL3 sequence was replaced by mmECL3 sequence by fusion PCR (using 3 PCRs).

A first PCR (PCR1) was done using the hsCCR6 as template (GSD491), the forward primer GlnPr1778 (containing a NheI restriction site and the beginning of the hsCCR6 sequence) and reverse primer GlnPr1951 (containing 25 bp of hsCCR6 before the hsECL3 and the first 46 bp of mmECL3).

A second PCR (PCR2) was done in parallel of the first PCR using the hsCCR6 as template (GSD491), the forward primer GlnPr1952 (containing the last 44 bp of mmECL3 and 27 bp of hsCCR6 after the hsECL3) and the reverse primer GlnPr1779 (containing the end of the hsCCR6 sequence and a XhoI restriction site).

The third PCR (PCR3) was done using PCR1 and PCR2 as template (overlap 18 bp) and GlnPr1778 and GlnPr1779 as forward and reverse primers.

For all three mutants, PCR product was inserted into a pT1 vector (GSD980) using the unique NheI and XhoI restriction sites. DNA was then transformed into E. coli bacteria and plated out on ampicillin plate. The next day, 2-4 clones per mutants were selected, their DNA was extracted and sent to Fastens for sequencing. Based on sequencing results, one clone for each mutant was chosen with GSB202 the mutant pT1-hsCCR6/mmECL1, GSB208 the mutant pT1-hsCCR6/mmECL2 and GSB206 the mutant pT1-hsCCR6/mmECL3. MidiPrep were done for all three mutants for transient transfection in HEK cells.

Primers sequences:
GlnPr1778:
(SEQ ID NO: 153)
GATCGCTAGCCACCATGAGCGGGGAATCAATGAA GlnPr1779:
(SEQ ID NO: 154)
GATCCTCGAGTCATCACATAGTGAAGGACGACG GlnPr1947:
(SEQ ID NO: 155)
CATCGCTGAAAACCCAAGTGTTGGTGGCATGAGTCACTGCCCAGAATGG
GAGAGTAAG GlnPr1948:
(SEQ ID NO: 156)
AACACTTGGGTTTTCAGCGATGCACTGTGTAAATTGCTAAAAGGCATCT
ATGCCATCA GlnPr1949:
(SEQ ID NO: 157)
CTCACAGACATCACGATCCTGCAGCTCGTATTTCTTGTTGAAGATAAAT
GTAGGGCTGGAGATGATGACTGACAGCCCCCAC GlnPr1950:
(SEQ ID NO: 158)
GATCGTGATGTCTGTGAGCCACGGTACAGGTCTGTCTCAGAGCCCATCA
CGTGGAAGCTGCTGATGTTGGGGCTTGAGCTAC GlnPr1951:
(SEQ ID NO: 159)
CGAGGACTTTCTCGGTGCTGCAGCTCCGGCCCACTTTGCCCGTGTTTGC
AGCCGTCACAAGCAGGACCATG GlnPr1952:
(SEQ ID NO: 160)
GCACCGAGAAAGTCCTCGCCTACACCAGGAACGTGGCCGAGGTCCTGGC
TTTCCTGCACTGCTGCCTGAAC Two other human/mouse mutants were generated: the mutant 4 consists of a human CCR6 receptor containing a mouse N-terminal region while the mutant 5 corresponds to a mouse CCR6 receptor containing a human N-terminal region.

The mutant 4 called hsCCR6/mmN-term corresponds to the sequence of the hsCCR6 where amino acids 1 to 47 (N-term of hsCCR6 until the first transmembrane domain) were replaced by amino acids 1 to 39 of mmCCR6 sequence (N-term of mmCCR6 until the first transmembrane domain). The mutant 5 called mmCCR6/hsN-term corresponds to the sequence of the mmCCR6 where amino acids 1 to 39 (N-term of mmCCR6 until the first transmembrane domain) were replaced by amino acids 1 to 47 of hsCCR6 sequence (N-term of hsCCR6 until the first transmembrane domain)

For the mutant hsCCR6/mmN-term, the hsN-term sequence was replaced by mmN-term sequence by fusion PCR (using 3 PCRs).

A first PCR (PCR1) was done using the mmCCR6 as template (GSD363), the forward primer GlnPr866 (containing a NheI restriction site and the beginning of the mmCCR6 sequence) and reverse primer GlnPr1983 (containing the end of the mmN-term sequence and the beginning of the hsCCR6 first transmembrane domain).

A second PCR (PCR2) was done in parallel of the first PCR using the hsCCR6 as template (GSD491), the forward primer GlnPr1984 (containing the end of the mmN-term sequence and the beginning of the hsCCR6 first transmembrane domain) and the reverse primer GlnPr1779 (containing the end of the hsCCR6 sequence and a XhoI restriction site).

The third PCR (PCR3) was done using PCR1 and PCR2 as template (overlap 40 bp) and GlnPr866 and GlnPr1779 as forward and reverse primers.

For the mutant mmCCR6/hsN-term, the mmN-term sequence was replaced by hsN-term sequence by fusion PCR (using 3 PCRs).

A first PCR (PCR1) was done using the hsCCR6 as template (GSD491), the forward primer GlnPr1778 (containing a NheI restriction site and the beginning of the hsCCR6 sequence) and reverse primer GlnPr1985 (containing the end of the hsN-term sequence and the beginning of the mmCCR6 first transmembrane domain).

A second PCR (PCR2) was done in parallel of the first PCR using the mmCCR6 as template (GSD363), the forward primer GlnPr1986 (containing the end of the hsN-term sequence and the beginning of the mmCCR6 first transmembrane domain) and the reverse primer GlnPr1987 (containing the end of the mmCCR6 sequence and a XhoI restriction site).

The third PCR (PCR3) was done using PCR1 and PCR2 as template (overlap 33 bp) and GlnPr1778 and GlnPr1987 as forward and reverse primers.

For both mutants 4 and 5, PCR product was inserted into a pT1 vector (GSD980) using the unique NheI and XhoI restriction sites. DNA was then transformed into E. coli bacteria and plated out on ampicillin plate. The next day, 4 clones per mutants were selected, their DNA was extracted and sent to Fastens for sequencing. Based on sequencing results, one clone for each mutant was chosen with GSB210 the mutant pT1-hsCCR6/mmN-term and GSB215 the mutant pT1-mmCCR6/hsN-term.

MaxiPrep were done for both mutants for the establishment of stable cell lines using BAF cells.

Primers sequences:
GlnPr866:
(SEQ ID NO: 161)
AGAGGCTAGCCACCATGAATTCCACAGAGTCCTA GlnPr1983:
(SEQ ID NO: 162)
CAAGGAGTAGGCAATCGGTACAAATACCTTGGTGAAGTTTCTGAC GlnPr1984:
(SEQ ID NO: 163)
AAACTTCACCAAGGTATTTGTACCGATTGCCTACTCCTTGATCTG GlnPr1779:
(SEQ ID NO: 154)
GATCCTCGAGTCATCACATAGTGAAGGACGACG GlnPr1778:
(SEQ ID NO: 153)
GATCGCTAGCCACCATGAGCGGGGAATCAATGAA GlnPr1985:
(SEQ ID NO: 164)
CAATTGGCACAAATAGCCTGGAGAACTGCCTGACCTCCTG GlnPr1986:
(SEQ ID NO: 165)
TCAGGCAGTTCTCCAGGCTATTTGTGCCAATTGCCTACTC GlnPr1987:
(SEQ ID NO: 166)
CCGCGATCCTCGAGTCATTACATGGTAAAGGACGATGCATTATCA A summary of all the 5 mutants described above is illustrated in table 3 below:

*Table 3*: *summary of the human/mouse CCR6 hybrid mutants used for epitope mapping* hsCCR6—SEQ ID NO: 71, mmCCR6—SEQ ID NO: 72, hsCCR6/mmECL1—SEQ ID NO: 13, hsCCR6/mmECL2—SEQ ID NO: 15, hsCCR6/mmECL3—SEQ ID NO: 17, hsCCR6/mmN-term—SEQ ID NO: 168, mmCCR6/hsN-term—SEQ ID NO: 170.

Flow Cytometry.

Binding of MAb to the surface of CCR6 transfected CHO cells was assessed using flow cytometry. $2\times10^5$ cells were distributed in a 96 well V bottom plate and centrifuged for three minutes at 1300 rpm. Cells were collected and incubated with the appropriate mAb at a final concentration of 10 µg/ml in a volume of 50 µl in FACS buffer. Cells were incubated for 30 minutes on ice, washed twice and resuspended in 50 µl of PE-labelled secondary antibody diluted at 1/200 in FACS buffer. Cells were incubated for 15 minutes on ice, washed once, resuspended in 400 µl of FACS buffer and analyzed on the FACS instrument (Cyan, Beckman Coulter) in channel FL-2. FACS analysis in FIG. 4 shows that the mouse-human hybrids mutants of CCR6 were correctly expressed on cell surface as all the transfectants were either recognized by commercial anti-mouse or anti-human CCR6 antibodies. As shown in FIG. 4, chimeric 4H11 mAb recognized all the hybrid mutants containing a human N-terminal region (Figures A, D, E and F) while it did not bind to the chimeric construct containing a mouse N-terminus region (FIG. 4C), suggesting that the N-terminal region of human CCR6 is essential for the interaction between CCR6 and chimeric 4H11 mAb.

In order to identify key residues important for the binding of chimeric 4H11 mAb on the N-terminal region of CCR6, two other mutants were generated within the N-terminal region.

Generation of Mouse-Human Hybrid Mutants within the N-Terminal Region of CCR6

The aim was to replace two small regions ("blocks") within the N-terminal sequence of mouse CCR6 (mmCCR6) with their human (hsCCR6) counterparts, and to evaluate by FACS binding activity of chimeric 4H11 antibody on these hybrid constructs.

The two different locations were identified and named block 1, from amino acids 3 to 11 (mmCCR6) and block 2 from amino acids 8 to 16. The first mutant called mmCCR6 block1 hsCCR6 corresponds to the sequence of the mmCCR6 where amino acids 3 to 11 were replaced by amino acids 21 to 27 of hsCCR6 sequence. The second mutant called mmCCR6 block2 hsCCR6 corresponds to the sequence of the mmCCR6 where amino acids 8 to 16 were replaced by amino acids 29 to 35 of hsCCR6 sequence.

For the mutant "block 1", mmCCR6 sequence was replaced by hsCCR6 sequence by PCR using the mmCCR6 as the template (GSD363a) and the primer GlnPr2188 (containing the hsCCR6 sequence and a NHeI restriction site) and the primer GlnPr2189 (containing the codon stop and XhoI restriction site).

For the mutant "block 2", mmCCR6 sequence was replaced by hsCCR6 sequence by fusion PCR using the mmCCR6 as the template (GSD363a). The primer GlnPr2190 (containing the codon start and a NHeI restriction site) and the primer GlnPr2191 (containing the hsCCR6 sequence) were used to create a first product. In parallel, the primer GlnPr2192 (containing the hsCCR6 sequence) and the primer GlnPr2193 (containing the codon stop and XhoI restriction site) were used to create a second product. Knowing that the two PCR products have an overlap of 27 bp, they were used as templates for the second round of PCR with the two most external primers GlnPr2190 (containing the codon start and a NHeI restriction site) and GlnPr2193 (containing the codon stop and XhoI restriction site).

For both mutants ("block 1" and "block 2"), PCR product was inserted into a pT1 vector (GSD980) using the unique NheI and XhoI restriction sites. DNA was then transformed into *E. coli* bacteria and plated out on ampicillin plate. The next day, 4 clones per mutants were selected, their DNA was extracted and sent to Fasteris for sequencing. Based on sequencing results, one clone for each mutant was chosen with GSA32 the mutant pT1-mmCCR6 block1 hsCCR6 and GSA33 the mutant pT1-mmCCR6 block2 hsCCR6.

Transient Transfection of CHO Cells

CHO cells were transfected with the mmCCR6 mutants using PEI reagents. To this end, the day prior the transfection cells were split to obtain a cell density of $1\cdot10^6$ cells/mL. The day of transfection cells were spun down and re-suspended in 5 mL of transfection medium (Opti-MEM from Gibco) up to a cell density of 2.106 cells/mL ($10\cdot10^6$ cells had to be spun down). 12.5 μg of DNA was added to 2504 of 150 mM NaCl. In parallel 25 μg of PEI was added to 250 μL of 150 mM NaCl. Then both solutions were mixed up and incubated 10 min at RT in order to allow the complexes to form. DNA cocktail was poured onto the cells and cells were incubated 4-5 h at 37° C. on a shaker (105 rpm, 5% CO2). 5 mL of growth medium (Power CHO 2 from Lonza containing 4 mM Glutamine) was added to the cells to have a final density of $1\cdot10^6$ cells/mL. Finally cells were incubated 4 days on a shaker (37° C., 105 rpm, 5% CO2) before being analyzed on FACS.

Results from FIG. 5 show that chimeric 4H11 bound to mutant 1 containing a human block 1 in a mouse CCR6 receptor but did not bind to the mutant 2 consisting of a human block 2 sequence in a human CCR6 receptor. Thus, the epitope of 4H11 is located within the N-terminal region of CCR6 receptor, and more precisely in a sequence composed of 9 residues between Phe in position 18 and Glu in position 16.

A summary of the N-terminal human/mouse hybrids constructs is shown in Table 4 below.

Table 4: summary of the hybrids human/mouse N-terminal CCR6 sequences used for epitope mapping

| | |
|---|---|
| HsCCR6 N-terminal sequence | MNFSDVFDSSEDYFVSVNTSYYSVDSEMLLCSLQEVRQFSRL |
| Mo CCR6 N-terminal sequence | MNSTESYFGTDDYDNTEYYSPPDHGPCSLEEVRNFTKV |
| Mutant mmCCR6 block 1 hsCCR6 | MNFSDVFDSSEDYDNTEYYS<u>PPDHGP</u>CSLEEVRNFTKV (Human / Mouse) |
| Mutant mmCCR6 block 2 hsCCR6 | MN<u>STESYFGTD</u>DYDNTEYYSVDSEMLLCSLEEVRNFTKV (Mouse / Human) | hsCCR6 N-terminal sequence—SEQ ID NO:172, mmCCR6 Nterminal sequence—SEQ ID NO: 174, mutant mmCCR6 block1 hsCCR6—SEQ ID NO: 180, mutant mmCCR6 block2 hsCCR6—SEQ ID NO: 185.

Example 6: Humanization of Mouse Monoclonal Antibody 4H11

Humanizing the anti-human CCR6 mouse antibody 4H11 including selection of human acceptor frameworks, back mutations, and mutations that substantially retain and/or improve the binding properties of human CDR-grafted acceptor frameworks is described herein.
Design of the Reshaped Variable Regions Homology matching was used to choose human acceptor frameworks to graft 4H11 CDRs. Databases e.g. a database of germline variable genes from the immunoglobulin loci of human and mouse (the IMGT database, supra) or the VBASE2 (Retter I et al., (2005) Nucleic Acids Res. 33, Database issue D671-D674) or the Kabat database (Johnson G et al., (2000) Nucleic Acids Res. 28: 214-218) or publications (e.g., Kabat E A et al., supra) may be used to identify the human subfamilies to which the murine heavy and light chain V regions (SEQ ID NO: 7 and 8, respectively) belong and determine the best-fit human germline framework to use as the acceptor molecule. Selection of heavy and light chain variable sequences (VH and VL) within these subfamilies to be used as acceptor may be based upon sequence homology and/or a match of structure of the CDR1 and CDR2 regions to help preserve the appropriate relative presentation of the six CDRs after grafting.

For example, use of the IMGT database indicates good homology between the 4H11 heavy chain variable domain framework and the members of the human heavy chain variable domain subfamily 3. Highest homologies and identities of both CDRs and framework sequences were observed for germline sequences: IGHV3-11*04 (SEQ ID NO: 77), IGHV3-11*01 (SEQ ID NO: 78), IGHV3-48*03 (SEQ ID NO: 79), IGHV3-23*04 (SEQ ID NO: 80), and IGHV3-66*04 (SEQ ID NO: 81), all of which had sequence identity above 74% for the whole sequence up to CDR3. IGHV3-11*04 and IGHV3-11*01 showed 76% sequence identity while IGHV3-48*03 and IGHV3-23*04 showed a sequence identity of 75%. IGHV3-23*04 was selected as the VH framework due to its stability.

Using the same approach, 4H11 light chain variable domain sequence showed good homology to the members of the human light chain variable domain kappa subfamily 2. Highest homologies and identities of both CDRs and framework sequences were observed for germline sequences: IGKV2-30*02 (SEQ ID NO: 82) and IGKV2-30*01 (SEQ ID NO: 83) exhibited the highest identity with respectively 82% and 81%, closely followed by another group consisting of IGKV2D-30*01 (SEQ ID NO: 84), IGKV2-29*02 (SEQ ID NO: 85), and IGKV2-29*03 (SEQ ID NO: 86) all exhibiting sequence identity above 78%.

As starting point to the humanization process, human IGHV3-23*04 (SEQ ID NO: 80), and IGKV2-30*02 (SEQ ID NO: 82) variable domains were selected as acceptors to the 4H11 CDRs. A first humanized antibody of human gamma one isotype was prepared (see below). The antibody encompassed a human-mouse hybrid heavy chain variable domain and a human-mouse hybrid light chain variable domain. The hybrid heavy chain variable domain was based on the human heavy chain variable domain IGHV3-23*04 wherein germline CDR1 and 2 where respectively replaced for 4H11 heavy chain CDR1 and 2. Best matching JH segment sequence to the human acceptor framework was identified from the IMGT searches mentioned above. The resulting human-mouse hybrid heavy chain variable sequence had human IGHV3-23*04 framework regions, 4H11 mouse CDRs, and best matching JH segment. Similarly, the human-mouse hybrid light chain variable domain had human IGKV2-30*02 framework regions, 4H11 mouse CDRs, and best matching JK to human acceptor. To accommodate CDRs on to the human acceptor framework key positions were modified by substituting human residues to mouse residues. This process is called back-mutation and is the most unpredictable procedure in the humanization of monoclonal antibodies. It necessitates the identification and the selection of critical framework residues from the mouse antibody that need to be retained in order to preserve affinity while at the same time minimizing potential immunogenicity in the humanized antibody.

To identify residues that may impact the most CDR conformation and/or inter-variable domain packing, a 3D model for the human-mouse hybrid VH-VL pair of variable domains was calculated using the structure homology-modelling server SWISS-MODEL (Arnold K et al., (2006) Bioinformatics, 22(2): 195-201; swissmodel.expasy.org) set in automated mode. Model analysis allowed the selection of a subset of positions based on their putative influence on CDR regions and/or heavy chain-light chain variable domain packing. This subset of positions consisted of variable heavy chain positions: 24 and 49 as well as variable light chain positions: 36 and 46 (Kabat numbering).

The newly designed variable domains are referred herein as heavy chain variable domain VH1 with SEQ ID NO: 75, and as light chain variable domain VL1 with SEQ ID NO: 38. The first humanized antibody encompassing VH1 and VL1 is abbreviated herein VH1/VL1 antibody.
Production of the First Humanized Antibody Prototype Coding DNA sequences (cDNAs) for VH1 and VL1 were synthesized in a scFv format by GENEART AG (Regensburg, Germany) thereby allowing for a single cDNA sequence to encompass both variable domains (SEQ ID NO: 167). Individual variable domain cDNAs were retrieved from this scFv construct by PCR, and further assembled upstream of their respective constant domain cDNA sequence(s) using PCR assembly techniques. Finally, the complete heavy and light chain cDNAs were ligated in independent vectors that are based on a modified pcDNA3.1 vector (Invitrogen, CA, USA) carrying the CMV promoter and a Bovine Growth Hormone poly-adenylation signal. The light chain specific vector allowed expression of human kappa isotype light chains by ligation of the light chain variable domain cDNA of interest in front of the kappa light chain constant domain cDNA using BamHI and BsiWI restriction enzyme sites; while the heavy chain specific vector was engineered to allow ligation of the heavy chain variable domain cDNA of interest in front of the cDNA sequence encoding the human IGHG1 CH1, IGHG1 hinge region, IGHG1 CH2, and IGHG1 CH3 constant domains using BamHI and SalI restriction enzyme sites. In both heavy and light chain expression vectors, secretion was driven by the mouse VJ2C leader peptide containing the BamHI site. The BsiWI restriction enzyme site is located in the kappa constant domain; whereas the SalI restriction enzyme site is found in the IGHG1 CH1 domain.

The VH1/VL1 antibody (having heavy chain SEQ ID NO: 173 and light chain SEQ ID NO: 30) was transiently produced by co-transfecting equal quantities of heavy and light chains vectors into suspension-adapted HEK293-EBNA1 cells (ATCC® catalogue number: CRL-10852)

using polyethylenimine (PEI, Sigma, Buchs, Switzerland). Typically, 100 ml of cells in suspension at a density of 0.8-1.2 million cells per ml is transfected with a DNA-PEI mixture containing 50 μg of expression vector encoding the heavy chain and 50 μg of expression vector encoding the light chain. When recombinant expression vectors encoding antibody genes are introduced into the host cells, antibodies are produced by further culturing the cells for a period of 4 to 5 days to allow for secretion into the culture medium (EX-CELL 293, HEK293-serum-free medium; Sigma, Buchs, Switzerland), supplemented with 0.1% pluronic acid, 4 mM glutamine, and 0.25 μg/ml geneticin).

The VH1/VL1 antibody was purified from cell-free supernatant using recombinant protein-A streamline media (GE Healthcare Europe GmbH, Glattbrugg, Switzerland), and buffered exchanged into phosphate buffer saline prior to assays.

Cell ELISA on CHO Cells Expressing Human CCR6

CHO cells transfected with human CCR6 were generated as described in example 1. In order to detect interaction of humanized candidates with CCR6 expressed in CHO cells, a cell ELISA was developed. Briefly, ninety-six well-microtiter plates (Costar, USA; distributor VWR AG, Nyon, Switzerland) were coated with 100 μl of Poly-D lysine (Sigma-Aldrich Chemie GmbH, Buchs, Switzerland) at 1 μg/ml in PBS and incubated overnight at 4° C. The day after, plates were washed and CCR6-expressing CHO cells were centrifuged at 1300 rpm for 3 minutes and plated overnight at 37° C., 5% $CO_2$ at $1\times10^6$ cells/well in Dulbecco's Modified Eagle Medium (DMEM, PAA Laboratories, Pasching, Austria) supplemented with 10% FBS (PAA Laboratories, Pasching, Austria), 2 mM L-glutamine (Lonza, Leuven, Belgium), 100 U/ml penicillin, 100 μg/ml streptomycin (Biochrom AG, Berlin, Germany. The day after, cells were incubated for one hour at room temperature with various concentrations (ranging from 10 to 0.0137 μg/ml) of humanized 4H11 candidates. Following cell incubation, samples were washed three times with DMEM containing 10% FCS and fixed with 50 μl of PBS containing 4% of PFA (Sigma-Aldrich Chemie GmbH, Buchs, Switzerland) at room temperature for 15 minutes. Cells were washed with PBS containing 2% BSA (Bovine Serum Albumine, PAA Laboratories, Pasching, Austria), and blocked with 200 μl of the same buffer for one hour at room temperature. Samples were incubated with a Horseradish Peroxidase (HRP) labelled-goat-anti human Ig Fc fragment specific-HRP (Jackson ImmunoResearch Europe Ltd, Newmarket, UK). Cells were washed 5 times with PBS containing 2% BSA, and the plates were incubated with TMB Substrate (Sigma-Aldrich Chemie GmbH, Buchs, Switzerland) to reveal antibody binding. Absorbance was read by a microplate reader (Biotek, USA; distributor: WITTEC AG, Littau, Switzerland).

Back Mutations from Mouse to Human Residues

Since VH1/VL1 antibody led to a binding comparable to the chimeric antibody VH1 and VL1 were used as a starting point for further mutagenesis. To decrease the immunogenic potential of 4H11, further humanized candidates were designed by back-mutating framework mouse residues at position 24 and 49 in VH and position 36 and 46 in VL to human residues. An additional variant includes a conservative mutation in the CDR H2 at the position 62, where the mouse residue, a threonine, is substituted by a human residue, a serine.

Antibody expression and purification followed the methods described above. Humanized antibody candidates were assayed for their binding by Cell ELISA as previously described.

FIG. 6 shows that amongst humanized variants, VH5/VL1 antibody showed a similar or better binding than other candidates on CHO expressing human CCR6. Similarly, FIG. 7 shows that VH5/VL1 antibody displays a similar or better inhibitory function than other candidates on Ab Hunter anti-CCR6 bioassay. Moreover, VH5 (SEQ ID NO: 37) has the highest identity to the human framework IGHV3-23*04 (SEQ ID NO: 80) with a sequence identity of 89.5%, resulting in a lower immunogenic risk.

Thermostability of Selected Humanized Anti-CCR6 Antibodies by Differential Scanning Calorimetry The thermal stabilities of the humanized antibodies were measured using differential scanning calorimetry (DSC). Monoclonal antibodies melting profiles are characteristic of their isotypes (Garber E & Demarest S J (2007) Biochem. Biophys. Res. Commun. 355: 751-7), however the mid-point melting temperature of the FAB fragment can be easily identified even in the context of a full-length IgG. Such mid-point melting of FAB portion was used to monitor monoclonal stability of the humanized candidates.

Calorimetric measurements were carried out on a VP-DSC differential scanning microcalorimeter (GE Healthcare Europe GmbH). The cell volume was 0.128 ml, the heating rate was 200° C./h, and the excess pressure was kept at 65 p.s.i. All antibodies were used at a concentration of 1 mg/ml in PBS (pH 7.4). The molar heat capacity of antibody was estimated by comparison with duplicate samples containing identical buffer from which the antibody had been omitted. The partial molar heat capacities and melting curves were analyzed using standard procedures. Thermograms were baseline corrected and concentration normalized before being further analyzed using a Non-Two State model in the software Origin v7.0.

Humanized variant VH5/VL1 FAB fragment displayed a single transition at 79.4° C. with a shape and amplitude consistent with a cooperative unfolding which is generally observed for a compactly folded FAB fragments indicating that the engineering process was successful at retaining FAB stability. Overall the humanized variant showed a good thermal stability.

TABLE 5 humanized anti human CCR6 antibodies

| Antibody variant (IGHG1) | SEQ ID NOs | Back-mutations VH/VL | EC50s | DSC (° C.) |
|---|---|---|---|---|
| Chimera | 175/176 | — | 1.89 | 76.1 |
| H1/L1 | 173/30 | —/— | 1.27 | 78.7 |
| H1/L2 | 173, 186 | —/Y36F | 1.42 | 77.2 |
| H1/L3 | 173, 187 | —/Y36F-R46L | ND | 76.9 |
| H2/L1 | 183, 30 | T24A/— | 0.3195 | 79.6 |
| H2/L2 | 183, 186 | T24A/Y36F | 1.93 | 77.9 |
| H2/L3 | 183, 187 | T24A/Y36F-R46L | ND | 76.5 |
| H3/L1 | 184, 30 | A49S/— | 0.84 | 77.2 |
| H3/L2 | 184, 186 | A49S/Y36F | 1.04 | 76 |
| H3/L3 | 184, 187 | A49S/Y36F-R46L | ND | 76 |
| H5/L1 | 37, 30 | T24A-A49S-T62S/— | 0.95 | 79.4 |

The H5/L1 antibody described in the above table was formatted as an IgG1 format and was also formatted as a hinge stabilised human IgG4 to create a non cytotoxic anti-CCR6 humanised antibody.

Example 7

Testing Binding Activity of 4H11 Humanized Candidates on Soluble N-Terminal Region of CCR6 from Both Human and Cynomologus Species Since the epitope of chimeric 4H11 was localized in the N-terminal region of CCR6, a soluble peptide corresponding to this N-terminal fragment was generated and used to evaluate the affinity of 4H11 VH5/VL1 IgG4HS candidate in both human and cynomologus species. The soluble N-terminal peptide region was generated as follows:

Expression of a Soluble Fusion Construct of the N-Terminus of Human and Cynomolgus CCR6 and a Human Fc of the IgG1 Isotype.

Cloning of the soluble fusion construct of the N-terminus of human CCR6: The DNA coding for the soluble fusion construct of the N-terminus of human CCR6 was ordered at LifeTechnology (GeneArt®; Carlsbad, Calif.). The amino acid construct was designed by first fusing a signal peptide to the extracellular N-terminus of human CCR6 (amino acids 1 to 47 in swissprot entry P51684). This construct was linked to the Fc part of the human IgG1 isotype (amino acids 104 to 330 in swissprot entry P01857) via a modified glycin linker (GGGGT), as shown in SEQ ID NO: 258 [see human CCR6-Fc for correct number]. GeneArt reverse-translated this amino acid into a DNA sequence and attached an NheI restriction site and a Kozak sequence 5' and a XhoI restriction site 3' of the open reading frame coding for the fusion protein. This construct was cloned in plasmid 13ABRC6P and delivered to Glenmark.

Plasmid 13ABRC6P was cut using NheI/XhoI and the insert cloned into the backbone of pGLEX18 (a Glenmark proprietary vector with an expression cassette under control of the human CMV promoter and the oriP element) that was cut in the MCS using the same enzymes and CIPed in order to prevent recircularization. The resulting construct was named pGLEX18-hsCCR6-Nter-Fc and confirmed by sequencing (Fastens, Geneva, Switzerland).

The procedure for cloning of the cynomolgus fusion construct was similar. The fusion construct ordered at LifeTechnologies was different only in the extracellular N-terminus of cynomolgus CCR6 (amino acids 6 to 52 in swissprot entry G7MR72) and was delivered cloned in plasmid GeneArt Sequence #31. The final construct was named pGLEX18-cynoCCR6-Nter-Fc and confirmed by sequencing (Fastens, Geneva, Switzerland).

Expression:

Suspension HEK293-EBNA cells were transfected with the expression vectors using polyethyleneimine (JetPEI®, Polyplus-transfection, Illkirch, France) in 1 L Schott bottles using 150 ml of medium. For this purpose, exponential growing cells were seeded at a density of 8 E6 cells/mL in 75 mL of OptiMEM medium (#31985-047, Invitrogen). A JetPEI®:DNA complex was added to the cells in a weight ratio of 3 (µg/µg). Final DNA concentration in the cell suspension was 2.5 µg/mL. After 5 hours incubation at 37° C. under shaking (200 rpm), 75 mL of fresh culture medium were added to the cell suspension. Then the cells were incubated on a shaken platform at 37° C., 5% $CO_2$ and 80% humidity for 5 days until harvest. The supernatants of the cells were clarified using 0.2 µm filters and the protein was purified using protein A.

[human CCR6-Fc]

SEQ ID NO: 188
METDTLLLWVLLLWVPGSTGMSGESMNFSDVFDSSEDYFVSVNTSYYSVD
SEMLLCSLQEVRQFSRLGGGGTDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

[Cyno CCR6-Fc]

SEQ ID NO: 189
METDTLLLWVLLLWVPGSTGMSGESMNFSDVFDSSEDYFASVNTSYYTVD
SEMLLCTLHEVRQFSRLGGGGTDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

ELISA:

A binding ELISA was performed to test the reactivity of 4H11 VH5/VL1 IgG1 and 4H11 VH5/VL1 IgG4HS antibodies on peptides consisting of the N-terminal region of CCR6 from human and cynomologus species. Briefly, 96 well-microtiter plates (Costar USA, distributor VWR AG, Nyon, Switzerland) were coated with 100 µl of recombinant human and cynomologus N-terminus peptide-Fc at 2 µg/ml in PBS. Plates were incubated overnight at 4° C. and were then blocked with PBS 2% BSA (Bovine Serum Albumine, PAA Laboratories, Pasching, Austria) at room temperature (RT) for one hour. The blocking solution was removed and various concentrations of 4H11 VH5/VL1 IgG1 and 4H11 VH5/VL1 IgG4HS were added. The plates were incubated at RT for 1 hour, then washed six times with PBS 0.01% Tween-20 (Sigma-Aldrich Chemie GmbH, Buchs, Switzerland) and a goat-anti human Ig F(ab')2 fragment specific-HRP (Jackson ImmunoResearch Europe Ltd, Newmarket, UK). After washing, the plates were incubated with TMB substrate (Bio-Rad Laboratories AG, Reinach, Switzerland) to reveal antibody binding. The reaction was stopped by adding 2M $H_2SO_4$ and the optical density was read at 450 nM (OD 450 nM) on a Synergy HT2 spectrophotometer (Biotek, USA; distributor: WITTEC AG, Littau, Switzerland). FIG. 8 shows that 4H11 VH5/VL1 IgG1 and 4H11 VH5/VL1 IgG4HS antibodies recognize similarly the N-terminal peptides corresponding to the N-terminal region of CCR6 from both human (FIG. 8A) and cynomologus (FIG. 8B) species.

Kinetic Binding Affinity Constants by Surface Plasmon Resonance (SPR):

Kinetic binding affinity constants (KD) were measured on Fc-fused huCCR6 N-terminal and cynoCCR6 N-terminal peptides with the 4H11 VH5/VL1 IgG4hs antibody as analyte. Same measurements were performed using the 4H11 VH5/VL1 IgG1 antibody and chimeric 4H11 antibody for comparison. Measurements were conducted on a BIAcore 2000 (GE Healthcare—BIAcore, GE Healthcare Europe GmbH, Glattbrugg, Switzerland) at room temperature, and analyzed with the BiaEvaluation software (BIAcore; v4.1, GE Healthcare Europe GmbH) using a bivalent analyte kinetic affinity model.

A CM5 research grade sensor chip (GE Healthcare Europe GmbH; ref. BR-1000-14) was activated by injecting 35 µl of a 1:1 N-hydroxysulfosuccinimide (NHS)/1-Ethyl- 3-[3-dimethylaminopropyl]carbodiimide Hydrochloride (EDC) solution (v/v; 5 μl/min flow-rate; on flow paths 1 and 2). Fc-fused human or cynomologus CCR6 N-terminal peptides were diluted to a final concentration of 25 nM in acetate buffer pH 4.5 (GE Healthcare Europe GmbH, BR-1003-50; one pH unit below pI) and subsequently immobilized on the previously activated CM5 sensor chip by injecting 20 μl on both flow path 1 and 2 (5 μl/min); this corresponded to approximately 300 response units (RUs). The human or cynomologus CCR6 N-terminal peptides coupled CM5 sensor chip was then deactivated by injecting 35 μl of ethanolamine solution (5 μl/min). Finally, two injections of 3M MgCl2 solution (GE Healthcare Europe GmbH, ref. BR100839) were performed to release non-crosslinked Fc-fused peptides.

For affinity measurements, the recombinant 4H11 antibodies stored in 1×PBS buffer were diluted in HBS-EP buffer (GE Healthcare Europe GmbH, ref. BR-1001-88; 0.01 M HEPES, 0.15 M NaCl, EDTA 3 mM, 0.005% Surfactant P20, pH 7.4) and injected at different concentrations (3.8 nM to 1 μM) on the flow-path 1 and 2 (flow-path 1 being used as reference) at a 30 μl/min flow rate for 4 min, followed by a 10 min dissociation time period in running buffer. After each binding event, surface was regenerated with 3M MgCl2 for 10 sec (30 μl/min flow rate).

Measurements (sensorgram: fc2-fc1) were best fitted with a bivalent analyte model. The measurements included zero-concentration samples for referencing. This model fits binding data to two sequential reactions leading to the determination of two equilibrium dissociation constant sets and then two KD values, KD1 and KD2. The format used to determine kinetics data, which mimics the interaction occurring in vivo between the IgG its membrane bound target, allows avidity which increases apparent affinity.

The Chi2 value represents the sum of squared differences between the experimental data and reference data at each point; while the plots of residuals indicate the difference between the experimental and reference data for each point in the fit. Both Chi2 and residual values were used to evaluate the quality of a fit between the experimental data and individual binding models.

FIG. 9 shows that the 4H11 VH5/VL1 IgG4hs antibody recognizes Fc-fused human and cynomologus N terminal peptides with KD values of 1.56 nM and 4.67 nM, respectively.

Inhibition of CCL20-Induced Migration of BAF Cells Transfected with Chimeric Human-Mouse CCR6 Constructs:

As shown in FIG. 8 and FIG. 9, 4H11 VH5/VL1 IgG4HS recognizes specifically the N-terminal portion of CCR6 receptor. To further explore the biological function of the N-terminal region of CCR6, BAF cells transfected with either hybrid mouse CCR6 containing a human N-terminal region or human CCR6 containing a mouse N-terminal region were used in the presence of blocking anti-mouse CCR6 or 4H11 VH5/VL1 IgG4HS. A migration assay was assessed according to the protocol described in example 3. Results from FIG. 10 show that 4H11 VH5/VL1 IgG4HS was able to neutralize human CCL20-mediated migration of BAF cells transfected with, but not murine CCL20-mediated migration of BAF cells transfected with human CCR6 receptor containing a mouse N-terminal region. Therefore, this antibody blocked specifically the biological function mediated by the N-terminal region of CCR6. As a control, a blocking rat anti-mouse CCR6 antibody (R&D Systems, clone 140706) was used at a final concentration of 10 μg/ml.

Inhibition of CCL20-CCR6 Interaction:

To determine whether 4H11 VH5/VL1 IgG4HS neutralizes CCR6-mediated biological function through a direct inhibition of CCL20-CCR6 interaction, an assay using flow cytometry approach was set up. Briefly, BAF cells transfected with CCR6 were counted and diluted at $1*10^6$ cells/ml in FACS buffer containing 0.1% of azide. 100 μl of these cells were then incubated at 4° C. for 20 minutes with various concentrations of 4H11 VH5/VL1 IgG4HS diluted in FACS buffer 0.1% azide. Following incubation, cells were centrifuged and washed twice and incubated for 20 minutes with a fix concentration (0.5 μg/ml) of recombinant CCL20 (R&D systems) diluted in FACS buffer containing 0.1% of azide. Then, CCL20 was detected using a biotinylated anti-human CCL20 (R&D Systems, clone BAF360) followed by allophycocyanin (APC)-labelled streptavidin diluted in FACS buffer+0.1% azide at 1 μg/ml and 1/100, respectively. Cells were washed two times in FACS buffer, 0.1% azide and samples were analysed by flow cytometry. The relative percentage of binding of CCL20 to CCR6 was calculated considering fluorescent signal in conditions using chimeric IgG1 isotype control as 100% of fluorescence activity. FIG. 11 shows that 4H11 VH5/VL1 IgG4HS significantly reduces binding of CCL20 to CCR6 receptor signalling in a dose dependent manner as compared to an isotype matched control. In addition, 4H11 VH5/VL1 IgG4HS is still active at low concentrations (below 0.5 μg/ml).

Example 8

Evaluation of Binding and Neutralizing Potentials of Bivalent and Monovalent 4H11 VH5/VL1.

Testing of Bivalent and Monovalent VH5/VL1 mAbs in Binding Assay.

Binding activities of bivalent VH5/VL1 IgG1 (SEQ ID NO: 10 and 30) and monovalent BEAT® VH5/VL1 antibodies (SEQ ID NO: 218, 219 and 220) were evaluated by Flow cytometry using BAF cells transfected with human CCR6 full length protein, following the protocol described in Example 3. In the assay, transfected cells were incubated with various concentrations of both antibodies (ranging from 3 to 0.01 μg/ml). An anti-human H+L-Phycoerithrin-PE (BD Biosciences, Allschwil, Switzerland) diluted at 1/200 was used as secondary antibody to detect both bivalent IgG1 and monovalent BEAT® antibody molecules. FIG. 12 shows that both IgG1 and BEAT® VH5/VL1 antibodies recognized CCR6 on the cell surface in a dose dependent manner. However, the bivalent VH5/VL1 antibody displayed a better binding profile compared to the monovalent fragment, the former showing a maximum binding activity higher than the latter.

Testing of Bivalent and Monovalent VH5/VL1 mAbs in CCL20-Mediated Migration Bioassay.

In order to evaluate and compare neutralization efficiencies of the monovalent BEAT® VH5/VL1 and bivalent VH5/VL1 IgG1 antibodies, both molecules were tested at different concentrations (ranging from 50 to 0.4 μg/ml) in a chemotaxis assay, following the protocol detailed in Example 3. As shown in FIG. 13, both antibodies tested showed reduced cellular migration compared to isotype control, even though the monovalent VH5/VL1 antibody showed a reduced activity in comparison to the bivalent format.

Taken together, the results from FIGS. 12 and 13 show that as monovalent antibody, VH5/VL1 is still active, despite reduced binding and functional effect as compared to the bivalent molecule. These observations support the use of VH5/VL1 as a component of an antibody able to bind to more than one antigen such as a bispecific antibody.

Example 9

Engineering of Humanized VH5/VL1 Antibody
Affinity Maturation

The VH5/VL1 affinity for the N-terminal region of human CCR6 was further engineered by phage display. Techniques to affinity mature antibodies using phage display are known (Benhar I (2007) Expert Opin Biol Ther., 7(5): 763-79). The VH5/VL1 antibody gene sequence was formatted as a scFv fragment for display and diversity was introduced by site directed mutagenesis.

Two different phage libraries were built: a first phage library was diversified in CDR-H2 (using NNK codons at Kabat residues: 52, 53, 56, and 58) with the others CDRs unchanged, and a second phage library was diversified in CDR-L3 (NNK codon at Kabat residues: 92, 93, and 94, while Kabat residue 96 was diversified for Leu, Phe, Ile, Tyr, and Trp via a mix of five different oligonucleotides) with the others CDRs unchanged. The resulting affinity maturation libraries had a diversity >2×10e7 and three rounds of selection using biotinylated antigen (N-terminal region of human CCR6 fused to a human IgG1 Fc fragment) and streptavidin capture were performed. Antigen concentration was decreased between the three rounds (round1: 50 nM, round 2: 5 nM, and round 3: 0.5 nM) and competition steps with non-biotinylated antigen were added to select for high affinity variants (1 µM in round 2 and 3). Affinity matured scFv candidates were evaluated by Surface Plasmon Resonance (SPR) for improved binding off-rates onto the fusion protein (FIG. 14). Variants from the CDR-H2 library exhibited no or only a moderate off-rate improvement while variants from the CDR-L3 library showed moderate to significant off-rate improvement.

One preferred CDR-H2 variant was the VH5/VL1-H2-B3 scFv clone (FIG. 14A) which carried substitutions N53T and I56R (Kabat numbering). This variant had a moderate off-rate improvement compared to the parental control with the added benefit of removing a putative deamidation site found in the parental CDR-H2 sequence at position Kabat 53 and 54. Two preferred CDR-L3 variants were identified for their off-rate improvement over the parental control, the VH5/VL1-L3-C9 and VH5/VL1-L3-G8 variants (FIG. 14B). VH5/VL1-L3-C9 had the following CDR-L3 substitutions: S92T, H93Y, and V94Y (Kabat numbering) while VH5/VL1-L3-G8 sequence differed only at position 94 from VH5/VL1-L3-C9, and substituted as follows: S92T, H93Y, and V94L (Kabat numbering).

All preferred amino acid changes in CDR-H2 and CDR-L3 identified from these improved clones were used to format new FAB fragments and antibodies as described below.

Removal of a Putative Deamidation Motif in CDR-L1

CDR-L1 of VH5/VL1 has a deamidation motif at position Kabat 28 and 29. Several substitutions were undertaken to abrogate its consensus sequence. VH5/VL1 FAB fragments substituted at position N28T, N28S, N28Q, N28E, and G29A in CDR-L1 were produced. All substitutions at CDR-L1 position 28 impaired binding as judged by SPR on human or cynomolgus monkey fusion proteins (FIG. 15); only G29A did not impact VH5/VL1 affinity for human CCR6 or its FAB stability (FIG. 16).

Formatting

CDR-L3 and CDR-H2 substitutions identified from phage display screens were used to produce engineered VH5/VL1 antibodies and fragments thereof which also included the aforementioned G29A modification thereby removing the deamidation site located in CDR L1. Formats included human FAB fragments, human IgG1 antibodies, human monovalent BEAT® antibodies (PCT publications NO: WO 2012/131555 and WO 2014/049003) and hinge stabilised IgG4 antibodies, as described in FIG. 17. FAB constructs were used for KD determination by SPR with the human or cynomolgus monkey CCR6 fusion protein coupled onto the sensor chip.

A first pair of engineered FABs was produced using the variable domains of the preferred CDR-L3 library scFv clones VH5/VL1-L3-C9 and VH5/VL1-L3-G8 with the added CDR-L1 G29A modification. Both FABs referred herein as VH5/VL1-C9-G29A and VH5/VL1-G8-G29A exhibited about a twenty-fold improvement in KD value compared to the parental FAB (FIG. 18)—which was used as a control in same set of experiments. Note that the parental FAB had a KD value of about 20 nM as opposed to the 48 nM previously measured (Example 7), the difference is explained by a variation in the quality of the fusion proteins, the quality of the antigens used being greater in this set of experiments.

A second pair of engineered FABs encompassing the preferred CDR-L3 substitutions (S92T, H93Y, and V94Y or S92T, H93Y, and V94L) combined with the preferred CDR-H2 substitutions (N53T and I56R) and the CDR-L1 G29A modification was also produced. FABs referred herein as VH5/VL1-B3C9-G29A and VH5/VL1-B3G8-G29A differed only in CDR-H2 from the first pair of FAB constructs and exhibited a further two-fold improvement in KD value. Both VH5/VL1-B3C9-G29A and VH5/VL1-B3G8-G29A had a KD value of about 0.5 nM for the N-terminal region of human CCR6 and about 1 nM for the N-terminal region of cynomolgus monkey CCR6, representing about a forty-fold improvement in affinity compared to the parental VH5/VL1 FAB for human CCR6, and about a thirty-fold improvement in affinity for cynomolgus monkey CCR6.

Example 10

Improved Blocking Potential of Affinity-Matured VH5/VL1 Variants.

To evaluate the impact of affinity maturation of VH5/VL1 IgG1 on chemotaxis activity, four engineered variants of VH5/VL1 in either bivalent IgG1 or monovalent BEAT® formats were tested at various concentrations (ranging from 20 to 0.75 µg/ml) in a migration assay using BAF cells transfected with full length human CCR6. Briefly, 100000 of cells were added to the upper chambers of the HTS Transwell®-96 plates [Corning, Chemie Brunschwig AG, Switzerland] in the presence of affinity-matured variants. The lower chamber of the Transwell contained recombinant human CCL20 (R&D Systems) diluted at 10 ng/ml in 235 µl of BAF medium (RPMI-1640 (Sigma-Aldrich Chemie GmbH, Basel, Switzerland) containing 10% of FCS (Amimed distributed by Bioconcept, Allschwil, Switzerland)). Following 4 hrs of incubation at 37° C., 5% CO2, cells from lower and upper chambers were harvested and counted using the Guava Easycyte HT (Millipore AG, Zug, Switzerland). As a negative control, a human IgG1 irrelevant antibody was used at 20 µg/ml. Non affinity-matured bivalent VH5/VL1 IgG1 and monovalent VH5/VL1 BEAT® molecules were used as references in the bioassay. For all the tested molecules, a migration ratio was calculated by dividing the number of cells in the lower chamber by the total number of cells in the upper and lower chamber. The percentage of inhibition of migration was calculated as the percentage of that seen for the isotype control. FIG. 19 demonstrates that VH5/VL1 variants which exhibit increased affinities to human CCR6-Nterminal peptide (B3G8 G29A and B3C9 G29A as shown in FIG. 18) inhibited more effectively the migration of CCR6-expressing BAF cells. The four engineered variants showed a high blocking potential, even at low concentrations (for example 0.75 µg/ml). Interestingly, the monovalent versions of the affinity-matured variants also showed increased neutralizing potential, compared to the monovalent VH5/VL1 antibody before affinity maturation. In particular, at low concentrations, B3G8 G29A and B3C9 G29A mutants displayed a higher inhibition profile (approximately 35%) than the non-engineered monovalent VH5/VL1 BEAT® at 20 µg/ml (approximately 20%).

Taken together, data from FIG. 19 demonstrate a direct relationship between the increase of affinity of the four different engineered VH5/VL1 variants and their increased blocking potential in the migration assay.

```
                        SEQUENCE LISTING

<160> NUMBER OF SEQ ID NOS: 258

<210> SEQ ID NO 1
    <211> LENGTH: 10
    <212> TYPE: PRT
    <213> ORGANISM: Mus musculus

<400> SEQUENCE: 1

Gly Phe Ser Phe Ser Asp Tyr Tyr Met Tyr
    1               5                   10

<210> SEQ ID NO 2
    <211> LENGTH: 16
    <212> TYPE: PRT
    <213> ORGANISM: Mus musculus

<400> SEQUENCE: 2

Tyr Ile Thr Asn Gly Gly Ile Thr Tyr Tyr Pro Asp Thr Val Lys Gly
    1               5                   10                  15

<210> SEQ ID NO 3
    <211> LENGTH: 11
    <212> TYPE: PRT
    <213> ORGANISM: Mus musculus

<400> SEQUENCE: 3

Thr Ser Pro Leu Arg Gly Ala Trp Phe Ala Tyr
    1               5                   10

<210> SEQ ID NO 4
    <211> LENGTH: 13
    <212> TYPE: PRT
    <213> ORGANISM: Mus musculus

<400> SEQUENCE: 4

Gln Ser Ile Val His Ser Asn Gly Asn Thr Tyr Leu Glu
    1               5                   10

<210> SEQ ID NO 5
    <211> LENGTH: 7
    <212> TYPE: PRT
    <213> ORGANISM: Mus musculus

<400> SEQUENCE: 5

Lys Val Ser Asn Arg Phe Ser
    1               5

<210> SEQ ID NO 6
    <211> LENGTH: 9
    <212> TYPE: PRT
    <213> ORGANISM: Mus musculus

<400> SEQUENCE: 6

Phe Gln Gly Ser His Val Pro Leu Thr
```

```
<210> SEQ ID NO 7
<211> LENGTH: 117
<212> TYPE: PRT
<213> ORGANISM: Mus musculus

<400> SEQUENCE: 7

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Ser Phe Ser Asp Tyr
            20                  25                  30

Tyr Met Tyr Trp Ile Arg Gln Thr Pro Glu Lys Arg Leu Glu Trp Val
        35                  40                  45

Ala Tyr Ile Thr Asn Gly Gly Ile Thr Tyr Tyr Pro Asp Thr Val Lys
    50                  55                  60

Gly Arg Phe Thr Ile Ser Arg Asp Asn Ala Lys Asn Thr Leu Tyr Leu
65                  70                  75                  80

Gln Met Ser Arg Leu Arg Ser Glu Asp Thr Ala Met Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser
        115

<210> SEQ ID NO 8
<211> LENGTH: 112
<212> TYPE: PRT
<213> ORGANISM: Mus musculus

<400> SEQUENCE: 8

Asp Val Ile Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Lys Leu Glu Ile Lys
            100                 105                 110

<210> SEQ ID NO 9
<211> LENGTH: 220
<212> TYPE: PRT
<213> ORGANISM: Artificial Sequence
<220> FEATURE:
<223> OTHER INFORMATION: 4H11VH5-CH1FabHC

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ser Gly Phe Ser Phe Ser Asp Tyr
            20                  25                  30
```

```
Tyr Met Tyr Trp Val Arg Gln Ala Pro Gly Lys Gly Leu Glu Trp Val
            35                  40                  45

Ser Tyr Ile Thr Asn Gly Gly Ile Thr Tyr Tyr Pro Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95

Ser Pro Leu Arg Gly Ala Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys
210                 215                 220

<210> SEQ ID NO 10
<211> LENGTH: 447
<212> TYPE: PRT
<213> ORGANISM: Artificial Sequence
<220> FEATURE:
<223> OTHER INFORMATION: 4H11VH5 IgG1

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
            35                  40                  45

Ser Tyr Ile Thr Asn Gly Gly Ile Thr Tyr Tyr Pro Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95

Ser Pro Leu Arg Gly Ala Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 11
<211> LENGTH: 1125
<212> TYPE: DNA
<213> ORGANISM: Homo sapiens

<400> SEQUENCE: 11
atgagcgggg aatcaatgaa tttcagcgat gttttcgact ccagtgaaga ttattttgtg    60
tcagtcaata cttcatatta ctcagttgat tctgagatgt tactgtgctc cttgcaggag   120
gtcaggcagt ctccaggct atttgtaccg attgcctact ccttgatctg tgtctttggc   180
ctcctgggga atattctggt ggtgatcacc tttgctttt ataagaaggc caggtctatg   240
acagacgtct atctcttgaa catggccatt gcagacatcc tctttgttct tactctccca   300
ttctgggcag tgagtcatgc cactggtgcg tgggttttca gcaatgccac gtgcaagttg   360
ctaaaaggca tctatgccat caactttaac tgcgggatgc tgcctctgac ttgcattagc   420
atggaccggt acatcgccat tgtacaggcg actaagtcat ccggctccg atccagaaca   480
ctaccgcgca gcaaaatcat ctgccttgtt gtgtggggc tgtcagtcat catctcccagc   540
tcaactttg tcttcaacca aaaatacaac acccaaggca gcgatgtctg tgaacccaag   600
```

| | | |
|---|---|---|
| taccagactg tctcggagcc catcaggtgg aagctgctga tgttggggct tgagctactc | 660 | |
| tttggtttct ttatcccttt gatgttcatg atattttgtt acacgttcat tgtcaaaacc | 720 | |
| ttggtgcaag ctcagaattc taaaaggcac aaagccatcc gtgtaatcat agctgtggtg | 780 | |
| cttgtgtttc tggcttgtca gattcctcat aacatggtcc tgcttgtgac ggctgcaaat | 840 | |
| ttgggtaaaa tgaaccgatc ctgccagagc gaaaagctaa ttggctatac gaaaactgtc | 900 | |
| acagaagtcc tggcttttcct gcactgctgc ctgaaccctg tgctctacgc ttttattggg | 960 | |
| cagaagttca gaaactactt tctgaagatc ttgaaggacc tgtggtgtgt gagaaggaag | 1020 | |
| tacaagtcct caggcttctc ctgtgccggg aggtactcag aaaacatttc tcggcagacc | 1080 | |
| agtgagaccg cagataacga caatgcgtcg tccttcacta tgtga | 1125 | |

<210> SEQ ID NO 12
<211> LENGTH: 1104
<212> TYPE: DNA
<213> ORGANISM: Mus musculus

<400> SEQUENCE: 12

| | | |
|---|---|---|
| atgaattcca cagagtccta ctttggaacg gatgattatg acaacacaga gtattattct | 60 | |
| attcctccag accatgggcc atgctcccta gaagaggtca gaaacttcac caaggtattt | 120 | |
| gtgccaattg cctactcctt aatatgtgtc tttggcctcc tgggcaacat tatggtggtg | 180 | |
| atgacctttg ccttctacaa gaaagccaga tccatgactg acgtctacct gttgaacatg | 240 | |
| gccatcacag acatactctt tgtcctcacc ctaccgttct gggcagttac tcatgccacc | 300 | |
| aacacttggg ttttcagcga tgcactgtgt aaactgatga aggcacata tgcggtcaac | 360 | |
| tttaactgtg ggatgctgct cctggcctgt atcagcatgg accggtacat tgccatcgtc | 420 | |
| caggcaacca atctttccg ggtacgctcc agaacactga cgcacagtaa ggtcatctgt | 480 | |
| gtggcagtgt ggttcatctc catcatcatc tcaagcccta catttatctt caacaagaaa | 540 | |
| tacgagctgc aggatcgtga tgtctgtgag ccacggtaca ggtctgtctc agagcccatc | 600 | |
| acgtggaagc tgctgggtat gggactggag ctgttctttg gttcttcac ccctttgctg | 660 | |
| tttatggtgt tctgctatct gttcattatc aagaccttgg tgcaggccca gaactccaag | 720 | |
| aggcacagag ccatccgagt cgtgatcgct gtggttctcg tgttcctggc ttgtcagatc | 780 | |
| cctcacaaca tggtcctcct cgtgactgcg gtcaacacgg gcaaagtggg ccggagctgc | 840 | |
| agcaccgaga agtcctcgc ctacaccagg aacgtggccg aggtcctggc tttcctgcat | 900 | |
| tgctgcctca ccccgtgtt gtatgcgttt attggacaga attcagaaa ctacttcatg | 960 | |
| aagatcatga aggatgtgtg gtgtatgaga aggaagaata gatgcctgg cttcctctgt | 1020 | |
| gcccgggttt actcggaaag ctacatctcc aggcagacca gtgagaccgt cgaaaatgat | 1080 | |
| aatgcatcgt cctttaccat gtaa | 1104 | |

<210> SEQ ID NO 13
<211> LENGTH: 374
<212> TYPE: PRT
<213> ORGANISM: Artificial Sequence
<220> FEATURE:
<223> OTHER INFORMATION: Human-Mouse CCR6 fusion

<400> SEQUENCE: 13

Met Ser Gly Glu Ser Met Asn Phe Ser Asp Val Phe Asp Ser Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
 50                  55                  60

Ile Leu Val Val Ile Thr Phe Ala Phe Tyr Lys Lys Ala Arg Ser Met
 65                  70                  75                  80

Thr Asp Val Tyr Leu Leu Asn Met Ala Ile Ala Asp Ile Leu Phe Val
                 85                  90                  95

Leu Thr Leu Pro Phe Trp Ala Val His Ala Thr Asn Thr Trp Val
                100                 105                 110

Phe Ser Asp Ala Leu Cys Lys Leu Leu Lys Gly Ile Tyr Ala Ile Asn
                115                 120                 125

Phe Asn Cys Gly Met Leu Leu Leu Thr Cys Ile Ser Met Asp Arg Tyr
                130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
                180                 185                 190

Gly Ser Asp Val Cys Glu Pro Lys Tyr Gln Thr Val Ser Glu Pro Ile
                195                 200                 205

Arg Trp Lys Leu Leu Met Leu Gly Leu Glu Leu Leu Phe Gly Phe Phe
                210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
                260                 265                 270

Val Leu Leu Val Thr Ala Ala Asn Leu Gly Lys Met Asn Arg Ser Cys
                275                 280                 285

Gln Ser Glu Lys Leu Ile Gly Tyr Thr Lys Thr Val Thr Glu Val Leu
                290                 295                 300

Ala Phe Leu His Cys Cys Leu Asn Pro Val Leu Tyr Ala Phe Ile Gly
305                 310                 315                 320

Gln Lys Phe Arg Asn Tyr Phe Leu Lys Ile Leu Lys Asp Leu Trp Cys
                325                 330                 335

Val Arg Arg Lys Tyr Lys Ser Ser Gly Phe Ser Cys Ala Gly Arg Tyr
                340                 345                 350

Ser Glu Asn Ile Ser Arg Gln Thr Ser Glu Thr Ala Asp Asn Asp Asn
                355                 360                 365

Ala Ser Ser Phe Thr Met
    370

<210> SEQ ID NO 14
<211> LENGTH: 1125
<212> TYPE: DNA
<213> ORGANISM: Artificial Sequence
<220> FEATURE:
<223> OTHER INFORMATION: Human-Mouse CCR6 fusion

<400> SEQUENCE: 14
atgagcgggg aatcaatgaa tttcagcgat gttttcgact ccagtgaaga ttattttgtg    60

| | |
|---|---|
| tcagtcaata cttcatatta ctcagttgat tctgagatgt tactgtgctc cttgcaggag | 120 |
| gtcaggcagt tctccaggct atttgtaccg attgcctact ccttgatctg tgtctttggc | 180 |
| ctcctgggga atattctggt ggtgatcacc tttgcttttt ataagaaggc caggtctatg | 240 |
| acagacgtct atctcttgaa catggccatt gcagacatcc tctttgttct tactctccca | 300 |
| ttctgggcag tgactcatgc caccaacact tgggttttca gcgatgcact gtgtaaattg | 360 |
| ctaaaaggca tctatgccat caactttaac tgcgggatgc tgctcctgac ttgcattagc | 420 |
| atggaccggt acatcgccat tgtacaggcg actaagtcat tccggctccg atccagaaca | 480 |
| ctaccgcgca gcaaaatcat ctgccttgtt gtgtgggggc tgtcagtcat catctccagc | 540 |
| tcaactttg tcttcaacca aaatacaac acccaaggca gcgatgtctg tgaacccaag | 600 |
| taccagactg tctcggagcc catcaggtgg aagctgctga tgttggggct tgagctactc | 660 |
| tttggtttct ttatcccttt gatgttcatg atattttgtt acacgttcat tgtcaaaacc | 720 |
| ttggtgcaag ctcagaattc taaaaggcac aaagccatcc gtgtaatcat agctgtggtg | 780 |
| cttgtgtttc tggcttgtca gattcctcat aacatggtcc tgcttgtgac ggctgcaaat | 840 |
| ttgggtaaaa tgaaccgatc ctgccagagc gaaaagctaa ttggctatac gaaaactgtc | 900 |
| acagaagtcc tggcttttcct gcactgctgc ctgaaccctg tgctctacgc ttttattggg | 960 |
| cagaagttca gaaactactt tctgaagatc ttgaaggacc tgtggtgtgt gagaaggaag | 1020 |
| tacaagtcct caggcttctc ctgtgccggg aggtactcag aaaacatttc tcggcagacc | 1080 |
| agtgagaccg cagataacga caatgcgtcg tccttcacta tgtga | 1125 |

<210> SEQ ID NO 15
<211> LENGTH: 374
<212> TYPE: PRT
<213> ORGANISM: Artificial Sequence
<220> FEATURE:
<223> OTHER INFORMATION: Human-Mouse CCR6 fusion

<400> SEQUENCE: 15

```
Met Ser Gly Glu Ser Met Asn Phe Ser Asp Val Phe Asp Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
            100                 105                 110

Phe Ser Asn Ala Thr Cys Lys Leu Leu Lys Gly Ile Tyr Ala Ile Asn
        115                 120                 125

Phe Asn Cys Gly Met Leu Leu Leu Thr Cys Ile Ser Met Asp Arg Tyr
    130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175
```

| | | | | | | | | | | | |
|---|---|---|---|---|---|---|---|---|---|---|---|
|Ile|Ile|Ser|Ser|Pro|Thr|Phe|Ile|Phe|Asn|Lys|Lys|Tyr|Glu|Leu|Gln|
| | | |180| | | |185| | | |190| | | | |

Asp Arg Asp Val Cys Glu Pro Arg Tyr Arg Ser Val Ser Glu Pro Ile
    195                        200                    205

Thr Trp Lys Leu Leu Met Leu Gly Leu Glu Leu Leu Phe Gly Phe Phe
    210                        215                    220

Ile Pro Leu Met Phe Met Ile Phe Cys Tyr Thr Phe Ile Val Lys Thr
225                      230                    235              240

Leu Val Gln Ala Gln Asn Ser Lys Arg His Lys Ala Ile Arg Val Ile
            245                    250                255

Ile Ala Val Val Leu Val Phe Leu Ala Cys Gln Ile Pro His Asn Met
    260                        265                    270

Val Leu Leu Val Thr Ala Ala Asn Leu Gly Lys Met Asn Arg Ser Cys
    275                        280                    285

Gln Ser Glu Lys Leu Ile Gly Tyr Thr Lys Thr Val Thr Glu Val Leu
            290                    295                300

Ala Phe Leu His Cys Cys Leu Asn Pro Val Leu Tyr Ala Phe Ile Gly
305                      310                    315              320

Gln Lys Phe Arg Asn Tyr Phe Leu Lys Ile Leu Lys Asp Leu Trp Cys
            325                    330              335

Val Arg Arg Lys Tyr Lys Ser Ser Gly Phe Ser Cys Ala Gly Arg Tyr
    340                        345                    350

Ser Glu Asn Ile Ser Arg Gln Thr Ser Glu Thr Ala Asp Asn Asp Asn
            355                    360                365

Ala Ser Ser Phe Thr Met
    370

<210> SEQ ID NO 16
<211> LENGTH: 1125
<212> TYPE: DNA
<213> ORGANISM: Artificial Sequence
<220> FEATURE:
<223> OTHER INFORMATION: Human-Mouse CCR6 fusion

<400> SEQUENCE: 16

| | |
|---|---:|
|atgagcgggg aatcaatgaa tttcagcgat gttttcgact ccagtgaaga ttattttgtg|60|
|tcagtcaata cttcatatta ctcagttgat tctgagatgt tactgtgctc cttgcaggag|120|
|gtcaggcagt tctccaggct atttgtaccg attgcctact ccttgatctg tgtctttggc|180|
|ctcctgggga atattctggt ggtgatcacc tttgcttttt ataagaaggc caggtctatg|240|
|acagacgtct atctcttgaa catggccatt gcagacatcc tctttgttct tactctccca|300|
|ttctgggcag tgagtcatgc cactggtgcg tgggttttca gcaatgccac gtgcaagttg|360|
|ctaaaaggca tctatgccat caactttaac tgcgggatgc tgctcctgac ttgcattagc|420|
|atggaccggt acatcgccat tgtacaggcg actaagtcat tccggctccg atccagaaca|480|
|ctaccgcgca gcaaaatcat ctgccttgtt gtgtgggggc tgtcagtcat catctccagc|540|
|cctacattta tcttcaacaa gaaatacgag ctgcaggatc gtgatgtctg tgagccacgg|600|
|tacaggtctg tctcagagcc catcacgtgg aagctgctga tgttggggct gagctactc|660|
|tttggtttct ttatcccttt gatgttcatg atattttgtt acacgttcat tgtcaaaacc|720|
|ttggtgcaag ctcagaattc taaaaggcac aaagccatcc gtgtaatcat agctgtggtg|780|
|cttgtgtttc tggcttgtca gattcctcat aacatggtcc tgcttgtgac ggctgcaaat|840|
|ttgggtaaaa tgaaccgatc ctgccagagc gaaaagctaa ttggctatac gaaaactgtc|900|

```
acagaagtcc tggctttcct gcactgctgc ctgaaccctg tgctctacgc tttattggg      960 cagaagttca gaaactactt tctgaagatc ttgaaggacc tgtggtgtgt gagaaggaag    1020
tacaagtcct caggcttctc ctgtgccggg aggtactcag aaaacatttc tcggcagacc    1080
agtgagaccg cagataacga caatgcgtcg tccttcacta tgtga                    1125
```

<210> SEQ ID NO 17  
<211> LENGTH: 374  
<212> TYPE: PRT  
<213> ORGANISM: Artificial Sequence  
<220> FEATURE:  
<223> OTHER INFORMATION: Human-Mouse CCR6 fusion

<400> SEQUENCE: 17

```
Met Ser Gly Glu Ser Met Asn Phe Ser Asp Val Phe Asp Ser Glu
1               5                   10                  15

Asp Tyr Phe Val Ser Val Asn Thr Ser Tyr Ser Val Asp Ser Glu
                20                  25                  30

Met Leu Leu Cys Ser Leu Gln Glu Val Arg Gln Phe Ser Arg Leu Phe
            35                  40                  45

Val Pro Ile Ala Tyr Ser Leu Ile Cys Val Phe Gly Leu Leu Gly Asn
50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
            100                 105                 110

Phe Ser Asn Ala Thr Cys Lys Leu Leu Lys Gly Ile Tyr Ala Ile Asn
        115                 120                 125

Phe Asn Cys Gly Met Leu Leu Leu Thr Cys Ile Ser Met Asp Arg Tyr
130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
            180                 185                 190

Gly Ser Asp Val Cys Glu Pro Lys Tyr Gln Thr Val Ser Glu Pro Ile
        195                 200                 205

Arg Trp Lys Leu Leu Met Leu Gly Leu Glu Leu Leu Phe Gly Phe Phe
210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
            260                 265                 270

Val Leu Leu Val Thr Ala Ala Asn Thr Gly Lys Val Gly Arg Ser Cys
        275                 280                 285

Ser Thr Glu Lys Val Leu Ala Tyr Thr Arg Asn Val Ala Glu Val Leu
290                 295                 300

Ala Phe Leu His Cys Cys Leu Asn Pro Val Leu Tyr Ala Phe Ile Gly
305                 310                 315                 320

Gln Lys Phe Arg Asn Tyr Phe Leu Lys Ile Leu Lys Asp Leu Trp Cys
```

```
                325                 330                 335
Val Arg Arg Lys Tyr Lys Ser Ser Gly Phe Ser Cys Ala Gly Arg Tyr
            340                 345                 350

Ser Glu Asn Ile Ser Arg Gln Thr Ser Glu Thr Ala Asp Asn Asp Asn
            355                 360                 365

Ala Ser Ser Phe Thr Met
        370

<210> SEQ ID NO 18
<211> LENGTH: 1125
<212> TYPE: DNA
<213> ORGANISM: Artificial Sequence
<220> FEATURE:
<223> OTHER INFORMATION: Human-Mouse CCR6 fusion

<400> SEQUENCE: 18
atgagcgggg aatcaatgaa tttcagcgat gttttcgact ccagtgaaga ttattttgtg      60
tcagtcaata cttcatatta ctcagttgat tctgagatgt tactgtgctc cttgcaggag    120
gtcaggcagt tctccaggct atttgtaccg attgcctact ccttgatctg tgtctttggc    180
ctcctgggga atattctggt ggtgatcacc tttgcttttt ataagaaggc caggtctatg    240
acagacgtct atctcttgaa catggccatt gcagacatcc tctttgttct tactctccca    300
ttctgggcag tgagtcatgc cactggtgcg tgggttttca gcaatgccac gtgcaagttg    360
ctaaaaggca tctatgccat caactttaac tgcgggatgc tgctcctgac ttgcattagc    420
atggaccggt acatcgccat gtacaggcg actaagtcat tccggctccg atccagaaca    480
ctaccgcgca gcaaaatcat ctgccttgtt gtgtggggc tgtcagtcat catctccagc    540 tcaactttg tcttcaacca aaatacaac acccaaggca gcgatgtctg tgaacccaag    600
taccagactg tctcggagcc catcaggtgg aagctgctga tgttggggct tgagctactc    660
tttggtttct ttatcccttt gatgttcatg atattttgtt acacgttcat tgtcaaaacc    720
ttggtgcaag ctcagaattc taaaaggcac aaagccatcc gtgtaatcat agctgtggtg    780
cttgtgtttc tggcttgtca gattcctcat aacatggtcc tgcttgtgac ggctgcaaac    840
acgggcaaag tgggccggag ctgcagcacc gagaaagtcc tcgcctacac caggaacgtg    900
gccgaggtcc tggctttcct gcactgctgc ctgaaccctg tgctctacgc ttttattggg    960
cagaagttca gaaactactt tctgaagatc ttgaaggacc tgtggtgtgt gagaaggaag   1020
tacaagtcct caggcttctc ctgtgccggg aggtactcag aaaacatttc tcggcagacc   1080
agtgagaccg cagataacga caatgcgtcg tccttcacta tgtga                   1125

<210> SEQ ID NO 19
<211> LENGTH: 447
<212> TYPE: PRT
<213> ORGANISM: Mus musculus

<400> SEQUENCE: 19

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Ser Phe Ser Asp Tyr
            20                  25                  30

Tyr Met Tyr Trp Ile Arg Gln Thr Pro Glu Lys Arg Leu Glu Trp Val
        35                  40                  45

Ala Tyr Ile Thr Asn Gly Gly Ile Thr Tyr Tyr Pro Asp Thr Val Lys
    50                  55                  60
```

Gly Arg Phe Thr Ile Ser Arg Asp Asn Ala Lys Asn Thr Leu Tyr Leu
 65                  70                  75                  80

Gln Met Ser Arg Leu Arg Ser Glu Asp Thr Ala Met Tyr Tyr Cys Thr
             85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 20
<211> LENGTH: 448
<212> TYPE: PRT
<213> ORGANISM: Mus musculus

<400> SEQUENCE: 20

-continued

```
Glu Val Lys Leu Val Glu Ser Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Thr Asn Gly Val Gly Asn Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Ser Pro Leu Arg Gly Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 21
<211> LENGTH: 448
<212> TYPE: PRT
<213> ORGANISM: Mus musculus

<400> SEQUENCE: 21

Glu Val Lys Leu Val Glu Ser Gly Gly Gly Leu Val Gln Pro Gly Gly
1               5                   10                  15

Ser Leu Lys Leu Ser Cys Thr Thr Ser Gly Phe Thr Phe Ser Asp Tyr
                20                  25                  30

Tyr Met Tyr Trp Val Arg Gln Thr Pro Glu Lys Arg Leu Glu Trp Val
            35                  40                  45

Ala Tyr Ile Thr Asn Gly Val Gly Asn Thr Tyr Tyr Pro Asn Thr Val
        50                  55                  60

Asn Gly Arg Phe Thr Ile Ser Arg Asp Asn Ala Lys Asn Ala Leu Tyr
65                  70                  75                  80

Leu Gln Met Ser Arg Leu Lys Ser Glu Asp Thr Ala Met Tyr Tyr Cys
                85                  90                  95

Ala Ser Pro Ile Arg Gly Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 22
<211> LENGTH: 448
<212> TYPE: PRT
<213> ORGANISM: Mus musculus

<400> SEQUENCE: 22

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Ser Phe Ser Asp Tyr
            20                  25                  30

Tyr Met Tyr Trp Val Arg Gln Thr Pro Glu Lys Gly Leu Glu Trp Val
        35                  40                  45

Ala Tyr Ile Ser Asn Gly Val Gly Asn Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Ser Pro Leu Arg Gly Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

```
            275                 280                 285
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 23
<211> LENGTH: 448
<212> TYPE: PRT
<213> ORGANISM: Mus musculus

<400> SEQUENCE: 23

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Arg Arg Leu Glu Trp Val
        35                  40                  45

Ala Tyr Ile Thr Asn Asp Val Gly Lys Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
            85                  90                  95

Ala Ser Pro Ile Arg Gly Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

-continued

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 24
<211> LENGTH: 451
<212> TYPE: PRT
<213> ORGANISM: Artificial Sequence
<220> FEATURE:
<223> OTHER INFORMATION: VH5IgG4S228PHC

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Ser Pro Leu Arg Gly Ala Trp Phe Ala Tyr Trp Gly Gln Gly Thr Leu
        100                 105                 110

Val Thr Val Ser Ser Ala Ser Thr Lys Gly Pro Ser Val Phe Pro Leu
    115                 120                 125

```
Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
                260                 265                 270

Glu Asp Pro Glu Val Gln Phe Asn Trp Tyr Val Asp Gly Val Glu Val
                275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Gln Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
                435                 440                 445

Leu Gly Lys
    450

<210> SEQ ID NO 25
<211> LENGTH: 219
<212> TYPE: PRT
<213> ORGANISM: Mus musculus

<400> SEQUENCE: 25

Asp Val Ile Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45
```

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215

<210> SEQ ID NO 26
<211> LENGTH: 219
<212> TYPE: PRT
<213> ORGANISM: Mus musculus

<400> SEQUENCE: 26

Asp Val Ile Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
                35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser

Pro Val Thr Lys Ser Phe Asn Arg Gly Glu Cys
    210                 215

<210> SEQ ID NO 27
<211> LENGTH: 219
<212> TYPE: PRT
<213> ORGANISM: Mus musculus

<400> SEQUENCE: 27

Asp Ile Val Leu Thr Gln Ser Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro Leu Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 28
<211> LENGTH: 219
<212> TYPE: PRT
<213> ORGANISM: Mus musculus

<400> SEQUENCE: 28

Asp Val Ile Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly

```
            85                  90                  95
Ser His Val Pro Leu Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 29
<211> LENGTH: 219
<212> TYPE: PRT
<213> ORGANISM: Mus musculus

<400> SEQUENCE: 29

```
Asp Val Ile Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 30
<211> LENGTH: 219

```
<212> TYPE: PRT
<213> ORGANISM: Artificial Sequence
<220> FEATURE:
<223> OTHER INFORMATION: VL1LC

<400> SEQUENCE: 30
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 31
<211> LENGTH: 10
<212> TYPE: PRT
<213> ORGANISM: Mus musculus

<400> SEQUENCE: 31
```

Gly Phe Ser Phe Ser Asp Tyr Tyr Met Tyr
1               5                   10

```
<210> SEQ ID NO 32
<211> LENGTH: 16
<212> TYPE: PRT
<213> ORGANISM: Mus musculus

<400> SEQUENCE: 32
```

Tyr Ile Thr Asn Gly Gly Ile Thr Tyr Tyr Pro Asp Ser Val Lys Gly
1               5                   10                  15

```
<210> SEQ ID NO 33
<211> LENGTH: 11
<212> TYPE: PRT
<213> ORGANISM: Mus musculus

<400> SEQUENCE: 33
```

```
Thr Ser Pro Leu Arg Gly Ala Trp Phe Ala Tyr
1               5                   10
```

<210> SEQ ID NO 34
<211> LENGTH: 13
<212> TYPE: PRT
<213> ORGANISM: Mus musculus

<400> SEQUENCE: 34

```
Gln Ser Ile Val His Ser Asn Gly Asn Thr Tyr Leu Glu
1               5                   10
```

<210> SEQ ID NO 35
<211> LENGTH: 7
<212> TYPE: PRT
<213> ORGANISM: Mus musculus

<400> SEQUENCE: 35

```
Lys Val Ser Asn Arg Phe Ser
1               5
```

<210> SEQ ID NO 36
<211> LENGTH: 9
<212> TYPE: PRT
<213> ORGANISM: Mus musculus

<400> SEQUENCE: 36

```
Phe Gln Gly Ser His Val Pro Leu Thr
1               5
```

<210> SEQ ID NO 37
<211> LENGTH: 117
<212> TYPE: PRT
<213> ORGANISM: Artificial Sequence
<220> FEATURE:
<223> OTHER INFORMATION: VH5 IgG4 S228P HC variable

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser
        115
```

<210> SEQ ID NO 38
<211> LENGTH: 112
<212> TYPE: PRT
<213> ORGANISM: Artificial Sequence
<220> FEATURE:
<223> OTHER INFORMATION: VL1 LC variable

<400> SEQUENCE: 38

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 39
<211> LENGTH: 118
<212> TYPE: PRT
<213> ORGANISM: Mus musculus

<400> SEQUENCE: 39

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Thr Asn Gly Val Gly Asn Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Ser Pro Leu Arg Gly Ala Trp Phe Ala Tyr Trp Gly Gln Gly Thr
            100                 105                 110

Leu Val Thr Val Ser Ser
        115

<210> SEQ ID NO 40
<211> LENGTH: 118
<212> TYPE: PRT
<213> ORGANISM: Mus musculus

<400> SEQUENCE: 40

Glu Val Lys Leu Val Glu Ser Gly Gly Gly Leu Val Gln Pro Gly Gly
1               5                   10                  15

Ser Leu Lys Leu Ser Cys Thr Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Thr Asn Gly Val Gly Asn Thr Tyr Tyr Pro Asn Thr Val
    50                  55                  60

Asn Gly Arg Phe Thr Ile Ser Arg Asp Asn Ala Lys Asn Ala Leu Tyr
65                  70                  75                  80

Leu Gln Met Ser Arg Leu Lys Ser Glu Asp Thr Ala Met Tyr Tyr Cys
                85                  90                  95

```
Ala Ser Pro Ile Arg Gly Ala Trp Phe Ala Tyr Trp Gly Gln Gly Thr
            100                 105                 110

Leu Val Thr Val Ser Ser
        115

<210> SEQ ID NO 41
<211> LENGTH: 118
<212> TYPE: PRT
<213> ORGANISM: Mus musculus

<400> SEQUENCE: 41

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Ser Phe Ser Asp Tyr
            20                  25                  30

Tyr Met Tyr Trp Val Arg Gln Thr Pro Glu Lys Gly Leu Glu Trp Val
        35                  40                  45

Ala Tyr Ile Ser Asn Gly Val Gly Asn Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
            85                  90                  95

Ala Ser Pro Leu Arg Gly Ala Trp Phe Ala Tyr Trp Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Mus musculus

<400> SEQUENCE: 42

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Arg Arg Leu Glu Trp Val
        35                  40                  45

Ala Tyr Ile Thr Asn Asp Val Gly Lys Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
            85                  90                  95

Ala Ser Pro Ile Arg Gly Ala Trp Phe Ala Tyr Trp Gly Gln Gly Thr
            100                 105                 110

Leu Val Thr Val Ser Ser
        115

<210> SEQ ID NO 43
<211> LENGTH: 112
<212> TYPE: PRT
<213> ORGANISM: Mus musculus

<400> SEQUENCE: 43
```

Asp Val Ile Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Lys Leu Glu Ile Lys
            100                 105                 110

<210> SEQ ID NO 44
<211> LENGTH: 112
<212> TYPE: PRT
<213> ORGANISM: Mus musculus

<400> SEQUENCE: 44

Asp Ile Val Leu Thr Gln Ser Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro Leu Thr Phe Gly Ala Gly Thr Lys Leu Glu Ile Lys
            100                 105                 110

<210> SEQ ID NO 45
<211> LENGTH: 112
<212> TYPE: PRT
<213> ORGANISM: Mus musculus

<400> SEQUENCE: 45

Asp Val Ile Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Lys Leu Glu Ile Lys
            100                 105                 110

<210> SEQ ID NO 46
<211> LENGTH: 112
<212> TYPE: PRT
<213> ORGANISM: Mus musculus

<400> SEQUENCE: 46

Asp Val Ile Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Lys Leu Glu Ile Lys
            100                 105                 110

<210> SEQ ID NO 47
<211> LENGTH: 10
<212> TYPE: PRT
<213> ORGANISM: Mus musculus

<400> SEQUENCE: 47

Gly Phe Thr Phe Ser Asp Tyr Tyr Met Tyr
1               5                   10

<210> SEQ ID NO 48
<211> LENGTH: 10
<212> TYPE: PRT
<213> ORGANISM: Mus musculus

<400> SEQUENCE: 48

Gly Phe Thr Phe Ser Asp Tyr Tyr Met Tyr
1               5                   10

<210> SEQ ID NO 49
<211> LENGTH: 10
<212> TYPE: PRT
<213> ORGANISM: Mus musculus

<400> SEQUENCE: 49

Gly Phe Ser Phe Ser Asp Tyr Tyr Met Tyr
1               5                   10

<210> SEQ ID NO 50
<211> LENGTH: 10
<212> TYPE: PRT
<213> ORGANISM: Mus musculus

<400> SEQUENCE: 50

Gly Phe Thr Phe Ser Asp Tyr Tyr Met Tyr
1               5                   10

<210> SEQ ID NO 51
<211> LENGTH: 13
<212> TYPE: PRT
<213> ORGANISM: Mus musculus

```
<400> SEQUENCE: 51

Gln Ser Ile Val His Ser Asn Gly Asn Thr Tyr Leu Glu
1               5                   10

<210> SEQ ID NO 52
<211> LENGTH: 13
<212> TYPE: PRT
<213> ORGANISM: Mus musculus

<400> SEQUENCE: 52

Gln Asn Ile Val His Ser Asn Gly Asn Thr Tyr Leu Glu
1               5                   10

<210> SEQ ID NO 53
<211> LENGTH: 13
<212> TYPE: PRT
<213> ORGANISM: Mus musculus

<400> SEQUENCE: 53

Gln Ser Ile Val His Ser Asn Gly Asn Thr Tyr Leu Glu
1               5                   10

<210> SEQ ID NO 54
<211> LENGTH: 13
<212> TYPE: PRT
<213> ORGANISM: Mus musculus

<400> SEQUENCE: 54

Gln Ser Ile Val His Ser Asn Gly Asn Thr Tyr Leu Glu
1               5                   10

<210> SEQ ID NO 55
<211> LENGTH: 16
<212> TYPE: PRT
<213> ORGANISM: Mus musculus

<400> SEQUENCE: 55

Ile Thr Asn Gly Val Gly Asn Thr Tyr Tyr Pro Asp Thr Val Lys Gly
1               5                   10                  15

<210> SEQ ID NO 56
<211> LENGTH: 16
<212> TYPE: PRT
<213> ORGANISM: Mus musculus

<400> SEQUENCE: 56

Ile Thr Asn Gly Val Gly Asn Thr Tyr Tyr Pro Asn Thr Val Asn Gly
1               5                   10                  15

<210> SEQ ID NO 57
<211> LENGTH: 16
<212> TYPE: PRT
<213> ORGANISM: Mus musculus

<400> SEQUENCE: 57

Ile Ser Asn Gly Val Gly Asn Thr Tyr Tyr Pro Asp Thr Val Lys Gly
1               5                   10                  15

<210> SEQ ID NO 58
<211> LENGTH: 16
<212> TYPE: PRT
<213> ORGANISM: Mus musculus

<400> SEQUENCE: 58
```

Ile Thr Asn Asp Val Gly Lys Thr Tyr Tyr Ser Asp Thr Val Lys Gly
1               5                   10                  15

<210> SEQ ID NO 59
<211> LENGTH: 7
<212> TYPE: PRT
<213> ORGANISM: Mus musculus

<400> SEQUENCE: 59

Lys Val Ser Asn Arg Phe Ser
1               5

<210> SEQ ID NO 60
<211> LENGTH: 7
<212> TYPE: PRT
<213> ORGANISM: Mus musculus

<400> SEQUENCE: 60

Lys Val Ser Asn Arg Phe Ser
1               5

<210> SEQ ID NO 61
<211> LENGTH: 7
<212> TYPE: PRT
<213> ORGANISM: Mus musculus

<400> SEQUENCE: 61

Lys Val Ser Asn Arg Phe Ser
1               5

<210> SEQ ID NO 62
<211> LENGTH: 7
<212> TYPE: PRT
<213> ORGANISM: Mus musculus

<400> SEQUENCE: 62

Lys Val Ser Asn Arg Phe Ser
1               5

<210> SEQ ID NO 63
<211> LENGTH: 11
<212> TYPE: PRT
<213> ORGANISM: Mus musculus

<400> SEQUENCE: 63

Ala Ser Pro Leu Arg Gly Ala Trp Phe Ala Tyr
1               5                   10

<210> SEQ ID NO 64
<211> LENGTH: 11
<212> TYPE: PRT
<213> ORGANISM: Mus musculus

<400> SEQUENCE: 64

Ala Ser Pro Ile Arg Gly Ala Trp Phe Ala Tyr
1               5                   10

<210> SEQ ID NO 65
<211> LENGTH: 11
<212> TYPE: PRT
<213> ORGANISM: Mus musculus

<400> SEQUENCE: 65

Ala Ser Pro Leu Arg Gly Ala Trp Phe Ala Tyr
1               5                   10

<210> SEQ ID NO 66
<211> LENGTH: 11
<212> TYPE: PRT
<213> ORGANISM: Mus musculus

<400> SEQUENCE: 66

Ala Ser Pro Ile Arg Gly Ala Trp Phe Ala Tyr
1               5                   10

<210> SEQ ID NO 67
<211> LENGTH: 9
<212> TYPE: PRT
<213> ORGANISM: Mus musculus

<400> SEQUENCE: 67

Phe Gln Gly Ser His Val Pro Leu Thr
1               5

<210> SEQ ID NO 68
<211> LENGTH: 9
<212> TYPE: PRT
<213> ORGANISM: Mus musculus

<400> SEQUENCE: 68

Phe Gln Gly Ser His Val Pro Leu Thr
1               5

<210> SEQ ID NO 69
<211> LENGTH: 9
<212> TYPE: PRT
<213> ORGANISM: Mus musculus

<400> SEQUENCE: 69

Phe Gln Gly Ser His Val Pro Leu Thr
1               5

<210> SEQ ID NO 70
<211> LENGTH: 9
<212> TYPE: PRT
<213> ORGANISM: Mus musculus

<400> SEQUENCE: 70

Phe Gln Gly Ser His Val Pro Leu Thr
1               5

<210> SEQ ID NO 71
<211> LENGTH: 374
<212> TYPE: PRT
<213> ORGANISM: Homo sapiens

<400> SEQUENCE: 71

Met Ser Gly Glu Ser Met Asn Phe Ser Asp Val Phe Asp Ser Glu
1               5                   10                  15

Asp Tyr Phe Val Ser Val Asn Thr Ser Tyr Tyr Ser Val Asp Ser Glu
                20                  25                  30

Met Leu Leu Cys Ser Leu Gln Glu Val Arg Gln Phe Ser Arg Leu Phe
            35                  40                  45

Val Pro Ile Ala Tyr Ser Leu Ile Cys Val Phe Gly Leu Leu Gly Asn
        50                  55                  60

Ile Leu Val Val Ile Thr Phe Ala Phe Tyr Lys Lys Ala Arg Ser Met
65                  70                  75                  80

```
Thr Asp Val Tyr Leu Leu Asn Met Ala Ile Ala Asp Ile Leu Phe Val
            85                  90                  95

Leu Thr Leu Pro Phe Trp Ala Val Ser His Ala Thr Gly Ala Trp Val
       100                 105                 110

Phe Ser Asn Ala Thr Cys Lys Leu Leu Lys Gly Ile Tyr Ala Ile Asn
       115                 120                 125

Phe Asn Cys Gly Met Leu Leu Thr Cys Ile Ser Met Asp Arg Tyr
130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
                180                 185                 190

Gly Ser Asp Val Cys Glu Pro Lys Tyr Gln Thr Val Ser Glu Pro Ile
                195                 200                 205

Arg Trp Lys Leu Leu Met Leu Gly Leu Glu Leu Phe Gly Phe Phe
        210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
                260                 265                 270

Val Leu Leu Val Thr Ala Ala Asn Leu Gly Lys Met Asn Arg Ser Cys
        275                 280                 285

Gln Ser Glu Lys Leu Ile Gly Tyr Thr Lys Thr Val Thr Glu Val Leu
        290                 295                 300

Ala Phe Leu His Cys Cys Leu Asn Pro Val Leu Tyr Ala Phe Ile Gly
305                 310                 315                 320

Gln Lys Phe Arg Asn Tyr Phe Leu Lys Ile Leu Lys Asp Leu Trp Cys
                325                 330                 335

Val Arg Arg Lys Tyr Lys Ser Ser Gly Phe Ser Cys Ala Gly Arg Tyr
                340                 345                 350

Ser Glu Asn Ile Ser Arg Gln Thr Ser Glu Thr Ala Asp Asn Asp Asn
                355                 360                 365

Ala Ser Ser Phe Thr Met
        370

<210> SEQ ID NO 72
<211> LENGTH: 367
<212> TYPE: PRT
<213> ORGANISM: Mus musculus

<400> SEQUENCE: 72

Met Asn Ser Thr Glu Ser Tyr Phe Gly Thr Asp Asp Tyr Asp Asn Thr
1               5                   10                  15

Glu Tyr Tyr Ser Ile Pro Pro Asp His Gly Pro Cys Ser Leu Glu Glu
            20                  25                  30

Val Arg Asn Phe Thr Lys Val Phe Val Pro Ile Ala Tyr Ser Leu Ile
        35                  40                  45

Cys Val Phe Gly Leu Leu Gly Asn Ile Met Val Val Met Thr Phe Ala
    50                  55                  60

Phe Tyr Lys Lys Ala Arg Ser Met Thr Asp Val Tyr Leu Leu Asn Met
65                  70                  75                  80
```

Ala Ile Thr Asp Ile Leu Phe Val Leu Thr Leu Pro Phe Trp Ala Val
                85                  90                  95

Thr His Ala Thr Asn Thr Trp Val Phe Ser Asp Ala Leu Cys Lys Leu
            100                 105                 110

Met Lys Gly Thr Tyr Ala Val Asn Phe Asn Cys Gly Met Leu Leu Leu
        115                 120                 125

Ala Cys Ile Ser Met Asp Arg Tyr Ile Ala Ile Val Gln Ala Thr Lys
130                 135                 140

Ser Phe Arg Val Arg Ser Arg Thr Leu Thr His Ser Lys Val Ile Cys
145                 150                 155                 160

Val Ala Val Trp Phe Ile Ser Ile Ile Ser Ser Pro Thr Phe Ile
                165                 170                 175

Phe Asn Lys Lys Tyr Glu Leu Gln Asp Arg Asp Val Cys Glu Pro Arg
                180                 185                 190

Tyr Arg Ser Val Ser Glu Pro Ile Thr Trp Lys Leu Leu Gly Met Gly
            195                 200                 205

Leu Glu Leu Phe Phe Gly Phe Phe Thr Pro Leu Leu Phe Met Val Phe
        210                 215                 220

Cys Tyr Leu Phe Ile Ile Lys Thr Leu Val Gln Ala Gln Asn Ser Lys
225                 230                 235                 240

Arg His Arg Ala Ile Arg Val Val Ile Ala Val Val Leu Val Phe Leu
                245                 250                 255

Ala Cys Gln Ile Pro His Asn Met Val Leu Leu Val Thr Ala Val Asn
                260                 265                 270

Thr Gly Lys Val Gly Arg Ser Cys Ser Thr Glu Lys Val Leu Ala Tyr
            275                 280                 285

Thr Arg Asn Val Ala Glu Val Leu Ala Phe Leu His Cys Cys Leu Asn
        290                 295                 300

Pro Val Leu Tyr Ala Phe Ile Gly Gln Lys Phe Arg Asn Tyr Phe Met
305                 310                 315                 320

Lys Ile Met Lys Asp Val Trp Cys Met Arg Arg Lys Asn Lys Met Pro
                325                 330                 335

Gly Phe Leu Cys Ala Arg Val Tyr Ser Glu Ser Tyr Ile Ser Arg Gln
                340                 345                 350

Thr Ser Glu Thr Val Glu Asn Asp Asn Ala Ser Ser Phe Thr Met
            355                 360                 365

<210> SEQ ID NO 73
<211> LENGTH: 366
<212> TYPE: PRT
<213> ORGANISM: Rattus rattus

<400> SEQUENCE: 73

Met Asn Phe Thr Glu Ala Asn Tyr Gly Met Glu Asp Tyr Thr Gly Ser
1               5                   10                  15

Asp Tyr Ser Met Phe Pro Glu Thr Glu Pro Cys Ser Leu Gln Glu Val
            20                  25                  30

Arg Asp Phe Thr Lys Val Phe Val Pro Ile Ala Tyr Ser Leu Ile Cys
        35                  40                  45

Val Phe Gly Leu Leu Gly Asn Ile Met Val Val Ile Thr Phe Ala Phe
    50                  55                  60

Tyr Lys Lys Ala Arg Ser Met Thr Asp Val Tyr Leu Leu Asn Met Ala
65                  70                  75                  80

Ile Thr Asp Ile Leu Phe Val Leu Thr Leu Pro Phe Trp Ala Val Thr

```
                        85                  90                  95
His Ala Thr Asp Thr Trp Ile Phe Gly Asn Thr Met Cys Lys Leu Met
                100                 105                 110
Lys Gly Thr Tyr Ala Val Asn Phe Asn Cys Gly Met Leu Leu Leu Ala
                115                 120                 125
Cys Ile Ser Met Asp Arg Tyr Ile Ala Ile Val Gln Ala Thr Lys Ser
                130                 135                 140
Phe Arg Val Arg Ser Arg Thr Leu Thr His Ser Lys Val Ile Cys Leu
145                 150                 155                 160
Thr Val Trp Phe Val Ser Ile Ile Ile Ser Ser Pro Thr Phe Phe
                    165                 170                 175
Asn Lys Gln Tyr Lys Leu Gln Gly Arg Asp Val Cys Glu Pro Gln Tyr
                180                 185                 190
Lys Leu Val Ser Glu Pro Ile Thr Trp Lys Leu Gly Met Gly Leu
                195                 200                 205
Glu Leu Leu Phe Gly Phe Phe Ile Pro Leu Leu Phe Met Val Phe Cys
210                 215                 220
Tyr Leu Phe Ile Ile Lys Thr Leu Val Gln Ala Gln Asn Ser Lys Arg
225                 230                 235                 240
His Arg Ala Ile Arg Val Ile Ala Val Val Leu Val Phe Leu Ala
                    245                 250                 255
Cys Gln Ile Pro His Asn Met Val Leu Leu Val Thr Ala Ala Asn Thr
                260                 265                 270
Gly Lys Met Gly Arg Ser Cys Ser Ala Glu Lys Ala Leu Ala Tyr Ala
                275                 280                 285
Arg Asn Val Ala Glu Val Leu Ala Phe Leu His Cys Cys Leu Asn Pro
                290                 295                 300
Val Leu Tyr Ala Phe Ile Gly Gln Lys Phe Arg Ser Tyr Phe Met Lys
305                 310                 315                 320
Ile Met Lys Asp Val Trp Cys Met Arg Arg Lys Ser Lys Val Pro Thr
                    325                 330                 335
Phe Phe Cys Ala Arg Val Tyr Ser Glu Ser Tyr Ile Ser Arg Gln Thr
                340                 345                 350
Ser Glu Thr Val Glu Asn Asp Asn Ala Ser Ser Phe Thr Met
                355                 360                 365

<210> SEQ ID NO 74
<211> LENGTH: 374
<212> TYPE: PRT
<213> ORGANISM: Macaca mulatta

<400> SEQUENCE: 74

Met Ser Gly Glu Ser Met Asn Phe Ser Asp Val Phe Asp Ser Ser Glu
1               5                   10                  15
Asp Tyr Phe Ala Ser Val Asn Thr Ser Tyr Tyr Thr Val Asp Ser Glu
                20                  25                  30
Met Leu Leu Cys Thr Leu His Glu Val Arg Gln Phe Ser Arg Leu Phe
                35                  40                  45
Val Pro Ile Ala Tyr Ser Leu Ile Cys Val Phe Gly Leu Leu Gly Asn
                50                  55                  60
Ile Leu Val Val Ile Thr Phe Ala Phe Tyr Lys Lys Ala Arg Ser Met
65                  70                  75                  80
Thr Asp Val Tyr Leu Leu Asn Met Ala Ile Ala Asp Ile Leu Phe Val
                85                  90                  95
```

Leu Thr Leu Pro Phe Trp Ala Val Ser His Ala Thr Gly Ala Trp Val
                100                 105                 110

Phe Ser Asn Ala Met Cys Lys Leu Met Lys Gly Ile Tyr Ala Ile Asn
            115                 120                 125

Phe Asn Cys Gly Met Leu Leu Leu Thr Cys Ile Ser Met Asp Arg Tyr
        130                 135                 140

Ile Ala Ile Val Gln Ala Thr Lys Ser Phe Arg Leu Arg Tyr Arg Thr
145                 150                 155                 160

Leu Leu Arg Ser Lys Val Ile Cys Leu Ile Val Trp Gly Gly Ser Val
                165                 170                 175

Val Ile Ser Ser Ser Thr Phe Ile Phe Asn Gln Lys Tyr Asn Ile Gln
            180                 185                 190

Gly Ser Asp Val Cys Glu Pro Lys Tyr Gln Thr Val Ser Glu Pro Ile
        195                 200                 205

Lys Trp Lys Leu Leu Met Leu Gly Leu Glu Leu Leu Phe Gly Phe Phe
210                 215                 220

Ile Pro Leu Met Val Met Ile Phe Trp Tyr Met Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
            260                 265                 270

Val Leu Leu Val Thr Ala Ala Asn Leu Gly Asn Met Asn Arg Ser Cys
        275                 280                 285

His Ser Glu Lys Leu Leu Gly Tyr Thr Lys Thr Val Thr Glu Val Leu
290                 295                 300

Ala Phe Leu His Cys Cys Leu Asn Pro Val Leu Tyr Ala Phe Ile Gly
305                 310                 315                 320

Gln Lys Phe Arg Asn Tyr Phe Leu Lys Ile Met Lys Asp Leu Trp Cys
                325                 330                 335

Val Arg Arg Lys Tyr Lys Ser Ser Gly Phe Ser Cys Ala Gly Arg Tyr
            340                 345                 350

Ser Glu Asn Ile Ser Arg Gln Thr Ser Glu Thr Ala Asp Asn Asp Asn
        355                 360                 365

Ala Ser Ser Phe Thr Met
    370

<210> SEQ ID NO 75
<211> LENGTH: 117
<212> TYPE: PRT
<213> ORGANISM: Artificial Sequence
<220> FEATURE:
<223> OTHER INFORMATION: VH1 HC variable

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Thr Asn Gly Gly Ile Thr Tyr Tyr Pro Asp Thr Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser
            115

<210> SEQ ID NO 76
<211> LENGTH: 96
<212> TYPE: PRT
<213> ORGANISM: Homo sapiens

<400> SEQUENCE: 76

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
                20                  25                  30

Cys Leu Gly Tyr Thr Asp Arg Ile Leu His Pro Lys Phe Ile Val Gly
            35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 77
<211> LENGTH: 98
<212> TYPE: PRT
<213> ORGANISM: Homo sapiens

<400> SEQUENCE: 77

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 78
<211> LENGTH: 98
<212> TYPE: PRT
<213> ORGANISM: Homo sapiens

<400> SEQUENCE: 78

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

-continued

Ser Tyr Ile Ser Ser Gly Ser Thr Ile Tyr Tyr Ala Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 79
<211> LENGTH: 98
<212> TYPE: PRT
<213> ORGANISM: Homo sapiens

<400> SEQUENCE: 79

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Ser Ser Gly Ser Thr Ile Tyr Tyr Ala Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 80
<211> LENGTH: 98
<212> TYPE: PRT
<213> ORGANISM: Homo sapiens

<400> SEQUENCE: 80

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys

<210> SEQ ID NO 81
<211> LENGTH: 97
<212> TYPE: PRT
<213> ORGANISM: Homo sapiens

<400> SEQUENCE: 81

Glu Val Gln Leu Val Glu Ser Gly Gly Gly Leu Val Gln Pro Gly Gly
 1               5                  10                  15

-continued

```
Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 82
<211> LENGTH: 100
<212> TYPE: PRT
<213> ORGANISM: Homo sapiens

<400> SEQUENCE: 82

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 83
<211> LENGTH: 100
<212> TYPE: PRT
<213> ORGANISM: Homo sapiens

<400> SEQUENCE: 83

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 84
<211> LENGTH: 100
<212> TYPE: PRT
```

<213> ORGANISM: Homo sapiens

<400> SEQUENCE: 84

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 85
<211> LENGTH: 100
<212> TYPE: PRT
<213> ORGANISM: Homo sapiens

<400> SEQUENCE: 85

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 86
<211> LENGTH: 100
<212> TYPE: PRT
<213> ORGANISM: Homo sapiens

<400> SEQUENCE: 86

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
          100

<210> SEQ ID NO 87
<211> LENGTH: 720
<212> TYPE: DNA
<213> ORGANISM: Mus musculus

<400> SEQUENCE: 87

| | | | | | |
|---|---|---|---|---|---|
| atggagagcc | ctgcccagct | gctgttcctg | ctgctcctgt | ggcttccgga | cacccaggcc | 60 |
| gatgttataa | tgacccagtc | tccactctcc | ctgcctgtca | gtcttggaga | tcaagcctcc | 120 |
| atctcttgca | gatctagtca | gagcattgta | catagtaatg | gaaacaccta | tttagaatgg | 180 |
| tacctgcaga | aaccaggcca | gtctccaaag | ctcctgatct | acaaagtctc | caaccgattt | 240 |
| tctggggtcc | cagacaggtt | cagtggcagt | ggatcaggga | cagatttcac | actcaagatc | 300 |
| agcagagtgg | aggctgagga | tctgggactt | tattactgct | ttcaaggttc | acatgttccg | 360 |
| ctcacgttcg | gtgctgggac | caagctggaa | ataaaacgga | ccgtggccgc | tcccagcgtg | 420 |
| ttcatcttcc | cccccagcga | cgagcagctg | aagagcggca | ccgcctccgt | ggtgtgcctg | 480 |
| ctgaacaact | tctaccccg | gaggccaag | gtgcagtgga | aggtggacaa | cgccctgcag | 540 |
| agcggcaaca | gccaggaaag | cgtcaccgag | caggacagca | aggactccac | ctacagcctg | 600 |
| agcagcaccc | tgaccctgag | caaggccgac | tacgagaagc | acaaggtgta | cgcctgcgag | 660 |
| gtgacccacc | agggactgtc | cagccccgtg | accaagagct | caacagggg | cgagtgctga | 720 |

<210> SEQ ID NO 88
<211> LENGTH: 1404
<212> TYPE: DNA
<213> ORGANISM: Mus musculus

<400> SEQUENCE: 88

| | | | | | |
|---|---|---|---|---|---|
| atggagagcc | ctgcccagct | gctgttcctg | ctgctcctgt | ggcttccgga | cacccaggcc | 60 |
| gaggtgaagc | tggtggagtc | tggggaggc | ttagtgcagc | ctggagggtc | cctgaaactc | 120 |
| tcctgtgcaa | cttctggatt | cagtttcagt | gactattaca | tgtattggat | cgccagact | 180 |
| ccagagaaga | ggctggagtg | ggtcgcatac | attactaatg | gtggtatcac | ctattatcca | 240 |
| gacactgtaa | agggccgatt | caccatctcc | agagacaatg | ccaagaacac | cctgtacctg | 300 |
| caaatgagcc | gtctgaggtc | tgaggacaca | gccatgtatt | actgtacaag | tccattacgg | 360 |
| ggggcctggt | ttgcttactg | gggccaaggg | actctggtca | ctgtctcctc | agcctccacc | 420 |
| aagggcccca | gcgtgttccc | cctggccccc | agcagcaagt | ctaccagcgg | cggcacagca | 480 |
| gccctgggat | gcctggtgaa | ggactacttc | cccgagcccg | tgaccgtgag | ctggaacagc | 540 |
| ggagccctga | cctccggcgt | gcacaccttc | cccgccgtgc | tgcagagcag | cggcctgtac | 600 |
| agcctgagca | gcgtggtgac | cgtgcccagc | agcagcctgg | gcacccagac | ctacatctgc | 660 |
| aacgtgaacc | acaagcccag | caacaccaag | gtggacaaga | aggtggagcc | caagagctgc | 720 |
| gacaagaccc | acacctgccc | tccctgtcct | gctcctgagc | tgctcggcgg | accctccgtg | 780 |
| ttcctgttcc | cccccaagcc | caaggacacc | ctgatgatca | gcaggacccc | cgaggtgacc | 840 |
| tgcgtggtgg | tggacgtgag | ccacgaggac | ccagaggtga | agttcaactg | gtacgtggac | 900 |
| ggcgtggagg | tgcacaacgc | caagaccaag | cccagagagg | aacagtacaa | cagcacctac | 960 |
| agggtggtgt | ccgtgctgac | cgtgctgcac | caggactggc | tgaacggcaa | agagtacaag | 1020 |
| tgcaaggtct | ccaacaaggc | cctgccagcc | cccatcgaga | aaaccatcag | caaggccaag | 1080 |

```
ggccagccac gggagcccca ggtgtacacc ctgcccccct cccgcgagga gatgaccaag   1140
aaccaggtgt ccctgacatg tctggtgaaa ggcttctacc ccagcgacat cgccgtggag   1200
tgggagagca acggccagcc cgagaacaac tacaagacca cccccccagt gctggacagc   1260
gacggcagct tcttcctgta cagcaagctg accgtggaca agagcaggtg gcagcagggc   1320
aacgtgttca gctgcagcgt gatgcacgag gccctgcaca accactacac ccagaagagc   1380
ctgagcctgt cccccggcaa gtga                                          1404
```

<210> SEQ ID NO 89
<211> LENGTH: 720
<212> TYPE: DNA
<213> ORGANISM: Mus musculus

<400> SEQUENCE: 89

```
atggagagcc ctgcccagct gctgttcctg ctgctcctgt ggcttccgga cacccaggcc     60
gatgttataa tgacccagtc tccactctcc ctgcctgtca gtcttggaga tcaagcctcc    120
atctcttgca gatctagtca gagcattgta catagtaatg gaaacaccta tttagaatgg    180
tacctgcaga aaccaggcca gtctccaaag ctcctgatct acaaagtctc caaccgattt    240
tctggggtcc cagacaggtt cagtggcagt ggatcaggga cagatttcac actcaagatc    300
agcagagtgg aggctgagga tctgggactt tattactgct ttcaaggttc acatgttccg    360
ctcacgttcg gtgctgggac caagctggaa ataaaacgga ccgtggccgc tcccagcgtg    420
ttcatcttcc cccccagcga cgagcagctg aagagcggca ccgcctccgt ggtgtgcctg    480
ctgaacaact tctacccccg ggaggccaag gtgcagtgga aggtggacaa cgccctgcag    540
agcggcaaca gccaggaaag cgtcaccgag caggacagca aggactccac ctacagcctg    600
agcagcaccc tgaccctgag caaggccgac tacgagaagc acaaggtgta cgcctgcgag    660
gtgacccacc agggactgtc cagccccgtg accaagagct tcaacagggg cgagtgctga    720
```

<210> SEQ ID NO 90
<211> LENGTH: 1407
<212> TYPE: DNA
<213> ORGANISM: Mus musculus

<400> SEQUENCE: 90

```
atggagagcc ctgcccagct gctgttcctg ctgctcctgt ggcttccgga cacccaggcc     60
gaggtgaagc tggtggagtc tgggggaggc ttagtgcagc ctggagggtc cctgaaactc    120
tcctgtgcaa cctctggatt cactttcagc gactattaca tgtattgggt tcgccagact    180
ccagagaaga ggctggagtg ggtcgcatac attactaatg gtgttggtaa cacctattat    240
ccagacactg taaagggccg attcaccatc tccagagaca atgccaagaa caccctgtac    300
ctgcaaatga gccgtctgaa gtctgaggac acagccatgt attactgtgc aagtccatta    360
cggggggcct ggtttgctta ctggggccaa gggactctgg tcactgtctc ctcagcctcc    420
accaagggcc ccagcgtgtt ccccctggcc cccagcagca agtctaccag cggcggcaca    480
gcagccctgg gatgcctggt gaaggactac ttccccgagc ccgtgaccgt gagctggaac    540
agcggagccc tgacctccgg cgtgcacacc ttccccgccg tgctgcagag cagcggcctg    600
tacagcctga gcagcgtggt gaccgtgccc agcagcagcc tgggcaccca gacctacatc    660
tgcaacgtga accacaagcc cagcaacacc aaggtggaca agaaggtgga gcccaagagc    720
tgcgacaaga cccacacctg ccctccctgt cctgctcctg agctgctcgg cggaccctcc    780
```

| | |
|---|---|
| gtgttcctgt tcccccccaa gcccaaggac accctgatga tcagcaggac ccccgaggtg | 840 |
| acctgcgtgg tggtggacgt gagccacgag gacccgagg tgaagttcaa ctggtacgtg | 900 |
| gacggcgtgg aggtgcacaa cgccaagacc aagcccagag aggaacagta acagcacc | 960 |
| tacagggtgt gtccgtgct gaccgtgctg caccaggact ggctgaacgg caaagagtac | 1020 |
| aagtgcaagg tctccaacaa ggccctgcca gccccatcg agaaaaccat cagcaaggcc | 1080 |
| aagggccagc cacgggagcc ccaggtgtac accctgcccc cctcccgcga ggagatgacc | 1140 |
| aagaaccagg tgtccctgac atgtctggtg aaaggcttct accccagcga catcgccgtg | 1200 |
| gagtgggaga gcaacggcca gcccgagaac aactacaaga ccacccccc agtgctggac | 1260 |
| agcgacggca gcttcttcct gtacagcaag ctgaccgtgg acaagagcag gtggcagcag | 1320 |
| ggcaacgtgt tcagctgcag cgtgatgcac gaggccctgc acaaccacta cacccagaag | 1380 |
| agcctgagcc tgtcccccgg caagtga | 1407 |

<210> SEQ ID NO 91
<211> LENGTH: 720
<212> TYPE: DNA
<213> ORGANISM: Mus musculus

<400> SEQUENCE: 91

| | |
|---|---|
| atggagagcc ctgcccagct gctgttcctg ctgctcctgt ggcttccgga cacccaggcc | 60 |
| gatattgtac tcacccagtc tccactctcc ctgcctgtca gtcttggaga tcaagcctcc | 120 |
| atctcttgca gatctagtca gaacattgta catagtaatg gaaacactta tttagaatgg | 180 |
| tacctgcaga aaccaggcca gtctccgaag ctcctgatct acaaagtttc caaccgattt | 240 |
| tctggggttc cagacaggtt cagtggcagt ggatcaggga cagatttcac actcaagatc | 300 |
| agcagagtgg aggctgagga tctgggagtt tatttctgct ttcaaggttc acatgttccg | 360 |
| ctcacgttcg gtgctgggac caagctggaa ataaaacgga ccgtggccgc tcccagcgtg | 420 |
| ttcatcttcc cccccagcga cgagcagctg aagagcggca ccgcctccgt ggtgtgcctg | 480 |
| ctgaacaact ctacccccg ggaggccaag gtgcagtgga aggtggacaa cgccctgcag | 540 |
| agcggcaaca gccaggaaag cgtcaccgag caggacagca aggactccac ctacagcctg | 600 |
| agcagcaccc tgaccctgag caaggccgac tacgagaagc acaaggtgta cgcctgcgag | 660 |
| gtgacccacc agggactgtc cagccccgtg accaagagct caacaggg cgagtgctga | 720 |

<210> SEQ ID NO 92
<211> LENGTH: 1407
<212> TYPE: DNA
<213> ORGANISM: Mus musculus

<400> SEQUENCE: 92

| | |
|---|---|
| atggagagcc ctgcccagct gctgttcctg ctgctcctgt ggcttccgga cacccaggcc | 60 |
| gaggtgaagc tggtggagtc tggggaggc ttagtgcagc ctggagggtc cctgaaactc | 120 |
| tcctgtacaa cctctggatt cactttcagt gactattata tgtattgggt tcgccagact | 180 |
| ccagagaaga ggctggagtg ggtcgcatac attactaatg gtgttggtaa tacctattat | 240 |
| ccaaacactg taaacggccg attcaccatc tccagagaca atgccaagaa cgccctgtac | 300 |
| ctgcaaatga gccgtctgaa gtctgaggac acagccatgt attactgtgc aagtccaata | 360 |
| cggggggcct ggtttgctta ctggggccaa gggactctgg tcactgtctc ctcagcctcc | 420 |
| accaagggcc cagcgtgtt ccccctggcc ccagcagca gtctaccag cggcggcaca | 480 |
| gcagccctgg gatgcctggt gaaggactac ttccccgagc ccgtgaccgt gagctggaac | 540 |

```
agcggagccc tgacctccgg cgtgcacacc ttccccgccg tgctgcagag cagcggcctg      600
tacagcctga gcagcgtggt gaccgtgccc agcagcagcc tgggcaccca gacctacatc      660
tgcaacgtga accacaagcc cagcaacacc aaggtggaca agaaggtgga gcccaagagc      720
tgcgacaaga cccacacctg ccctcccgt cctgctcctg agctgctcgg cggacccctcc     780 gtgttcctgt tcccccccaa gcccaaggac accctgatga tcagcaggac ccccgaggtg      840
acctgcgtgg tggtggacgt gagccacgag gacccagagg tgaagttcaa ctggtacgtg      900
gacggcgtgg aggtgcacaa cgccaagacc aagcccagag aggaacagta caacagcacc      960
tacagggtgg tgtccgtgct gaccgtgctg caccaggact ggctgaacgg caaagagtac     1020
aagtgcaagg tctccaacaa ggccctgcca gccccatcg agaaaaccat cagcaaggcc      1080
aagggccagc cacgggagcc ccaggtgtac accctgcccc cctcccgcga ggagatgacc     1140
aagaaccagg tgtccctgac atgtctggtg aaaggcttct accccagcga catcgccgtg     1200
gagtgggaga gcaacggcca gcccgagaac aactacaaga ccaccccccc agtgctggac     1260
agcgacggca gcttcttcct gtacagcaag ctgaccgtgg acaagagcag gtggcagcag     1320
ggcaacgtgt tcagctgcag cgtgatgcac gaggccctgc acaaccacta cacccagaag     1380
agcctgagcc tgtcccccgg caagtga                                         1407

<210> SEQ ID NO 93
<211> LENGTH: 720
<212> TYPE: DNA
<213> ORGANISM: Mus musculus

<400> SEQUENCE: 93
atggagagcc ctgcccagct gctgttcctg ctgctcctgt ggcttccgga cacccaggcc       60
gatgttataa tgacccagtc tccactctcc ctgcctgtca gtcttggaga tcaagcctcc      120
atctcttgca gatctagtca gagcattgta catagtaatg aaacacccta tttagaatgg      180
tacctgcaga accaggcca gtctccaaag ctcctgatct acaaagtctc caaccgattt      240
tctggggtcc cagacaggtt cagtggcagt ggatcaggga cagatttcac actcaagatc      300
agcagagtgg aggctgagga tctgggactt tattactgct tcaaggttc acatgttccg       360 ctcacgttcg gtgctgggac caagctggaa ataaaacgga ccgtggccgc tcccagcgtg      420
ttcatcttcc cccccagcga cgagcagctg aagagcggca ccgcctccgt ggtgtgcctg      480
ctgaacaact ctaccccccg ggaggccaag gtgcagtgga aggtggacaa cgccctgcag      540
agcggcaaca gccaggaaag cgtcaccgag caggacagca aggactccac ctacagcctg      600
agcagcaccc tgaccctgag caaggccgac tacgagaagc acaaggtgta cgcctgcgag      660
gtgacccacc agggactgtc cagccccgtg accaagagct tcaacagggg cgagtgctga      720

<210> SEQ ID NO 94
<211> LENGTH: 1407
<212> TYPE: DNA
<213> ORGANISM: Mus musculus

<400> SEQUENCE: 94
atggagagcc ctgcccagct gctgttcctg ctgctcctgt ggcttccgga cacccaggcc       60
gaggtgaagc tggtggaatc tggggaggc ttagtgcagc ctggagggtc cctgaaactc      120
tcctgtgcaa cctctggatt ctcttttcagt gactattaca tgtattgggt tcgccagact      180
ccagagaagg ggctggagtg ggtcgcatac attagtaatg gtgttggtaa cacctattat      240
```

```
ccagacactg taaagggccg attcaccatc tccagagaca atgccaagaa caccctgtac    300
ctgcaaatga gccgtctgaa gtctgaggac acagccatgt attactgtgc aagtccatta    360
cggggggcct ggtttgctta ctggggccaa gggactctgg tcactgtctc ctcagcctcc    420
accaagggcc ccagcgtgtt ccccctggcc ccagcagca agtctaccag cggcggcaca     480
gcagccctgg gatgcctggt gaaggactac ttccccgagc ccgtgaccgt gagctggaac    540
agcggagccc tgacctccgg cgtgcacacc ttccccgccg tgctgcagag cagcggcctg    600
tacagcctga gcagcgtggt gaccgtgccc agcagcagcc tgggcaccca gacctacatc    660
tgcaacgtga accacaagcc cagcaacacc aaggtggaca gaaggtggag gcccaagagc    720
tgcgacaaga cccacacctg ccctccctgt cctgctcctg agctgctcgg cggaccctcc    780
gtgttcctgt tcccccccaa gcccaaggac accctgatga tcagcaggac ccccgaggtg    840
acctgcgtgg tggtggacgt gagccacgag gacccagagg tgaagttcaa ctggtacgtg    900
gacggcgtgg aggtgcacaa cgccaagacc aagcccagag aggaacagta caacagcacc    960
tacagggtgg tgtccgtgct gaccgtgctg caccaggact ggctgaacgg caaagagtac   1020
aagtgcaagg tctccaacaa ggcccctgcca gcccccatcg agaaaaccat cagcaaggcc   1080
aagggccagc cacgggagcc ccaggtgtac accctgcccc cctcccgcga ggagatgacc   1140
aagaaccagg tgtccctgac atgtctggtg aaaggcttct accccagcga catcgccgtg   1200
gagtgggaga gcaacggcca gcccgagaac aactacaaga ccacccccccc agtgctggac   1260 agcgacggca gcttcttcct gtacagcaag ctgaccgtgg acaagagcag gtggcagcag   1320
ggcaacgtgt tcagctgcag cgtgatgcac gaggccctgc acaaccacta cacccagaag   1380
agcctgagcc tgtcccccgg caagtga                                       1407
```

<210> SEQ ID NO 95
<211> LENGTH: 720
<212> TYPE: DNA
<213> ORGANISM: Mus musculus

<400> SEQUENCE: 95

```
atggagagcc ctgcccagct gctgttcctg ctgctcctgt ggcttccgga cacccaggcc     60
gatgttataa tgacccagtc tccactctcc ctgcctgtca gtcttggaga tcaagcctcc    120
atctcttgca gatctagtca gagcattgta catagtaatg aaacacccta tttagaatgg    180
tacctgcaga aaccaggcca gtctccaaag ctcctgatct acaaagtctc caaccgattt    240
tctggggtcc cagacaggtt cagtggcagt ggatcaggga cagatttcac actcaagatc    300
agcagagtgg aggctgagga tctgggactt tattactgct ttcaaggttc acatgttccg    360
ctcacgttcg gtgctgggac caagctggaa ataaaacgga ccgtggccgc tcccagcgtg    420
ttcatcttcc ccccagcga cgagcagctg aagagcggca ccgcctccgt ggtgtgcctg    480
ctgaacaact tctaccccccg ggaggccaag gtgcagtgga aggtggacaa cgccctgcag    540
agcggcaaca gccaggaaag cgtcaccgag caggacagca aggactccac ctacagcctg    600
agcagcaccc tgaccctgag caaggccgac tacgagaagc acaaggtgta cgcctgcgag    660
gtgacccacc agggactgtc cagccccgtg accaagagct tcaacagggg cgagtgctga    720
```

<210> SEQ ID NO 96
<211> LENGTH: 1407
<212> TYPE: DNA
<213> ORGANISM: Mus musculus

<400> SEQUENCE: 96

```
atggagagcc ctgcccagct gctgttcctg ctgctcctgt ggcttccgga cacccaggcc      60
gaggtgaagc tggtggagtc tgggggaggc ttagtgcagc ctggagggtc cctgaaactc     120
tcctgtgcaa cctctggatt cactttcagt gactattaca tgtattgggt tcgccagact     180
ccagagagga ggctggagtg ggtcgcatac attactaatg atgttggtaa aacctattat     240
tcagacactg taaagggccg attcaccatc tccagagata tgccaagaa caccctgtac      300
ctacaaatga gtcgtctgaa gtctgaggac acagccatgt attactgtgc aagtccaata     360
cgggggggcct ggtttgctta ctggggccaa gggactctgg tcactgtctc ctcagcctcc    420
accaagggcc cagcgtgtt cccctggcc ccagcagca gtctaccag cggcggcaca         480
gcagccctgg gatgcctggt gaaggactac ttccccgagc ccgtgaccgt gagctggaac     540
agcggagccc tgacctccgg cgtgcacacc ttccccgccg tgctgcagag cagcggcctg     600
tacagcctga gcagcgtggt gaccgtgccc agcagcagcc tgggcaccca gacctacatc     660
tgcaacgtga accacaagcc cagcaacacc aaggtggaca gaaaggtgga gcccaagagc     720
tgcgacaaga cccacacctg ccctcccgt cctgctcctg agctgctcgg cggaccctcc      780
gtgttcctgt tcccccccaa gcccaaggac accctgatga tcagcaggac ccccgaggtg    840
acctgcgtgg tggtggacgt gagccacgag gacccagagg tgaagttcaa ctggtacgtg     900
gacggcgtgg aggtgcacaa cgccaagacc aagcccagag aggaacagta caacagcacc     960
tacagggtgg tgtccgtgct gaccgtgctg caccaggact ggctgaacgg caaagagtac    1020
aagtgcaagg tctccaacaa ggccctgcca gcccccatcg agaaaaccat cagcaaggcc    1080
aagggccagc cacgggagcc ccaggtgtac accctgcccc cctcccgcga ggagatgacc    1140
aagaaccagg tgtccctgac atgtctggtg aaaggcttct accccagcga catcgccgtg    1200
gagtgggaga gcaacggcca gcccgagaac aactacaaga ccacccccc agtgctggac    1260
agcgacggca gcttcttcct gtacagcaag ctgaccgtgg acaagagcag gtggcagcag    1320
ggcaacgtgt tcagctgcag cgtgatgcac gaggccctgc acaaccacta cacccagaag    1380
agcctgagcc tgtcccccgg caagtga                                        1407
```

<210> SEQ ID NO 97  
<211> LENGTH: 723  
<212> TYPE: DNA  
<213> ORGANISM: Artificial Sequence  
<220> FEATURE:  
<223> OTHER INFORMATION: 4H11 VL1 LC Nucleotide

<400> SEQUENCE: 97

```
atggagacag acacactcct gctatgggta ctgctgctct gggttccagg atccactggt      60
gatgtcgtga tgacccagag ccccctgagc ctgcctgtga cactgggaca gcctgccagc     120
atcagctgca gatccagcca gagcatcgtg cacagcaacg gcaataccta tctggaatgg     180
tatcagcagc ggcctggcca gtcccccaga ctgctgatct acaaggtgtc caaccggttc     240
agcggcgtgc ccgacagatt ttctggctct ggcagcggca ccgacttcac cctgaagatc     300
tcccggggtgg aagccgagga cgtgggcgtg tactactgtt ttcaaggcag ccacgtgccc     360
ctgaccttcg gccagggaac aaagctggaa atcaagcgta cggtggccgc tcccagcgtg    420
ttcatcttcc cccccagcga cgagcagctg aagagcggca ccgcctccgt ggtgtgcctg    480
ctgaacaact tctaccccgg ggaggccaag gtgcagtgga aggtggacaa cgccctccag    540
agcggcaaca gccaggaaag cgtcaccgag caggacagca aggactccac ctacagcctg    600
```

| | |
|---|---|
| agcagcaccc tgaccctgag caaggccgac tacgagaagc acaaggtgta cgcctgcgag | 660 |
| gtgacccacc agggcctgtc cagccccgtg accaagagct tcaaccgggg cgagtgctga | 720 |
| taa | 723 |

<210> SEQ ID NO 98
<211> LENGTH: 1398
<212> TYPE: DNA
<213> ORGANISM: Artificial Sequence
<220> FEATURE:
<223> OTHER INFORMATION: 4H11 VH5 IgG4 S228P Nucleotide

<400> SEQUENCE: 98

| | |
|---|---|
| atggagacag acacactcct gctatgggta ctgctgctct gggttccagg atccactggt | 60 |
| gaagtgcagc tggtggaatc tggcggcgga ctggtgcagc ctggcggatc tctgagactg | 120 |
| agctgtgccg ccagcggctt cagcttcagc gactactaca tgtactgggt gcgccaggcc | 180 |
| cctggcaagg gactggaatg ggtgtcctac atcaccaacg gcggcatcac ctactacccc | 240 |
| gactccgtga agggccggtt caccatcagc cgggacaaca gcaagaacac cctgtacctg | 300 |
| cagatgaaca gcctgcgggc cgaggacacc gccgtgtact actgtaccag cccccctgaga | 360 |
| ggcgcttggt ttgcctattg gggccagggc accctcgtga ccgtgtctag tgcgtcgacc | 420 |
| aagggcccca gcgtgttccc cctggccccc tgcagcagaa gcaccagcga gtccacagcc | 480 |
| gccctgggct gtctggtgaa ggactacttc cccgagcccg tgaccgtgtc ctggaacagc | 540 |
| ggagccctga ccagcggcgt gcacaccttc cccgccgtgc tgcagagcag cggcctgtac | 600 |
| agcctgagca gcgtggtgac agtgcccagc agcagcctgg gcaccaagac ctacacctgc | 660 |
| aacgtggacc acaagcccag caacaccaag gtggacaaga gggtggagag caagtacggc | 720 |
| ccaccctgcc cccatgccc agcccccgag ttcctgggcg acccctccgt gttcctgttc | 780 |
| ccccccaagc ccaaggacac cctgatgatc agcaggaccc ccgaggtgac ctgcgtggtg | 840 |
| gtggacgtga gccaggagga cccagaggtc cagttcaact ggtacgtgga cggcgtggag | 900 |
| gtgcacaacg ccaagaccaa gcccagagag gagcagttta acagcaccta caggtggtg | 960 |
| tccgtgctga ccgtgctgca ccaggactgg ctgaacggca aggaatacaa gtgcaaggtc | 1020 |
| tccaacaagg gcctgcccag ctccatcgag aaaaccatca gcaaggccaa gggccagcca | 1080 |
| cgggagcccc aggtgtacac cctgccaccc tcccaggagg agatgaccaa gaaccaggtg | 1140 |
| tccctgacct gcctggtgaa gggcttctac cccagcgaca tcgccgtgga gtgggagagc | 1200 |
| aacggccagc ccgagaacaa ctacaagacc acccccccag tgctggacag cgacggcagc | 1260 |
| ttcttcctgt acagcaggct gaccgtggac aagtccaggt ggcaggaggg caacgtcttt | 1320 |
| agctgcagcg tgatgcacga ggccctgcac aaccactaca cccagaagag cctgagcctg | 1380 |
| tccctgggca agtgatag | 1398 |

<210> SEQ ID NO 99
<211> LENGTH: 33
<212> TYPE: DNA
<213> ORGANISM: Artificial Sequence
<220> FEATURE:
<223> OTHER INFORMATION: primer

<400> SEQUENCE: 99

| | |
|---|---|
| gaggctagcc accatgagcg gggaatcaat gaa | 33 |

<210> SEQ ID NO 100
<211> LENGTH: 33

<212> TYPE: DNA
<213> ORGANISM: Artificial Sequence
<220> FEATURE:
<223> OTHER INFORMATION: primer

<400> SEQUENCE: 100
aggggcatcg attcacatag tgaaggacga cgc                                        33

<210> SEQ ID NO 101
<211> LENGTH: 1126
<212> TYPE: DNA
<213> ORGANISM: Homo sapiens

<400> SEQUENCE: 101
atgagcgggg aatcaatgaa tttcagcgat gttttcgact ccagtgaaga ttattttgtg          60
tcagtcaata cttcatatta ctcagttgat tctgagatgt tactgtgctc cttgcaggag         120
gtcaggcagt tctccaggct atttgtaccg attgcctact ccttgatctg tgtctttggc         180
ctcctgggga atattctggt ggtgatcacc tttgcttttt ataagaaggc caggtctatg         240
acagacgtct atctcttgaa catggccatt gcagacatcc tctttgttct tactctccca         300
ttctgggcag tgagtcatgc caccggtgcg tgggttttca gcaatgccac gtgcaagttg         360
ctaaaaggca tctatgccat caactttaac tgcgggatgc tgctcctgac ttgcattagc         420
atggaccggt acatcgccat tgtacaggcg actaagtcat tccggctccg atccagaaca         480
ctaccgcgca gcaaaatcat ctgccttgtt gtgtggggc tgtcagtcat catctccagc         540 tcaactttg tcttcaacca aaaatacaac acccaaggca gcgatgtctg tgaacccaag         600
taccagactg tctcggagcc catcaggtgg aagctgctga tgttggggct tgagctactc         660
tttggtttct ttatcccttt gatgttcatg atattttgtt acacgttcat tgtcaaaacc         720
ttggtgcaag ctcagaattc taaaaggcac aaagccatcc gtgtaatcat agctgtggtg         780
cttgtgtttc tggcttgtca gattcctcat aacatggtcc tgcttgtgac ggctgcaaat         840
ttgggtaaaa tgaaccgatc ctgccagagc gaaaagctaa ttggctatac gaaaactgtc         900
acagaagtcc tggctttcct gcactgctgc ctgaaccctg tgctctacgc ttttattggg         960
cagaagttca gaaactactt tctgaagatc ttgaaggacc tgtggtgtgt gagaaggaag        1020
tacaagtcct caggcttctc ctgtgccggg aggtactcag aaaacatttc tcggcagacc        1080
agtgagaccg cagataacga caatgcgtcg tccttcacta tgtgaa                       1126

<210> SEQ ID NO 102
<211> LENGTH: 41
<212> TYPE: DNA
<213> ORGANISM: Artificial Sequence
<220> FEATURE:
<223> OTHER INFORMATION: primer

<400> SEQUENCE: 102
gtgatcgcca tggcgtcgac cgakgtrmag cttcaggagt c                              41

<210> SEQ ID NO 103
<211> LENGTH: 41
<212> TYPE: DNA
<213> ORGANISM: Artificial Sequence
<220> FEATURE:
<223> OTHER INFORMATION: Primer

<400> SEQUENCE: 103
gtgatcgcca tggcgtcgac cgaggtbcag ctbcagcagt c                              41

```
<210> SEQ ID NO 104
<211> LENGTH: 41
<212> TYPE: DNA
<213> ORGANISM: Artificial Sequence
<220> FEATURE:
<223> OTHER INFORMATION: primer

<400> SEQUENCE: 104
gtgatcgcca tggcgtcgac ccaggtgcag ctgaagsart c         41

<210> SEQ ID NO 105
<211> LENGTH: 41
<212> TYPE: DNA
<213> ORGANISM: Artificial Sequence
<220> FEATURE:
<223> OTHER INFORMATION: primer

<400> SEQUENCE: 105
gtgatcgcca tggcgtcgac cgaggtccar ctgcaacart c         41

<210> SEQ ID NO 106
<211> LENGTH: 41
<212> TYPE: DNA
<213> ORGANISM: Artificial Sequence
<220> FEATURE:
<223> OTHER INFORMATION: primer

<400> SEQUENCE: 106
gtgatcgcca tggcgtcgac ccaggtycag ctbcagcart c         41

<210> SEQ ID NO 107
<211> LENGTH: 41
<212> TYPE: DNA
<213> ORGANISM: Artificial Sequence
<220> FEATURE:
<223> OTHER INFORMATION: primer

<400> SEQUENCE: 107
gtgatcgcca tggcgtcgac ccaggtycar ctgcagcart c         41

<210> SEQ ID NO 108
<211> LENGTH: 41
<212> TYPE: DNA
<213> ORGANISM: Artificial Sequence
<220> FEATURE:
<223> OTHER INFORMATION: primer

<400> SEQUENCE: 108
gtgatcgcca tggcgtcgac ccaggtccac gtgaagcart c         41

<210> SEQ ID NO 109
<211> LENGTH: 41
<212> TYPE: DNA
<213> ORGANISM: Artificial Sequence
<220> FEATURE:
<223> OTHER INFORMATION: primer

<400> SEQUENCE: 109
gtgatcgcca tggcgtcgac cgaggtgaas stggtggart c         41

<210> SEQ ID NO 110
<211> LENGTH: 41
<212> TYPE: DNA
<213> ORGANISM: Artificial Sequence
<220> FEATURE:
<223> OTHER INFORMATION: primer
```

```
<400> SEQUENCE: 110
gtgatcgcca tggcgtcgac cgavgtgawg stggtggagt c            41

<210> SEQ ID NO 111
<211> LENGTH: 41
<212> TYPE: DNA
<213> ORGANISM: Artificial Sequence
<220> FEATURE:
<223> OTHER INFORMATION: primer

<400> SEQUENCE: 111
gtgatcgcca tggcgtcgac cgaggtgcag stggtggart c            41

<210> SEQ ID NO 112
<211> LENGTH: 41
<212> TYPE: DNA
<213> ORGANISM: Artificial Sequence
<220> FEATURE:
<223> OTHER INFORMATION: primer

<400> SEQUENCE: 112
gtgatcgcca tggcgtcgac cgakgtgcam ctggtggart c            41

<210> SEQ ID NO 113
<211> LENGTH: 41
<212> TYPE: DNA
<213> ORGANISM: Artificial Sequence
<220> FEATURE:
<223> OTHER INFORMATION: primer

<400> SEQUENCE: 113
gtgatcgcca tggcgtcgac cgaggtgaag ctgatggart c            41

<210> SEQ ID NO 114
<211> LENGTH: 41
<212> TYPE: DNA
<213> ORGANISM: Artificial Sequence
<220> FEATURE:
<223> OTHER INFORMATION: primer

<400> SEQUENCE: 114
gtgatcgcca tggcgtcgac cgaggtgcar cttgttgart c            41

<210> SEQ ID NO 115
<211> LENGTH: 41
<212> TYPE: DNA
<213> ORGANISM: Artificial Sequence
<220> FEATURE:
<223> OTHER INFORMATION: primer

<400> SEQUENCE: 115
gtgatcgcca tggcgtcgac cgargtraag cttctcgart c            41

<210> SEQ ID NO 116
<211> LENGTH: 41
<212> TYPE: DNA
<213> ORGANISM: Artificial Sequence
<220> FEATURE:
<223> OTHER INFORMATION: primer

<400> SEQUENCE: 116
gtgatcgcca tggcgtcgac cgaagtgaar sttgaggart c            41

<210> SEQ ID NO 117
```

```
<211> LENGTH: 41
<212> TYPE: DNA
<213> ORGANISM: Artificial Sequence
<220> FEATURE:
<223> OTHER INFORMATION: primer

<400> SEQUENCE: 117
gtgatcgcca tggcgtcgac ccaggttact ctraaasart c                           41

<210> SEQ ID NO 118
<211> LENGTH: 41
<212> TYPE: DNA
<213> ORGANISM: Artificial Sequence
<220> FEATURE:
<223> OTHER INFORMATION: primer

<400> SEQUENCE: 118
gtgatcgcca tggcgtcgac ccaggtccaa ctvcagcarc c                           41

<210> SEQ ID NO 119
<211> LENGTH: 41
<212> TYPE: DNA
<213> ORGANISM: Artificial Sequence
<220> FEATURE:
<223> OTHER INFORMATION: primer

<400> SEQUENCE: 119
gtgatcgcca tggcgtcgac cgatgtgaac ttggaasart c                           41

<210> SEQ ID NO 120
<211> LENGTH: 41
<212> TYPE: DNA
<213> ORGANISM: Artificial Sequence
<220> FEATURE:
<223> OTHER INFORMATION: primer

<400> SEQUENCE: 120
gtgatcgcca tggcgtcgac cgaggtgaag gtcatcgart c                           41

<210> SEQ ID NO 121
<211> LENGTH: 38
<212> TYPE: DNA
<213> ORGANISM: Artificial Sequence
<220> FEATURE:
<223> OTHER INFORMATION: primer

<400> SEQUENCE: 121
cctccaccac tcgagcccga ggaaacggtg accgtggt                               38

<210> SEQ ID NO 122
<211> LENGTH: 38
<212> TYPE: DNA
<213> ORGANISM: Artificial Sequence
<220> FEATURE:
<223> OTHER INFORMATION: primer

<400> SEQUENCE: 122
cctccaccac tcgagcccga ggagactgtg agagtggt                               38

<210> SEQ ID NO 123
<211> LENGTH: 38
<212> TYPE: DNA
<213> ORGANISM: Artificial Sequence
<220> FEATURE:
<223> OTHER INFORMATION: primer

<400> SEQUENCE: 123
```
cctccaccac tcgagcccgc agagacagtg accagagt                           38

<210> SEQ ID NO 124
<211> LENGTH: 38
<212> TYPE: DNA
<213> ORGANISM: Artificial Sequence
<220> FEATURE:
<223> OTHER INFORMATION: primer

<400> SEQUENCE: 124
cctccaccac tcgagcccga ggagacggtg actgaggt                           38

<210> SEQ ID NO 125
<211> LENGTH: 35
<212> TYPE: DNA
<213> ORGANISM: Artificial Sequence
<220> FEATURE:
<223> OTHER INFORMATION: primer

<400> SEQUENCE: 125
ggcggtggcg ctagcgayat ccagctgact cagcc                              35

<210> SEQ ID NO 126
<211> LENGTH: 35
<212> TYPE: DNA
<213> ORGANISM: Artificial Sequence
<220> FEATURE:
<223> OTHER INFORMATION: primer

<400> SEQUENCE: 126
ggcggtggcg ctagccaaat tgttctcacc cagtc                              35

<210> SEQ ID NO 127
<211> LENGTH: 35
<212> TYPE: DNA
<213> ORGANISM: Artificial Sequence
<220> FEATURE:
<223> OTHER INFORMATION: primer

<400> SEQUENCE: 127
ggcggtggcg ctagcgayat tgtgmtmact cagtc                              35

<210> SEQ ID NO 128
<211> LENGTH: 35
<212> TYPE: DNA
<213> ORGANISM: Artificial Sequence
<220> FEATURE:
<223> OTHER INFORMATION: primer

<400> SEQUENCE: 128
ggcggtggcg ctagcgayat tgtgytraca cagtc                              35

<210> SEQ ID NO 129
<211> LENGTH: 35
<212> TYPE: DNA
<213> ORGANISM: Artificial Sequence
<220> FEATURE:
<223> OTHER INFORMATION: primer

<400> SEQUENCE: 129
ggcggtggcg ctagcgayat tgtratgacm cagtc                              35

<210> SEQ ID NO 130
<211> LENGTH: 35
<212> TYPE: DNA

```
<213> ORGANISM: Artificial Sequence
<220> FEATURE:
<223> OTHER INFORMATION: primer

<400> SEQUENCE: 130
ggcggtggcg ctagcgayat tmagatramc cagtc                                35

<210> SEQ ID NO 131
<211> LENGTH: 35
<212> TYPE: DNA
<213> ORGANISM: Artificial Sequence
<220> FEATURE:
<223> OTHER INFORMATION: primer

<400> SEQUENCE: 131
ggcggtggcg ctagcgayat tcagatgayd cagtc                                35

<210> SEQ ID NO 132
<211> LENGTH: 35
<212> TYPE: DNA
<213> ORGANISM: Artificial Sequence
<220> FEATURE:
<223> OTHER INFORMATION: primer

<400> SEQUENCE: 132
ggcggtggcg ctagcgayat ycagatgaca cagac                                35

<210> SEQ ID NO 133
<211> LENGTH: 35
<212> TYPE: DNA
<213> ORGANISM: Artificial Sequence
<220> FEATURE:
<223> OTHER INFORMATION: primer

<400> SEQUENCE: 133
ggcggtggcg ctagcgayat tgttctcawc cagtc                                35

<210> SEQ ID NO 134
<211> LENGTH: 35
<212> TYPE: DNA
<213> ORGANISM: Artificial Sequence
<220> FEATURE:
<223> OTHER INFORMATION: primer

<400> SEQUENCE: 134
ggcggtggcg ctagcgayat tgwgctsacc caatc                                35

<210> SEQ ID NO 135
<211> LENGTH: 35
<212> TYPE: DNA
<213> ORGANISM: Artificial Sequence
<220> FEATURE:
<223> OTHER INFORMATION: primer

<400> SEQUENCE: 135
ggcggtggcg ctagcgayat tstratgacc cartc                                35

<210> SEQ ID NO 136
<211> LENGTH: 35
<212> TYPE: DNA
<213> ORGANISM: Artificial Sequence
<220> FEATURE:
<223> OTHER INFORMATION: primer

<400> SEQUENCE: 136
ggcggtggcg ctagcgayrt tktgatgacc carac                                35
```

```
<210> SEQ ID NO 137
<211> LENGTH: 35
<212> TYPE: DNA
<213> ORGANISM: Artificial Sequence
<220> FEATURE:
<223> OTHER INFORMATION: primer

<400> SEQUENCE: 137
ggcggtggcg ctagcgayat tgtgatgacb cagkc                              35

<210> SEQ ID NO 138
<211> LENGTH: 35
<212> TYPE: DNA
<213> ORGANISM: Artificial Sequence
<220> FEATURE:
<223> OTHER INFORMATION: primer

<400> SEQUENCE: 138
ggcggtggcg ctagcgayat tgtgataacy cagga                              35

<210> SEQ ID NO 139
<211> LENGTH: 35
<212> TYPE: DNA
<213> ORGANISM: Artificial Sequence
<220> FEATURE:
<223> OTHER INFORMATION: primer

<400> SEQUENCE: 139
ggcggtggcg ctagcgayat tgtgatgacc cagwt                              35

<210> SEQ ID NO 140
<211> LENGTH: 35
<212> TYPE: DNA
<213> ORGANISM: Artificial Sequence
<220> FEATURE:
<223> OTHER INFORMATION: primer

<400> SEQUENCE: 140
ggcggtggcg ctagcgayat tgtgatgaca caacc                              35

<210> SEQ ID NO 141
<211> LENGTH: 35
<212> TYPE: DNA
<213> ORGANISM: Artificial Sequence
<220> FEATURE:
<223> OTHER INFORMATION: primer

<400> SEQUENCE: 141
ggcggtggcg ctagcgayat tttgctgact cagtc                              35

<210> SEQ ID NO 142
<211> LENGTH: 35
<212> TYPE: DNA
<213> ORGANISM: Artificial Sequence
<220> FEATURE:
<223> OTHER INFORMATION: primer

<400> SEQUENCE: 142
ggcggtggcg ctagcgaaac aactgtgacc cagtc                              35

<210> SEQ ID NO 143
<211> LENGTH: 35
<212> TYPE: DNA
<213> ORGANISM: Artificial Sequence
<220> FEATURE:
```

<223> OTHER INFORMATION: primer

<400> SEQUENCE: 143
ggcggtggcg ctagcgaaaa tgtkctsacc cagtc    35

<210> SEQ ID NO 144
<211> LENGTH: 38
<212> TYPE: DNA
<213> ORGANISM: Artificial Sequence
<220> FEATURE:
<223> OTHER INFORMATION: primer

<400> SEQUENCE: 144
ggcggtggcg ctagccaggc tgttgtgact caggaatc    38

<210> SEQ ID NO 145
<211> LENGTH: 36
<212> TYPE: DNA
<213> ORGANISM: Artificial Sequence
<220> FEATURE:
<223> OTHER INFORMATION: primer

<400> SEQUENCE: 145
atgctgacgc ggccgcacgt ttkatttcca gcttgg    36

<210> SEQ ID NO 146
<211> LENGTH: 36
<212> TYPE: DNA
<213> ORGANISM: Artificial Sequence
<220> FEATURE:
<223> OTHER INFORMATION: primer

<400> SEQUENCE: 146
atgctgacgc ggccgcacgt tttatttcca actttg    36

<210> SEQ ID NO 147
<211> LENGTH: 36
<212> TYPE: DNA
<213> ORGANISM: Artificial Sequence
<220> FEATURE:
<223> OTHER INFORMATION: primer

<400> SEQUENCE: 147
atgctgacgc ggccgcacgt ttcagctcca gcttgg    36

<210> SEQ ID NO 148
<211> LENGTH: 36
<212> TYPE: DNA
<213> ORGANISM: Artificial Sequence
<220> FEATURE:
<223> OTHER INFORMATION: primer

<400> SEQUENCE: 148
atgctgacgc ggccgcacct aggacagtca gtttgg    36

<210> SEQ ID NO 149
<211> LENGTH: 17
<212> TYPE: DNA
<213> ORGANISM: Artificial Sequence
<220> FEATURE:
<223> OTHER INFORMATION: primer

<400> SEQUENCE: 149
gtaaaacgac ggccagt    17

```
<210> SEQ ID NO 150
<211> LENGTH: 16
<212> TYPE: DNA
<213> ORGANISM: Artificial Sequence
<220> FEATURE:
<223> OTHER INFORMATION: primer

<400> SEQUENCE: 150
aacagctatg accatg                                                    16

<210> SEQ ID NO 151
<211> LENGTH: 19
<212> TYPE: DNA
<213> ORGANISM: Artificial Sequence
<220> FEATURE:
<223> OTHER INFORMATION: primer

<400> SEQUENCE: 151
taatacgact cactatagg                                                 19

<210> SEQ ID NO 152
<211> LENGTH: 19
<212> TYPE: DNA
<213> ORGANISM: Artificial Sequence
<220> FEATURE:
<223> OTHER INFORMATION: primer

<400> SEQUENCE: 152
gatttaggtg acactatag                                                 19

<210> SEQ ID NO 153
<211> LENGTH: 34
<212> TYPE: DNA
<213> ORGANISM: Artificial Sequence
<220> FEATURE:
<223> OTHER INFORMATION: primer

<400> SEQUENCE: 153
gatcgctagc caccatgagc ggggaatcaa tgaa                                34

<210> SEQ ID NO 154
<211> LENGTH: 33
<212> TYPE: DNA
<213> ORGANISM: Artificial Sequence
<220> FEATURE:
<223> OTHER INFORMATION: primer

<400> SEQUENCE: 154
gatcctcgag tcatcacata gtgaaggacg acg                                 33

<210> SEQ ID NO 155
<211> LENGTH: 58
<212> TYPE: DNA
<213> ORGANISM: Artificial Sequence
<220> FEATURE:
<223> OTHER INFORMATION: primer

<400> SEQUENCE: 155
catcgctgaa aacccaagtg ttggtggcat gagtcactgc ccagaatggg agagtaag      58

<210> SEQ ID NO 156
<211> LENGTH: 58
<212> TYPE: DNA
<213> ORGANISM: Artificial Sequence
<220> FEATURE:
<223> OTHER INFORMATION: primer
```

```
<400> SEQUENCE: 156
aacacttggg ttttcagcga tgcactgtgt aaattgctaa aaggcatcta tgccatca      58

<210> SEQ ID NO 157
<211> LENGTH: 82
<212> TYPE: DNA
<213> ORGANISM: Artificial Sequence
<220> FEATURE:
<223> OTHER INFORMATION: primer

<400> SEQUENCE: 157
ctcacagaca tcacgatcct gcagctcgta tttcttgttg aagataaatg tagggctgga   60
gatgatgact gacagccccc ac                                            82

<210> SEQ ID NO 158
<211> LENGTH: 82
<212> TYPE: DNA
<213> ORGANISM: Artificial Sequence
<220> FEATURE:
<223> OTHER INFORMATION: primer

<400> SEQUENCE: 158
gatcgtgatg tctgtgagcc acggtacagg tctgtctcag agcccatcac gtggaagctg   60
ctgatgttgg ggcttgagct ac                                            82

<210> SEQ ID NO 159
<211> LENGTH: 71
<212> TYPE: DNA
<213> ORGANISM: Artificial Sequence
<220> FEATURE:
<223> OTHER INFORMATION: primer

<400> SEQUENCE: 159
cgaggacttt ctcggtgctg cagctccggc ccactttgcc cgtgtttgca gccgtcacaa   60
gcaggaccat g                                                        71

<210> SEQ ID NO 160
<211> LENGTH: 71
<212> TYPE: DNA
<213> ORGANISM: Artificial Sequence
<220> FEATURE:
<223> OTHER INFORMATION: primer

<400> SEQUENCE: 160
gcaccgagaa agtcctcgcc tacaccagga acgtggccga ggtcctggct ttcctgcact   60
gctgcctgaa c                                                        71

<210> SEQ ID NO 161
<211> LENGTH: 34
<212> TYPE: DNA
<213> ORGANISM: Artificial Sequence
<220> FEATURE:
<223> OTHER INFORMATION: primer

<400> SEQUENCE: 161
agaggctagc caccatgaat tccacagagt ccta                               34

<210> SEQ ID NO 162
<211> LENGTH: 45
<212> TYPE: DNA
<213> ORGANISM: Artificial Sequence
<220> FEATURE:
<223> OTHER INFORMATION: primer
```

<400> SEQUENCE: 162
caaggagtag gcaatcggta caaataccct ggtgaagttt ctgac          45

<210> SEQ ID NO 163
<211> LENGTH: 45
<212> TYPE: DNA
<213> ORGANISM: Artificial Sequence
<220> FEATURE:
<223> OTHER INFORMATION: primer

<400> SEQUENCE: 163
aaacttcacc aaggtatttg taccgattgc ctactccttg atctg          45

<210> SEQ ID NO 164
<211> LENGTH: 40
<212> TYPE: DNA
<213> ORGANISM: Artificial Sequence
<220> FEATURE:
<223> OTHER INFORMATION: primer

<400> SEQUENCE: 164
caattggcac aaatagcctg gagaactgcc tgacctcctg               40

<210> SEQ ID NO 165
<211> LENGTH: 40
<212> TYPE: DNA
<213> ORGANISM: Artificial Sequence
<220> FEATURE:
<223> OTHER INFORMATION: primer

<400> SEQUENCE: 165
tcaggcagtt ctccaggcta tttgtgccaa ttgcctactc               40

<210> SEQ ID NO 166
<211> LENGTH: 45
<212> TYPE: DNA
<213> ORGANISM: Artificial Sequence
<220> FEATURE:
<223> OTHER INFORMATION: primer

<400> SEQUENCE: 166
ccgcgatcct cgagtcatta catggtaaag gacgatgcat tatca          45

<210> SEQ ID NO 167
<211> LENGTH: 747
<212> TYPE: DNA
<213> ORGANISM: Artificial Sequence
<220> FEATURE:
<223> OTHER INFORMATION: scFvformatcDNAof4H11VH1andVL1

<400> SEQUENCE: 167
gaagtgcagc tggtggaatc tggcggcgga ctggtgcagc ctggcggatc tctgagactg          60
agctgtgcca ccagcggctt cagcttcagc gactactaca tgtactgggt gcgccaggcc         120
cctggcaagg gactggaatg ggtggcctac atcaccaacg gcggcatcac ctactacccc         180
gacaccgtga agggcggtt caccatcagc cggacaaca gcaagaacac cctgtacctg          240
cagatgaaca gcctgcgggc cgaggacacc gccgtgtact actgtaccag ccccctgaga         300
ggcgcttggt ttgcctattg gggccagggc accaccgtga ccgtgtctag tggaggcgga         360
ggatctggcg gcggaggaag tggcggaggg ggatctgggg gaggcggatc tgatgtcgtg         420
atgacccaga gcccctgag cctgcctgtg acactgggac agcctgccag catcagctgc         480

```
agatccagcc agagcatcgt gcacagcaac ggcaatacct atctggaatg gtatcagcag      540
cggcctggcc agtcccccag actgctgatc tacaaggtgt ccaaccggtt cagcggcgtg      600
cccgacagat ttctggctc tggcagcggc accgacttca ccctgaagat ctcccgggtg       660
gaagccgagg acgtgggcgt gtactactgt tttcaaggca gccacgtgcc cctgaccttc      720
ggccagggaa caaagctgga aatcaag                                          747
```

<210> SEQ ID NO 168
<211> LENGTH: 366
<212> TYPE: PRT
<213> ORGANISM: Artificial Sequence
<220> FEATURE:
<223> OTHER INFORMATION: hsCCR6-mmNterm

<400> SEQUENCE: 168

```
Met Asn Ser Thr Glu Ser Tyr Phe Gly Thr Asp Asp Tyr Asp Asn Thr
1               5                   10                  15

Glu Tyr Tyr Ser Ile Pro Pro Asp His Gly Pro Cys Ser Leu Glu Glu
            20                  25                  30

Val Arg Asn Phe Thr Lys Val Phe Val Pro Ile Ala Tyr Ser Leu Ile
        35                  40                  45

Cys Val Phe Gly Leu Leu Gly Asn Ile Leu Val Val Ile Thr Phe Ala
    50                  55                  60

Phe Tyr Lys Lys Ala Arg Ser Met Thr Asp Val Tyr Leu Leu Asn Met
65                  70                  75                  80

Ala Ile Ala Asp Ile Leu Phe Val Leu Thr Leu Pro Phe Trp Ala Val
                85                  90                  95

Ser His Ala Thr Gly Ala Trp Val Phe Ser Asn Ala Thr Cys Lys Leu
            100                 105                 110

Leu Lys Gly Ile Tyr Ala Ile Asn Phe Asn Cys Gly Met Leu Leu Leu
        115                 120                 125

Thr Cys Ile Ser Met Asp Arg Tyr Ile Ala Ile Val Gln Ala Thr Lys
    130                 135                 140

Ser Phe Arg Leu Arg Ser Arg Thr Leu Pro Arg Ser Lys Ile Ile Cys
145                 150                 155                 160

Leu Val Val Trp Gly Leu Ser Val Ile Ser Ser Ser Thr Phe Val
                165                 170                 175

Phe Asn Gln Lys Tyr Asn Thr Gln Gly Ser Asp Val Cys Glu Pro Lys
            180                 185                 190

Tyr Gln Thr Val Ser Glu Pro Ile Arg Trp Lys Leu Leu Met Leu Gly
        195                 200                 205

Leu Glu Leu Leu Phe Gly Phe Phe Ile Pro Leu Met Phe Met Ile Phe
    210                 215                 220

Cys Tyr Thr Phe Ile Val Lys Thr Leu Val Gln Ala Gln Asn Ser Lys
225                 230                 235                 240

Arg His Lys Ala Ile Arg Val Ile Ile Ala Val Val Leu Val Phe Leu
                245                 250                 255

Ala Cys Gln Ile Pro His Asn Met Val Leu Leu Val Thr Ala Ala Asn
            260                 265                 270

Leu Gly Lys Met Asn Arg Ser Cys Gln Ser Glu Lys Leu Ile Gly Tyr
        275                 280                 285

Thr Lys Thr Val Thr Glu Val Leu Ala Phe Leu His Cys Cys Leu Asn
    290                 295                 300

Pro Val Leu Tyr Ala Phe Ile Gly Gln Lys Phe Arg Asn Tyr Phe Leu
305                 310                 315                 320
```

```
Lys Ile Leu Lys Asp Leu Trp Cys Val Arg Arg Lys Tyr Lys Ser Ser
            325                 330                 335

Gly Phe Ser Cys Ala Gly Arg Tyr Ser Glu Asn Ile Ser Arg Gln Thr
            340                 345                 350

Ser Glu Thr Ala Asp Asn Asp Asn Ala Ser Ser Phe Thr Met
            355                 360                 365

<210> SEQ ID NO 169
<211> LENGTH: 1101
<212> TYPE: DNA
<213> ORGANISM: Artificial Sequence
<220> FEATURE:
<223> OTHER INFORMATION: hsCCR6-mmNtermDNA

<400> SEQUENCE: 169
atgaattcca cagagtccta ctttggaacg gatgattatg caacacaga gtattattct      60
attcctccag accatgggcc atgctcccta gaagaggtca gaaacttcac caaggtattt    120
gtaccgattg cctactcctt gatctgtgtc tttggcctcc tggggaatat tctggtggtg    180
atcacctttg cttttttataa gaaggccagg tctatgacag acgtctatct cttgaacatg    240
gccattgcag acatcctctt tgttcttact ctcccattct gggcagtgag tcatgccact    300
ggtgcgtggg ttttcagcaa tgccacgtgc aagttgctaa aaggcatcta tgccatcaac    360
tttaactgcg ggatgctgct cctgacttgc attagcatgg accggtacat cgccattgta    420
caggcgacta gtcattccg gctccgatcc agaacactac cgcgcagcaa aatcatctgc    480
cttgttgtgt gggggctgtc agtcatcatc tccagctcaa ctttgtctt caaccaaaaa      540
tacaacaccc aaggcagcga tgtctgtgaa cccaagtacc agactgtctc ggagcccatc    600
aggtggaagc tgctgatgtt ggggcttgag ctactctttg gtttctttat ccctttgatg    660
ttcatgatat tttgttacac gttcattgtc aaaaccttgg tgcaagctca gaattctaaa    720
aggcacaaag ccatccgtgt aatcatagct gtggtgcttg tgtttctggc ttgtcagatt    780
cctcataaca tggtcctgct tgtgacggct gcaaatttgg gtaaaatgaa ccgatcctgc    840
cagagcgaaa agctaattgg ctatacgaaa actgtcacag aagtcctggc tttcctgcac    900
tgctgcctga accctgtgct ctacgctttt attgggcaga gttcagaaaa ctactttctg    960
aagatcttga aggacctgtg gtgtgtgaga aggaagtaca agtcctcagg cttctcctgt   1020
gccgggaggt actcagaaaa catttctcgg cagaccagtg agaccgcaga taacgacaat   1080
gcgtcgtcct tcactatgtg a                                              1101

<210> SEQ ID NO 170
<211> LENGTH: 375
<212> TYPE: PRT
<213> ORGANISM: Artificial Sequence
<220> FEATURE:
<223> OTHER INFORMATION: mmCCR6-hsNterm

<400> SEQUENCE: 170

Met Ser Gly Glu Ser Met Asn Phe Ser Asp Val Phe Asp Ser Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
            35                  40                  45

Val Pro Ile Ala Tyr Ser Leu Ile Cys Val Phe Gly Leu Leu Gly Asn
            50                  55                  60
```

```
Ile Met Val Val Met Thr Phe Ala Phe Tyr Lys Lys Ala Arg Ser Met
 65                  70                  75                  80

Thr Asp Val Tyr Leu Leu Asn Met Ala Ile Thr Asp Ile Leu Phe Val
                 85                  90                  95

Leu Thr Leu Pro Phe Trp Ala Val Thr His Ala Thr Asn Thr Trp Val
            100                 105                 110

Phe Ser Asp Ala Leu Cys Lys Leu Met Lys Gly Thr Tyr Ala Val Asn
        115                 120                 125

Phe Asn Cys Gly Met Leu Leu Leu Ala Cys Ile Ser Met Asp Arg Tyr
    130                 135                 140

Ile Ala Ile Val Gln Ala Thr Lys Ser Phe Arg Val Arg Ser Arg Thr
145                 150                 155                 160

Leu Thr His Ser Lys Val Ile Cys Val Ala Val Trp Phe Ile Ser Ile
                165                 170                 175

Ile Ile Ser Ser Pro Thr Phe Ile Phe Asn Lys Lys Tyr Glu Leu Gln
            180                 185                 190

Asp Arg Asp Val Cys Glu Pro Arg Tyr Arg Ser Val Ser Glu Pro Ile
        195                 200                 205

Thr Trp Lys Leu Leu Gly Met Gly Leu Glu Leu Phe Phe Gly Phe Phe
    210                 215                 220

Thr Pro Leu Leu Phe Met Val Phe Cys Tyr Leu Phe Ile Ile Lys Thr
225                 230                 235                 240

Leu Val Gln Ala Gln Asn Ser Lys Arg His Arg Ala Ile Arg Val Val
                245                 250                 255

Ile Ala Val Val Leu Val Phe Leu Ala Cys Gln Ile Pro His Asn Met
            260                 265                 270

Val Leu Leu Val Thr Ala Val Asn Thr Gly Lys Val Gly Arg Ser Cys
        275                 280                 285

Ser Thr Glu Lys Val Leu Ala Tyr Thr Arg Asn Val Ala Glu Val Leu
    290                 295                 300

Ala Phe Leu His Cys Cys Leu Asn Pro Val Leu Tyr Ala Phe Ile Gly
305                 310                 315                 320

Gln Lys Phe Arg Asn Tyr Phe Met Lys Ile Met Lys Asp Val Trp Cys
                325                 330                 335

Met Arg Arg Lys Asn Lys Met Pro Gly Phe Leu Cys Ala Arg Val Tyr
            340                 345                 350

Ser Glu Ser Tyr Ile Ser Arg Gln Thr Ser Glu Thr Val Glu Asn Asp
        355                 360                 365

Asn Ala Ser Ser Phe Thr Met
    370                 375

<210> SEQ ID NO 171
<211> LENGTH: 1128
<212> TYPE: DNA
<213> ORGANISM: Artificial Sequence
<220> FEATURE:
<223> OTHER INFORMATION: mmCCR6-hsNtermDNA

<400> SEQUENCE: 171
atgagcgggg aatcaatgaa tttcagcgat gttttcgact ccagtgaaga ttattttgtg     60
tcagtcaata cttcatatta ctcagttgat tctgagatgt tactgtgctc cttgcaggag    120
gtcaggcagt tctccaggct atttgtgcca attgcctact ccttaatatg tgtctttggc    180
ctcctgggca acattatggt ggtgatgacc tttgccttct acaagaaagc cagatccatg    240
```

```
actgacgtct  acctgttgaa  catggccatc  acagacatac  tctttgtcct  caccctaccg    300
ttctgggcag  ttactcatgc  caccaacact  tgggttttca  gcgatgcact  gtgtaaactg    360
atgaaaggca  catatgcggt  caactttaac  tgtgggatgc  tgctcctggc  ctgtatcagc    420
atggaccggt  acattgccat  cgtccaggca  accaaatctt  tccgggtacg  ctccagaaca    480
ctgacgcaca  gtaaggtcat  ctgtgtggca  gtgtggttca  tctccatcat  catctcaagc    540
cctacattta  tcttcaacaa  gaaatacgag  ctgcaggatc  gtgatgtctg  tgagccacgg    600
tacaggtctg  tctcagagcc  catcacgtgg  aagctgctgg  gtatgggact  ggagctgttc    660
tttgggttct  tcacccctt  gctgtttatg  gtgttctgct  atctgttcat  tatcaagacc    720
ttggtgcagg  cccagaactc  caagaggcac  agagccatcc  gagtcgtgat  cgctgtggtt    780
ctcgtgttcc  tggcttgtca  gatccctcac  aacatggtcc  tcctcgtgac  tgcggtcaac    840
acgggcaaag  tgggccggag  ctgcagcacc  gagaaagtcc  tcgcctacac  caggaacgtg    900
gccgaggtcc  tggctttcct  gcattgctgc  ctcaaccccg  tgttgtatgc  gtttattgga    960
cagaaattca  gaaactactt  catgaagatc  atgaaggatg  tgtggtgtat  gagaaggaag   1020
aataagatgc  ctggcttcct  ctgtgcccgg  gtttactcgg  aaagctacat  ctccaggcag   1080
accagtgaga  ccgtcgaaaa  tgataatgca  tcgtccttta  ccatgtaa                 1128
```

<210> SEQ ID NO 172
<211> LENGTH: 39
<212> TYPE: PRT
<213> ORGANISM: Artificial Sequence
<220> FEATURE:
<223> OTHER INFORMATION: hsCCR6 N-terminal sequence

<400> SEQUENCE: 172

Met Asn Phe Ser Asp Val Phe Asp Ser Ser Glu Asp Tyr Asp Asn Thr
1               5                   10                  15

Glu Tyr Tyr Ser Val Asp Ser Glu Met Leu Leu Cys Ser Leu Gly Glu
            20                  25                  30

Val Arg Gln Phe Ser Arg Leu
        35

<210> SEQ ID NO 173
<211> LENGTH: 447
<212> TYPE: PRT
<213> ORGANISM: Artificial Sequence
<220> FEATURE:
<223> OTHER INFORMATION: 4H11 VH1 heavy chain IgG1

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Thr Asn Gly Gly Ile Thr Tyr Tyr Pro Asp Thr Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 174
<211> LENGTH: 39
<212> TYPE: PRT
<213> ORGANISM: Artificial Sequence
<220> FEATURE:
<223> OTHER INFORMATION: mmCCR6Nterminalsequence

<400> SEQUENCE: 174

Met Asn Ser Thr Glu Ser Tyr Phe Gly Thr Asp Asp Tyr Asp Asn Thr
1               5                   10                  15

Glu Tyr Tyr Ser Ile Pro Pro Asp His Gly Pro Cys Ser Leu Gly Glu
            20                  25                  30

Val Arg Gln Phe Ser Arg Leu
            35

<210> SEQ ID NO 175
<211> LENGTH: 447
<212> TYPE: PRT
<213> ORGANISM: Artificial Sequence
<220> FEATURE:
<223> OTHER INFORMATION: chimera 4H11 heavy chain IgG1

<400> SEQUENCE: 175

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Ser Phe Ser Asp Tyr
            20                  25                  30

Tyr Met Tyr Trp Ile Arg Gln Thr Pro Glu Lys Arg Leu Glu Trp Val
        35                  40                  45

Ala Tyr Ile Thr Asn Gly Gly Ile Thr Tyr Tyr Pro Asp Thr Val Lys
    50                  55                  60

Gly Arg Phe Thr Ile Ser Arg Asp Asn Ala Lys Asn Thr Leu Tyr Leu
65                  70                  75                  80

Gln Met Ser Arg Leu Arg Ser Glu Asp Thr Ala Met Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 176
<211> LENGTH: 219
<212> TYPE: PRT
<213> ORGANISM: Artificial Sequence
<220> FEATURE:
<223> OTHER INFORMATION: chimera 4H11 light chain

<400> SEQUENCE: 176

Asp Val Ile Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 177
<211> LENGTH: 117
<212> TYPE: PRT
<213> ORGANISM: Artificial Sequence
<220> FEATURE:
<223> OTHER INFORMATION: 4H11 VH2
```

<400> SEQUENCE: 177

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Thr Asn Gly Gly Ile Thr Tyr Tyr Pro Asp Thr Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Ser Pro Leu Arg Gly Ala Trp Phe Ala Tyr Trp Gly Gln Gly Thr Leu
            100                 105                 110

Val Thr Val Ser Ser
        115

<210> SEQ ID NO 178
<211> LENGTH: 117
<212> TYPE: PRT
<213> ORGANISM: Artificial Sequence
<220> FEATURE:
<223> OTHER INFORMATION: 4H11 VH3

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Thr Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Ser Pro Leu Arg Gly Ala Trp Phe Ala Tyr Trp Gly Gln Gly Thr Leu
            100                 105                 110

Val Thr Val Ser Ser
        115

<210> SEQ ID NO 179
<211> LENGTH: 117
<212> TYPE: PRT
<213> ORGANISM: Artificial Sequence
<220> FEATURE:
<223> OTHER INFORMATION: 4H11 VH4

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

```
Ser Tyr Ile Thr Asn Gly Gly Ile Thr Tyr Tyr Pro Asp Thr Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Thr
                85                  90                  95
Ser Pro Leu Arg Gly Ala Trp Phe Ala Tyr Trp Gly Gln Gly Thr Leu
            100                 105                 110
Val Thr Val Ser Ser
            115

<210> SEQ ID NO 180
<211> LENGTH: 39
<212> TYPE: PRT
<213> ORGANISM: Artificial Sequence
<220> FEATURE:
<223> OTHER INFORMATION: mutantmmCCR6block1hsCCR6

<400> SEQUENCE: 180

Met Asn Phe Ser Asp Val Phe Asp Ser Ser Glu Asp Tyr Asp Asn Thr
1               5                   10                  15
Glu Tyr Tyr Ser Ile Pro Pro Asp His Gly Pro Cys Ser Leu Glu Glu
            20                  25                  30
Val Arg Asn Phe Thr Lys Val
            35

<210> SEQ ID NO 181
<211> LENGTH: 112
<212> TYPE: PRT
<213> ORGANISM: Artificial Sequence
<220> FEATURE:
<223> OTHER INFORMATION: 4H11 VL2

<400> SEQUENCE: 181

Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Ile Val His Ser
            20                  25                  30
Asn Gly Asn Thr Tyr Leu Glu Trp Phe Gln Gln Arg Pro Gly Gln Ser
        35                  40                  45
Pro Arg Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Leu Thr Phe Gly Gln Gly Thr Lys Leu Glu Ile Lys
            100                 105                 110

<210> SEQ ID NO 182
<211> LENGTH: 112
<212> TYPE: PRT
<213> ORGANISM: Artificial Sequence
<220> FEATURE:
<223> OTHER INFORMATION: 4H11 VL3

<400> SEQUENCE: 182

Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Ile Val His Ser
```

```
                    20                  25                  30
Asn Gly Asn Thr Tyr Leu Glu Trp Phe Gln Gln Arg Pro Gly Gln Ser
            35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 183
<211> LENGTH: 447
<212> TYPE: PRT
<213> ORGANISM: Artificial Sequence
<220> FEATURE:
<223> OTHER INFORMATION: 411VH2heavychainIgG1

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Thr Asn Gly Gly Ile Thr Tyr Tyr Pro Asp Thr Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
```

```
                275                 280                 285
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 184
<211> LENGTH: 447
<212> TYPE: PRT
<213> ORGANISM: Artificial Sequence
<220> FEATURE:
<223> OTHER INFORMATION: VH3 heavy chain IgG1

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Ser Phe Ser Asp Tyr
                20                  25                  30

Tyr Met Tyr Trp Val Arg Gln Ala Pro Gly Lys Gly Leu Glu Trp Val
            35                  40                  45

Ser Tyr Ile Thr Asn Gly Gly Ile Thr Tyr Tyr Pro Asp Thr Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
```

```
              195                 200                 205
Thr Lys Val Asp Lys Val Glu Pro Lys Ser Cys Asp Lys Thr His
        210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 185
<211> LENGTH: 39
<212> TYPE: PRT
<213> ORGANISM: Artificial Sequence
<220> FEATURE:
<223> OTHER INFORMATION: mutantmmCCR6block2hsCCR6

<400> SEQUENCE: 185

Met Asn Ser Thr Glu Ser Tyr Phe Gly Thr Asp Tyr Asp Asn Thr
1               5                   10                  15
Glu Tyr Tyr Ser Val Asp Ser Glu Met Leu Leu Cys Ser Leu Glu Glu
            20                  25                  30
Val Arg Asn Phe Thr Lys Val
        35

<210> SEQ ID NO 186
<211> LENGTH: 219
<212> TYPE: PRT
<213> ORGANISM: Artificial Sequence
<220> FEATURE:
<223> OTHER INFORMATION: 4H11 VL2 light chain

<400> SEQUENCE: 186

Asp Val Val Met Thr Gln Ser Pro Leu Ser Leu Pro Val Thr Leu Gly
1               5                   10                  15
```

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
                35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 187
<211> LENGTH: 219
<212> TYPE: PRT
<213> ORGANISM: Artificial Sequence
<220> FEATURE:
<223> OTHER INFORMATION: 4H11 VL3 light chain

<400> SEQUENCE: 187

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
                35                  40                  45

Pro Arg Arg Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

```
Ser Gly Asn Ser Gln Glu Ser Val Thr Glu Gln Asp Ser Lys Asp Ser
            165                 170                 175
Thr Tyr Ser Leu Ser Ser Thr Leu Thr Leu Ser Lys Ala Asp Tyr Glu
        180                 185                 190
Lys His Lys Val Tyr Ala Cys Glu Val Thr His Gln Gly Leu Ser Ser
    195                 200                 205
Pro Val Thr Lys Ser Phe Asn Arg Gly Glu Cys
    210                 215

<210> SEQ ID NO 188
<211> LENGTH: 299
<212> TYPE: PRT
<213> ORGANISM: Artificial Sequence
<220> FEATURE:
<223> OTHER INFORMATION: human CCR6-Fc

<400> SEQUENCE: 188

Met Glu Thr Asp Thr Leu Leu Leu Trp Val Leu Leu Leu Trp Val Pro
1               5                   10                  15
Gly Ser Thr Gly Met Ser Gly Glu Ser Met Asn Phe Ser Asp Val Phe
            20                  25                  30
Asp Ser Ser Glu Asp Tyr Phe Val Ser Val Asn Thr Ser Tyr Tyr Ser
        35                  40                  45
Val Asp Ser Glu Met Leu Leu Cys Ser Leu Gln Glu Val Arg Gln Phe
    50                  55                  60
Ser Arg Leu Gly Gly Gly Thr Asp Lys Thr His Thr Cys Pro Pro
65                  70                  75                  80
Cys Pro Ala Pro Glu Leu Leu Gly Gly Pro Ser Val Phe Leu Phe Pro
                85                  90                  95
Pro Lys Pro Lys Asp Thr Leu Met Ile Ser Arg Thr Pro Glu Val Thr
            100                 105                 110
Cys Val Val Val Asp Val Ser His Glu Asp Pro Glu Val Lys Phe Asn
        115                 120                 125
Trp Tyr Val Asp Gly Val Glu Val His Asn Ala Lys Thr Lys Pro Arg
    130                 135                 140
Glu Glu Gln Tyr Asn Ser Thr Tyr Arg Val Val Ser Val Leu Thr Val
145                 150                 155                 160
Leu His Gln Asp Trp Leu Asn Gly Lys Glu Tyr Lys Cys Lys Val Ser
                165                 170                 175
Asn Lys Ala Leu Pro Ala Pro Ile Glu Lys Thr Ile Ser Lys Ala Lys
            180                 185                 190
Gly Gln Pro Arg Glu Pro Gln Val Tyr Thr Leu Pro Pro Ser Arg Asp
        195                 200                 205
Glu Leu Thr Lys Asn Gln Val Ser Leu Thr Cys Leu Val Lys Gly Phe
    210                 215                 220
Tyr Pro Ser Asp Ile Ala Val Glu Trp Glu Ser Asn Gly Gln Pro Glu
225                 230                 235                 240
Asn Asn Tyr Lys Thr Thr Pro Pro Val Leu Asp Ser Asp Gly Ser Phe
                245                 250                 255
Phe Leu Tyr Ser Lys Leu Thr Val Asp Lys Ser Arg Trp Gln Gln Gly
            260                 265                 270
Asn Val Phe Ser Cys Ser Val Met His Glu Ala Leu His Asn His Tyr
        275                 280                 285
Thr Gln Lys Ser Leu Ser Leu Ser Pro Gly Lys
    290                 295
```

<210> SEQ ID NO 189
<211> LENGTH: 299
<212> TYPE: PRT
<213> ORGANISM: Artificial Sequence
<220> FEATURE:
<223> OTHER INFORMATION: Cyno CCR6-Fc

<400> SEQUENCE: 189

```
Met Glu Thr Asp Thr Leu Leu Leu Trp Val Leu Leu Trp Val Pro
1               5                   10                  15

Gly Ser Thr Gly Met Ser Gly Glu Ser Met Asn Phe Ser Asp Val Phe
            20                  25                  30

Asp Ser Glu Asp Tyr Phe Ala Ser Val Asn Thr Ser Tyr Tyr Thr
        35                  40                  45

Val Asp Ser Glu Met Leu Leu Cys Thr Leu His Glu Val Arg Gln Phe
    50                  55                  60

Ser Arg Leu Gly Gly Gly Thr Asp Lys Thr His Thr Cys Pro Pro
65              70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Asp
        195                 200                 205

Glu Leu Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys
    290                 295
```

<210> SEQ ID NO 190
<211> LENGTH: 16
<212> TYPE: PRT
<213> ORGANISM: Artificial Sequence
<220> FEATURE:
<223> OTHER INFORMATION: Affinity matured CDRH2

<400> SEQUENCE: 190

```
Tyr Ile Thr Thr Gly Gly Arg Thr Tyr Tyr Pro Asp Ser Val Lys Gly
1               5                   10                  15
```

<210> SEQ ID NO 191
<211> LENGTH: 13
<212> TYPE: PRT
<213> ORGANISM: Artificial Sequence
<220> FEATURE:
<223> OTHER INFORMATION: CDRL1 G29A

<400> SEQUENCE: 191

Gln Ser Ile Val His Ser Asn Ala Asn Thr Tyr Leu Glu
1               5                   10

<210> SEQ ID NO 192
<211> LENGTH: 9
<212> TYPE: PRT
<213> ORGANISM: Artificial Sequence
<220> FEATURE:
<223> OTHER INFORMATION: CDRL3 G8

<400> SEQUENCE: 192

Phe Gln Gly Thr Tyr Leu Pro Leu Thr
1               5

<210> SEQ ID NO 193
<211> LENGTH: 9
<212> TYPE: PRT
<213> ORGANISM: Artificial Sequence
<220> FEATURE:
<223> OTHER INFORMATION: CDRL3 C9

<400> SEQUENCE: 193

Phe Gln Gly Thr Tyr Tyr Pro Leu Thr
1               5

<210> SEQ ID NO 194
<211> LENGTH: 447
<212> TYPE: PRT
<213> ORGANISM: Artificial Sequence
<220> FEATURE:
<223> OTHER INFORMATION: G8 G29A igG1 HC

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 195
<211> LENGTH: 219
<212> TYPE: PRT
<213> ORGANISM: Artificial Sequence
<220> FEATURE:
<223> OTHER INFORMATION: G8 G29A IgG1 LC

<400> SEQUENCE: 195

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Phe Gln Gly
            85                  90                  95

Thr Tyr Leu Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 196
<211> LENGTH: 447
<212> TYPE: PRT
<213> ORGANISM: Artificial Sequence
<220> FEATURE:
<223> OTHER INFORMATION: C9 G29A IgG1 HC

<400> SEQUENCE: 196

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220
```

```
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 197
<211> LENGTH: 219
<212> TYPE: PRT
<213> ORGANISM: Artificial Sequence
<220> FEATURE:
<223> OTHER INFORMATION: C9 G29A IgG1 LC

<400> SEQUENCE: 197

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 198
<211> LENGTH: 894
<212> TYPE: PRT
<213> ORGANISM: Artificial Sequence
<220> FEATURE:
<223> OTHER INFORMATION: B3G8 G29A IgG1 HC

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Thr Gly Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Glu
        435                 440                 445

Val Gln Leu Val Glu Ser Gly Gly Leu Val Gln Pro Gly Gly Ser
450                 455                 460

Leu Arg Leu Ser Cys Ala Ala Ser Gly Phe Ser Phe Ser Asp Tyr Tyr
465                 470                 475                 480

Met Tyr Trp Val Arg Gln Ala Pro Gly Lys Gly Leu Glu Trp Val Ser
                485                 490                 495

Tyr Ile Thr Thr Gly Gly Arg Thr Tyr Tyr Pro Asp Ser Val Lys Gly
                500                 505                 510

Arg Phe Thr Ile Ser Arg Asp Asn Ser Lys Asn Thr Leu Tyr Leu Gln
        515                 520                 525

Met Asn Ser Leu Arg Ala Glu Asp Thr Ala Val Tyr Tyr Cys Thr Ser
530                 535                 540

Pro Leu Arg Gly Ala Trp Phe Ala Tyr Trp Gly Gln Gly Thr Leu Val
545                 550                 555                 560

Thr Val Ser Ser Ala Ser Thr Lys Gly Pro Ser Val Phe Pro Leu Ala
                565                 570                 575

Pro Ser Ser Lys Ser Thr Ser Gly Gly Thr Ala Ala Leu Gly Cys Leu
                580                 585                 590

Val Lys Asp Tyr Phe Pro Glu Pro Val Thr Val Ser Trp Asn Ser Gly
        595                 600                 605

Ala Leu Thr Ser Gly Val His Thr Phe Pro Ala Val Leu Gln Ser Ser
610                 615                 620

Gly Leu Tyr Ser Leu Ser Ser Val Val Thr Val Pro Ser Ser Ser Leu
625                 630                 635                 640

Gly Thr Gln Thr Tyr Ile Cys Asn Val Asn His Lys Pro Ser Asn Thr
                645                 650                 655

Lys Val Asp Lys Lys Val Glu Pro Lys Ser Cys Asp Lys Thr His Thr
                660                 665                 670

Cys Pro Pro Cys Pro Ala Pro Glu Leu Leu Gly Gly Pro Ser Val Phe
        675                 680                 685

Leu Phe Pro Pro Lys Pro Lys Asp Thr Leu Met Ile Ser Arg Thr Pro
690                 695                 700
```

Glu Val Thr Cys Val Val Asp Val Ser His Glu Asp Pro Glu Val
705                 710                 715                 720

Lys Phe Asn Trp Tyr Val Asp Gly Val Glu Val His Asn Ala Lys Thr
                725                 730                 735

Lys Pro Arg Glu Glu Gln Tyr Asn Ser Thr Tyr Arg Val Val Ser Val
            740                 745                 750

Leu Thr Val Leu His Gln Asp Trp Leu Asn Gly Lys Glu Tyr Lys Cys
        755                 760                 765

Lys Val Ser Asn Lys Ala Leu Pro Ala Pro Ile Glu Lys Thr Ile Ser
    770                 775                 780

Lys Ala Lys Gly Gln Pro Arg Glu Pro Gln Val Tyr Thr Leu Pro Pro
785                 790                 795                 800

Ser Arg Asp Glu Leu Thr Lys Asn Gln Val Ser Leu Thr Cys Leu Val
                805                 810                 815

Lys Gly Phe Tyr Pro Ser Asp Ile Ala Val Glu Trp Glu Ser Asn Gly
            820                 825                 830

Gln Pro Glu Asn Asn Tyr Lys Thr Thr Pro Pro Val Leu Asp Ser Asp
        835                 840                 845

Gly Ser Phe Phe Leu Tyr Ser Lys Leu Thr Val Asp Lys Ser Arg Trp
    850                 855                 860

Gln Gln Gly Asn Val Phe Ser Cys Ser Val Met His Glu Ala Leu His
865                 870                 875                 880

Asn His Tyr Thr Gln Lys Ser Leu Ser Leu Ser Pro Gly Lys
                885                 890

<210> SEQ ID NO 199
<211> LENGTH: 219
<212> TYPE: PRT
<213> ORGANISM: Artificial Sequence
<220> FEATURE:
<223> OTHER INFORMATION: B3G8 G29A IgG1 LC

<400> SEQUENCE: 199

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Leu Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 200
<211> LENGTH: 447
<212> TYPE: PRT
<213> ORGANISM: Artificial Sequence
<220> FEATURE:
<223> OTHER INFORMATION: B3C9 G29A IgG1 HC

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Thr Gly Gly Arg Thr Tyr Tyr Pro Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Ser Pro Leu Arg Gly Ala Trp Phe Ala Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445
```

<210> SEQ ID NO 201
<211> LENGTH: 219
<212> TYPE: PRT
<213> ORGANISM: Artificial Sequence
<220> FEATURE:
<223> OTHER INFORMATION: B3C9 G29A IgG1 LC

<400> SEQUENCE: 201

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 202
<211> LENGTH: 220

```
<212> TYPE: PRT
<213> ORGANISM: Artificial Sequence
<220> FEATURE:
<223> OTHER INFORMATION: G8 G29A Fab HC

<400> SEQUENCE: 202
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Ser Pro Leu Arg Gly Ala Trp Phe Ala Tyr Trp Gly Gln Gly Thr Leu
        100                 105                 110

Val Thr Val Ser Ser Ala Ser Thr Lys Gly Pro Ser Val Phe Pro Leu
115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys
210                 215                 220

```
<210> SEQ ID NO 203
<211> LENGTH: 219
<212> TYPE: PRT
<213> ORGANISM: Artificial Sequence
<220> FEATURE:
<223> OTHER INFORMATION: G8 G29A Fab LC

<400> SEQUENCE: 203
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Thr Tyr Leu Pro Leu Thr Phe Gly Gln Gly Thr Lys Leu Glu Ile Lys
        100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 204
<211> LENGTH: 220
<212> TYPE: PRT
<213> ORGANISM: Artificial Sequence
<220> FEATURE:
<223> OTHER INFORMATION: C9 G29A Fab HC

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Ser Pro Leu Arg Gly Ala Trp Phe Ala Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 205
<211> LENGTH: 219
<212> TYPE: PRT
<213> ORGANISM: Artificial Sequence
<220> FEATURE:
<223> OTHER INFORMATION: C9 G29A Fab LC

<400> SEQUENCE: 205

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 206
<211> LENGTH: 220
<212> TYPE: PRT
<213> ORGANISM: Artificial Sequence
<220> FEATURE:
<223> OTHER INFORMATION: B3G8 G29A Fab HC

<400> SEQUENCE: 206

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Thr Gly Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu

```
                115                 120                 125
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 207
<211> LENGTH: 219
<212> TYPE: PRT
<213> ORGANISM: Artificial Sequence
<220> FEATURE:
<223> OTHER INFORMATION: B3G8 G29A Fab LC

<400> SEQUENCE: 207

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Leu Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 208
<211> LENGTH: 220
<212> TYPE: PRT
<213> ORGANISM: Artificial Sequence
<220> FEATURE:
<223> OTHER INFORMATION: B3C9 G29A Fab HC
```

<400> SEQUENCE: 208

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Thr Gly Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 209
<211> LENGTH: 219
<212> TYPE: PRT
<213> ORGANISM: Artificial Sequence
<220> FEATURE:
<223> OTHER INFORMATION: B3C9 G29A Fab LC

<400> SEQUENCE: 209

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

```
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 210
<211> LENGTH: 444
<212> TYPE: PRT
<213> ORGANISM: Artificial Sequence
<220> FEATURE:
<223> OTHER INFORMATION: G8 G29A IgG4 S228P HC

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Ser Pro Leu Arg Gly Ala Trp Phe Ala Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270
```

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 211
<211> LENGTH: 219
<212> TYPE: PRT
<213> ORGANISM: Artificial Sequence
<220> FEATURE:
<223> OTHER INFORMATION: G8 G29A IgG4 S228P LC

<400> SEQUENCE: 211

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Leu Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 212
<211> LENGTH: 444
<212> TYPE: PRT
<213> ORGANISM: Artificial Sequence
<220> FEATURE:
<223> OTHER INFORMATION: C9 G29A IgG4 S228P HC

<400> SEQUENCE: 212

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Ser Pro Leu Arg Gly Ala Trp Phe Ala Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Lys Thr Tyr Thr Cys Asn Val Asp His Lys Pro Ser Asn
    195                 200                 205

Thr Lys Val Asp Lys Arg Val Glu Ser Lys Tyr Gly Pro Pro Cys Pro
            210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 213
<211> LENGTH: 219
<212> TYPE: PRT
<213> ORGANISM: Artificial Sequence
<220> FEATURE:
<223> OTHER INFORMATION: C9 G29A IgG4 S228P LC

<400> SEQUENCE: 213

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 214
<211> LENGTH: 444
<212> TYPE: PRT
<213> ORGANISM: Artificial Sequence
<220> FEATURE:

<223> OTHER INFORMATION: B3G8 G29A IgG4 S228P HC

<400> SEQUENCE: 214

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Thr Gly Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400
```

```
Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 215
<211> LENGTH: 219
<212> TYPE: PRT
<213> ORGANISM: Artificial Sequence
<220> FEATURE:
<223> OTHER INFORMATION: B3G8 G29A IgG4 S228P LC

<400> SEQUENCE: 215

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Leu Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 216
<211> LENGTH: 444
<212> TYPE: PRT
<213> ORGANISM: Artificial Sequence
<220> FEATURE:
<223> OTHER INFORMATION: B3C9 G29A IgG4 S228P HC

<400> SEQUENCE: 216

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45
```

```
Ser Tyr Ile Thr Thr Gly Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                      70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 217
<211> LENGTH: 219
```

```
<212> TYPE: PRT
<213> ORGANISM: Artificial Sequence
<220> FEATURE:
<223> OTHER INFORMATION: B3C9 G29A IgG4 S228P LC

<400> SEQUENCE: 217
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 218
<211> LENGTH: 446
<212> TYPE: PRT
<213> ORGANISM: Artificial Sequence
<220> FEATURE:
<223> OTHER INFORMATION: 4H11 VH5 (N82AS)/VL1 monovalent HC

<400> SEQUENCE: 218
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Lys Trp Tyr Val Asp Gly Val Glu Val His Asn Ala Lys
        275                 280                 285

Thr Lys Pro Arg Glu Glu Gln Tyr Asn Ser Thr Phe Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Thr Lys Gly Gln Pro Arg Glu Pro Ala Val Tyr Thr Leu Pro
            340                 345                 350

Pro Ser Arg Glu Glu Met Thr Lys Asn Gln Val Lys Leu Val Cys Leu
        355                 360                 365

Val Thr Gly Phe Tyr Pro Ser Asp Ile Ala Val Glu Trp Glu Ser Ser
    370                 375                 380

Gly Gln Pro Glu Asn Asn Tyr Tyr Thr Thr Pro Pro Met Leu Asp Ser
385                 390                 395                 400

Asp Gly Ser Phe Ser Leu Val Ser Trp Leu Asn Val Asp Lys Ser Arg
                405                 410                 415

Trp Gln Gln Gly Asn Ile Phe Ser Cys Ser Val Met His Glu Ala Leu
            420                 425                 430

His Asn Arg Phe Thr Gln Lys Ser Leu Ser Leu Ser Pro Gly
        435                 440                 445

<210> SEQ ID NO 219
<211> LENGTH: 219
<212> TYPE: PRT
<213> ORGANISM: Artificial Sequence
<220> FEATURE:
<223> OTHER INFORMATION: 4H11 VH5 (N82AS)/VL1 monovalent LC

<400> SEQUENCE: 219

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

```
Asn Gly Asn Thr Tyr Leu Glu Trp Tyr Gln Gln Arg Pro Gly Gln Ser
            35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 220
<211> LENGTH: 227
<212> TYPE: PRT
<213> ORGANISM: Artificial Sequence
<220> FEATURE:
<223> OTHER INFORMATION: 4H11 VH5 (N82AS)/VL1 monovalent Fc

<400> SEQUENCE: 220

Asp Lys Thr His Thr Cys Pro Pro Cys Pro Ala Pro Glu Ala Ala Gly
1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
            115                 120                 125

Ala Thr Phe Pro Pro Ser Arg Asp Glu Leu Thr Lys Asn Gln Val Thr
130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Lys Thr Asp Pro Pro
                165                 170                 175
```

```
Leu Leu Glu Ser Gln Gly Ser Phe Ala Leu Ser Ser Arg Leu Arg Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 221
<211> LENGTH: 446
<212> TYPE: PRT
<213> ORGANISM: Artificial Sequence
<220> FEATURE:
<223> OTHER INFORMATION: G8 G29A monovalent HC

<400> SEQUENCE: 221

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Lys Trp Tyr Val Asp Gly Val Glu Val His Asn Ala Lys
        275                 280                 285

Thr Lys Pro Arg Glu Glu Gln Tyr Asn Ser Thr Phe Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Thr Lys Gly Gln Pro Arg Glu Pro Ala Val Tyr Thr Leu Pro
            340                 345                 350

Pro Ser Arg Glu Glu Met Thr Lys Asn Gln Val Lys Leu Val Cys Leu
        355                 360                 365

Val Thr Gly Phe Tyr Pro Ser Asp Ile Ala Val Glu Trp Glu Ser Ser
    370                 375                 380

Gly Gln Pro Glu Asn Asn Tyr Tyr Thr Thr Pro Pro Met Leu Asp Ser
385                 390                 395                 400

Asp Gly Ser Phe Ser Leu Val Ser Trp Leu Asn Val Asp Lys Ser Arg
                405                 410                 415

Trp Gln Gln Gly Asn Ile Phe Ser Cys Ser Val Met His Glu Ala Leu
            420                 425                 430

His Asn Arg Phe Thr Gln Lys Ser Leu Ser Leu Ser Pro Gly
        435                 440                 445

<210> SEQ ID NO 222
<211> LENGTH: 219
<212> TYPE: PRT
<213> ORGANISM: Artificial Sequence
<220> FEATURE:
<223> OTHER INFORMATION: G8 G29A monovalent LC

<400> SEQUENCE: 222

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Leu Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 223
<211> LENGTH: 227
<212> TYPE: PRT
<213> ORGANISM: Artificial Sequence
<220> FEATURE:
<223> OTHER INFORMATION: G8 G29A monovalent Fc

<400> SEQUENCE: 223

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Ala Thr Phe Pro Pro Ser Arg Asp Glu Leu Thr Lys Asn Gln Val Thr
    130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Lys Thr Asp Pro Pro
                165                 170                 175

Leu Leu Glu Ser Gln Gly Ser Phe Ala Leu Ser Ser Arg Leu Arg Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 224
<211> LENGTH: 446
<212> TYPE: PRT
<213> ORGANISM: Artificial Sequence
<220> FEATURE:
<223> OTHER INFORMATION: C9 G29A monovalent HC

<400> SEQUENCE: 224

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu

```
                65                  70                  75                  80
        Gln Met Ser Ser Leu Arg Ala Glu Asp Thr Ala Val Tyr Tyr Cys Thr
                            85                  90                  95

Ser Pro Leu Arg Gly Ala Trp Phe Ala Tyr Trp Gly Gln Gly Thr Leu
                        100                 105                 110

Val Thr Val Ser Ser Ala Ser Thr Lys Gly Pro Ser Val Phe Pro Leu
                        115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
        145                 150                 155                 160

Gly Ala Leu Thr Ser Gly Val His Thr Phe Pro Ala Val Leu Gln Ser
                        165                 170                 175

Ser Gly Leu Tyr Ser Leu Ser Ser Val Val Thr Val Pro Ser Ser Ser
                        180                 185                 190

Leu Gly Thr Gln Thr Tyr Ile Cys Asn Val Asn His Lys Pro Ser Asn
                        195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Ala Ala Gly Gly Pro Ser Val
        225                 230                 235                 240

Phe Leu Phe Pro Pro Lys Pro Lys Asp Thr Leu Met Ile Ser Arg Thr
                        245                 250                 255

Pro Glu Val Thr Cys Val Val Val Asp Val Ser His Glu Asp Pro Glu
                        260                 265                 270

Val Gln Phe Lys Trp Tyr Val Asp Gly Val Glu Val His Asn Ala Lys
                        275                 280                 285

Thr Lys Pro Arg Glu Glu Gln Tyr Asn Ser Thr Phe Arg Val Val Ser
                        290                 295                 300

Val Leu Thr Val Leu His Gln Asp Trp Leu Asn Gly Lys Glu Tyr Lys
        305                 310                 315                 320

Cys Lys Val Ser Asn Lys Ala Leu Pro Ala Pro Ile Glu Lys Thr Ile
                        325                 330                 335

Ser Lys Thr Lys Gly Gln Pro Arg Glu Pro Ala Val Tyr Thr Leu Pro
                        340                 345                 350

Pro Ser Arg Glu Glu Met Thr Lys Asn Gln Val Lys Leu Val Cys Leu
                        355                 360                 365

Val Thr Gly Phe Tyr Pro Ser Asp Ile Ala Val Glu Trp Glu Ser Ser
                        370                 375                 380

Gly Gln Pro Glu Asn Asn Tyr Tyr Thr Thr Pro Pro Met Leu Asp Ser
        385                 390                 395                 400

Asp Gly Ser Phe Ser Leu Val Ser Trp Leu Asn Val Asp Lys Ser Arg
                        405                 410                 415

Trp Gln Gln Gly Asn Ile Phe Ser Cys Ser Val Met His Glu Ala Leu
                        420                 425                 430

His Asn Arg Phe Thr Gln Lys Ser Leu Ser Leu Ser Pro Gly
                        435                 440                 445

<210> SEQ ID NO 225
<211> LENGTH: 219
<212> TYPE: PRT
<213> ORGANISM: Artificial Sequence
<220> FEATURE:
<223> OTHER INFORMATION: C9 G29A monovalent LC
```

<400> SEQUENCE: 225

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 226
<211> LENGTH: 227
<212> TYPE: PRT
<213> ORGANISM: Artificial Sequence
<220> FEATURE:
<223> OTHER INFORMATION: C9 G29A monovalent Fc

<400> SEQUENCE: 226

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Ala Thr Phe Pro Pro Ser Arg Asp Glu Leu Thr Lys Asn Gln Val Thr

```
                130                 135                 140
Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Lys Thr Asp Pro Pro
                165                 170                 175

Leu Leu Glu Ser Gln Gly Ser Phe Ala Leu Ser Ser Arg Leu Arg Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225

<210> SEQ ID NO 227
<211> LENGTH: 446
<212> TYPE: PRT
<213> ORGANISM: Artificial Sequence
<220> FEATURE:
<223> OTHER INFORMATION: B3G8 G29A monovalent HC

<400> SEQUENCE: 227

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
                20                  25                  30

Tyr Met Tyr Trp Val Arg Gln Ala Pro Gly Lys Gly Leu Glu Trp Val
                35                  40                  45

Ser Tyr Ile Thr Thr Gly Gly Arg Thr Tyr Tyr Pro Asp Ser Val Lys
            50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
```

```
                260                 265                 270
Val Gln Phe Lys Trp Tyr Val Asp Gly Val Glu Val His Asn Ala Lys
            275                 280                 285

Thr Lys Pro Arg Glu Glu Gln Tyr Asn Ser Thr Phe Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Thr Lys Gly Gln Pro Arg Glu Pro Ala Val Tyr Thr Leu Pro
            340                 345                 350

Pro Ser Arg Glu Glu Met Thr Lys Asn Gln Val Lys Leu Val Cys Leu
            355                 360                 365

Val Thr Gly Phe Tyr Pro Ser Asp Ile Ala Val Glu Trp Glu Ser Ser
            370                 375                 380

Gly Gln Pro Glu Asn Asn Tyr Tyr Thr Thr Pro Pro Met Leu Asp Ser
385                 390                 395                 400

Asp Gly Ser Phe Ser Leu Val Ser Trp Leu Asn Val Asp Lys Ser Arg
                405                 410                 415

Trp Gln Gln Gly Asn Ile Phe Ser Cys Ser Val Met His Glu Ala Leu
            420                 425                 430

His Asn Arg Phe Thr Gln Lys Ser Leu Ser Leu Ser Pro Gly
            435                 440                 445

<210> SEQ ID NO 228
<211> LENGTH: 219
<212> TYPE: PRT
<213> ORGANISM: Artificial Sequence
<220> FEATURE:
<223> OTHER INFORMATION: B3G8 G29A monovalent LC

<400> SEQUENCE: 228

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala As

```
                    180                 185                 190
Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215

<210> SEQ ID NO 229
<211> LENGTH: 227
<212> TYPE: PRT
<213> ORGANISM: Artificial Sequence
<220> FEATURE:
<223> OTHER INFORMATION: B3G8 G29A monovalent Fc

<400> SEQUENCE: 229

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Ala Thr Phe Pro Pro Ser Arg Asp Glu Leu Thr Lys Asn Gln Val Thr
    130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Lys Thr Asp Pro Pro
                165                 170                 175

Leu Leu Glu Ser Gln Gly Ser Phe Ala Leu Ser Ser Arg Leu Arg Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 230
<211> LENGTH: 446
<212> TYPE: PRT
<213> ORGANISM: Artificial Sequence
<220> FEATURE:
<223> OTHER INFORMATION: B3C9 G29A monovalent HC

<400> SEQUENCE: 230

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30
```

Tyr Met Tyr Trp Val Arg Gln Ala Pro Gly Lys Gly Leu Glu Trp Val
          35                  40                  45

Ser Tyr Ile Thr Thr Gly Gly Arg Thr Tyr Tyr Pro Asp Ser Val Lys
 50                  55                  60

Gly Arg Phe Thr Ile Ser Arg Asp Asn Ser Lys Asn Thr Leu Tyr Leu
 65                  70                  75                  80

Gln Met Ser Ser Leu Arg Ala Glu Asp Thr Ala Val Tyr Tyr Cys Thr
                 85                  90                  95

Ser Pro Leu Arg Gly Ala Trp Phe Ala Tyr Trp Gly Gln Gly Thr Leu
             100                 105                 110

Val Thr Val Ser Ser Ala Ser Thr Lys Gly Pro Ser Val Phe Pro Leu
         115                 120                 125

Ala Pro Ser Ser Lys Ser Thr Ser Gly Gly Thr Ala Ala Leu Gly Cys
     130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Gln Phe Lys Trp Tyr Val Asp Gly Val Glu Val His Asn Ala Lys
        275                 280                 285

Thr Lys Pro Arg Glu Glu Gln Tyr Asn Ser Thr Phe Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Thr Lys Gly Gln Pro Arg Glu Pro Ala Val Tyr Thr Leu Pro
            340                 345                 350

Pro Ser Arg Glu Glu Met Thr Lys Asn Gln Val Lys Leu Val Cys Leu
        355                 360                 365

Val Thr Gly Phe Tyr Pro Ser Asp Ile Ala Val Glu Trp Glu Ser Ser
    370                 375                 380

Gly Gln Pro Glu Asn Asn Tyr Tyr Thr Thr Pro Pro Met Leu Asp Ser
385                 390                 395                 400

Asp Gly Ser Phe Ser Leu Val Ser Trp Leu Asn Val Asp Lys Ser Arg
                405                 410                 415

Trp Gln Gln Gly Asn Ile Phe Ser Cys Ser Val Met His Glu Ala Leu
            420                 425                 430

His Asn Arg Phe Thr Gln Lys Ser Leu Ser Leu Ser Pro Gly
        435                 440                 445

<210> SEQ ID NO 231
<211> LENGTH: 219
<212> TYPE: PRT
<213> ORGANISM: Artificial Sequence
<220> FEATURE:
<223> OTHER INFORMATION: B3C9 G29A monovalent LC

<400> SEQUENCE: 231

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 232
<211> LENGTH: 227
<212> TYPE: PRT
<213> ORGANISM: Artificial Sequence
<220> FEATURE:
<223> OTHER INFORMATION: B3C9 G29A monovalent Fc

<400> SEQUENCE: 232

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Glu Val
            115                 120                 125

Ala Thr Phe Pro Pro Ser Arg Asp Glu Leu Thr Lys Asn Gln Val Thr
        130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Lys Thr Asp Pro Pro
                165                 170                 175

Leu Leu Glu Ser Gln Gly Ser Phe Ala Leu Ser Ser Arg Leu Arg Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 233
<211> LENGTH: 220
<212> TYPE: PRT
<213> ORGANISM: Artificial Sequence
<220> FEATURE:
<223> OTHER INFORMATION: 4H11 VH5/VL1 Fab HC

<400> SEQUENCE: 233

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 234
<211> LENGTH: 219
<212> TYPE: PRT
<213> ORGANISM: Artificial Sequence
<220> FEATURE:
<223> OTHER INFORMATION: 4H11 VH5/VL1 Fab LC

<400> SEQUENCE: 234

```
Asp Val Val Met Thr Gln Ser Pro Leu Ser Leu Pro Val Thr Leu Gly
1               5                   10                  15

Gln Pro Ala Ser Ile Ser Cys Arg Ser Gln Ser Ile Val His Ser
            20                  25                  30

Asn Gly Asn Thr Tyr Leu Glu Trp Tyr Gln Gln Arg Pro Gly Gln Ser
            35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 235
<211> LENGTH: 444
<212> TYPE: PRT
<213> ORGANISM: Artificial Sequence
<220> FEATURE:
<223> OTHER INFORMATION: 4H11 VH5/VL1 IgG4 S228P HC

<400> SEQUENCE: 235

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
            35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95
```

Ser Pro Leu Arg Gly Ala Trp Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
            210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 236
<211> LENGTH: 219
<212> TYPE: PRT
<213> ORGANISM: Artificial Sequence
<220> FEATURE:
<223> OTHER INFORMATION: 4H11 VH5/VL1 IgG4 S228P LC

<400> SEQUENCE: 236

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 237
<211> LENGTH: 246
<212> TYPE: PRT
<213> ORGANISM: Artificial Sequence
<220> FEATURE:
<223> OTHER INFORMATION: VH5/VL1 scFv

<400> SEQUENCE: 237

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Asn Gly Gly Ile Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Thr Asp Val Val Met Thr Gln Ser Pro Leu Ser Leu
130                 135                 140

Pro Val Thr Leu Gly Gln Pro Ala Ser Ile Ser Cys Arg Ser Ser Gln
145                 150                 155                 160

```
Ser Ile Val His Ser Asn Gly Asn Thr Tyr Leu Glu Trp Tyr Gln Gln
            165                 170                 175

Arg Pro Gly Gln Ser Pro Arg Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Phe Gln Gly Ser His Val Pro Leu Thr Phe Gly Gln Gly Thr
225                 230                 235                 240

Lys Leu Glu Ile Lys Arg
            245

<210> SEQ ID NO 238
<211> LENGTH: 11
<212> TYPE: PRT
<213> ORGANISM: Artificial Sequence
<220> FEATURE:
<223> OTHER INFORMATION: hCDR1 VH5 extended

<400> SEQUENCE: 238

Gly Phe Ser Phe Ser Asp Tyr Tyr Met Tyr Trp
1               5                   10

<210> SEQ ID NO 239
<211> LENGTH: 7
<212> TYPE: PRT
<213> ORGANISM: Artificial Sequence
<220> FEATURE:
<223> OTHER INFORMATION: hCDR2 standard

<400> SEQUENCE: 239

Ile Thr Asn Gly Gly Ile Thr
1               5

<210> SEQ ID NO 240
<211> LENGTH: 7
<212> TYPE: PRT
<213> ORGANISM: Artificial Sequence
<220> FEATURE:
<223> OTHER INFORMATION: hCDR2 B3 standard

<400> SEQUENCE: 240

Ile Thr Thr Gly Gly Arg Thr
1               5

<210> SEQ ID NO 241
<211> LENGTH: 19
<212> TYPE: PRT
<213> ORGANISM: Artificial Sequence
<220> FEATURE:
<223> OTHER INFORMATION: hCDR2 VH5 B3 extended

<400> SEQUENCE: 241

Trp Val Ser Tyr Ile Thr Thr Gly Gly Arg Thr Tyr Tyr Pro Asp Ser
1               5                   10                  15

Val Lys Gly

<210> SEQ ID NO 242
<211> LENGTH: 19
<212> TYPE: PRT
<213> ORGANISM: Artificial Sequence
<220> FEATURE:
```

<223> OTHER INFORMATION: hCDR2 4H11 B3 extended

<400> SEQUENCE: 242

Trp Val Ala Tyr Ile Thr Thr Gly Gly Arg Thr Tyr Tyr Pro Asp Thr
1               5                   10                  15

Val Lys Gly

<210> SEQ ID NO 243
<211> LENGTH: 11
<212> TYPE: PRT
<213> ORGANISM: Artificial Sequence
<220> FEATURE:
<223> OTHER INFORMATION: lCDR1 VL1 standard

<400> SEQUENCE: 243

Gln Ser Ile Val His Ser Asn Gly Asn Thr Tyr
1               5                   10

<210> SEQ ID NO 244
<211> LENGTH: 18
<212> TYPE: PRT
<213> ORGANISM: Artificial Sequence
<220> FEATURE:
<223> OTHER INFORMATION: lCDR1 VL1 extended

<400> SEQUENCE: 244

Arg Ser Ser Gln Ser Ile Val His Ser Asn Gly Asn Thr Tyr Leu Glu
1               5                   10                  15

Trp Tyr

<210> SEQ ID NO 245
<211> LENGTH: 11
<212> TYPE: PRT
<213> ORGANISM: Artificial Sequence
<220> FEATURE:
<223> OTHER INFORMATION: lCDR1 G29A standard

<400> SEQUENCE: 245

Gln Ser Ile Val His Ser Asn Ala Asn Thr Tyr
1               5                   10

<210> SEQ ID NO 246
<211> LENGTH: 18
<212> TYPE: PRT
<213> ORGANISM: Artificial Sequence
<220> FEATURE:
<223> OTHER INFORMATION: lCDR1 G29A extended

<400> SEQUENCE: 246

Arg Ser Ser Gln Ser Ile Val His Ser Asn Ala Asn Thr Tyr Leu Glu
1               5                   10                  15

Trp Tyr

<210> SEQ ID NO 247
<211> LENGTH: 3
<212> TYPE: PRT
<213> ORGANISM: Artificial Sequence
<220> FEATURE:
<223> OTHER INFORMATION: lCDR2 standard

<400> SEQUENCE: 247

Lys Val Ser
1

```
<210> SEQ ID NO 248
<211> LENGTH: 11
<212> TYPE: PRT
<213> ORGANISM: Artificial Sequence
<220> FEATURE:
<223> OTHER INFORMATION: lCDR2 extended

<400> SEQUENCE: 248

Leu Leu Ile Tyr Lys Val Ser Asn Arg Phe Ser
1               5                   10

<210> SEQ ID NO 249
<211> LENGTH: 117
<212> TYPE: PRT
<213> ORGANISM: Artificial Sequence
<220> FEATURE:
<223> OTHER INFORMATION: Hevay chain variable region IgG4 B3

<400> SEQUENCE: 249

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Thr Thr Gly Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Ser Pro Leu Arg Gly Ala Trp Phe Ala Tyr Trp Gly Gln Gly Thr Leu
            100                 105                 110

Val Thr Val Ser Ser
        115

<210> SEQ ID NO 250
<211> LENGTH: 112
<212> TYPE: PRT
<213> ORGANISM: Artificial Sequence
<220> FEATURE:
<223> OTHER INFORMATION: variable light VL1 G8

<400> SEQUENCE: 250

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Leu Pro Leu Thr Phe Gly Gln Gly Thr Lys Leu Glu Ile Lys
            100                 105                 110

<210> SEQ ID NO 251
```

```
<211> LENGTH: 112
<212> TYPE: PRT
<213> ORGANISM: Artificial Sequence
<220> FEATURE:
<223> OTHER INFORMATION: variable light VL1 G29A G8

<400> SEQUENCE: 251

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Leu Pro Leu Thr Phe Gly Gln Gly Thr Lys Leu Glu Ile Lys
            100                 105                 110

<210> SEQ ID NO 252
<211> LENGTH: 112
<212> TYPE: PRT
<213> ORGANISM: Artificial Sequence
<220> FEATURE:
<223> OTHER INFORMATION: variable light VL1 C9

<400> SEQUENCE: 252

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr Tyr Tyr Pro Leu Thr Phe Gly Gln Gly Thr Lys Leu Glu Ile Lys
            100                 105                 110

<210> SEQ ID NO 253
<211> LENGTH: 112
<212> TYPE: PRT
<213> ORGANISM: Artificial Sequence
<220> FEATURE:
<223> OTHER INFORMATION: variable light VL1 G29A C9

<400> SEQUENCE: 253

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Tyr Gln Gln Arg Pro Gly Gln Ser
        35                  40                  45
```

-continued

```
Pro Arg Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Thr Tyr Tyr Pro Leu Thr Phe Gly Gln Gly Thr Lys Leu Glu Ile Lys
            100                 105                 110
```

<210> SEQ ID NO 254
<211> LENGTH: 19
<212> TYPE: PRT
<213> ORGANISM: Artificial Sequence
<220> FEATURE:
<223> OTHER INFORMATION: hCDR2 4H11 extended

<400> SEQUENCE: 254

```
Trp Val Ala Tyr Ile Thr Asn Gly Gly Ile Thr Tyr Tyr Pro Asp Thr
1               5                   10                  15
Val Lys Gly
```

<210> SEQ ID NO 255
<211> LENGTH: 19
<212> TYPE: PRT
<213> ORGANISM: Artificial Sequence
<220> FEATURE:
<223> OTHER INFORMATION: hCDR2 VH5 extended

<400> SEQUENCE: 255

```
Trp Val Ser Tyr Ile Thr Asn Gly Gly Ile Thr Tyr Tyr Pro Asp Ser
1               5                   10                  15
Val Lys Gly
```

<210> SEQ ID NO 256
<211> LENGTH: 18
<212> TYPE: PRT
<213> ORGANISM: Artificial Sequence
<220> FEATURE:
<223> OTHER INFORMATION: lCDR1 4H11

<400> SEQUENCE: 256

```
Arg Ser Ser Gln Ser Ile Val His Ser Asn Gly Asn Thr Tyr Leu Glu
1               5                   10                  15
Trp Tyr
```

<210> SEQ ID NO 257
<211> LENGTH: 11
<212> TYPE: PRT
<213> ORGANISM: Artificial Sequence
<220> FEATURE:
<223> OTHER INFORMATION: lCDR2 4H11

<400> SEQUENCE: 257

```
Leu Leu Ile Tyr Lys Val Ser Asn Arg Phe Ser
1               5                   10
```

<210> SEQ ID NO 258
<211> LENGTH: 5
<212> TYPE: PRT
<213> ORGANISM: Artificial Sequence
<220> FEATURE:
<223> OTHER INFORMATION: glycin linker

<400> SEQUENCE: 258

Gly Gly Gly Gly Thr
1               5

The invention claimed is:

1. An antibody or antigen-binding fragment thereof that binds to CCR6 comprising a heavy chain CDR1 comprising the amino acid sequence of SEQ ID NO: 31, and a heavy chain CDR2 comprising the amino acid sequence of SEQ ID NO: 32, SEQ ID NO: 190, SEQ ID NO: 239, SEQ ID NO: 240, SEQ ID NO: 241, SEQ ID NO: 242, SEQ ID NO: 254 or SEQ ID NO: 255 and a heavy chain CDR3 comprising the amino acid sequence of SEQ ID NO: 33; and comprising a light chain CDR1 comprising the amino acid sequence of SEQ ID NO: 34, SEQ ID NO: 191, SEQ ID NO:244, SEQ ID NO:245, SEQ ID NO: 246 or SEQ ID NO: 256, and a light chain CDR2 comprising the amino acid sequence of SEQ ID NO: 35, SEQ ID NO: 247, SEQ ID NO: 248 or SEQ ID NO:257 and a light chain CDR3 comprising the amino acid sequence of SEQ ID NO: 36 or SEQ ID NO: 192 or SEQ ID NO: 193.

2. The antibody or antigen-binding fragment thereof of claim 1, wherein the antibody or fragment thereof is a murine antibody, chimeric antibody or a humanized antibody.

3. The antibody or antigen-binding fragment thereof of claim 1, wherein the antibody or fragment thereof comprises a heavy chain variable region sequence comprising the amino acid sequence comprising SEQ ID NO: 37 or SEQ ID NO: 249 and wherein the antibody or fragment thereof comprises a light chain variable region sequence comprising the amino acid sequence of SEQ ID NO: 38, SEQ ID NO: 251 or SEQ ID NO: 253.

4. The antibody or antigen-binding fragment thereof of claim 1, wherein said antibody or fragment comprises human heavy and/or light chain constant regions and wherein the human heavy constant region is selected from the group of human immunoglobulins consisting of IGHG1, non fucosylated IGHG1 and IGHG4.

5. The antibody or antigen-binding fragment thereof of claim 1, wherein the antibody is a full length antibody or an antibody fragment selected from the group consisting of Fab, Fab', Fab'-SH, Fd, Fv, dAb, F(ab')2, scFv, bispecific single chain Fv dimers, diabodies, triabodies and scFv genetically fused to the same or a different antibody.

6. A composition comprising the antibody or antigen-binding fragment thereof of claim 1 and a pharmaceutically acceptable carrier.

7. An immunoconjugate comprising the antibody or antigen-binding fragment thereof of claim 1 linked to a therapeutic agent.

8. The antibody or antigen-binding fragment thereof of claim 1, wherein the antibody or fragment thereof comprises the heavy chain CDR1 comprising: SEQ ID NO: 31; the heavy chain CDR2 comprising: SEQ ID NO: 32, SEQ ID NO: 190, SEQ ID NO: 239, SEQ ID NO: 240, SEQ ID NO: 241, SEQ ID NO: 242, SEQ ID NO: 254 or SEQ ID NO: 255; and the heavy chain CDR3 comprising: SEQ ID NO: 33, and wherein the antibody or fragment thereof comprises a sequence at least 95% identical to the non-CDR region of heavy chain variable region sequence comprising SEQ ID NO: 37 or SEQ ID NO: 249.

9. The antibody or antigen-binding fragment thereof of claim 1, wherein the antibody or fragment thereof comprises the light chain CDR1 comprising: SEQ ID NO: 34, SEQ ID NO: 191, SEQ ID NO:244, SEQ ID NO:245, SEQ ID NO: 246 or SEQ ID NO: 256; the heavy chain CDR2 comprising: SEQ ID NO: 35, SEQ ID NO: 247, SEQ ID NO: 248 or SEQ ID NO:257; and the heavy chain CDR3 comprising: SEQ ID NO: 36 or SEQ ID NO: 192 or SEQ ID NO: 193, and wherein the antibody or fragment thereof comprises a sequence at least 95% identical to the non-CDR region of light chain variable region sequence comprising SEQ ID NO: 38, SEQ ID NO: 251, or SEQ ID NO: 253.

* * * * *